(12) United States Patent
Hilpert et al.

(10) Patent No.: US 9,718,774 B2
(45) Date of Patent: Aug. 1, 2017

(54) INDOLE CARBOXAMIDE DERIVATIVES AS P2X7 RECEPTOR ANTAGONIST

(71) Applicant: ACTELION PHARMACEUTICALS LTD, Allschwil (CH)

(72) Inventors: Kurt Hilpert, Allschwil (CH); Francis Hubler, Allschwil (CH); Thierry Kimmerlin, Allschwil (CH); Dorte Renneberg, Allschwil (CH); Simon Stamm, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 14/651,922

(22) PCT Filed: Dec. 11, 2013

(86) PCT No.: PCT/IB2013/060794
§ 371 (c)(1),
(2) Date: Jun. 12, 2015

(87) PCT Pub. No.: WO2014/091415
PCT Pub. Date: Jun. 19, 2014

(65) Prior Publication Data
US 2015/0322008 A1 Nov. 12, 2015

(30) Foreign Application Priority Data
Dec. 12, 2012 (EP) .................................... 12196711

(51) Int. Cl.
| | | |
|---|---|---|
| C07D 209/08 | (2006.01) |
| C07D 491/08 | (2006.01) |
| C07D 403/12 | (2006.01) |
| C07D 401/14 | (2006.01) |
| C07D 405/14 | (2006.01) |
| C07D 413/14 | (2006.01) |
| C07D 401/12 | (2006.01) |
| C07D 403/14 | (2006.01) |
| C07D 413/12 | (2006.01) |
| C07D 417/12 | (2006.01) |
| C07D 498/08 | (2006.01) |

(52) U.S. Cl.
CPC ......... *C07D 209/08* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 417/12* (2013.01); *C07D 491/08* (2013.01); *C07D 498/08* (2013.01)

(58) Field of Classification Search
CPC ............................ C07D 209/08; C07D 401/12
See application file for complete search history.

(56) References Cited

U.S. PATENT DOCUMENTS

| | | |
|---|---|---|
| 2007/0281939 A1 | 12/2007 | Dombrowski et al. |
| 2012/0157494 A1 | 6/2012 | Harris, III et al. |
| 2014/0073651 A1 | 3/2014 | Hilpert et al. |
| 2014/0163035 A1 | 6/2014 | Hilpert et al. |
| 2015/0025075 A1 | 1/2015 | Hilpert et al. |

FOREIGN PATENT DOCUMENTS

| | | |
|---|---|---|
| EP | 2243772 | 10/2010 |
| WO | WO 00/61569 | 10/2000 |
| WO | WO 01/42194 | 6/2001 |
| WO | WO 01/44170 | 6/2001 |
| WO | WO 01/94338 | 12/2001 |
| WO | WO 03/041707 | 5/2003 |
| WO | WO 03/042190 | 5/2003 |
| WO | WO 03/042191 | 5/2003 |
| WO | WO 03/080579 | 10/2003 |
| WO | WO 2004/058270 | 7/2004 |
| WO | WO 2004/058731 | 7/2004 |
| WO | WO 2004/074224 | 9/2004 |
| WO | WO 2004/099146 | 11/2004 |
| WO | WO 2004/106305 | 12/2004 |
| WO | WO 2005/009968 | 2/2005 |
| WO | WO 2005/014529 | 2/2005 |
| WO | WO 2005/111003 | 11/2005 |
| WO | WO 2006/025783 | 3/2006 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
PCT/IB2013/060794 Written Opinion dated Mar. 19, 2014.
PCT/IB2013/060794 International Search Report dated Mar. 19, 2014.
Abberley, et al. "Identification Of 2-Oxo-N-(Phenylmethyl)-4-Imidazolidinecarboxamide Antagonists Of The P2x7 Receptor" Bioorganic & Medicinal Chemistry Letters, vol. 20, (2010), p. 6370-6374.

(Continued)

*Primary Examiner* — Shawquia Jackson
(74) *Attorney, Agent, or Firm* — Hoxie & Associates LLC

(57) ABSTRACT

The invention relates to indole carboxamide derivatives of formula (I),

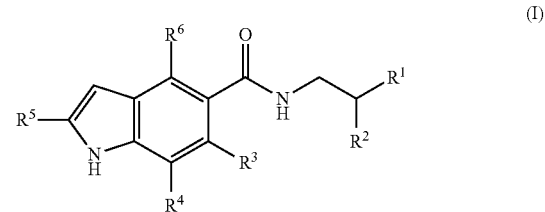

wherein $R^1$, $R^2$, $R^3$, $R^4$, $R^5$ and $R^6$ are as defined in the description, their preparation and their use as pharmaceutically active compounds.

19 Claims, No Drawings

(56) References Cited

FOREIGN PATENT DOCUMENTS

| | | |
|---|---|---|
| WO | WO 2006/059945 | 6/2006 |
| WO | WO 2006/080884 | 8/2006 |
| WO | WO 2006/102610 | 9/2006 |
| WO | WO 2007/055374 | 5/2007 |
| WO | WO 2007/109154 | 9/2007 |
| WO | WO 2007/109160 | 9/2007 |
| WO | WO 2007/109172 | 9/2007 |
| WO | WO 2007/109182 | 9/2007 |
| WO | WO 2007/109192 | 9/2007 |
| WO | WO 2007/109201 | 9/2007 |
| WO | WO 2007/141267 | 12/2007 |
| WO | WO 2007/141269 | 12/2007 |
| WO | WO 2008/003697 | 1/2008 |
| WO | WO 2008/066789 | 6/2008 |
| WO | WO 2008/094473 | 8/2008 |
| WO | WO 2008/112205 | 9/2008 |
| WO | WO 2008/114002 | 9/2008 |
| WO | WO 2008/116814 | 10/2008 |
| WO | WO 2008/116845 | 10/2008 |
| WO | WO 2008/119685 | 10/2008 |
| WO | WO 2008/119825 | 10/2008 |
| WO | WO 2008/124153 | 10/2008 |
| WO | WO 2008/125600 | 10/2008 |
| WO | WO 2008/138876 | 11/2008 |
| WO | WO 2009/012482 | 1/2009 |
| WO | WO 2009/023623 | 2/2009 |
| WO | WO 2009/070116 | 6/2009 |
| WO | WO 2009/074518 | 6/2009 |
| WO | WO 2009/074519 | 6/2009 |
| WO | WO 2009/077362 | 6/2009 |
| WO | WO 2009/077559 | 6/2009 |
| WO | WO 2009/108551 | 9/2009 |
| WO | WO 2009/118175 | 10/2009 |
| WO | WO 2009/132000 | 10/2009 |
| WO | WO 2010/118921 | 10/2010 |
| WO | WO 2011/054947 | 5/2011 |
| WO | WO 2012/114268 | 8/2012 |
| WO | WO 2012/163792 | 12/2012 |
| WO | WO 2013/014587 | 1/2013 |
| WO | WO 2013/108227 | 7/2013 |
| WO | WO 2014/057078 | 4/2014 |
| WO | WO 2014/057080 | 4/2014 |
| WO | WO 2014/097140 | 6/2014 |
| WO | WO 2014/115072 | 7/2014 |
| WO | WO 2014/115078 | 7/2014 |

OTHER PUBLICATIONS

Abdi, et al. "Discovery and Structure-Activity Relationships Of A Series Of Pyroglutamic Acid Amide Antagonists Of The P2x7 Receptor" Bioorganic & Medicinal Chemistry Letters, vol. 20, (2010), p. 5080-5084.
Arbeloa et al., "P2X7 receptor blockade prevents ATP excitotoxicity in neurons and reduces brain damage after ischemia." Neurobiol Dis., vol. 45(3), (2012), p. 954-961.
Brown, et al. "1,3,6-Trisubstituted Indoles As Peptidoleukotriene Antagonists: Benefits Of A Second, Polar, Pyrrole Substituent" Journal Of Medicinal Chemistry, vol. 35 (13), (1992), p. 2419-2439.
Chen, et al. "Discovery Of 2-Chloro-N-((4,4-Difluoro-1-Hdroxycyclohexyl)Methyl)-5-(5-Fluoropyrimidin-2-Y1)Benzamide As A Portent and Cns Penetrable P2x7 Receptor Antagonist" Bioorganic & Medicinal Chemistry Letters, vol. 20, (2010), p. 3107-3111.
Chessell, et al. "Disruption Of The P2x7 Purinoceptor Gene Abolishes Chronic Inflammatory And Neuropathic Pain" Pain, vol. 114, (2005), p. 386-396.
Dell'Antonio et al., "Antinociceptive effect of a new P(2Z)/P2X7 antagonist, oxidized ATP, in arthritic rats." Neurosci Lett., vol. 327(2), (2002), p. 87-90.
Deuchars, et al. "Neuronal P2x7 Receptors Are Targeted to Presynaptic Terminals in the Central and Peripheral Nervous Systems" The Journal Of Neuroscience, vol. 21 (18), (2001), p. 7143-7152.
Duplantier, et al. "Optimization Of The Physicochemical And Pharmacokinetic Attributes In A 6-Azauracil Series of P2x7 Receptor Antagonists Leading To The Discovery Of The Clinical Candidate Ce-224,535" Bioorganic & Medcinal Chemistry Letters vol. 21, (2011), p. 3708-3711.
Eltom et al., "P2X7 receptor and caspase 1 activation are central to airway inflammation observed after exposure to tobacco smoke." PLoS One, vol. 6(9), (2011), p. e24097.
Engel et al., "P2X7 receptor in epilepsy; role in pathophysiology and potential targeting for seizure control." Int J Physiol Pathophysiol Pharmacol, vol. 4(4), (2012), p. 174-187.
Eser et al., "Safety and Efficacy of an Oral Inhibitor of the Purinergic Receptor P2X7 in Adult Patients with Moderately to Severely Active Crohn's Disease: A Randomized Placebo-controlled, Double-blind, Phase IIa Study." Inflamm Bowel Dis., vol. 0(0), (2015), p. 1-7.
Ferrari, et al. "Atp-Mediated Cytotoxicity In Microglial Cells" Neuropharmacology, vol. 36, No. 9 (1997), p. 1295-1301.
Furber, et al. "Discovery Of Potent And Selective Adamantane-Based Small-Molecule P2x7 Receptor Antagonistss/Interleukin-1β Inhibitors" Journal Of Medicinal Chemistry, vol. 50 (2007), p. 5882-5885.
Gandelman et al., "Extracellular ATP and the P2X7 receptor in astrocyte-mediated motor neuron death: implications for amyotrophic lateral sclerosis", J Neuroinflammation, vol. 7(33), (2010), p. 1-9.
Gould et al., "Salt Selection for Basic Drugs" International Journal Of Pharmaceutics, vol. 33, (1986), p. 201-217.
Greene, et al. "Protective Groups in Organic Synthesis" Wiley Interscience (1999).
Guile, et al., "Antagonists Of The P2x7 Eceptor. From Lead Identification To Drug Development" Journal Of Medicinal Chemistry, vol. 52(10), (2009), p. 3123-3141.
Gulbransen et al., "Activation of neuronal P2X7 receptor-pannexin-1 mediates death of enteric neurons during colitis." Nat Med., vol. 18(4), (2012), p. 600-604.
Honore et al., "A-740003 [N-(1-{[cyanoimino)(5-quinolinylamino)methyl]amino}-2,2-dimethylpropyl)-2-(3,4-dimethoxyphenyl)acetamide], a novel and selective P2X7 receptor antagonist, dose-dependently reduces neuropathic pain in the rat", J Pharmacol Exp Ther, vol. 319(3), (2006), p. 1376-1385.
J.S. Wiley, et al. "Transduction Mechanisms Of P2z Purinoceptors" Ciba Foundation Symposia vol. 198 (1996), p. 149-160 and 160-165.
Jacobs, et al. "Synthesis, Structure-Acivity Relationships, And Pharmacoloogical Evalation Of A Series of Luorinated 3-Benzyl-5-Indolecarboxamides: Identification of 4-[[5-[((2r)-2-Methyl-4,4,4-Trifluorobutyl)Carbamoyl]-1-Methylindol-3-Y1]Methyl]-3-Methoxy-N-[(2-Methylphenyl)Sulfonyl]Benzamide, A Ptent, Orally Active Antagonist Of Leukotrienes D4 and E4" Journal of Medicinal Chemistry, vol. 37 (1994), p. 1282-1297.
Keating et al., "P2X7 receptor-dependent intestinal afferent hypersensitivity in a mouse model of postinfectious irritable bowel syndrome." J Immunol., vol. 187(3), (2011), p. 1467-1474.
Lang et al., "Oxidized ATP inhibits T-cell-mediated autoimmunity." Eur J Immunol., vol. 40(9), (2010), p. 2401-2408.
Letavic, et al. "Synthesis and Pharmacological Characterization Of Two Novel, Brain Penetrating P2x7 Antagonists" American Chemical Society Medicinal Chemisty Letters, vol. 4 (2013), p. 419-422.
Mezzaroma et al., "The inflammasome promotes adverse cardiac remodeling following acute myocardial infarction in the mouse." Proc Natl Acad Sci U S A 108(49), (2011), p. 19725-19730.
Muller et al., "A potential role for P2X7R in allergic airway inflammation in mice and humans", Am J Respir Cell Mol Biol, vol. 44(4), (2011), p. 456-464.
North et al., "Molecular Physiology of P2x Receptors" Physiology Review, vol. 82 (2002), p. 1013-1067.
Pastore et al., "Stimulation of purinergic receptors modulates chemokine expression in human keratinocytes." J Invest Dermatol., vol. 127(3), (2007), p. 660-667.

(56) References Cited

OTHER PUBLICATIONS

Peng et al., "Systemic administration of an antagonist of the ATP-sensitive receptor P2X7 improves recovery after spinal cord injury." Proc Natl Acad Sci U S A., vol. 106(30), (2009), p. 12489-12493.
Remington, The Science And Practice Of Pharmacy, 21$^{st}$ Edition (2005).
Sanz et al., "Activation of microglia by amyloid {beta} requires P2X7 receptor expression." J Immunol, vol. 182(7), (2009), p. 4378-4385.
Solle, et al., "Mechanisms Of Signal Transduction: Altered Cytokine Production In Mice Lacking P2x7 Receptors" The Journal Of Biological Chemistry, vol. 276(1), (2001), p. 125-132.
Sperlagh, et al., "Involvement Of P2x7 Receptors In The Regulation Of Neurotransmitter Release In The Rat Hippocampus" Journal Of Neurochemistry, vol. 81 (2002), p. 1196-1211.
Subramanyam, et al., "Discovery, Synthesis And Sar Of Azinyl- and Azolylbenzamides Antagonists Of The P2x7 Receptor" Bioorganic & Medicinal Chemisty Letters, vol. 21 (2011), p. 5475-5479.
Surprenant, et al. "The Cytolytic P2z Receptor for Extracellular Atp Identified As a P2x Receptor (P2x7)" Science, vol. 272 (1996), p. 735-738.
Taylor et al., "P2X7 deficiency attenuates renal injury in experimental glomerulonephritis." J Am Soc Nephrol., vol. 20(6), (2009), p. 1275-1281.
Velcicky, et al. "Palladium-Catalyzed Cyanomethylation Of Aryl Halides Through Domino Suzuki Coupling-Isoxazole Fragmentation" Journal Of The American Chemical Society, vol. 133 (2011), p. 2948-6951.
Virginio, et al., "Kinetics Of Cell Lysis, Dye Uptake And Permeability Changes In Cells Expressing The Rat P2x7 Receptor" Journal of Physiology, vol. 519.2 (1999), p. 335-346.
Wang, et al., "Palladium-Catalyzed One-Pot Synthesis Of 2-Alkyl-2-Arylcyanoacetates" Journal Organic Chemistry, vol. 73 (4), (2008), p. 1643-1645.
Wesselius et al., "Role of purinergic receptor polymorphisms in human bone." Front Biosci (Landmark Ed), vol. 16, (2011), p. 2572-2585.
Yu, et al., "Cellular Localization Of P2x7 Receptor Mrna in the Rat Brain" Brain Research, vol. 1194 (2008), p. 45-55.

* cited by examiner

INDOLE CARBOXAMIDE DERIVATIVES AS P2X7 RECEPTOR ANTAGONIST

CROSS REFERENCE TO RELATED APPLICATIONS

This application is a U.S. National Phase Application filed under 35 U.S.C. 371 of International Application No. PCT/IB2013/060794 filed Dec. 11, 2013, which claims priority to European Application No. 12196711.1 filed Dec. 12, 2012.

The present invention relates to indole carboxamide derivatives of formula (I) and their use as pharmaceuticals. The invention also concerns related aspects including processes for the preparation of the compounds, pharmaceutical compositions containing one or more compounds of formula (I), and especially their use as $P2X_7$ receptor antagonists.

The $P2X_7$ receptors (P2RX7) belong to the family of P2X ionotropic receptors that are activated by extracellular nucleotides, in particular adenosine triphosphate (ATP). P2RX7 is distinguished from other P2X family members by the high concentrations (mM range) of ATP required to activate it and its ability to form a large pore upon prolonged or repeated stimulation (North, R. A., Physiol. Rev. 2002, 82(4), 1013-67; Surprenant, A., Rassendren, F. et al., Science 1996, 272(5262), 735-8; Virginio, C., MacKenzie, A. et al., J. Physiol., 1999, 519, 335-46). P2RX7 is present on many cell types, especially ones known to be involved in inflammatory and immune processes. This is reflected within both the periphery and the CNS as Lipopolysaccharide S (LPS) priming of monocytes and microglia followed by ATP stimulation has been shown to lead to the local release and processing of IL1β and other family members including IL18 through a P2RX7 mediated mechanism. Indeed mice lacking the P2RX7 receptor are unable to release IL1β following LPS priming and ATP stimulation providing further evidence of its role in this pathway (Solle, M., Labasi, J. et al., J. Biol. Chem., 2001, 276(1), 125-32). In addition L-selectin shedding from monocytes, macrophages and lymphocytes, degranulation in mast cells and apoptosis in lymphocytes are all associated with P2RX7 stimulation. P2RX7 is also expressed on epithelial and endothelial cells (Ferrari, D., Chiozzi, P. et al., Neuropharmacology 1997, 36(9), 1295-301; Wiley, J. S., Chen, J. R. et al., Ciba Found Symp. 1996, 198, 149-60 and 160-5; North, R. A., Physiol. Rev. 2002, 82(4), 1013-67). In addition to its role in the periphery it may have an important function in neurotransmission within the CNS through its activation on postsynaptic and/or presynaptic central and peripheral neurons and glia (Deuchars, S. A., Atkinson, L. et al., J. Neurosci. 2001, 21(18), 7143-52; Sperlagh, B., Kofalvi, A. et al., J. Neurochem. 2002, 81(6), 1196-211). Recent data that has emerged using in situ hybridization demonstrated that P2X7 receptor mRNA was widely distributed throughout the rat brain. Specifically, among the areas of high P2X7mRNA expression noted were the piriform cortex, hippocampus, pontine nuclei and the anterior horn of the spinal cord (Yu, Y., Ugawa, S. et al., Brain. Res. 2008, 1194, 45-55). Hence there is therapeutic rationale for the use of P2X7 ion channel blockers in the treatment of a variety of disease states. These include but are not limited to diseases associated with the central nervous system such as stroke or injury and diseases associated with neuro-degeneration and neuroinflammation such as Alzheimer's disease, Huntington's disease, epilepsy, Amyotrophic lateral sclerosis, acute spinal cord injury additionally to meningitis, sleep disorders, mood and anxiety disorders as well as chronic and neuropathic and inflammatory pain. Furthermore, peripheral inflammatory disorders and autoimmune diseases including but not limited to rheumatoid arthritis, osteoarthritis, psoriasis, allergic dermatitis, asthma, chronic obstructive pulmonary disease, airways hyper-responsiveness, septic shock, bronchitis, glomerulonephritis, irritable bowel disease, skin injury, lung emphysema, Limb girdle dystrophy type 2B, fibrosis, Syndrome of synovitis Acne Pustulosis, atherosclerosis, burn injury, spinal cord injury, Hyperostosis Osteitis, Crohn's disease, ulcerative colitis, growth and metastases of malignant cells, myoblastic leukaemia, diabetes, trauma, meningitis, osteoporosis, burn injury, ischemic heart disease, and varicose veins and trauma, are all examples where the involvement of P2X7 channels has been implicated. In addition a recent report suggests a link between P2RX7 and chronic, inflammatory and neuropathic pain (Chessell, I. P., Hatcher, J. P. et al., Pain, 2005, 114(3), 386-96). Overall, these findings indicate a role for the P2X7 receptor in the process of neuronal synaptic transmission and therefore a potential role for P2X7 antagonists as novel therapeutic tools to treat neuropathic pain.

In view of the above observations, there is significant requirement for P2X7 antagonists that can be efficiently used in treating neuropathic pain, chronic inflammatory pain, inflammation, and neurodegenerative conditions.

Different indole carboxamide derivatives, which are also $P2X_7$ receptor antagonists, have been disclosed in WO 2009/023623, WO 2009/108551 and WO 2009/118175. Quinoline and isoquinoline derivatives which are also $P2X_7$ receptor antagonists, have been disclosed in WO2009/132000.

Various embodiments of the invention are presented hereafter:

1) The present invention relates to indole carboxamide derivatives of formula (I),

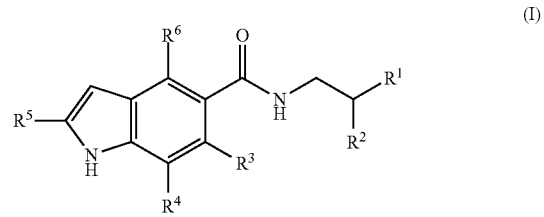

wherein $R^1$ represents a heteroaryl or an aryl group which groups are independently unsubstituted, mono-, di-, or tri-substituted, wherein the substituents are independently selected from the group consisting of $(C_1-C_4)$alkyl, $(C_3-C_6)$cycloalkyl, $(C_1-C_4)$alkoxy, $(C_1-C_3)$fluoroalkyl, $(C_1-C_3)$fluoroalkoxy, hydroxy, halogen and phenoxy;

$R^2$ represents
- heterocyclyl which is unsubstituted, mono- or di-substituted, wherein the substituents are independently selected from $(C_1-C_4)$alkyl, $(C_1-C_4)$alkylcarbonyl, $(C_1-C_4)$alkoxycarbonyl, $(C_1-C_4)$alkylsulfonyl, and halogen;
- heterocyclyloxy;
- $(C_3-C_6)$cycloalkyl which is unsubstituted or mono- or di-substituted with halogen;
- $(C_3-C_6)$cycloalkyloxy;
- N—$(C_3-C_6)$cycloalkyl-amino;
- N—$(C_3-C_6)$cycloalkylmethyl-amino;
- $(C_3-C_6)$alkyl;
- $(C_2-C_6)$alkoxy;
- N—$(C_1-C_4)$alkylamino;

N,N-di-[($C_1$-$C_4$)alkyl]-amino; or
N-arylmethyl-N—($C_1$-$C_4$)alkyl-amino;

$R^3$ represents hydrogen or halogen;

$R^4$ represents hydrogen, fluoro, chloro, ($C_1$-$C_4$)alkyl, ($C_1$-$C_4$)alkoxy, ($C_1$-$C_4$)alkyl-carbonyl, hydroxy-($C_1$-$C_4$)alkyl, hydroxy-($C_2$-$C_4$)alkoxy, ($C_1$-$C_2$)alkoxy-($C_1$-$C_4$)alkyl or ($C_1$-$C_4$)alkoxy-($C_2$-$C_4$)alkoxy;

$R^5$ represents hydrogen or ($C_1$-$C_4$)alkyl; and $R^6$ represents fluoro, chloro, methyl, ethyl or ($C_1$-$C_2$)fluoroalkyl;

and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

DEFINITIONS

The following paragraphs provide definitions of the various chemical moieties for the compounds according to the invention and are intended to apply uniformly throughout the specification and claims unless an otherwise expressly set out definition provides a broader or narrower definition.

The term "alkyl", used alone or in combination, refers to a straight or branched chain alkyl group containing one to six carbon atoms. The term "($C_x$-$C_y$)alkyl" (x and y each being an integer), refers to an alkyl group as defined before containing x to y carbon atoms. For example a ($C_1$-$C_4$)alkyl group contains from one to four carbon atoms. Representative examples of ($C_1$-$C_4$)alkyl groups include methyl, ethyl, n-propyl, iso-propyl, n-butyl, iso-butyl, sec-butyl and tert-butyl. A ($C_3$-$C_6$)alkyl group contains from three to six carbon atoms. Representative examples of ($C_3$-$C_6$)alkyl groups include n-propyl, iso-propyl, n-butyl, iso-butyl, sec-butyl, tert-butyl, pent-1-yl, pent-2-yl, pent-3-yl, 2-methyl-but-1-yl, 3-methyl-but-1-yl, 2-methyl-but-2-yl, 3-methyl-but-2-yl, hex-1-yl, hex-2-yl, hex-3-yl, 2-methyl-pent-2-yl, 3-methyl-pent-2-yl, 4-methyl-pent-2-yl, 2-methyl-pent-3-yl, 3-methyl-pent-3-yl, 2,3-dimethyl-but-2-yl and 3,3-dimethyl-but-2-yl.

The term "alkoxy", used alone or in combination, refers to an alkyl-O— group wherein the alkyl group is as defined above. The term "($C_x$-$C_y$)alkoxy" (x and y each being an integer) refers to an alkoxy group as defined before containing x to y carbon atoms. For example a ($C_1$-$C_4$)alkoxy group contains from one to four carbon atoms. Representative examples of ($C_1$-$C_4$)alkoxy groups include methoxy, ethoxy, n-propoxy, iso-propoxy, n-butoxy, iso-butoxy, sec-butoxy and tert-butoxy. A ($C_2$-$C_6$)alkoxy group contains from two to six carbon atoms. Representative examples of ($C_2$-$C_6$)alkoxy groups include ethoxy, n-propoxy, iso-propoxy, n-butoxy, iso-butoxy, sec-butoxy, tert-butoxy, pent-1-yloxy, pent-2-yloxy, pent-3-yloxy, 2-methyl-but-1-yloxy, 3-methyl-but-1-yloxy, 2-methyl-but-2-yloxy, 3-methyl-but-2-yloxy, hex-1-yloxy, hex-2-yloxy, hex-3-yloxy, 2-methyl-pent-2-yloxy, 3-methyl-pent-2-yloxy, 4-methyl-pent-2-yloxy, 2-methyl-pent-3-yloxy, 3-methyl-pent-3-yloxy, 2,3-dimethyl-but-2-yloxy and 3,3-dimethyl-but-2-yloxy.

The term "hydroxy-($C_1$-$C_4$)alkyl", used alone or in combination, refers to an alkyl group as defined before containing from one to four carbon atoms in which one hydrogen atom has been replaced with hydroxy. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl.

The term "hydroxy-($C_2$-$C_4$)alkoxy", used alone or in combination, refers to an alkoxy group as defined before containing from two to four carbon atoms in which one hydrogen atom has been replaced with hydroxy. Examples of said groups are 2-hydroxy-ethoxy, 2-hydroxy-prop-1-yloxy, 3-hydroxy-prop-1-yloxy, 1-hydroxy-prop-2-yloxy, 2-hydroxy-but-1-yloxy, 3-hydroxy-but-1-yloxy, 4-hydroxy-but-1-yloxy, 1-hydroxy-but-2-yloxy, 3-hydroxy-but-2-yloxy, 4-hydroxy-but-2-yloxy, 2-hydroxy-2-methyl-prop-1-yloxy, 3-hydroxy-2-methyl-prop-1-yloxy, and 2-hydroxy-1,1-dimethyl-eth-1-yloxy.

The term "($C_1$-$C_2$)alkoxy-($C_1$-$C_4$)alkyl", used alone or in combination, refers to an alkyl group as defined before containing from one to four carbon atoms in which one hydrogen atom has been replaced with ($C_1$-$C_2$)alkoxy as defined before. Examples of said groups are methoxy-methyl, methoxy-ethyl, methoxy-propyl, methoxy-butyl, ethoxy-methyl, ethoxy-ethyl, ethoxy-propyl and ethoxy-butyl.

The term "($C_1$-$C_4$)alkoxy-($C_2$-$C_4$)alkoxy", used alone or in combination, refers to an alkoxy group as defined before containing from two to four carbon atoms in which one hydrogen atom has been replaced with ($C_1$-$C_4$)alkoxy as defined before. A preferred example of said groups is 2-tert-butoxy-ethoxy.

The term "($C_1$-$C_4$)alkylcarbonyl", used alone or in combination, refers to a ($C_1$-$C_4$)alkyl-C(O)— group wherein the ($C_1$-$C_4$)alkyl group is as defined before, which is attached to the rest of the molecule via the carbonyl-C-atom. Representative examples of ($C_1$-$C_4$)alkyl-carbonyl groups include methylcarbonyl, ethylcarbonyl, n-propylcarbonyl, iso-propylcarbonyl, n-butylcarbonyl, iso-butylcarbonyl, sec-butylcarbonyl and tert-butylcarbonyl.

The term "($C_1$-$C_4$)alkoxycarbonyl", used alone or in combination, refers to a ($C_1$-$C_4$)alkyl-O—C(O)— group wherein the ($C_1$-$C_4$)alkyl group is as defined before, which is attached to the rest of the molecule via the carboxyl-C-atom. Representative examples of ($C_1$-$C_4$)alkoxy-carbonyl groups include methoxycarbonyl, ethoxycarbonyl, n-propoxycarbonyl, iso-propoxycarbonyl, n-butoxycarbonyl, iso-butoxycarbonyl, sec-butoxycarbonyl and tert-butoxycarbonyl.

The term "($C_1$-$C_4$)alkylsulfonyl", used alone or in combination, refers to a ($C_1$-$C_4$)alkyl-S(O)$_2$— group wherein the ($C_1$-$C_4$)alkyl group is as defined before, which is attached to the rest of the molecule via the sulfonyl-S-atom. Representative examples of ($C_1$-$C_4$)alkyl-sulfonyl groups include methylsulfonyl, ethylsulfonyl, n-propylsulfonyl, iso-propylsulfonyl, n-butylsulfonyl, iso-butylsulfonyl, sec-butylsulfonyl and tert-butylsulfonyl.

The term "N—($C_1$-$C_4$)alkylamino", used alone or in combination, refers to an amino group (—NH$_2$) wherein one hydrogen atom has been replaced with ($C_1$-$C_4$)alkyl as defined before. Representative examples of N—($C_1$-$C_4$)alkylamino groups include methylamino, ethylamino, n-propylamino, iso-propylamino, n-butylamino, iso-butylamino, sec-butylamino and tert-butylamino.

The term "N,N-di-[($C_1$-$C_4$)alkyl]-amino", used alone or in combination, refers to an amino group (—$NH_2$) wherein both hydrogen atoms have been replaced with ($C_1$-$C_4$)alkyl groups as defined before, wherein the two alkyl groups are the same or different. Representative examples of N,N-di-[($C_1$-$C_4$)alkyl]-amino groups include dimethylamino, methyl-ethylamino, methyl-n-propylamino, methyl-iso-propylamino, methyl-n-butylamino, methyl-iso-butylamino, methyl-sec-butylamino, methyl-tert-butylamino, diethylamino, ethyl-n-propylamino, ethyl-iso-propylamino, ethyl-n-butylamino, ethyl-iso-butylamino, ethyl-sec-butylamino and ethyl-tert-butylamino.

The term "N-arylmethyl-N—($C_1$-$C_4$)alkyl-amino", used alone or in combination, refers to an amino group (—$NH_2$) wherein one hydrogen atom has been replaced with ($C_1$-$C_4$) alkyl as defined before and the other hydrogen atom has been replaced with arylmethyl, wherein the term aryl refers to phenyl or naphthyl. Representative examples of N-arylmethyl-N—($C_1$-$C_4$)alkyl-amino groups include benzyl-methylamino, benzyl-ethylamino, benzyl-n-propylamino, benzyl-iso-propylamino, benzyl-n-butylamino, benzyl-iso-butylamino, benzyl-sec-butylamino, benzyl-tert-butylamino, naphthylmethyl-methylamino, naphthylmethyl-ethylamino, naphthylmethyl-n-propylamino, naphthylmethyl-iso-propylamino, naphthylmethyl-n-butylamino, naphthylmethyl-iso-butylamino, naphthylmethyl-sec-butylamino and naphthylmethyl-tert-butylamino.

The term "($C_x$-$C_y$)fluoroalkyl" (x and y each being an integer) refers to an alkyl group as defined before containing x to y carbon atoms in which one or more (and possibly all) hydrogen atoms have been replaced with fluoro. For example a ($C_1$-$C_3$)fluoroalkyl group contains from one to three carbon atoms in which one to seven hydrogen atoms have been replaced with fluoro. In analogy, a ($C_1$-$C_2$) fluoroalkyl group contains one or two carbon atoms in which one to five hydrogen atoms have been replaced with fluoro. Representative examples of said groups are difluoromethyl, trifluoromethyl, 2,2-difluoro-ethyl and 2,2,2-trifluoroethyl.

The term "($C_x$-$C_y$)fluoroalkoxy" (x and y each being an integer) refers to an alkoxy group as defined before containing x to y carbon atoms in which one or more (and possibly all) hydrogen atoms have been replaced with fluoro. For example a ($C_1$-$C_3$)fluoroalkoxy group contains from one to three carbon atoms in which one to seven hydrogen atoms have been replaced with fluoro. Representative examples of said groups are difluoromethoxy, trifluoromethoxy, 2,2-difluoroethoxy and 2,2,2-trifluoroethoxy.

The term "($C_3$-$C_6$)cycloalkyl", used alone or in combination, refers to a cycloalkyl group with 3 to 6 carbon atoms. Examples of ($C_3$-$C_6$)cycloalkyl groups are cyclopropyl, cyclobutyl, cyclopentyl and cyclohexyl.

The term "($C_3$-$C_6$)cycloalkyloxy", used alone or in combination, refers to a ($C_3$-$C_6$)cycloalkyl-O— group wherein the ($C_3$-$C_6$)cycloalkyl group is as defined above. Examples of ($C_3$-$C_6$)cycloalkyloxy groups are cyclopropyloxy, cyclobutyloxy, cyclopentyloxy and cyclohexyloxy.

The term "N—($C_3$-$C_6$)cycloalkyl-amino", used alone or in combination, refers to an amino group (—$NH_2$) wherein one hydrogen atom has been replaced with ($C_3$-$C_6$)cycloalkyl as defined before. Representative examples of N—($C_3$-$C_6$)cycloalkyl-amino groups include cyclopropyl-amino, cyclobutyl-amino, cyclopentyl-amino and cyclohexyl-amino.

The term "N—($C_3$-$C_6$)cycloalkylmethyl-amino", used alone or in combination, refers to an amino group (—$NH_2$) wherein one hydrogen atom has been replaced with a ($C_3$-$C_6$)cycloalkylmethyl group wherein the ($C_3$-$C_6$)cycloalkyl group is as defined before.

Representative examples of N—($C_3$-$C_6$)cycloalkylmethyl-amino groups include cyclopropylmethyl-amino, cyclobutylmethyl-amino, cyclopentylmethyl-amino and cyclohexylmethyl-amino.

The term halogen means fluoro, chloro, bromo or iodo.

The term "aryl", used alone or in combination, means a phenyl or a naphthyl group. The aryl group is unsubstituted or substituted as explicitly defined. Examples of unsubstituted or substituted aryl groups are 2-fluoro-phenyl, 3-fluoro-phenyl, 4-fluoro-phenyl, 2,4-difluoro-phenyl, 3,4-difluoro-phenyl, 3,5-difluoro-phenyl, 2,4,6-trifluoro-phenyl, 4-chloro-phenyl, 4-chloro-2-fluoro-phenyl, 2,4-dichloro-phenyl, 4-methyl-phenyl, 4-methoxy-phenyl, 4-trifluoromethyl-phenyl, 4-trifluoromethoxy-phenyl and 4-phenoxy-phenyl.

The term "heteroaryl", used alone or in combination, means a 5- to 10-membered monocyclic or bicyclic aromatic ring containing 1, 2 or 3 heteroatoms independently selected from oxygen, nitrogen and sulfur. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, cinnolinyl, quinazolinyl, quinoxalinyl and phthalazinyl. The heteroaryl groups are unsubstituted or substituted as explicitly defined. Examples of such unsubstituted or substituted heteroaryl groups are 3,5-dimethyl-isoxazolyl (notably 3,5-dimethyl-isoxazol-4-yl), thiazolyl (notably thiazol-5-yl), isothiazolyl (notably isothiazol-5-yl), 1-methyl-pyrazolyl (notably 1-methyl-pyrazol-4-yl), pyridyl (notably pyridin-3-yl), 5-fluoro-pyridyl (notably 5-fluoro-pyridin-2-yl), 6-chloro-pyridyl (notably 6-chloro-pyridin-3-yl), 6-methyl-pyridyl (notably 6-methyl-pyridin-3-yl), 6-methoxy-pyridyl (notably 6-methoxy-pyridin-3-yl), 6-trifluoromethyl-pyridyl (notably 6-trifluoromethyl-pyridin-3-yl), 2-hydroxy-pyridyl (notably 2-hydroxy-pyridin-4-yl), pyrimidyl (notably pyrimidin-5-yl), 2-methyl-pyrimidyl (notably 2-methyl-pyrimidin-5-yl), 2-cyclopropyl-pyrimidyl (notably 2-cyclopropyl-pyrimidin-5-yl), 2-trifluoromethyl-pyrimidyl (notably 2-trifluoromethyl-pyrimidin-5-yl), pyridazinyl (notably pyridazin-3-yl) and 5-methyl-pyrazinyl (notably 5-methyl-pyrazin-2-yl).

The term "5- or 6-membered monocyclic heteroaryl", used alone or in combination, means a 5- or 6-membered monocyclic aromatic ring containing one nitrogen atom and optionally one additional heteroatom selected from oxygen, nitrogen and sulfur. Examples of such heteroaryl groups are oxazolyl, isoxazolyl, thiazolyl, isothiazolyl, pyrrolyl, imidazolyl, pyrazolyl, pyridyl, pyrimidyl, pyridazinyl and pyrazinyl. The heteroaryl groups are unsubstituted or substituted as explicitly defined. Examples of such unsubstituted or substituted heteroaryl groups are 3,5-dimethyl-isoxazolyl (notably 3,5-dimethyl-isoxazol-4-yl), thiazolyl (notably thiazol-5-yl), isothiazolyl (notably isothiazol-5-yl), 1-methyl-pyrazolyl (notably 1-methyl-pyrazol-4-yl), pyridyl (notably pyridin-3-yl), 5-fluoro-pyridyl (notably 5-fluoro-pyridin-2-yl), 6-chloro-pyridyl (notably 6-chloro-pyridin-3-yl), 6-methyl-pyridyl (notably 6-methyl-pyridin-3-yl), 6-methoxy-pyridyl (notably 6-methoxy-pyridin-3-yl), 6-trifluoromethyl-pyridyl (notably 6-trifluoromethyl-pyridin-3-yl), 2-hydroxy-pyridyl (notably 2-hydroxy-pyridin-4-yl), pyrimidyl (notably pyrimidin-5-yl), 2-methyl-pyrimidyl (notably 2-methyl-pyrimidin-5-yl), 2-cyclopropyl-pyrimidyl (notably 2-cyclopropyl-pyrimidin-5-yl), 2-trifluoromethyl-pyrimidyl (notably 2-trifluoromethyl-pyrimidin-5-yl), pyridazinyl (notably pyridazin-3-yl) and 5-methyl-pyrazinyl (notably 5-methyl-pyrazin-2-yl).

The term "heterocyclyl", used alone or in combination, refers to a saturated mono- or bicyclic moiety of 4 to 8 ring members containing one heteroatom selected from nitrogen, oxygen and sulfur and optionally one additional nitrogen atom. The sulfur atom of a heterocyclyl group may be in an oxidised form, i.e. as a sulfoxide or sulfonyl. Examples of such heterocyclyl groups are azetidinyl, pyrrolidinyl, piperidinyl, piperazinyl, tetrahydropyranyl, morpholinyl, thiomorpholinyl, 1-oxo-thiomorpholinyl, 1,1-dioxo-thiomorpholinyl, azepanyl, 1,4-oxazepanyl, 6-oxa-3-azabicyclo[3.1.1]heptanyl and 2-oxa-5-azabicyclo[2.2.1]heptanyl. The heterocyclyl groups are unsubstituted or substituted as explicitly defined. Examples of such unsubstituted or substituted heterocyclyl groups are azetidin-1-yl, pyrrolidin-1-yl, 3,3-difluoro-pyrrolidin-1-yl, piperidin-1-yl, 4-fluoro-piperidin-1-yl, 3,3-difluoro-piperidin-1-yl, 4,4-difluoro-piperidin-1-yl, 2-methyl-piperidin-1-yl, 4-methyl-piperidin-1-yl, 4-(tert-butoxy-carbonyl)-piperidin-1-yl, piperidin-4-yl, 1-methyl-piperidin-4-yl, 1-acetyl-piperidin-4-yl, 1-(tert-butoxy-carbonyl)-piperidin-4-yl, 1-methylsulfonyl-piperidin-4-yl, 4-(tert-butoxy-carbonyl)-piperazin-1-yl, tetrahydropyran-4-yl, morpholin-4-yl, 2,6-dimethyl-morpholin-4-yl, 1,1-dioxo-thiomorpholin-4-yl, azepan-1-yl, 1,4-oxazepan-4-yl, 6-oxa-3-azabicyclo[3.1.1]heptan-3-yl and 2-oxa-5-azabicyclo[2.2.1]heptan-5-yl.

The term "heterocyclyloxy", used alone or in combination, refers to a heterocyclyl-O— group, wherein the heterocyclyl group is as defined above. An example of such a heterocyclyl group is tetrahydropyranoxy (notably tetrahydropyran-4-oxy).

Further embodiments of the invention are presented hereinafter:

1P) A further embodiment of the invention relates to compounds according to embodiment 1), wherein
$R^1$ represents a heteroaryl or an aryl group which groups are independently unsubstituted, mono-, di-, or tri-substituted, wherein the substituents are independently selected from the group consisting of $(C_1-C_4)$alkyl, $(C_3-C_6)$cycloalkyl, $(C_1-C_4)$alkoxy, $(C_1-C_3)$fluoroalkyl, $(C_1-C_3)$fluoroalkoxy, hydroxy, halogen and phenoxy;
$R^2$ represents
heterocyclyl which is unsubstituted, mono- or di-substituted, wherein the substituents are independently selected from $(C_1-C_4)$alkyl, $(C_1-C_4)$alkylcarbonyl, $(C_1-C_4)$alkoxycarbonyl, $(C_1-C_4)$alkylsulfonyl, and halogen;
heterocyclyloxy;
$(C_3-C_6)$cycloalkyl which is unsubstituted or mono- or di-substituted with halogen;
$(C_3-C_6)$cycloalkyloxy;
N—$(C_3-C_6)$cycloalkyl-amino;
N—$(C_3-C_6)$cycloalkylmethyl-amino;
$(C_3-C_6)$alkyl;
$(C_2-C_6)$alkoxy;
N—$(C_1-C_4)$alkylamino;
N,N-di-[$(C_1-C_4)$alkyl]-amino; or
N-arylmethyl-N—$(C_1-C_4)$alkyl-amino;
$R^3$ represents hydrogen or halogen;
$R^4$ represents hydrogen, $(C_1-C_4)$alkyl or $(C_1-C_2)$alkoxy-$(C_1-C_4)$alkyl;
$R^5$ represents hydrogen or $(C_1-C_4)$alkyl; and
$R^6$ represents chloro or methyl;
and to the salts (in particular pharmaceutically acceptable salts) of such compounds.

2) A further embodiment of the invention relates to compounds according to any one of embodiments 1) or 1P), wherein
$R^1$ represents a 5- or 6-membered monocyclic heteroaryl or a phenyl group which groups are independently unsubstituted, mono- or di-substituted, wherein the substituents are independently selected from the group consisting of methyl, cyclopropyl, methoxy, trifluoromethyl, trifluoromethoxy, hydroxy, fluoro, chloro and phenoxy;
$R^2$ represents
heterocyclyl which is unsubstituted, mono- or di-substituted, wherein the substituents are independently selected from methyl, methylcarbonyl, tert-butoxy-carbonyl, methylsulfonyl, and fluoro;
tetrahydropyran-4-oxy;
cyclohexyl which is unsubstituted or mono- or di-substituted with fluoro;
cyclopentyloxy; cyclohexyloxy;
cylopentyl-amino;
cylopentylmethyl-amino;
iso-butyl; pent-3-yl;
ethoxy; pent-3-yloxy;
iso-butylamino;
dimethylamino; diethylamino; methyl-iso-butylamino; or N-benzyl-N-methyl-amino;
$R^3$ represents hydrogen or chloro;
$R^4$ represents hydrogen, methyl, iso-butyl or 3-methoxy-prop-1-yl;
$R^5$ represents hydrogen or methyl; and
$R^6$ represents chloro or methyl;
and to the salts (in particular pharmaceutically acceptable salts) of such compounds.

3) A further embodiment of the invention relates to compounds according to any one of embodiments 1) or 1P), wherein
$R^1$ represents a heteroaryl or an aryl group which groups are independently unsubstituted, mono- or di-substituted, wherein the substituents are independently selected from the group consisting of $(C_1-C_4)$alkyl, $(C_3-C_6)$cycloalkyl, $(C_1-C_4)$alkoxy, $(C_1-C_3)$fluoroalkyl and halogen;
$R^2$ represents
heterocyclyl which is unsubstituted, mono- or di-substituted, wherein the substituents are independently selected from $(C_1-C_4)$alkyl and halogen;
$(C_3-C_6)$cycloalkyl which is unsubstituted or mono- or di-substituted with fluoro;
cyclopentyloxy;
$(C_3-C_6)$alkyl; or
pent-3-yloxy;
$R^3$ represents hydrogen;
$R^4$ represents hydrogen, $(C_1-C_4)$alkyl or $(C_1-C_2)$alkoxy-$(C_1-C_4)$alkyl;
$R^5$ represents hydrogen; and
$R^6$ represents chloro or methyl;
and to the salts (in particular pharmaceutically acceptable salts) of such compounds.

4) A further embodiment of the invention relates to compounds according to any one of embodiments 1) or 1P), wherein
$R^1$ represents a 5- or 6-membered monocyclic heteroaryl group which is unsubstituted, mono- or di-substituted, wherein the substituents are independently selected from the group consisting of $(C_1-C_4)$alkyl, $(C_3-C_6)$cycloalkyl, $(C_1-C_4)$alkoxy, $(C_1-C_3)$fluoroalkyl and halogen;
$R^2$ represents
heterocyclyl which is unsubstituted, mono- or di-substituted, wherein the substituents are independently selected from methyl and fluoro; or ($C_3$-$C_6$)cycloalkyl which is unsubstituted or mono- or di-substituted with fluoro;
$R^3$ represents hydrogen;
$R^4$ represents hydrogen or ($C_1$-$C_4$)alkyl;
$R^5$ represents hydrogen; and
$R^6$ represents chloro or methyl;
and to the salts (in particular pharmaceutically acceptable salts) of such compounds.

5) A further embodiment of the invention relates to compounds according to any one of embodiments 1) or 1P), wherein
$R^1$ represents a pyrimidyl or pyridyl group which is unsubstituted or mono-substituted with methyl, cyclopropyl, methoxy, trifluoromethyl or chloro;
$R^2$ represents heterocyclyl, wherein the heterocyclyl is selected from 3,3-difluoro-pyrrolidin-1-yl, piperidin-1-yl, 4-fluoro-piperidin-1-yl, 3,3-difluoro-piperidin-1-yl, 4,4-difluoro-piperidin-1-yl, morpholin-4-yl, azepan-1-yl, 1,4-oxazepan-4-yl and 6-oxa-3-azabicyclo[3.1.1]heptan-3-yl;
$R^3$ represents hydrogen;
$R^4$ represents hydrogen or methyl;
$R^5$ represents hydrogen; and
$R^6$ represents chloro or methyl;
and to the salts (in particular pharmaceutically acceptable salts) of such compounds.

6) A further embodiment of the invention relates to compounds according to any one of embodiments 1), 1P), 3) or 4), wherein the term "($C_1$-$C_4$)alkyl" means methyl;
and to the salts (in particular pharmaceutically acceptable salts) of such compounds.

7) A further embodiment of the invention relates to compounds according to any one of embodiments 1), 1P), 3) or 6), wherein the term "($C_3$-$C_6$)alkyl" means iso-butyl or pent-3-yl;
and to the salts (in particular pharmaceutically acceptable salts) of such compounds.

8) A further embodiment of the invention relates to compounds according to any one of embodiments 1), 1P), 3), 4), 6) or 7), wherein the term "($C_1$-$C_4$)alkoxy" means methoxy;
and to the salts (in particular pharmaceutically acceptable salts) of such compounds.

9) A further embodiment of the invention relates to compounds according to any one of embodiments 1), 1P), 3), 4) or 6) to 8), wherein the term "($C_3$-$C_6$)cycloalkyl", if representing a substituent to a heteroaryl or an aryl group, means cyclopropyl; and to the salts (in particular pharmaceutically acceptable salts) of such compounds.

10) A further embodiment of the invention relates to compounds according to any one of embodiments 1), 1P), 3), 4) or 6) to 9), wherein the term "($C_3$-$C_6$)cycloalkyl", if representing $R^2$, means cyclohexyl;
and to the salts (in particular pharmaceutically acceptable salts) of such compounds.

11) A further embodiment of the invention relates to compounds according to any one of embodiments 1), 1P), 3), 4) or 6) to 10), wherein the terms "($C_1$-$C_3$)fluoroalkyl" and, if present, "($C_1$-$C_2$)fluoroalkyl" mean trifluoromethyl;
and to the salts (in particular pharmaceutically acceptable salts) of such compounds.

12) A further embodiment of the invention relates to compounds according to any one of embodiments 1), 1P), 3) or 6) to 11), wherein the term "($C_1$-$C_2$)alkoxy-($C_1$-$C_4$)alkyl" means 3-methoxy-prop-1-yl;
and to the salts (in particular pharmaceutically acceptable salts) of such compounds.

13) A further embodiment of the invention relates to compounds according to any one of embodiments 1), 1P), 3), 4) or 6) to 12), wherein the term "halogen" means fluoro or chloro;
and to the salts (in particular pharmaceutically acceptable salts) of such compounds.

14) A further embodiment of the invention relates to compounds according to any one of embodiments 1), 1P), 3), 4) or 6) to 12), wherein the term "halogen" means fluoro;
and to the salts (in particular pharmaceutically acceptable salts) of such compounds.

15) A further embodiment of the invention relates to compounds according to any one of embodiments 1), 1P), 3) or 6) to 14), wherein the term "heteroaryl" means "5- or 6-membered monocyclic heteroaryl";
and to the salts (in particular pharmaceutically acceptable salts) of such compounds.

16) A further embodiment of the invention relates to compounds according to any one of embodiments 1) to 4) or 6) to 14), wherein the term "heteroaryl" or the term "5- or 6-membered monocyclic heteroaryl" means thiazolyl, isothiazolyl, pyridyl or pyrimidyl;
and to the salts (in particular pharmaceutically acceptable salts) of such compounds.

17) A further embodiment of the invention relates to compounds according to any one of embodiments 1) to 4) or 6) to 14), wherein the term "heteroaryl" or the term "5- or 6-membered monocyclic heteroaryl" means pyridyl or pyrimidyl;
and to the salts (in particular pharmaceutically acceptable salts) of such compounds.

18) A further embodiment of the invention relates to compounds according to any one of embodiments 1), 1P), 3) or 6) to 17), wherein the term "aryl" means phenyl;
and to the salts (in particular pharmaceutically acceptable salts) of such compounds.

19) A further embodiment of the invention relates to compounds according to any one of embodiments 1) to 4) or 6) to 18), wherein the term "heterocyclyl" means pyrrolidinyl, piperidinyl, tetrahydropyranyl, morpholinyl, azepanyl, 1,4-oxazepanyl or 6-oxa-3-azabicyclo[3.1.1]heptanyl;
and to the salts (in particular pharmaceutically acceptable salts) of such compounds.

20) A further embodiment of the invention relates to compounds according to any one of embodiments 1) to 4) or 6) to 18), wherein the term "heterocyclyl" means piperidin-1-yl, morpholin-4-yl, azepan-1-yl, 1,4-oxazepan-4-yl or 6-oxa-3-azabicyclo[3.1.1]heptan-3-yl;
and to the salts (in particular pharmaceutically acceptable salts) of such compounds.

21) A further embodiment of the invention relates to compounds according to any one of embodiments 1), 1P), 3), 6) to 14), 16), 17), 19) or 20), wherein
$R^1$ represents a 5- or 6-membered monocyclic heteroaryl or a phenyl group which groups are independently unsubstituted, mono- or di-substituted, wherein the substituents are independently selected from the group consisting of ($C_1$-$C_4$)alkyl, ($C_3$-$C_6$)cycloalkyl, ($C_1$-$C_3$)fluoroalkyl and halogen;
and to the salts (in particular pharmaceutically acceptable salts) of such compounds.

22) A further embodiment of the invention relates to compounds according to any one of embodiments 1), 1P), 3), 4), 6) to 14), 16), 17), 19) or 20), wherein
$R^1$ represents a 5- or 6-membered monocyclic heteroaryl group which is unsubstituted or mono-substituted with ($C_1$-$C_4$)alkyl, ($C_3$-$C_6$)cycloalkyl, ($C_1$-$C_3$)fluoroalkyl and halogen;
and to the salts (in particular pharmaceutically acceptable salts) of such compounds.

23) A further embodiment of the invention relates to compounds according to any one of embodiments 1), 1P), 3), 6) to 14), 19) or 20), wherein $R^1$ represents a phenyl group which is unsubstituted, mono- or di-substituted, wherein the substituents are independently selected from the group consisting of $(C_1-C_4)$alkyl, $(C_1-C_4)$alkoxy, $(C_1-C_3)$fluoroalkyl and halogen;
and to the salts (in particular pharmaceutically acceptable salts) of such compounds.

24) A further embodiment of the invention relates to compounds according to any one of embodiments 1), 1P), 3), 6) or 8) to 23), wherein $R^2$ represents
heterocyclyl which is unsubstituted or mono- or di-substituted with fluoro; or
$(C_3-C_6)$cycloalkyl which is unsubstituted or mono- or di-substituted with fluoro;
and to the salts (in particular pharmaceutically acceptable salts) of such compounds.

25) A further embodiment of the invention relates to compounds according to any one of embodiments 1) to 4), 6), 8), 9) or 11) to 23), wherein $R^2$ represents heterocyclyl which is unsubstituted or mono- or di-substituted with fluoro;
and to the salts (in particular pharmaceutically acceptable salts) of such compounds.

26) A further embodiment of the invention relates to compounds according to any one of embodiments 1), 1P), 3), 6) to 18) or 21) to 23), wherein $R^2$ represents $(C_3-C_6)$alkyl; or $(C_3-C_6)$cycloalkyl which is unsubstituted or mono- or di-substituted with fluoro;
and to the salts (in particular pharmaceutically acceptable salts) of such compounds.

27) A further embodiment of the invention relates to compounds according to any one of embodiments 1), 1P), 6), 8) to 18) or 21) to 23), wherein $R^2$ represents $(C_3-C_6)$cycloalkyloxy or $(C_2-C_6)$alkoxy;
and to the salts (in particular pharmaceutically acceptable salts) of such compounds.

28) A further embodiment of the invention relates to compounds according to any one of embodiments 1), 1P), 2) or 6) to 27), wherein $R^3$ represents hydrogen;
and to the salts (in particular pharmaceutically acceptable salts) of such compounds.

29) A further embodiment of the invention relates to compounds according to any one of embodiments 1), 1P), 3), 6) to 11) or 13) to 28), wherein $R^4$ represents hydrogen or $(C_1-C_4)$alkyl;
and to the salts (in particular pharmaceutically acceptable salts) of such compounds.

30) A further embodiment of the invention relates to compounds according to any one of embodiments 1), 1P), 3) or 6) to 28), wherein $R^4$ represents $(C_1-C_2)$alkoxy-$(C_1-C_4)$alkyl;
and to the salts (in particular pharmaceutically acceptable salts) of such compounds.

31) A further embodiment of the invention relates to compounds according to any one of embodiments 1), 1P), 2) or 6) to 30), wherein $R^5$ represents hydrogen;
and to the salts (in particular pharmaceutically acceptable salts) of such compounds.

32) A further embodiment of the invention relates to compounds according to any one of embodiments 1) to 31), wherein $R^6$ represents chloro;
and to the salts (in particular pharmaceutically acceptable salts) of such compounds.

33) A further embodiment of the invention relates to compounds according to any one of embodiments 1) to 31), wherein $R^6$ represents methyl;
and to the salts (in particular pharmaceutically acceptable salts) of such compounds.

34) A further embodiment of the invention relates to compounds according to any one of embodiments 1) to 33), wherein the absolute configuration of the stereogenic center is as depicted in formula ($I_{St1}$)

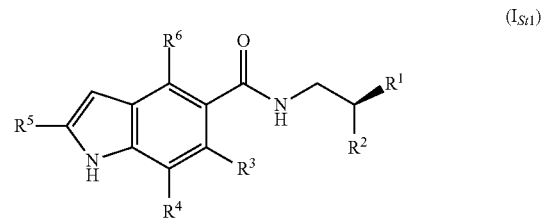

($I_{St1}$)

and to the salts (in particular pharmaceutically acceptable salts) of such compounds.

35) A further embodiment of the invention relates to compounds according to any one of embodiments 1) to 33), wherein the absolute configuration of the stereogenic center is as depicted in formula ($I_{St2}$)

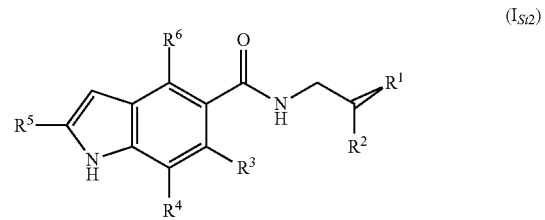

($I_{St2}$)

and to the salts (in particular pharmaceutically acceptable salts) of such compounds.

36) Preferred compounds of formula (I) as defined in embodiment 1) are selected from the group consisting of:
4-Chloro-1H-indole-5-carboxylic acid [2-morpholin-4-yl-2-(2-trifluoromethyl-pyrimidin-5-yl)-ethyl]-amide;
4-Chloro-1H-indole-5-carboxylic acid [2-(6-chloro-pyridin-3-yl)-2-(4,4-difluoro-piperidin-1-yl)-ethyl]-amide;
4-Chloro-1H-indole-5-carboxylic acid [(R)-2-(2-methyl-pyrimidin-5-yl)-2-morpholin-4-yl-ethyl]amide;
4-Chloro-1H-indole-5-carboxylic acid [(S)-2-(2-methyl-pyrimidin-5-yl)-2-morpholin-4-yl-ethyl]-amide;
4-Chloro-1H-indole-5-carboxylic acid [(R)-2-(4,4-difluoro-piperidin-1-yl)-2-(2-methyl-pyrimidin-5-yl)-ethyl]-amide;
4-Chloro-1H-indole-5-carboxylic acid [(S)-2-(4,4-difluoro-piperidin-1-yl)-2-(2-methyl-pyrimidin-5-yl)-ethyl]-amide;
4-Chloro-1H-indole-5-carboxylic acid [2-(6-methyl-pyridin-3-yl)-2-morpholin-4-yl-ethyl]-amide;
4-Chloro-1H-indole-5-carboxylic acid [2-(4,4-difluoro-piperidin-1-yl)-2-(2-trifluoromethyl-pyrimidin-5-yl)-ethyl]-amide;
4-Chloro-1H-indole-5-carboxylic acid [2-(2-cyclopropyl-pyrimidin-5-yl)-2-morpholin-4-yl-ethyl]-amide;
4-Chloro-1H-indole-5-carboxylic acid [2-morpholin-4-yl-2-(6-trifluoromethyl-pyridin-3-yl)-ethyl]-amide;

4-Chloro-1H-indole-5-carboxylic acid [2-(6-methoxy-pyridin-3-yl)-2-morpholin-4-yl-ethyl]-amide;
4-Chloro-1H-indole-5-carboxylic acid [2-dimethylamino-2-(2-methyl-pyrimidin-5-yl)-ethyl]-amide;
4-Chloro-1H-indole-5-carboxylic acid [2-azetidin-1-yl-2-(2-methyl-pyrimidin-5-yl)-ethyl]-amide;
4-Chloro-1H-indole-5-carboxylic acid [2-(2-methyl-pyrimidin-5-yl)-2-pyrrolidin-1-yl-ethyl]-amide;
4-Chloro-1H-indole-5-carboxylic acid [2-diethylamino-2-(2-methyl-pyrimidin-5-yl)-ethyl]-amide;
4-Chloro-1H-indole-5-carboxylic acid [2-(2-methyl-pyrimidin-5-yl)-2-piperidin-1-yl-ethyl]-amide;
4-Chloro-1H-indole-5-carboxylic acid [2-(4-fluoro-phenyl)-2-morpholin-4-yl-ethyl]amide;
4-Chloro-1H-indole-5-carboxylic acid [2-(3,5-difluoro-phenyl)-2-morpholin-4-yl-ethyl]-amide;
4-{2-[(4-Chloro-1H-indole-5-carbonyl)-amino]-1-pyridin-3-yl-ethyl}-piperidine-1-carboxylic acid tert-butyl ester;
4-Chloro-1H-indole-5-carboxylic acid (2-piperidin-4-yl-2-pyridin-3-yl-ethyl)-amide;
4-Chloro-1H-indole-5-carboxylic acid [2-(1-methyl-piperidin-4-yl)-2-pyridin-3-yl-ethyl]-amide;
4-Chloro-1H-indole-5-carboxylic acid [2-(1-acetyl-piperidin-4-yl)-2-pyridin-3-yl-ethyl]-amide;
4-Chloro-1H-indole-5-carboxylic acid [2-(1-methanesulfonyl-piperidin-4-yl)-2-pyridin-3-yl-ethyl]-amide;
4-Chloro-1H-indole-5-carboxylic acid [2-(6-chloro-pyridin-3-yl)-2-morpholin-4-yl-ethyl]-amide;
4-Chloro-1H-indole-5-carboxylic acid (2-morpholin-4-yl-2-pyridin-3-yl-ethyl)-amide;
4-Chloro-1H-indole-5-carboxylic acid (2-morpholin-4-yl-2-pyrimidin-5-yl-ethyl)-amide;
4-Chloro-1H-indole-5-carboxylic acid (2-piperidin-1-yl-2-pyrimidin-5-yl-ethyl)-amide;
4-Chloro-1H-indole-5-carboxylic acid [2-(1-methyl-1H-pyrazol-4-yl)-2-morpholin-4-yl-ethyl]-amide;
4-Chloro-1H-indole-5-carboxylic acid [2-(1-methyl-1H-pyrazol-4-yl)-2-piperidin-1-yl-ethyl]-amide;
4-Chloro-1H-indole-5-carboxylic acid [2-piperidin-1-yl-2-(2,4,6-trifluoro-phenyl)-ethyl]-amide;
4-Chloro-1H-indole-5-carboxylic acid [2-(2,4-difluoro-phenyl)-2-piperidin-1-yl-ethyl]-amide;
4-Chloro-1H-indole-5-carboxylic acid [2-(5-fluoro-pyridin-2-yl)-2-piperidin-1-yl-ethyl]-amide;
4-Chloro-1H-indole-5-carboxylic acid [2-morpholin-4-yl-2-(2,4,6-trifluoro-phenyl)-ethyl]-amide;
4-Chloro-1H-indole-5-carboxylic acid [2-(2,4-difluoro-phenyl)-2-morpholin-4-yl-ethyl]-amide;
4-Chloro-1H-indole-5-carboxylic acid [2-(2-fluoro-phenyl)-2-morpholin-4-yl-ethyl]-amide;
4-Chloro-1H-indole-5-carboxylic acid [2-(5-fluoro-pyridin-2-yl)-2-morpholin-4-yl-ethyl]-amide;
4-Chloro-1H-indole-5-carboxylic acid [2-(3-fluoro-phenyl)-2-morpholin-4-yl-ethyl]-amide;
4-Chloro-1H-indole-5-carboxylic acid [2-(4-chloro-phenyl)-2-morpholin-4-yl-ethyl]-amide;
4-Chloro-1H-indole-5-carboxylic acid [2-(2,4-dichloro-phenyl)-2-morpholin-4-yl-ethyl]-amide;
4-Chloro-1H-indole-5-carboxylic acid [2-(4-chloro-2-fluoro-phenyl)-2-morpholin-4-yl-ethyl]-amide;
4-Chloro-1H-indole-5-carboxylic acid [2-(cis-2,6-dimethyl-morpholin-4-yl)-2-(2-methyl-pyrimidin-5-yl)-ethyl]-amide;
4-Chloro-1H-indole-5-carboxylic acid [2-(trans-2,6-dimethyl-morpholin-4-yl)-2-(2-methyl-pyrimidin-5-yl)-ethyl]-amide;
4-Chloro-1H-indole-5-carboxylic acid [2-(3-fluoro-phenyl)-2-piperidin-1-yl-ethyl]-amide;
4-Chloro-1H-indole-5-carboxylic acid [2-piperidin-1-yl-2-(4-trifluoromethyl-phenyl)-ethyl]-amide;
4-Chloro-1H-indole-5-carboxylic acid [2-(3,4-difluoro-phenyl)-2-piperidin-1-yl-ethyl]-amide;
4-Chloro-1H-indole-5-carboxylic acid (2-piperidin-1-yl-2-pyridin-3-yl-ethyl)-amide;
4-Chloro-1H-indole-5-carboxylic acid (2-morpholin-4-yl-2-p-tolyl-ethyl)-amide;
4-Chloro-1H-indole-5-carboxylic acid [2-morpholin-4-yl-2-(4-trifluoromethoxy-phenyl)-ethyl]-amide;
4-Chloro-1H-indole-5-carboxylic acid [2-morpholin-4-yl-2-(4-trifluoromethyl-phenyl)-ethyl]-amide;
4-Chloro-1H-indole-5-carboxylic acid [2-(3,4-difluoro-phenyl)-2-morpholin-4-yl-ethyl]-amide;
4-Chloro-1H-indole-5-carboxylic acid [2-(2-methyl-pyrimidin-5-yl)-2-(tetrahydro-pyran-4-yl)-ethyl]-amide;
4-Chloro-1H-indole-5-carboxylic acid [2-cyclopentyloxy-2-(2-methyl-pyrimidin-5-yl)-ethyl]-amide;
4-Chloro-1H-indole-5-carboxylic acid [2-(3,5-dimethyl-isoxazol-4-yl)-2-morpholin-4-yl-ethyl]-amide;
4-Chloro-1H-indole-5-carboxylic acid [2-(3,5-dimethyl-isoxazol-4-yl)-2-piperidin-1-yl-ethyl]-amide;
4-Chloro-1H-indole-5-carboxylic acid (2-piperidin-1-yl-2-p-tolyl-ethyl)-amide;
4-Chloro-1H-indole-5-carboxylic acid [2-(6-chloro-pyridin-3-yl)-2-piperidin-1-yl-ethyl]-amide;
4-Chloro-1H-indole-5-carboxylic acid [2-(4-phenoxy-phenyl)-2-piperidin-1-yl-ethyl]-amide;
4-Chloro-1H-indole-5-carboxylic acid [2-morpholin-4-yl-2-(4-phenoxy-phenyl)-ethyl]-amide;
4-Chloro-1H-indole-5-carboxylic acid [2-(4-methoxy-phenyl)-2-morpholin-4-yl-ethyl]-amide;
4-Chloro-1H-indole-5-carboxylic acid [2-(5-methyl-pyrazin-2-yl)-2-piperidin-1-yl-ethyl]-amide;
4-Chloro-1H-indole-5-carboxylic acid (2-isothiazol-5-yl-2-piperidin-1-yl-ethyl)-amide;
4-Chloro-1H-indole-5-carboxylic acid (2-piperidin-1-yl-2-thiazol-5-yl-ethyl)-amide;
4-Chloro-1H-indole-5-carboxylic acid [2-(5-methyl-pyrazin-2-yl)-2-morpholin-4-yl-ethyl]-amide;
4-Chloro-1H-indole-5-carboxylic acid (2-morpholin-4-yl-2-thiazol-5-yl-ethyl)-amide;
4-Chloro-1H-indole-5-carboxylic acid [2-(6-chloro-pyridin-3-yl)-2-cyclohexyl-ethyl]-amide;
4-Chloro-1H-indole-5-carboxylic acid [2-(6-chloro-pyridin-3-yl)-4-methyl-pentyl]-amide;
4-Chloro-1H-indole-5-carboxylic acid [2-ethoxy-2-(2-methyl-pyrimidin-5-yl)-ethyl]-amide;
4-Chloro-1H-indole-5-carboxylic acid [2-(2-methyl-pyrimidin-5-yl)-2-(2-oxa-5-azabicyclo[2.2.1]hept-5-yl)-ethyl]-amide;
4-Chloro-1H-indole-5-carboxylic acid [2-cyclohexyloxy-2-(2-methyl-pyrimidin-5-yl)-ethyl]-amide;
4-Chloro-1H-indole-5-carboxylic acid [2-(2-methyl-pyrimidin-5-yl)-2-(tetrahydro-pyran-4-yloxy)-ethyl]-amide;
4-Chloro-1H-indole-5-carboxylic acid [2-(1-ethyl-propoxy)-2-(2-methyl-pyrimidin-5-yl)-ethyl]-amide;
4-Chloro-2-methyl-1H-indole-5-carboxylic acid [2-(2-methyl-pyrimidin-5-yl)-2-morpholin-4-yl-ethyl]-amide;
4-Chloro-1H-indole-5-carboxylic acid (2-piperidin-1-yl-2-pyridazin-3-yl-ethyl)-amide;
4-Chloro-1H-indole-5-carboxylic acid [2-(2-hydroxypyridin-4-yl)-2-piperidin-1-yl-ethyl]-amide;

1-[2-[(4-Chloro-1H-indole-5-carbonyl)-amino]-1-(2-methyl-pyrimidin-5-yl)-ethyl]-piperidine-4-carboxylic acid tert-butyl ester;
4-Chloro-1H-indole-5-carboxylic acid [2-(4-methyl-piperidin-1-yl)-2-(2-methyl-pyrimidin-5-yl)-ethyl]-amide;
4-Chloro-1H-indole-5-carboxylic acid [(R)-2-(2-methyl-piperidin-1-yl)-2-(2-methyl-pyrimidin-5-yl)-ethyl]-amide;
4-Chloro-1H-indole-5-carboxylic acid [2-(4-fluoro-piperidin-1-yl)-2-(2-methyl-pyrimidin-5-yl)-ethyl]-amide;
4-Chloro-1H-indole-5-carboxylic acid [2-(3,3-difluoro-piperidin-1-yl)-2-(2-methyl-pyrimidin-5-yl)-ethyl]-amide;
4-Chloro-1H-indole-5-carboxylic acid [2-azepan-1-yl-2-(2-methyl-pyrimidin-5-yl)-ethyl]-amide;
4-Chloro-1H-indole-5-carboxylic acid [2-(2-methyl-pyrimidin-5-yl)-2-[1,4]oxazepan-4-yl-ethyl]-amide;
4-Chloro-1H-indole-5-carboxylic acid [2-(3,3-difluoro-pyrrolidin-1-yl)-2-(2-methyl-pyrimidin-5-yl)-ethyl]-amide;
4-Chloro-1H-indole-5-carboxylic acid [2-cyclopentylamino-2-(2-methyl-pyrimidin-5-yl)-ethyl]-amide;
4-Chloro-1H-indole-5-carboxylic acid [2-(cyclopentylmethyl-amino)-2-(2-methyl-pyrimidin-5-yl)-ethyl]-amide;
4-Chloro-1H-indole-5-carboxylic acid [2-isobutylamino-2-(2-methyl-pyrimidin-5-yl)-ethyl]-amide;
4-Chloro-1H-indole-5-carboxylic acid [2-(isobutyl-methyl-amino)-2-(2-methyl-pyrimidin-5-yl)-ethyl]-amide;
4-Chloro-1H-indole-5-carboxylic acid [2-(benzyl-methyl-amino)-2-(2-methyl-pyrimidin-5-yl)-ethyl]-amide;
4-Chloro-1H-indole-5-carboxylic acid (3-ethyl-2-pyrimidin-5-yl-pentyl)-amide;
4-[2-[(4-Chloro-1H-indole-5-carbonyl)-amino]-1-(2-methyl-pyrimidin-5-yl)-ethyl]-piperazine-1-carboxylic acid tert-butyl ester;
4-Chloro-1H-indole-5-carboxylic acid (2-morpholin-4-yl-2-pyridazin-3-yl-ethyl)-amide;
4-Chloro-1H-indole-5-carboxylic acid [2-morpholin-4-yl-2-(2-hydroxypyridin-4-yl)-ethyl]-amide;
4-Chloro-1H-indole-5-carboxylic acid [2-(1,1-dioxo-thiomorpholin-4-yl)-2-(2-methyl-pyrimidin-5-yl)-ethyl]-amide;
4-Chloro-1H-indole-5-carboxylic acid [2-(4,4-difluoro-cyclohexyl)-2-(2-methyl-pyrimidin-5-yl)-ethyl]-amide;
4,6-Dichloro-1H-indole-5-carboxylic acid [2-(2-methyl-pyrimidin-5-yl)-2-morpholin-4-yl-ethyl]-amide;
4-Chloro-1H-indole-5-carboxylic acid [2-(2-methyl-pyrimidin-5-yl)-2-(6-oxa-3-azabicyclo[3.1.1]hept-3-yl)-ethyl]-amide;
4-Chloro-7-methyl-1H-indole-5-carboxylic acid [(R)-2-(2-methyl-pyrimidin-5-yl)-2-morpholin-4-yl-ethyl]-amide;
4-Chloro-7-methyl-1H-indole-5-carboxylic acid [(S)-2-(2-methyl-pyrimidin-5-yl)-2-morpholin-4-yl-ethyl]-amide;
4-Chloro-7-isobutyl-1H-indole-5-carboxylic acid [2-(2-methyl-pyrimidin-5-yl)-2-morpholin-4-yl-ethyl]-amide;
4-Chloro-7-(3-methoxy-propyl)-1H-indole-5-carboxylic acid [2-(2-methyl-pyrimidin-5-yl)-2-morpholin-4-yl-ethyl]-amide; and
4-Methyl-1H-indole-5-carboxylic acid [2-(2-methyl-pyrimidin-5-yl)-2-morpholin-4-yl-ethyl]-amide;
or salts (in particular pharmaceutically acceptable salts) of such compounds;
it is to be understood for any of the above listed compounds, that a stereogenic center, which is not specifically assigned, may be in absolute (R)- or absolute (S)-configuration; notably, the stereogenic center at the carbon atom attached to $R^1$ and $R^2$ may be in absolute (R)-configuration or absolute (S)-configuration. For example a compound listed as 4-Chloro-1H-indole-5-carboxylic acid [2-morpholin-4-yl-2-(2-trifluoromethyl-pyrimidin-5-yl)-ethyl]-amide may be 4-Chloro-1H-indole-5-carboxylic acid [(S)-2-morpholin-4-yl-2-(2-trifluoromethyl-pyrimidin-5-yl)-ethyl]-amide, 4-Chloro-1H-indole-5-carboxylic acid [(R)-2-morpholin-4-yl-2-(2-trifluoromethyl-pyrimidin-5-yl)-ethyl]-amide or any mixture thereof.

It is understood that in this specification the phrase "according to any one of embodiments 1) to X)", wherein "X" represents an integer between 2 and 36, refers to all embodiments between 1) and X) in the alternative, including embodiment 1P) as one of the alternatives; for instance the phrase "according to any one of embodiments 1) to 4)" means "according to any one of embodiments 1) or 1P) or 2) or 3) or 4)".

37) A further embodiment of the invention relates to compounds according to any one of embodiments 1), 34) or 35), which are also compounds of formula ($I_{Ar}$)

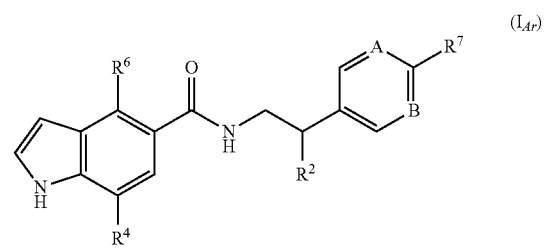

wherein
A represents N or CH;
B represents N or CH;
$R^2$ represents heterocyclyl which is unsubstituted or mono- or di-substituted with fluoro, wherein the heterocyclyl is selected from pyrrolidinyl, piperidinyl, tetrahydropyranyl, morpholinyl, azepanyl, 1,4-oxazepanyl and 6-oxa-3-azabicyclo[3.1.1]heptanyl; or $R^2$ represents cyclohexyl which is unsubstituted or mono- or di-substituted with fluoro;
$R^4$ represents hydrogen, fluoro, chloro, $(C_1-C_4)$alkyl, $(C_1-C_4)$alkoxy, hydroxy-$(C_2-C_4)$alkoxy or $(C_1-C_2)$alkoxy-$(C_1-C_4)$alkyl;
$R^6$ represents fluoro, chloro, methyl, ethyl or $(C_1-C_2)$fluoroalkyl; and
$R^7$ represents hydrogen, halogen, $(C_1-C_4)$alkyl, $(C_3-C_6)$cycloalkyl, $(C_1-C_4)$alkoxy or $(C_1-C_3)$fluoroalkyl;
and to the salts (in particular pharmaceutically acceptable salts) of such compounds.

38) A further embodiment of the invention relates to compounds according to embodiment 37), wherein
A represents N or CH;
B represents N or CH;
$R^2$ represents heterocyclyl which is unsubstituted or mono- or di-substituted with fluoro, wherein the heterocyclyl is selected from pyrrolidinyl, piperidinyl, tetrahydropyranyl, morpholinyl, azepanyl, 1,4-oxazepanyl and 6-oxa-3-azabicyclo[3.1.1]heptanyl; or
$R^2$ represents cyclohexyl which is unsubstituted or di-substituted with fluoro;
$R^4$ represents hydrogen, chloro, methyl, ethyl, n-propyl, iso-butyl, methoxy, ethoxy, 2-hydroxy-ethoxy or 3-methoxy-prop-1-yl;
$R^6$ represents fluoro, chloro, methyl, ethyl or trifluoromethyl; and
$R^7$ represents hydrogen, fluoro, chloro, methyl, cyclopropyl, methoxy or trifluoromethyl;

and to the salts (in particular pharmaceutically acceptable salts) of such compounds.

39) A further embodiment of the invention relates to compounds according to embodiment 37), wherein A and B represent N and $R^7$ represents hydrogen, $(C_1-C_4)$alkyl, $(C_3-C_6)$cycloalkyl or $(C_1-C_3)$fluoroalkyl; or A represents N, B represents CH and $R^7$ represents hydrogen, chloro, $(C_1-C_4)$alkyl, $(C_1-C_4)$alkoxy or $(C_1-C_3)$fluoroalkyl; or A and B represent CH and $R^7$ represents fluoro, chloro, $(C_1-C_4)$alkyl, $(C_1-C_4)$alkoxy or $(C_1-C_3)$fluoroalkyl;

$R^2$ represents pyrrolidinyl which is unsubstituted or di-substituted with fluoro; piperidinyl which is unsubstituted or mono- or di-substituted with fluoro; tetrahydropyranyl; morpholinyl; azepanyl; 1,4-oxazepanyl; 6-oxa-3-azabicyclo[3.1.1]heptanyl; or cyclohexyl which is unsubstituted or di-substituted with fluoro;

$R^4$ represents hydrogen, fluoro, chloro, $(C_1-C_4)$alkyl, $(C_1-C_4)$alkoxy, hydroxy-$(C_2-C_4)$alkoxy or $(C_1-C_2)$alkoxy-$(C_1-C_4)$alkyl; and $R^6$ represents fluoro, chloro, methyl, ethyl or $(C_1-C_2)$fluoroalkyl;

and to the salts (in particular pharmaceutically acceptable salts) of such compounds.

40) A further embodiment of the invention relates to compounds according to embodiment 37), wherein A and B represent N and $R^7$ represents hydrogen, methyl, cyclopropyl or trifluoromethyl; or A represents N, B represents CH and $R^7$ represents chloro, methyl, methoxy or trifluoromethyl; or A and B represent CH and $R^7$ represents fluoro or chloro;

$R^2$ represents 3,3-difluoro-pyrrolidin-1-yl, piperidin-1-yl, 4-fluoro-piperidin-1-yl, 3,3-difluoro-piperidin-1-yl, 4,4-difluoro-piperidin-1-yl, tetrahydropyran-4-yl, morpholin-4-yl, azepan-1-yl, 1,4-oxazepan-4-yl, or 6-oxa-3-azabicyclo[3.1.1]heptan-3-yl;

$R^4$ represents hydrogen, chloro, methyl, ethyl, n-propyl, iso-butyl, methoxy, ethoxy, 2-hydroxy-ethoxy or 3-methoxy-prop-1-yl;

$R^6$ represents fluoro, chloro, methyl, ethyl or trifluoromethyl;

and to the salts (in particular pharmaceutically acceptable salts) of such compounds.

41) A further embodiment of the invention relates to compounds according to any one of embodiments 37) to 40), wherein A and B represent N;

and to the salts (in particular pharmaceutically acceptable salts) of such compounds.

42) A further embodiment of the invention relates to compounds according to any one of embodiments 37) to 41), wherein $R^2$ represents piperidin-1-yl, 4-fluoro-piperidin-1-yl, 3,3-difluoro-piperidin-1-yl or 4,4-difluoro-piperidin-1-yl;

and to the salts (in particular pharmaceutically acceptable salts) of such compounds.

43) A further embodiment of the invention relates to compounds according to any one of embodiments 37) to 41), wherein $R^2$ represents morpholin-4-yl;

and to the salts (in particular pharmaceutically acceptable salts) of such compounds.

44) A further embodiment of the invention relates to compounds according to any one of embodiments 37) to 39) or 41), wherein $R^2$ represents 4,4-difluoro-cyclohexyl;

and to the salts (in particular pharmaceutically acceptable salts) of such compounds.

45) Further preferred compounds of formula (I) as defined in embodiment 1) are selected from the group consisting of:
4-Ethyl-1H-indole-5-carboxylic acid [2-(2-methyl-pyrimidin-5-yl)-2-morpholin-4-yl-ethyl]-amide;
7-Acetyl-4-chloro-1H-indole-5-carboxylic acid [2-(2-methyl-pyrimidin-5-yl)-2-morpholin-4-yl-ethyl]-amide;
7-Methyl-4-trifluoromethyl-1H-indole-5-carboxylic acid [2-(2-methyl-pyrimidin-5-yl)-2-morpholin-4-yl-ethyl]-amide;
4,7-Dimethyl-1H-indole-5-carboxylic acid [2-(2-methyl-pyrimidin-5-yl)-2-morpholin-4-yl-ethyl]-amide;
4-Methyl-1H-indole-5-carboxylic acid [(S)-2-(2-methyl-pyrimidin-5-yl)-2-morpholin-4-yl-ethyl]-amide;
4-Methyl-1H-indole-5-carboxylic acid [(R)-2-(2-methyl-pyrimidin-5-yl)-2-morpholin-4-yl-ethyl]-amide;
4-Chloro-7-ethyl-1H-indole-5-carboxylic acid [2-(2-methyl-pyrimidin-5-yl)-2-morpholin-4-yl-ethyl]-amide;
7-Chloro-4-methyl-1H-indole-5-carboxylic acid [2-(2-methyl-pyrimidin-5-yl)-2-morpholin-4-yl-ethyl]-amide;
7-Methoxy-4-methyl-1H-indole-5-carboxylic acid [2-(2-methyl-pyrimidin-5-yl)-2-morpholin-4-yl-ethyl]-amide;
4-Chloro-7-ethoxy-1H-indole-5-carboxylic acid [2-(2-methyl-pyrimidin-5-yl)-2-morpholin-4-yl-ethyl]-amide;
4-Chloro-7-propyl-1H-indole-5-carboxylic acid [2-(2-methyl-pyrimidin-5-yl)-2-morpholin-4-yl-ethyl]-amide;
7-(2-tert-Butoxy-ethoxy)-4-chloro-1H-indole-5-carboxylic acid [2-(2-methyl-pyrimidin-5-yl)-2-morpholin-4-yl-ethyl]-amide;
4-Chloro-7-(2-hydroxy-ethoxy)-1H-indole-5-carboxylic acid [2-(2-methyl-pyrimidin-5-yl)-2-morpholin-4-yl-ethyl]-amide;
4-Chloro-7-methoxy-1H-indole-5-carboxylic acid [(S)-2-(2-methyl-pyrimidin-5-yl)-2-morpholin-4-yl-ethyl]-amide;
4-Chloro-7-methoxy-1H-indole-5-carboxylic acid [(R)-2-(2-methyl-pyrimidin-5-yl)-2-morpholin-4-yl-ethyl]-amide;
4-Chloro-7-(1-hydroxy-1-methyl-ethyl)-1H-indole-5-carboxylic acid [2-(2-methyl-pyrimidin-5-yl)-2-morpholin-4-yl-ethyl]-amide;
4,7-Difluoro-1H-indole-5-carboxylic acid [2-(2-methyl-pyrimidin-5-yl)-2-morpholin-4-yl-ethyl]-amide; and
4-Fluoro-7-methoxy-1H-indole-5-carboxylic acid [2-(2-methyl-pyrimidin-5-yl)-2-morpholin-4-yl-ethyl]-amide;
or salts (in particular pharmaceutically acceptable salts) of such compounds;

it is to be understood for any of the above listed compounds, that a stereogenic center, which is not specifically assigned, may be in absolute (R)- or absolute (S)-configuration; notably, the stereogenic center at the carbon atom attached to $R^1$ and $R^2$ may be in absolute (R)-configuration or absolute (S)-configuration. For example a compound listed as 4-Chloro-7-ethoxy-1H-indole-5-carboxylic acid [2-(2-methyl-pyrimidin-5-yl)-2-morpholin-4-yl-ethyl]-amide may be 4-Chloro-7-ethoxy-1H-indole-5-carboxylic acid [(S)-2-(2-methyl-pyrimidin-5-yl)-2-morpholin-4-yl-ethyl]-amide, 4-Chloro-7-ethoxy-1H-indole-5-carboxylic acid [(R)-2-(2-methyl-pyrimidin-5-yl)-2-morpholin-4-yl-ethyl]-amide or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 45) as disclosed hereinabove and which are therefore intended and herewith specifically disclosed in individualized form are:

1, 1P+1, 2+1P+1, 3+1P+1, 4+1P+1, 5+1P+1, 6+1P+1, Y10, Y9, Y8, Y7, 7+Y10, 7+Y9, Y6, Y5, 8+Y10, 8+Y9, 8+Y8, 8+Y7, 8+7+Y10, 8+7+Y9, Y4, Y3, 9+Y10, 9+Y9, 9+Y6, 9+Y5, 9+8+Y10, 9+8+Y9, 9+8+Y8, 9+8+Y7, 9+8+7+Y10, 9+8+7+Y9, 10+3+1P+1, 10+6+1P+1, 10+Y10, 10+Y9, 10+Y4, 10+Y3, 10+9+Y10, 10+9+Y9, 10+9+Y6, 10+9+Y5, 10+9+8+Y10, 10+9+8+Y9, 10+9+8+Y8, 10+9+8+Y7, 10+9+8+7+Y10, 10+9+8+7+Y9, 11+3+1P+1, 11+6+1P+1, 11+Y10, 11+Y9, 11+10+3+1P+1, 11+10+6+1P+1, 11+10+Y10, 11+10+Y9, Y2+3+1P+1, Y2+6+1P+1, Y2+Y10, Y2+Y9, Y2+Y6, Y2+Y5, Y2+8+Y10, Y2+8+Y9, Y2+8+Y8, Y2+8+Y7, Y2+8+7+Y10, Y2+8+7+Y9, 12+3+1P+1, 12+6+1P+1, 12+Y10, 12+Y9, 12+Y6, 12+Y5, 12+8+Y10, 12+8+Y9, 12+8+Y8, 12+8+Y7, 12+8+7+Y10, 12+8+7+Y9, 12+11+3+1P+1, 12+11+6+1P+1, 12+11+Y10, 12+11+Y9, Y1+3+1P+1, Y1+6+1P+1, Y1+Y10, Y1+Y9, Y1+Y4, Y1+Y3, Y1+9+Y10, Y1+9+Y9, Y1+9+Y6, Y1+9+Y5, Y1+9+8+Y10, Y1+9+8+Y9, Y1+9+8+Y8, Y1+9+8+Y7, Y1+9+8+7+Y10, Y1+9+8+7+Y9, 13+3+1P+1, 13+6+1P+1, 13+Y10, 13+Y9, 13+11+3+1P+1, 13+11+6+1P+1, 13+11+Y10, 13+11+Y9, 13+11+10+3+1P+1, 13+11+10+6+1P+1, 13+11+10+Y10, 13+11+10+Y9, 13+Y2+3+1P+1, 13+Y2+6+1P+1, 13+Y2+Y10, 13+Y2+Y9, 13+Y2+Y6, 13+Y2+Y5, 13+Y2+8+Y10, 13+Y2+8+Y9, 13+Y2+8+Y8, 13+Y2+8+Y7, 13+Y2+8+7+Y10, 13+Y2+8+7+Y9, 13+12+3+1P+1, 13+12+6+1P+1, 13+12+Y10, 13+12+Y9, 13+12+Y6, 13+12+Y5, 13+12+8+Y10, 13+12+8+Y9, 13+12+8+Y8, 13+12+8+Y7, 13+12+8+7+Y10, 13+12+8+7+Y9, 13+12+11+3+1P+1, 13+12+11+6+1P+1, 13+12+11+Y10, 13+12+11+Y9, 13+Y1+3+1P+1, 13+Y1+6+1P+1, 13+Y1+Y10, 13+Y1+Y9, 13+Y1+Y4, 13+Y1+Y3, 13+Y1+9+Y10, 13+Y1+9+Y9, 13+Y1+9+Y6, 13+Y1+9+Y5, 13+Y1+9+8+Y10, 13+Y1+9+8+Y9, 13+Y1+9+8+Y8, 13+Y1+9+8+Y7, 13+Y1+9+8+7+Y10, 13+Y1+9+8+7+Y9, 14+3+1P+1, 14+6+1P+1, 14+Y10, 14+Y9, 14+12+3+1P+1, 14+12+6+1P+1, 14+12+Y10, 14+12+Y9, 14+12+Y6, 14+12+Y5, 14+12+8+Y10, 14+12+8+Y9, 14+12+8+Y8, 14+12+8+Y7, 14+12+8+7+Y10, 14+12+8+7+Y9, 14+12+11+3+1P+1, 14+12+11+6+1P+1, 14+12+11+Y10, 14+12+11+Y9, 14+Y1+3+1P+1, 14+Y1+6+1P+1, 14+Y1+Y10, 14+Y1+Y9, 14+Y1+Y4, 14+Y1+Y3, 14+Y1+9+Y10, 14+Y1+9+Y9, 14+Y1+9+Y6, 14+Y1+9+Y5, 14+Y1+9+8+Y10, 14+Y1+9+8+Y9, 14+Y1+9+8+Y8, 14+Y1+9+8+Y7, 14+Y1+9+8+7+Y10, 14+Y1+9+8+7+Y9, 15+13+3+1P+1, 15+13+6+1P+1, 15+13+Y10, 15+13+Y9, 15+13+11+3+1P+1, 15+13+11+6+1P+1, 15+13+11+Y10, 15+13+11+Y9, 15+13+11+10+3+1P+1, 15+13+11+10+6+1P+1, 15+13+11+10+Y10, 15+13+11+10+Y9, 15+13+Y2+3+1P+1, 15+13+Y2+6+1P+1, 15+13+Y2+Y10, 15+13+Y2+Y9, 15+13+Y2+Y6, 15+13+Y2+Y5, 15+13+Y2+8+Y10, 15+13+Y2+8+Y9, 15+13+Y2+8+Y8, 15+13+Y2+8+Y7, 15+13+Y2+8+7+Y10, 15+13+Y2+8+7+Y9, Z8+3+1P+1, Z8+6+1P+1, Z8+Y10, Z8+Y9, Z8+Y6, Z8+Y5, Z8+8+Y10, Z8+8+Y9, Z8+8+Y8, Z8+8+Y7, Z8+8+7+Y10, Z8+8+7+Y9, Z8+11+3+1P+1, Z8+11+6+1P+1, Z8+11+Y10, Z8+11+Y9, 15+13+Y1+3+1P+1, 15+13+Y1+6+1P+1, 15+13+Y1+Y10, 15+13+Y1+Y9, 15+13+Y1+Y4, 15+13+Y1+Y3, 15+13+Y1+9+Y10, 15+13+Y1+9+Y9, 15+13+Y1+9+Y6, 15+13+Y1+9+Y5, 15+13+Y1+9+8+Y10, 15+13+Y1+9+8+Y9, 15+13+Y1+9+8+Y8, 15+13+Y1+9+8+Y7, 15+13+Y1+9+8+7+Y10, 15+13+Y1+9+8+7+Y9, 16+13+3+1P+1, 16+13+6+1P+1, 16+13+Y10, 16+13+Y9, 16+13+11+3+1P+1, 16+13+11+6+1P+1, 16+13+11+Y10, 16+13+11+Y9, 16+13+11+10+3+1P+1, 16+13+11+10+6+1P+1, 16+13+11+10+Y10, 16+13+11+10+Y9, 16+13+Y2+3+1P+1, 16+13+Y2+6+1P+1, 16+13+Y2+Y10, 16+13+Y2+Y9, 16+13+Y2+Y6, 16+13+Y2+Y5, 16+13+Y2+8+Y10, 16+13+Y2+8+Y9, 16+13+Y2+8+Y8, 16+13+Y2+8+Y7, 16+13+Y2+8+7+Y10, 16+13+Y2+8+7+Y9, 16+13+12+3+1P+1, 16+13+12+6+1P+1, 16+13+12+Y10, 16+13+12+Y9, 16+13+12+Y6, 16+13+12+Y5, 16+13+12+8+Y10, 16+13+12+8+Y9, 16+13+12+8+Y8, 16+13+12+8+Y7, 16+13+12+8+7+Y10, 16+13+12+8+7+Y9, 16+13+12+11+3+1P+1, 16+13+12+11+6+1P+1, 16+13+12+11+Y10, 16+13+12+11+Y9, 16+13+Y1+3+1P+1, 16+13+Y1+6+1P+1, 16+13+Y1+Y10, 16+13+Y1+Y9, 16+13+Y1+Y4, 16+13+Y1+Y3, 16+13+Y1+9+Y10, 16+13+Y1+9+Y9, 16+13+Y1+9+Y6, 16+13+Y1+9+Y5, 16+13+Y1+9+8+Y10, 16+13+Y1+9+8+Y9, 16+13+Y1+9+8+Y8, 16+13+Y1+9+8+Y7, 16+13+Y1+9+8+7+Y10, 16+13+Y1+9+8+7+Y9, 17+13+3+1P+1, 17+13+6+1P+1, 17+13+Y10, 17+13+Y9, Z7+3+1P+1, Z7+6+1P+1, Z7+Y10, Z7+Y9, Z7+10+3+1P+1, Z7+10+6+1P+1, Z7+10+Y10, Z7+10+Y9, 17+13+Y2+3+1P+1, 17+13+Y2+6+1P+1, 17+13+Y2+Y10, 17+13+Y2+Y9, 17+13+Y2+Y6, 17+13+Y2+Y5, 17+13+Y2+8+Y10, 17+13+Y2+8+Y9, 17+13+Y2+8+Y8, 17+13+Y2+8+Y7, 17+13+Y2+8+7+Y10, 17+13+Y2+8+7+Y9, Z6+3+1P+1, Z6+6+1P+1, Z6+Y10, Z6+Y9, Z6+Y6, Z6+Y5, Z6+8+Y10, Z6+8+Y9, Z6+8+Y8, Z6+8+Y7, Z6+8+7+Y10, Z6+8+7+Y9, Z6+11+3+1P+1, Z6+11+6+1P+1, Z6+11+Y10, Z6+11+Y9, 17+13+Y1+3+1P+1, 17+13+Y1+6+1P+1, 17+13+Y1+Y10, 17+13+Y1+Y9, 17+13+Y1+Y4, 17+13+Y1+Y3, 17+13+Y1+9+Y10, 17+13+Y1+9+Y9, 17+13+Y1+9+Y6, 17+13+Y1+9+Y5, 17+13+Y1+9+8+Y10, 17+13+Y1+9+8+Y9, 17+13+Y1+9+8+Y8, 17+13+Y1+9+8+Y7, 17+13+Y1+9+8+7+Y10, 17+13+Y1+9+8+7+Y9, Z5+3+1P+1, Z5+6+1P+1, Z5+Y10, Z5+Y9, Z5+11+3+1P+1, Z5+11+6+1P+1, Z5+11+Y10, Z5+11+Y9, Z5+11+10+3+1P+1, Z5+11+10+6+1P+1, Z5+11+10+Y10, Z5+11+10+Y9, Z5+Y2+3+1P+1, Z5+Y2+6+1P+1, Z5+Y2+Y10, Z5+Y2+Y9, Z5+Y2+Y6, Z5+Y2+Y5, Z5+Y2+8+Y10, Z5+Y2+8+Y9, Z5+Y2+8+Y8, Z5+Y2+8+Y7, Z5+Y2+8+7+Y10, Z5+Y2+8+7+Y9, Z5+12+3+1P+1, Z5+12+6+1P+1, Z5+12+Y10, Z5+12+Y9, Z5+12+Y6, Z5+12+Y5, Z5+12+8+Y10, Z5+12+8+Y9, Z5+12+8+Y8, Z5+12+8+Y7, Z5+12+8+7+Y10, Z5+12+8+7+Y9, Z5+12+11+3+1P+1, Z5+12+11+6+1P+1, Z5+12+11+Y10, Z5+12+11+Y9, Z5+Y1+3+1P+1, Z5+Y1+6+1P+1, Z5+Y1+Y10, Z5+Y1+Y9, Z5+Y1+Y4, Z5+Y1+Y3, Z5+Y1+9+Y10, Z5+Y1+9+Y9, Z5+Y1+9+Y6, Z5+Y1+9+Y5, Z5+Y1+9+8+Y10, Z5+Y1+9+8+Y9, Z5+Y1+9+8+Y8, Z5+Y1+9+8+Y7, Z5+Y1+9+8+7+Y10, Z5+Y1+9+8+7+Y9, 18+17+13+3+1P+1, 18+17+13+6+1P+1, 18+17+13+Y10, 18+17+13+Y9, 18+Z7+3+1P+1, 18+Z7+6+1P+1, 18+Z7+Y10, 18+Z7+Y9, 18+Z7+10+3+1P+1, 18+Z7+10+6+1P+1, 18+Z7+10+Y10, 18+Z7+10+Y9, 18+17+13+Y2+3+1P+1, 18+17+13+Y2+6+1P+1, 18+17+13+Y2+Y10, 18+17+13+Y2+Y9, 18+17+13+Y2+Y6, 18+17+13+Y2+Y5, 18+17+

13+Y2+8+Y10, 18+17+13+Y2+8+Y9, 18+17+13+Y2+8+Y8, 18+17+13+Y2+8+Y7, 18+17+13+Y2+8+7+Y10, 18+17+13+Y2+8+7+Y9, 18+Z6+3+1P+1, 18+Z6+6+1P+1, 18+Z6+Y10, 18+Z6+Y9, 18+Z6+Y6, 18+Z6+Y5, 18+Z6+8+Y10, 18+Z6+8+Y9, 18+Z6+8+Y8, 18+Z6+8+Y7, 18+Z6+8+7+Y10, 18+Z6+8+7+Y9, 18+Z6+11+3+1P+1, 18+Z6+11+6+1P+1, 18+Z6+11+Y10, 18+Z6+11+Y9, 18+17+13+Y1+3+1P+1, 18+17+13+Y1+6+1P+1, 18+17+13+Y1+Y10, 18+17+13+Y1+Y9, 18+17+13+Y1+Y4, 18+17+13+Y1+Y3, 18+17+13+Y1+9+Y10, 18+17+13+Y1+9+Y9, 18+17+13+Y1+9+Y6, 18+17+13+Y1+9+Y5, 18+17+13+Y1+9+8+Y10, 18+17+13+Y1+9+8+Y9, 18+17+13+Y1+9+8+Y8, 18+17+13+Y1+9+8+Y7, 18+17+13+Y1+9+8+7+Y10, 18+17+13+Y1+9+8+7+Y9, Z4+3+1P+1, Z4+6+1P+1, Z4+Y10, Z4+Y9, Z4+11+3+1P+1, Z4+11+6+1P+1, Z4+11+Y10, Z4+11+Y9, Z4+11+10+3+1P+1, Z4+11+10+6+1P+1, Z4+11+10+Y10, Z4+11+10+Y9, Z4+Y2+3+1P+1, Z4+Y2+6+1P+1, Z4+Y2+Y10, Z4+Y2+Y9, Z4+Y2+Y6, Z4+Y2+Y5, Z4+Y2+8+Y10, Z4+Y2+8+Y9, Z4+Y2+8+Y8, Z4+Y2+8+Y7, Z4+Y2+8+7+Y10, Z4+Y2+8+7+Y9, Z4+12+3+1P+1, Z4+12+6+1P+1, Z4+12+Y10, Z4+12+Y9, Z4+12+Y6, Z4+12+Y5, Z4+12+8+Y10, Z4+12+8+Y9, Z4+12+8+Y8, Z4+12+8+Y7, Z4+12+8+7+Y10, Z4+12+8+7+Y9, Z4+12+11+3+1P+1, Z4+12+11+6+1P+1, Z4+12+11+Y10, Z4+12+11+Y9, Z4+Y1+3+1P+1, Z4+Y1+6+1P+1, Z4+Y1+Y10, Z4+Y1+Y9, Z4+Y1+Y4, Z4+Y1+Y3, Z4+Y1+9+Y10, Z4+Y1+9+Y9, Z4+Y1+9+Y6, Z4+Y1+9+Y5, Z4+Y1+9+8+Y10, Z4+Y1+9+8+Y9, Z4+Y1+9+8+Y8, Z4+Y1+9+8+Y7, Z4+Y1+9+8+7+Y10, Z4+Y1+9+8+7+Y9, Z3+3+1P+1, Z3+6+1P+1, Z3+Y10, Z3+Y9, Z3+11+3+1P+1, Z3+11+6+1P+1, Z3+11+Y10, Z3+11+Y9, Z3+11+10+3+1P+1, Z3+11+10+6+1P+1, Z3+11+10+Y10, Z3+11+10+Y9, Z3+Y2+3+1P+1, Z3+Y2+6+1P+1, Z3+Y2+Y10, Z3+Y2+Y9, Z3+Y2+Y6, Z3+Y2+Y5, Z3+Y2+8+Y10, Z3+Y2+8+Y9, Z3+Y2+8+Y8, Z3+Y2+8+Y7, Z3+Y2+8+7+Y10, Z3+Y2+8+7+Y9, Z3+12+3+1P+1, Z3+12+6+1P+1, Z3+12+Y10, Z3+12+Y9, Z3+12+Y6, Z3+12+Y5, Z3+12+8+Y10, Z3+12+8+Y9, Z3+12+8+Y8, Z3+12+8+Y7, Z3+12+8+7+Y10, Z3+12+8+7+Y9, Z3+12+11+3+1P+1, Z3+12+11+6+1P+1, Z3+12+11+Y10, Z3+12+11+Y9, Z3+Y1+3+1P+1, Z3+Y1+6+1P+1, Z3+Y1+Y10, Z3+Y1+Y9, Z3+Y1+Y4, Z3+Y1+Y3, Z3+Y1+9+Y10, Z3+Y1+9+Y9, Z3+Y1+9+Y6, Z3+Y1+9+Y5, Z3+Y1+9+8+Y10, Z3+Y1+9+8+Y9, Z3+Y1+9+8+Y8, Z3+Y1+9+8+Y7, Z3+Y1+9+8+7+Y10, Z3+Y1+9+8+7+Y9, Z2+3+1P+1, Z2+6+1P+1, Z2+Y10, Z2+Y9, Z2+11+3+1P+1, Z2+11+6+1P+1, Z2+11+Y10, Z2+11+Y9, Z2+11+10+3+1P+1, Z2+11+10+6+1P+1, Z2+11+10+Y10, Z2+11+10+Y9, Z2+Y2+3+1P+1, Z2+Y2+6+1P+1, Z2+Y2+Y10, Z2+Y2+Y9, Z2+Y2+Y6, Z2+Y2+Y5, Z2+Y2+8+Y10, Z2+Y2+8+Y9, Z2+Y2+8+Y8, Z2+Y2+8+Y7, Z2+Y2+8+7+Y10, Z2+Y2+8+7+Y9, Z2+12+3+1P+1, Z2+12+6+1P+1, Z2+12+Y10, Z2+12+Y9, Z2+12+Y6, Z2+12+Y5, Z2+12+8+Y10, Z2+12+8+Y9, Z2+12+8+Y8, Z2+12+8+Y7, Z2+12+8+7+Y10, Z2+12+8+7+Y9, Z2+12+11+3+1P+1, Z2+12+11+6+1P+1, Z2+12+11+Y10, Z2+12+11+Y9, Z2+Y1+3+1P+1, Z2+Y1+6+1P+1, Z2+Y1+Y10, Z2+Y1+Y9, Z2+Y1+Y4, Z2+Y1+Y3, Z2+Y1+9+Y10, Z2+Y1+9+Y9, Z2+Y1+9+Y6, Z2+Y1+9+Y5, Z2+Y1+9+8+Y10, Z2+Y1+9+8+Y9, Z2+Y1+9+8+Y8, Z2+Y1+9+8+Y7, Z2+Y1+9+8+7+Y10, Z2+Y1+9+8+7+Y9, Z1+3+1P+1, Z1+6+1P+1, Z1+Y10, Z1+Y9, Z1+11+3+1P+1, Z1+11+6+1P+1, Z1+11+Y10, Z1+11+Y9, Z1+11+10+3+1P+1, Z1+11+10+6+1P+1, Z1+11+10+Y10, Z1+11+10+Y9, Z1+Y2+3+1P+1, Z1+Y2+6+1P+1, Z1+Y2+Y10, Z1+Y2+Y9, Z1+Y2+Y6, Z1+Y2+Y5, Z1+Y2+8+Y10, Z1+Y2+8+Y9, Z1+Y2+8+Y8, Z1+Y2+8+Y7, Z1+Y2+8+7+Y10, Z1+Y2+8+7+Y9, Z1+12+3+1P+1, Z1+12+6+1P+1, Z1+12+Y10, Z1+12+Y9, Z1+12+Y6, Z1+12+Y5, Z1+12+8+Y10, Z1+12+8+Y9, Z1+12+8+Y8, Z1+12+8+Y7, Z1+12+8+7+Y10, Z1+12+8+7+Y9, Z1+12+11+3+1P+1, Z1+12+11+6+1P+1, Z1+12+11+Y10, Z1+12+11+Y9, Z1+Y1+3+1P+1, Z1+Y1+6+1P+1, Z1+Y1+Y10, Z1+Y1+Y9, Z1+Y1+Y4, Z1+Y1+Y3, Z1+Y1+9+Y10, Z1+Y1+9+Y9, Z1+Y1+9+Y6, Z1+Y1+9+Y5, Z1+Y1+9+8+Y10, Z1+Y1+9+8+Y9, Z1+Y1+9+8+Y8, Z1+Y1+9+8+Y7, Z1+Y1+9+8+7+Y10, Z1+Y1+9+8+7+Y9, 20+17+13+3+1P+1, 20+17+13+6+1P+1, 20+17+13+Y10, 20+17+13+Y9, 20+Z7+3+1P+1, 20+Z7+6+1P+1, 20+Z7+Y10, 20+Z7+Y9, 20+Z7+10+3+1P+1, 20+Z7+10+6+1P+1, 20+Z7+10+Y10, 20+Z7+10+Y9, 20+17+13+Y2+3+1P+1, 20+17+13+Y2+6+1P+1, 20+17+13+Y2+Y10, 20+17+13+Y2+Y9, 20+17+13+Y2+Y6, 20+17+13+Y2+Y5, 20+17+13+Y2+8+Y10, 20+17+13+Y2+8+Y9, 20+17+13+Y2+8+Y8, 20+17+13+Y2+8+Y7, 20+17+13+Y2+8+7+Y10, 20+17+13+Y2+8+7+Y9, 20+Z6+3+1P+1, 20+Z6+6+1P+1, 20+Z6+Y10, 20+Z6+Y9, 20+Z6+Y6, 20+Z6+Y5, 20+Z6+8+Y10, 20+Z6+8+Y9, 20+Z6+8+Y8, 20+Z6+8+Y7, 20+Z6+8+7+Y10, 20+Z6+8+7+Y9, 20+Z6+11+3+1P+1, 20+Z6+11+6+1P+1, 20+Z6+11+Y10, 20+Z6+11+Y9, 20+17+13+Y1+3+1P+1, 20+17+13+Y1+6+1P+1, 20+17+13+Y1+Y10, 20+17+13+Y1+Y9, 20+17+13+Y1+Y4, 20+17+13+Y1+Y3, 20+17+13+Y1+9+Y10, 20+17+13+Y1+9+Y9, 20+17+13+Y1+9+Y6, 20+17+13+Y1+9+Y5, 20+17+13+Y1+9+8+Y10, 20+17+13+Y1+9+8+Y9, 20+17+13+Y1+9+8+Y8, 20+17+13+Y1+9+8+Y7, 20+17+13+Y1+9+8+7+Y10, 20+17+13+Y1+9+8+7+Y9, 20+Z5+3+1P+1, 20+Z5+6+1P+1, 20+Z5+Y10, 20+Z5+Y9, 20+Z5+11+3+1P+1, 20+Z5+11+6+1P+1, 20+Z5+11+Y10, 20+Z5+11+Y9, 20+Z5+11+10+3+1P+1, 20+Z5+11+10+6+1P+1, 20+Z5+11+10+Y10, 20+Z5+11+10+Y9, 20+Z5+Y2+3+1P+1, 20+Z5+Y2+6+1P+1, 20+Z5+Y2+Y10, 20+Z5+Y2+Y9, 20+Z5+Y2+Y6, 20+Z5+Y2+Y5, 20+Z5+Y2+8+Y10, 20+Z5+Y2+8+Y9, 20+Z5+Y2+8+Y8, 20+Z5+Y2+8+Y7, 20+Z5+Y2+8+7+Y10, 20+Z5+Y2+8+7+Y9, 20+Z5+12+3+1P+1, 20+Z5+12+6+1P+1, 20+Z5+12+Y10, 20+Z5+12+Y9, 20+Z5+12+Y6, 20+Z5+12+Y5, 20+Z5+12+8+Y10, 20+Z5+12+8+Y9, 20+Z5+12+8+Y8, 20+Z5+12+8+Y7, 20+Z5+12+8+7+Y10, 20+Z5+12+8+7+Y9, 20+Z5+12+11+3+1P+1, 20+Z5+12+11+6+1P+1, 20+Z5+12+11+Y10, 20+Z5+12+11+Y9, 20+Z5+Y1+3+1P+1, 20+Z5+Y1+6+1P+1, 20+Z5+Y1+Y10, 20+Z5+Y1+Y9, 20+Z5+Y1+Y4, 20+Z5+Y1+Y3, 20+Z5+Y1+9+Y10, 20+Z5+Y1+9+Y9, 20+Z5+Y1+9+Y6, 20+Z5+Y1+9+Y5, 20+Z5+Y1+9+8+Y10, 20+Z5+Y1+9+8+Y9, 20+Z5+Y1+9+8+Y8, 20+Z5+Y1+9+8+Y7, 20+Z5+Y1+9+8+7+Y10, 20+Z5+Y1+9+8+7+Y9, 20+18+17+13+3+1P+1, 20+18+17+13+6+1P+1, 20+18+17+13+Y10, 20+18+17+13+Y9, 20+18+Z7+3+1P+1, 20+18+Z7+6+1P+1, 20+18+Z7+Y10, 20+18+Z7+Y9, 20+18+Z7+10+3+1P+1, 20+18+Z7+10+6+1P+1, 20+18+Z7+10+Y10, 20+18+Z7+10+Y9, 20+18+17+13+Y2+3+1P+1, 20+18+17+13+Y2+6+1P+1, 20+18+17+13+Y2+Y10, 20+18+17+13+Y2+Y9, 20+18+17+13+Y2+Y6, 20+18+17+13+Y2+Y5, 20+18+17+13+Y2+8+Y10, 20+18+17+13+Y2+8+Y9, 20+18+17+13+Y2+8+Y8, 20+18+17+13+Y2+8+Y7, 20+18+17+13+Y2+8+7+Y10, 20+18+17+13+Y2+8+7+Y9, 20+18+Z6+3+1P+1, 20+18+Z6+6+1P+1, 20+18+Z6+Y10, 20+18+Z6+Y9, 20+18+Z6+Y6, 20+18+Z6+Y5, 20+18+Z6+8+Y10, 20+18+Z6+8+Y9, 20+18+Z6+8+Y8, 20+18+Z6+8+Y7, 20+18+Z6+8+7+Y10, 20+18+Z6+8+7+Y9, 20+18+Z6+11+3+1P+1, 20+18+Z6+11+6+1P+1, 20+18+Z6+11+Y10, 20+18+Z6+11+Y9, 20+18+17+13+Y1+3+1P+1, 20+18+17+13+Y1+6+1P+1, 20+18+17+13+Y1+Y10, 20+18+17+13+Y1+Y9, 20+18+17+13+Y1+Y4,

20+18+17+13+Y1+Y3, 20+18+17+13+Y1+9+Y10, 20+18+17+13+Y1+9+Y9, 20+18+17+13+Y1+9+Y6, 20+18+17+13+Y1+9+Y5, 20+18+17+13+Y1+9+8+Y10, 20+18+17+13+Y1+9+8+Y9, 20+18+17+13+Y1+9+8+Y8, 20+18+17+13+Y1+9+8+Y7, 20+18+17+13+Y1+9+8+7+Y10, 20+18+17+13+Y1+9+8+7+Y9, 22+13+3+1P+1, 22+13+6+1P+1, 22+13+Y10, 22+13+Y9, 22+13+11+3+1P+1, 22+13+11+6+1P+1, 22+13+11+Y10, 22+13+11+Y9, 22+13+11+10+3+1P+1, 22+13+11+10+6+1P+1, 22+13+11+10+Y10, 22+13+11+10+Y9, 22+13+Y2+3+1P+1, 22+13+Y2+6+1P+1, 22+13+Y2+Y10, 22+13+Y2+Y9, 22+13+Y2+Y6, 22+13+Y2+Y5, 22+13+Y2+8+Y10, 22+13+Y2+8+Y9, 22+13+Y2+8+Y8, 22+13+Y2+8+Y7, 22+13+Y2+8+7+Y10, 22+13+Y2+8+7+Y9, 22+13+12+3+1P+1, 22+13+12+6+1P+1, 22+13+12+Y10, 22+13+12+Y9, 22+13+12+Y6, 22+13+12+Y5, 22+13+12+8+Y10, 22+13+12+8+Y9, 22+13+12+8+Y8, 22+13+12+8+Y7, 22+13+12+8+7+Y10, 22+13+12+8+7+Y9, 22+13+12+11+3+1P+1, 22+13+12+11+6+1P+1, 22+13+12+11+Y10, 22+13+12+11+Y9, 22+13+Y1+3+1P+1, 22+13+Y1+6+1P+1, 22+13+Y1+Y10, 22+13+Y1+Y9, 22+13+Y1+Y4, 22+13+Y1+Y3, 22+13+Y1+9+Y10, 22+13+Y1+9+Y9, 22+13+Y1+9+Y6, 22+13+Y1+9+Y5, 22+13+Y1+9+8+Y10, 22+13+Y1+9+8+Y9, 22+13+Y1+9+8+Y8, 22+13+Y1+9+8+Y7, 22+13+Y1+9+8+7+Y10, 22+13+Y1+9+8+7+Y9, 23+13+3+1P+1, 23+13+6+1P+1, 23+13+Y10, 23+13+Y9, 23+13+11+3+1P+1, 23+13+11+6+1P+1, 23+13+11+Y10, 23+13+11+Y9, 23+13+11+10+3+1P+1, 23+13+11+10+6+1P+1, 23+13+11+10+Y10, 23+13+11+10+Y9, 23+13+Y2+3+1P+1, 23+13+Y2+6+1P+1, 23+13+Y2+Y10, 23+13+Y2+Y9, 23+13+Y2+Y6, 23+13+Y2+Y5, 23+13+Y2+8+Y10, 23+13+Y2+8+Y9, 23+13+Y2+8+Y8, 23+13+Y2+8+Y7, 23+13+Y2+8+7+Y10, 23+13+Y2+8+7+Y9, 23+13+12+3+1P+1, 23+13+12+6+1P+1, 23+13+12+Y10, 23+13+12+Y9, 23+13+12+Y6, 23+13+12+Y5, 23+13+12+8+Y10, 23+13+12+8+Y9, 23+13+12+8+Y8, 23+13+12+8+Y7, 23+13+12+8+7+Y10, 23+13+12+8+7+Y9, 23+13+12+11+3+1P+1, 23+13+12+11+6+1P+1, 23+13+12+11+Y10, 23+13+12+11+Y9, 23+13+Y1+3+1P+1, 23+13+Y1+6+1P+1, 23+13+Y1+Y10, 23+13+Y1+Y9, 23+13+Y1+Y4, 23+13+Y1+Y3, 23+13+Y1+9+Y10, 23+13+Y1+9+Y9, 23+13+Y1+9+Y6, 23+13+Y1+9+Y5, 23+13+Y1+9+8+Y10, 23+13+Y1+9+8+Y9, 23+13+Y1+9+8+Y8, 23+13+Y1+9+8+Y7, 23+13+Y1+9+8+7+Y10, 23+13+Y1+9+8+7+Y9, 24+13+3+1P+1, 24+13+6+1P+1, 24+13+Y10, 24+13+Y9, 24+13+11+3+1P+1, 24+13+11+6+1P+1, 24+13+11+Y10, 24+13+11+Y9, 24+13+11+10+3+1P+1, 24+13+11+10+6+1P+1, 24+13+11+10+Y10, 24+13+11+10+Y9, 24+13+Y2+3+1P+1, 24+13+Y2+6+1P+1, 24+13+Y2+Y10, 24+13+Y2+Y9, 24+13+Y2+Y6, 24+13+Y2+Y5, 24+13+Y2+8+Y10, 24+13+Y2+8+Y9, 24+13+Y2+8+Y8, 24+13+Y2+8+Y7, 24+13+Y2+8+7+Y10, 24+13+Y2+8+7+Y9, 24+13+12+3+1P+1, 24+13+12+6+1P+1, 24+13+12+Y10, 24+13+12+Y9, 24+13+12+Y6, 24+13+12+Y5, 24+13+12+8+Y10, 24+13+12+8+Y9, 24+13+12+8+Y8, 24+13+12+8+Y7, 24+13+12+8+7+Y10, 24+13+12+8+7+Y9, 24+13+12+11+3+1P+1, 24+13+12+11+6+1P+1, 24+13+12+11+Y10, 24+13+12+11+Y9, 24+13+Y1+3+1P+1, 24+13+Y1+6+1P+1, 24+13+Y1+Y10, 24+13+Y1+Y9, 24+13+Y1+Y4, 24+13+Y1+Y3, 24+13+Y1+9+Y10, 24+13+Y1+9+Y9, 24+13+Y1+9+Y6, 24+13+Y1+9+Y5, 24+13+Y1+9+8+Y10, 24+13+Y1+9+8+Y9, 24+13+Y1+9+8+Y8, 24+13+Y1+9+8+Y7, 24+13+Y1+9+8+7+Y10, 24+13+Y1+9+8+7+Y9, 24+17+13+3+1P+1, 24+17+13+6+1P+1, 24+Z7+3+1P+1, 24+Z7+6+1P+1, 24+Z7+Y10, 24+Z7+Y9, 24+Z7+10+3+1P+1, 24+Z7+10+6+1P+1, 24+Z7+10+Y10, 24+Z7+10+Y9, 24+17+13+Y2+3+1P+1, 24+17+13+Y2+6+1P+1, 24+17+13+Y2+Y10, 24+17+13+Y2+Y9, 24+17+13+Y2+Y6, 24+17+13+Y2+Y5, 24+17+13+Y2+8+Y10, 24+17+13+Y2+8+Y9, 24+17+13+Y2+8+Y8, 24+17+13+Y2+8+Y7, 24+17+13+Y2+8+7+Y10, 24+17+13+Y2+8+7+Y9, 24+Z6+3+1P+1, 24+Z6+6+1P+1, 24+Z6+Y10, 24+Z6+Y9, 24+Z6+Y6, 24+Z6+Y5, 24+Z6+8+Y10, 24+Z6+8+Y9, 24+Z6+8+Y8, 24+Z6+8+Y7, 24+Z6+8+7+Y10, 24+Z6+8+7+Y9, 24+Z6+11+3+1P+1, 24+Z6+11+6+1P+1, 24+Z6+11+Y10, 24+Z6+11+Y9, 24+17+13+Y1+3+1P+1, 24+17+13+Y1+6+1P+1, 24+17+13+Y1+Y10, 24+17+13+Y1+Y9, 24+17+13+Y1+Y4, 24+17+13+Y1+Y3, 24+17+13+Y1+9+Y10, 24+17+13+Y1+9+Y9, 24+17+13+Y1+9+Y6, 24+17+13+Y1+9+Y5, 24+17+13+Y1+9+8+Y10, 24+17+13+Y1+9+8+Y9, 24+17+13+Y1+9+8+Y8, 24+17+13+Y1+9+8+Y7, 24+17+13+Y1+9+8+7+Y10, 24+17+13+Y1+9+8+7+Y9, 25+13+3+1P+1, 25+13+6+1P+1, 25+13+Y10, 25+13+Y9, 25+13+11+3+1P+1, 25+13+11+6+1P+1, 25+13+11+Y10, 25+13+11+Y9, 25+13+11+10+3+1P+1, 25+13+11+10+6+1P+1, 25+13+11+10+Y10, 25+13+11+10+Y9, 25+13+Y2+3+1P+1, 25+13+Y2+6+1P+1, 25+13+Y2+Y10, 25+13+Y2+Y9, 25+13+Y2+Y6, 25+13+Y2+Y5, 25+13+Y2+8+Y10, 25+13+Y2+8+Y9, 25+13+Y2+8+Y8, 25+13+Y2+8+Y7, 25+13+Y2+8+7+Y10, 25+13+Y2+8+7+Y9, 25+13+12+3+1P+1, 25+13+12+6+1P+1, 25+13+12+Y10, 25+13+12+Y9, 25+13+12+Y6, 25+13+12+Y5, 25+13+12+8+Y10, 25+13+12+8+Y9, 25+13+12+8+Y8, 25+13+12+8+Y7, 25+13+12+8+7+Y10, 25+13+12+8+7+Y9, 25+13+12+11+3+1P+1, 25+13+12+11+6+1P+1, 25+13+12+11+Y10, 25+13+12+11+Y9, 25+13+Y1+3+1P+1, 25+13+Y1+6+1P+1, 25+13+Y1+Y10, 25+13+Y1+Y9, 25+13+Y1+Y4, 25+13+Y1+Y3, 25+13+Y1+9+Y10, 25+13+Y1+9+Y9, 25+13+Y1+9+Y6, 25+13+Y1+9+Y5, 25+13+Y1+9+8+Y10, 25+13+Y1+9+8+Y9, 25+13+Y1+9+8+Y8, 25+13+Y1+9+8+Y7, 25+13+Y1+9+8+7+Y10, 25+13+Y1+9+8+7+Y9, 25+Z4+3+1P+1, 25+Z4+6+1P+1, 25+Z4+Y10, 25+Z4+Y9, 25+Z4+11+3+1P+1, 25+Z4+11+6+1P+1, 25+Z4+11+Y10, 25+Z4+11+Y9, 25+Z4+11+10+3+1P+1, 25+Z4+11+10+6+1P+1, 25+Z4+11+10+Y10, 25+Z4+11+10+Y9, 25+Z4+Y2+3+1P+1, 25+Z4+Y2+6+1P+1, 25+Z4+Y2+Y10, 25+Z4+Y2+Y9, 25+Z4+Y2+Y6, 25+Z4+Y2+Y5, 25+Z4+Y2+8+Y10, 25+Z4+Y2+8+Y9, 25+Z4+Y2+8+Y8, 25+Z4+Y2+8+Y7, 25+Z4+Y2+8+7+Y10, 25+Z4+Y2+8+7+Y9, 25+Z4+12+3+1P+1, 25+Z4+12+6+1P+1, 25+Z4+12+Y10, 25+Z4+12+Y9, 25+Z4+12+Y6, 25+Z4+12+Y5, 25+Z4+12+8+Y10, 25+Z4+12+8+Y9, 25+Z4+12+8+Y8, 25+Z4+12+8+Y7, 25+Z4+12+8+Y10, 25+Z4+12+8+7+Y9, 25+Z4+12+11+3+1P+1, 25+Z4+12+11+6+1P+1, 25+Z4+12+11+Y10, 25+Z4+12+11+Y9, 25+Z4+Y1+3+1P+1, 25+Z4+Y1+6+1P+1, 25+Z4+Y1+Y10, 25+Z4+Y1+Y9, 25+Z4+Y1+Y4, 25+Z4+Y1+Y3, 25+Z4+Y1+9+Y10, 25+Z4+Y1+9+Y9, 25+Z4+Y1+9+Y6, 25+Z4+Y1+9+Y5, 25+Z4+Y1+9+8+Y10, 25+Z4+Y1+9+8+Y9, 25+Z4+Y1+9+8+Y8, 25+Z4+Y1+9+8+Y7, 25+Z4+Y1+9+8+7+Y10, 25+Z4+Y1+9+8+7+Y9, 25+Z3+3+1P+1, 25+Z3+6+1P+1, 25+Z3+Y10, 25+Z3+Y9, 25+Z3+11+3+1P+1, 25+Z3+11+6+1P+1, 25+Z3+11+Y10, 25+Z3+11+Y9, 25+Z3+11+10+3+1P+1, 25+Z3+11+10+6+1P+1, 25+Z3+11+10+Y10, 25+Z3+11+10+Y9, 25+Z3+Y2+3+1P+1, 25+Z3+Y2+6+1P+1, 25+Z3+Y2+Y10, 25+Z3+Y2+Y9, 25+Z3+Y2+Y6, 25+Z3+Y2+Y5, 25+Z3+Y2+8+Y10, 25+Z3+Y2+8+Y9, 25+Z3+Y2+8+Y8, 25+Z3+Y2+8+Y7, 25+Z3+Y2+8+7+Y10, 25+Z3+Y2+8+7+Y9, 25+Z3+12+3+1P+1, 25+Z3+12+6+1P+1, 25+Z3+12+Y10, 25+Z3+12+Y9, 25+Z3+12+Y6, 25+Z3+12+Y5, 25+Z3+12+8+Y10, 25+Z3+12+8+Y9, 25+Z3+12+8+Y7, 25+Z3+12+8+7+Y10, 25+Z3+12+8+7+Y9, 25+Z3+12+11+3+1P+1, 25+Z3+12+11+6+1P+1, 25+Z3+12+11+Y10, 25+Z3+12+11+Y9, 25+Z3+Y1+3+

1P+1, 25+Z3+Y1+6+1P+1, 25+Z3+Y1+Y10, 25+Z3+Y1+Y9, 25+Z3+Y1+Y4, 25+Z3+Y1+Y3, 25+Z3+Y1+9+Y10, 25+Z3+Y1+9+Y9, 25+Z3+Y1+9+Y6, 25+Z3+Y1+9+Y5, 25+Z3+Y1+9+8+Y10, 25+Z3+Y1+9+8+Y9, 25+Z3+Y1+9+8+Y8, 25+Z3+Y1+9+8+Y7, 25+Z3+Y1+9+8+7+Y10, 25+Z3+Y1+9+8+7+Y9, 25+Z2+3+1P+1, 25+Z2+6+1P+1, 25+Z2+Y10, 25+Z2+Y9, 25+Z2+11+3+1P+1, 25+Z2+11+6+1P+1, 25+Z2+11+Y10, 25+Z2+11+Y9, 25+Z2+11+10+3+1P+1, 25+Z2+11+10+6+1P+1, 25+Z2+11+10+Y10, 25+Z2+11+10+Y9, 25+Z2+Y2+3+1P+1, 25+Z2+Y2+6+1P+1, 25+Z2+Y2+Y10, 25+Z2+Y2+Y9, 25+Z2+Y2+Y6, 25+Z2+Y2+Y5, 25+Z2+Y2+8+Y10, 25+Z2+Y2+8+Y9, 25+Z2+Y2+8+Y8, 25+Z2+Y2+8+Y7, 25+Z2+Y2+8+7+Y10, 25+Z2+Y2+8+7+Y9, 25+Z2+12+3+1P+1, 25+Z2+12+6+1P+1, 25+Z2+12+Y10, 25+Z2+12+Y9, 25+Z2+12+Y6, 25+Z2+12+Y5, 25+Z2+12+8+Y10, 25+Z2+12+8+Y9, 25+Z2+12+8+Y8, 25+Z2+12+8+Y7, 25+Z2+12+8+7+Y10, 25+Z2+12+8+7+Y9, 25+Z2+12+11+3+1P+1, 25+Z2+12+11+6+1P+1, 25+Z2+12+11+Y10, 25+Z2+12+11+Y9, 25+Z2+Y1+3+1P+1, 25+Z2+Y1+6+1P+1, 25+Z2+Y1+Y10, 25+Z2+Y1+Y9, 25+Z2+Y1+Y4, 25+Z2+Y1+Y3, 25+Z2+Y1+9+Y10, 25+Z2+Y1+9+Y9, 25+Z2+Y1+9+Y6, 25+Z2+Y1+9+Y5, 25+Z2+Y1+9+8+Y10, 25+Z2+Y1+9+8+Y9, 25+Z2+Y1+9+8+Y8, 25+Z2+Y1+9+8+Y7, 25+Z2+Y1+9+8+7+Y10, 25+Z2+Y1+9+8+7+Y9, 25+Z1+3+1P+1, 25+Z1+6+1P+1, 25+Z1+Y10, 25+Z1+Y9, 25+Z1+11+3+1P+1, 25+Z1+11+6+1P+1, 25+Z1+11+Y10, 25+Z1+11+Y9, 25+Z1+11+10+3+1P+1, 25+Z1+11+10+6+1P+1, 25+Z1+11+10+Y10, 25+Z1+11+10+Y9, 25+Z1+Y2+3+1P+1, 25+Z1+Y2+6+1P+1, 25+Z1+Y2+Y10, 25+Z1+Y2+Y9, 25+Z1+Y2+Y6, 25+Z1+Y2+Y5, 25+Z1+Y2+8+Y10, 25+Z1+Y2+8+Y9, 25+Z1+Y2+8+Y8, 25+Z1+Y2+8+Y7, 25+Z1+Y2+8+7+Y10, 25+Z1+Y2+8+7+Y9, 25+Z1+12+3+1P+1, 25+Z1+12+6+1P+1, 25+Z1+12+Y10, 25+Z1+12+Y9, 25+Z1+12+Y6, 25+Z1+12+Y5, 25+Z1+12+8+Y10, 25+Z1+12+8+Y9, 25+Z1+12+8+Y8, 25+Z1+12+8+Y7, 25+Z1+12+8+7+Y10, 25+Z1+12+8+7+Y9, 25+Z1+12+11+3+1P+1, 25+Z1+12+11+6+1P+1, 25+Z1+12+11+Y10, 25+Z1+12+11+Y9, 25+Z1+Y1+3+1P+1, 25+Z1+Y1+6+1P+1, 25+Z1+Y1+Y10, 25+Z1+Y1+Y9, 25+Z1+Y1+Y4, 25+Z1+Y1+Y3, 25+Z1+Y1+9+Y10, 25+Z1+Y1+9+Y9, 25+Z1+Y1+9+Y6, 25+Z1+Y1+9+Y5, 25+Z1+Y1+9+8+Y10, 25+Z1+Y1+9+8+Y9, 25+Z1+Y1+9+8+Y8, 25+Z1+Y1+9+8+Y7, 25+Z1+Y1+9+8+7+Y10, 25+Z1+Y1+9+8+7+Y9, 32+1P+1, 32+2+1P+1, 32+3+1P+1, 32+4+1P+1, 32+5+1P+1, 32+6+1P+1, 32+Y10, 32+Y9, 32+10+3+1P+1, 32+10+6+1P+1, 32+10+Y10, 32+10+Y9, 32+10+Y4, 32+10+Y3, 32+10+9+Y10, 32+10+9+Y9, 32+10+9+Y6, 32+10+9+Y5, 32+10+9+8+Y10, 32+10+9+8+Y9, 32+10+9+8+Y8, 32+10+9+8+Y7, 32+10+9+8+7+Y10, 32+10+9+8+7+Y9, 32+13+3+1P+1, 32+13+6+1P+1, 32+13+Y10, 32+13+Y9, 32+13+11+3+1P+1, 32+13+11+6+1P+1, 32+13+11+Y10, 32+13+11+Y9, 32+13+11+10+3+1P+1, 32+13+11+10+6+1P+1, 32+13+11+10+Y10, 32+13+11+10+Y9, 32+13+Y2+3+1P+1, 32+13+Y2+6+1P+1, 32+13+Y2+Y10, 32+13+Y2+Y9, 32+13+Y2+Y6, 32+13+Y2+Y5, 32+13+Y2+8+Y10, 32+13+Y2+8+Y9, 32+13+Y2+8+Y8, 32+13+Y2+8+Y7, 32+13+Y2+8+7+Y10, 32+13+Y2+8+7+Y9, 32+13+12+3+1P+1, 32+13+12+6+1P+1, 32+13+12+Y10, 32+13+12+Y9, 32+13+12+Y6, 32+13+12+Y5, 32+13+12+8+Y10, 32+13+12+8+Y9, 32+13+12+8+Y8, 32+13+12+8+Y7, 32+13+12+8+7+Y10, 32+13+12+8+7+Y9, 32+13+12+11+3+1P+1, 32+13+12+11+6+1P+1, 32+13+12+11+Y10, 32+13+12+11+Y9, 32+13+Y1+3+1P+1, 32+13+Y1+6+1P+1, 32+13+Y1+Y10, 32+13+Y1+Y9, 32+13+Y1+Y4, 32+13+Y1+Y3, 32+13+Y1+9+Y10, 32+13+Y1+9+Y9, 32+13+Y1+9+Y6, 32+13+Y1+9+Y5, 32+13+Y1+9+8+Y10, 32+13+Y1+9+8+Y9, 32+13+Y1+9+8+Y8, 32+13+Y1+9+8+Y7, 32+13+Y1+9+8+7+Y10, 32+14+3+1P+1, 32+14+6+1P+1, 32+14+Y10, 32+14+Y9, 32+14+12+3+1P+1, 32+14+12+6+1P+1, 32+14+12+Y10, 32+14+12+Y9, 32+14+12+Y6, 32+14+12+Y5, 32+14+12+8+Y10, 32+14+12+8+Y9, 32+14+12+8+Y8, 32+14+12+8+Y7, 32+14+12+8+7+Y10, 32+14+12+8+7+Y9, 32+14+12+11+3+1P+1, 32+14+12+11+6+1P+1, 32+14+12+11+Y10, 32+14+12+11+Y9, 32+14+Y1+3+1P+1, 32+14+Y1+6+1P+1, 32+14+Y1+Y10, 32+14+Y1+Y9, 32+14+Y1+Y4, 32+14+Y1+Y3, 32+14+Y1+9+Y10, 32+14+Y1+9+Y9, 32+14+Y1+9+Y6, 32+14+Y1+9+Y5, 32+14+Y1+9+8+Y10, 32+14+Y1+9+8+Y9, 32+14+Y1+9+8+Y8, 32+14+Y1+9+8+Y7, 32+14+Y1+9+8+7+Y10, 32+14+Y1+9+8+7+Y9, 32+15+13+3+1P+1, 32+15+13+6+1P+1, 32+15+13+Y10, 32+15+13+Y9, 32+15+13+11+3+1P+1, 32+15+13+11+6+1P+1, 32+15+13+11+Y10, 32+15+13+11+Y9, 32+15+13+11+10+3+1P+1, 32+15+13+11+10+6+1P+1, 32+15+13+11+10+Y10, 32+15+13+11+10+Y9, 32+15+13+Y2+3+1P+1, 32+15+13+Y2+6+1P+1, 32+15+13+Y2+Y10, 32+15+13+Y2+Y9, 32+15+13+Y2+Y6, 32+15+13+Y2+Y5, 32+15+13+Y2+8+Y10, 32+15+13+Y2+8+Y9, 32+15+13+Y2+8+Y8, 32+15+13+Y2+8+Y7, 32+15+13+Y2+8+7+Y10, 32+15+13+Y2+8+7+Y9, 32+Z8+3+1P+1, 32+Z8+6+1P+1, 32+Z8+Y10, 32+Z8+Y9, 32+Z8+Y6, 32+Z8+Y5, 32+Z8+8+Y10, 32+Z8+8+Y9, 32+Z8+8+Y8, 32+Z8+8+Y7, 32+Z8+8+7+Y10, 32+Z8+8+7+Y9, 32+Z8+11+3+1P+1, 32+Z8+11+6+1P+1, 32+Z8+11+Y10, 32+Z8+11+Y9, 32+15+13+Y1+3+1P+1, 32+15+13+Y1+6+1P+1, 32+15+13+Y1+Y10, 32+15+13+Y1+Y9, 32+15+13+Y1+Y4, 32+15+13+Y1+Y3, 32+15+13+Y1+9+Y10, 32+15+13+Y1+9+Y9, 32+15+13+Y1+9+Y6, 32+15+13+Y1+9+Y5, 32+15+13+Y1+9+8+Y10, 32+15+13+Y1+9+8+Y9, 32+15+13+Y1+9+8+Y8, 32+15+13+Y1+9+8+Y7, 32+15+13+Y1+9+8+7+Y10, 32+15+13+Y1+9+8+7+Y9, 32+17+13+3+1P+1, 32+17+13+6+1P+1, 32+17+13+Y10, 32+17+13+Y9, 32+Z7+3+1P+1, 32+Z7+6+1P+1, 32+Z7+Y10, 32+Z7+Y9, 32+Z7+10+3+1P+1, 32+Z7+10+6+1P+1, 32+Z7+10+Y10, 32+Z7+10+Y9, 32+17+13+Y2+3+1P+1, 32+17+13+Y2+6+1P+1, 32+17+13+Y2+Y10, 32+17+13+Y2+Y9, 32+17+13+Y2+Y6, 32+17+13+Y2+Y5, 32+17+13+Y2+8+Y10, 32+17+13+Y2+8+Y9, 32+17+13+Y2+8+Y8, 32+17+13+Y2+8+Y7, 32+17+13+Y2+8+7+Y10, 32+17+13+Y2+8+7+Y9, 32+Z6+3+1P+1, 32+Z6+6+1P+1, 32+Z6+Y10, 32+Z6+Y9, 32+Z6+Y6, 32+Z6+Y5, 32+Z6+8+Y10, 32+Z6+8+Y9, 32+Z6+8+Y8, 32+Z6+8+Y7, 32+Z6+8+7+Y10, 32+Z6+8+7+Y9, 32+Z6+11+3+1P+1, 32+Z6+11+6+1P+1, 32+Z6+11+Y10, 32+Z6+11+Y9, 32+17+13+Y1+3+1P+1, 32+17+13+Y1+6+1P+1, 32+17+13+Y1+Y10, 32+17+13+Y1+Y9, 32+17+13+Y1+Y4, 32+17+13+Y1+Y3, 32+17+13+Y1+9+Y10, 32+17+13+Y1+9+Y9, 32+17+13+Y1+9+Y6, 32+17+13+Y1+9+Y5, 32+17+13+Y1+9+8+Y10, 32+17+13+Y1+9+8+Y9, 32+17+13+Y1+9+8+Y8, 32+17+13+Y1+9+8+Y7, 32+17+13+Y1+9+8+7+Y10, 32+17+13+Y1+9+8+7+Y9, 32+Z5+3+1P+1, 32+Z5+6+1P+1, 32+Z5+Y10, 32+Z5+Y9, 32+Z5+11+3+1P+1, 32+Z5+11+6+1P+1, 32+Z5+11+Y10, 32+Z5+11+Y9, 32+Z5+11+10+3+1P+1, 32+Z5+11+10+6+1P+1, 32+Z5+11+10+Y10, 32+Z5+11+10+Y9, 32+Z5+Y2+3+1P+1, 32+Z5+Y2+6+1P+1, 32+Z5+Y2+Y10, 32+Z5+Y2+Y9, 32+Z5+Y2+Y6, 32+Z5+Y2+Y5, 32+Z5+Y2+8+Y10, 32+Z5+Y2+8+Y9, 32+Z5+Y2+8+Y8, 32+Z5+Y2+8+Y7, 32+Z5+Y2+8+7+Y10, 32+Z5+Y2+8+7+Y9, 32+Z5+12+3+1P+1, 32+Z5+12+6+1P+1, 32+Z5+12+Y10, 32+Z5+12+Y9, 32+Z5+12+Y6, 32+Z5+12+Y5, 32+Z5+12+8+Y10, 32+Z5+12+8+Y9, 32+Z5+12+8+Y8, 32+Z5+12+8+Y7, 32+Z5+12+8+7+Y10, 32+Z5+12+8+7+Y9, 32+Z5+12+11+

3+1P+1, 32+Z5+12+11+6+1P+1, 32+Z5+12+11+Y10, 32+Z5+12+11+Y9, 32+Z5+Y1+3+1P+1, 32+Z5+Y1+6+1P+1, 32+Z5+Y1+Y10, 32+Z5+Y1+Y9, 32+Z5+Y1+Y4, 32+Z5+Y1+Y3, 32+Z5+Y1+9+Y10, 32+Z5+Y1+9+Y9, 32+Z5+Y1+9+Y6, 32+Z5+Y1+9+Y5, 32+Z5+Y1+9+8+Y10, 32+Z5+Y1+9+8+Y9, 32+Z5+Y1+9+8+Y8, 32+Z5+Y1+9+8+Y7, 32+Z5+Y1+9+8+7+Y10, 32+Z5+Y1+9+8+7+Y9, 32+18+17+13+3+1P+1, 32+18+17+13+6+1P+1, 32+18+17+13+Y10, 32+18+17+13+Y9, 32+18+Z7+3+1P+1, 32+18+Z7+6+1P+1, 32+18+Z7+Y10, 32+18+Z7+Y9, 32+18+Z7+10+3+1P+1, 32+18+Z7+10+6+1P+1, 32+18+Z7+10+Y10, 32+18+Z7+10+Y9, 32+18+17+13+Y2+3+1P+1, 32+18+17+13+Y2+6+1P+1, 32+18+17+13+Y2+Y10, 32+18+17+13+Y2+Y9, 32+18+17+13+Y2+Y6, 32+18+17+13+Y2+Y5, 32+18+17+13+Y2+8+Y10, 32+18+17+13+Y2+8+Y9, 32+18+17+13+Y2+8+Y8, 32+18+17+13+Y2+8+Y7, 32+18+17+13+Y2+8+7+Y10, 32+18+17+13+Y2+8+7+Y9, 32+18+Z6+3+1P+1, 32+18+Z6+6+1P+1, 32+18+Z6+Y10, 32+18+Z6+Y9, 32+18+Z6+Y6, 32+18+Z6+Y5, 32+18+Z6+8+Y10, 32+18+Z6+8+Y9, 32+18+Z6+8+Y8, 32+18+Z6+8+Y7, 32+18+Z6+8+7+Y10, 32+18+Z6+8+7+Y9, 32+18+Z6+11+3+1P+1, 32+18+Z6+11+6+1P+1, 32+18+Z6+11+Y10, 32+18+Z6+11+Y9, 32+18+17+13+Y1+3+1P+1, 32+18+17+13+Y1+6+1P+1, 32+18+17+13+Y1+Y10, 32+18+17+13+Y1+Y9, 32+18+17+13+Y1+Y4, 32+18+17+13+Y1+Y3, 32+18+17+13+Y1+9+Y10, 32+18+17+13+Y1+9+Y9, 32+18+17+13+Y1+9+Y6, 32+18+17+13+Y1+9+Y5, 32+18+17+13+Y1+9+8+Y10, 32+18+17+13+Y1+9+8+Y9, 32+18+17+13+Y1+9+8+Y8, 32+18+17+13+Y1+9+8+Y7, 32+18+17+13+Y1+9+8+7+Y10, 32+18+17+13+Y1+9+8+7+Y9, 32+Z4+3+1P+1, 32+Z4+6+1P+1, 32+Z4+Y10, 32+Z4+Y9, 32+Z4+11+3+1P+1, 32+Z4+11+6+1P+1, 32+Z4+11+Y10, 32+Z4+11+Y9, 32+Z4+11+10+3+1P+1, 32+Z4+11+10+6+1P+1, 32+Z4+11+10+Y10, 32+Z4+11+10+Y9, 32+Z4+Y2+3+1P+1, 32+Z4+Y2+6+1P+1, 32+Z4+Y2+Y10, 32+Z4+Y2+Y9, 32+Z4+Y2+Y6, 32+Z4+Y2+Y5, 32+Z4+Y2+8+Y10, 32+Z4+Y2+8+Y9, 32+Z4+Y2+8+Y8, 32+Z4+Y2+8+Y7, 32+Z4+Y2+8+7+Y10, 32+Z4+Y2+8+7+Y9, 32+Z4+12+3+1P+1, 32+Z4+12+6+1P+1, 32+Z4+12+Y10, 32+Z4+12+Y9, 32+Z4+12+Y6, 32+Z4+12+Y5, 32+Z4+12+8+Y10, 32+Z4+12+8+Y9, 32+Z4+12+8+Y8, 32+Z4+12+8+Y7, 32+Z4+12+8+7+Y10, 32+Z4+12+8+7+Y9, 32+Z4+12+11+3+1P+1, 32+Z4+12+11+6+1P+1, 32+Z4+12+11+Y10, 32+Z4+12+11+Y9, 32+Z4+Y1+3+1P+1, 32+Z4+Y1+6+1P+1, 32+Z4+Y1+Y10, 32+Z4+Y1+Y9, 32+Z4+Y1+Y4, 32+Z4+Y1+Y3, 32+Z4+Y1+9+Y10, 32+Z4+Y1+9+Y9, 32+Z4+Y1+9+Y6, 32+Z4+Y1+9+Y5, 32+Z4+Y1+9+8+Y10, 32+Z4+Y1+9+8+Y9, 32+Z4+Y1+9+8+Y8, 32+Z4+Y1+9+8+Y7, 32+Z4+Y1+9+8+7+Y10, 32+Z4+Y1+9+8+7+Y9, 32+Z3+3+1P+1, 32+Z3+6+1P+1, 32+Z3+Y10, 32+Z3+Y9, 32+Z3+11+3+1P+1, 32+Z3+11+6+1P+1, 32+Z3+11+Y10, 32+Z3+11+Y9, 32+Z3+11+10+3+1P+1, 32+Z3+11+10+6+1P+1, 32+Z3+11+10+Y10, 32+Z3+11+10+Y9, 32+Z3+Y2+3+1P+1, 32+Z3+Y2+6+1P+1, 32+Z3+Y2+Y10, 32+Z3+Y2+Y9, 32+Z3+Y2+Y6, 32+Z3+Y2+Y5, 32+Z3+Y2+8+Y10, 32+Z3+Y2+8+Y9, 32+Z3+Y2+8+Y8, 32+Z3+Y2+8+Y7, 32+Z3+Y2+8+7+Y10, 32+Z3+Y2+8+7+Y9, 32+Z3+12+3+1P+1, 32+Z3+12+6+1P+1, 32+Z3+12+Y10, 32+Z3+12+Y9, 32+Z3+12+Y6, 32+Z3+12+Y5, 32+Z3+12+8+Y10, 32+Z3+12+8+Y9, 32+Z3+12+8+Y8, 32+Z3+12+8+Y7, 32+Z3+12+8+7+Y10, 32+Z3+12+8+7+Y9, 32+Z3+12+11+3+1P+1, 32+Z3+12+11+6+1P+1, 32+Z3+12+11+Y10, 32+Z3+12+11+Y9, 32+Z3+Y1+3+1P+1, 32+Z3+Y1+6+1P+1, 32+Z3+Y1+Y10, 32+Z3+Y1+Y9, 32+Z3+Y1+Y4, 32+Z3+Y1+Y3, 32+Z3+Y1+9+Y10, 32+Z3+Y1+9+Y9, 32+Z3+Y1+9+Y6, 32+Z3+Y1+9+Y5, 32+Z3+Y1+9+8+Y10, 32+Z3+Y1+9+8+Y9, 32+Z3+Y1+9+8+Y8, 32+Z3+Y1+9+8+Y7, 32+Z3+Y1+9+8+7+Y10, 32+Z3+Y1+9+8+7+Y9, 32+Z2+3+1P+1, 32+Z2+6+1P+1, 32+Z2+Y10, 32+Z2+Y9, 32+Z2+11+3+1P+1, 32+Z2+11+6+1P+1, 32+Z2+11+Y10, 32+Z2+11+Y9, 32+Z2+11+10+3+1P+1, 32+Z2+11+10+6+1P+1, 32+Z2+11+10+Y10, 32+Z2+11+10+Y9, 32+Z2+Y2+3+1P+1, 32+Z2+Y2+6+1P+1, 32+Z2+Y2+Y10, 32+Z2+Y2+Y9, 32+Z2+Y2+Y6, 32+Z2+Y2+Y5, 32+Z2+Y2+8+Y10, 32+Z2+Y2+8+Y9, 32+Z2+Y2+8+Y8, 32+Z2+Y2+8+Y7, 32+Z2+Y2+8+7+Y10, 32+Z2+Y2+8+7+Y9, 32+Z2+12+3+1P+1, 32+Z2+12+6+1P+1, 32+Z2+12+Y10, 32+Z2+12+Y9, 32+Z2+12+Y6, 32+Z2+12+Y5, 32+Z2+12+8+Y10, 32+Z2+12+8+Y9, 32+Z2+12+8+Y8, 32+Z2+12+8+Y7, 32+Z2+12+8+7+Y10, 32+Z2+12+8+7+Y9, 32+Z2+12+11+3+1P+1, 32+Z2+12+11+6+1P+1, 32+Z2+12+11+Y10, 32+Z2+12+11+Y9, 32+Z2+Y1+3+1P+1, 32+Z2+Y1+6+1P+1, 32+Z2+Y1+Y10, 32+Z2+Y1+Y9, 32+Z2+Y1+Y4, 32+Z2+Y1+Y3, 32+Z2+Y1+9+Y10, 32+Z2+Y1+9+Y9, 32+Z2+Y1+9+Y6, 32+Z2+Y1+9+Y5, 32+Z2+Y1+9+8+Y10, 32+Z2+Y1+9+8+Y9, 32+Z2+Y1+9+8+Y8, 32+Z2+Y1+9+8+Y7, 32+Z2+Y1+9+8+7+Y10, 32+Z2+Y1+9+8+7+Y9, 32+Z1+3+1P+1, 32+Z1+6+1P+1, 32+Z1+Y10, 32+Z1+Y9, 32+Z1+11+3+1P+1, 32+Z1+11+6+1P+1, 32+Z1+11+Y10, 32+Z1+11+Y9, 32+Z1+11+10+3+1P+1, 32+Z1+11+10+6+1P+1, 32+Z1+11+10+Y10, 32+Z1+11+10+Y9, 32+Z1+Y2+3+1P+1, 32+Z1+Y2+6+1P+1, 32+Z1+Y2+Y10, 32+Z1+Y2+Y9, 32+Z1+Y2+Y6, 32+Z1+Y2+Y5, 32+Z1+Y2+8+Y10, 32+Z1+Y2+8+Y9, 32+Z1+Y2+8+Y8, 32+Z1+Y2+8+Y7, 32+Z1+Y2+8+7+Y10, 32+Z1+Y2+8+7+Y9, 32+Z1+12+3+1P+1, 32+Z1+12+6+1P+1, 32+Z1+12+Y10, 32+Z1+12+Y9, 32+Z1+12+Y6, 32+Z1+12+Y5, 32+Z1+12+8+Y10, 32+Z1+12+8+Y9, 32+Z1+12+8+Y8, 32+Z1+12+8+Y7, 32+Z1+12+8+7+Y10, 32+Z1+12+8+7+Y9, 32+Z1+12+11+3+1P+1, 32+Z1+12+11+6+1P+1, 32+Z1+12+11+Y10, 32+Z1+12+11+Y9, 32+Z1+Y1+3+1P+1, 32+Z1+Y1+6+1P+1, 32+Z1+Y1+Y10, 32+Z1+Y1+Y9, 32+Z1+Y1+Y4, 32+Z1+Y1+Y3, 32+Z1+Y1+9+Y10, 32+Z1+Y1+9+Y9, 32+Z1+Y1+9+Y6, 32+Z1+Y1+9+Y5, 32+Z1+Y1+9+8+Y10, 32+Z1+Y1+9+8+Y9, 32+Z1+Y1+9+8+Y8, 32+Z1+Y1+9+8+Y7, 32+Z1+Y1+9+8+7+Y10, 32+Z1+Y1+9+8+7+Y9, 32+20+17+13+3+1P+1, 32+20+17+13+6+1P+1, 32+20+17+13+Y10, 32+20+17+13+Y9, 32+20+Z7+3+1P+1, 32+20+Z7+6+1P+1, 32+20+Z7+Y10, 32+20+Z7+Y9, 32+20+Z7+10+3+1P+1, 32+20+Z7+10+6+1P+1, 32+20+Z7+10+Y10, 32+20+Z7+10+Y9, 32+20+17+13+Y2+3+1P+1, 32+20+17+13+Y2+6+1P+1, 32+20+17+13+Y2+Y10, 32+20+17+13+Y2+Y9, 32+20+17+13+Y2+Y6, 32+20+17+13+Y2+Y5, 32+20+17+13+Y2+8+Y10, 32+20+17+13+Y2+8+Y9, 32+20+17+13+Y2+8+Y8, 32+20+17+13+Y2+8+Y7, 32+20+17+13+Y2+8+7+Y10, 32+20+17+13+Y2+8+7+Y9, 32+20+Z6+3+1P+1, 32+20+Z6+6+1P+1, 32+20+Z6+Y10, 32+20+Z6+Y9, 32+20+Z6+Y6, 32+20+Z6+Y5, 32+20+Z6+8+Y10, 32+20+Z6+8+Y9, 32+20+Z6+8+Y8, 32+20+Z6+8+Y7, 32+20+Z6+8+7+Y10, 32+20+Z6+8+7+Y9, 32+20+Z6+11+3+1P+1, 32+20+Z6+11+6+1P+1, 32+20+Z6+11+Y10, 32+20+Z6+11+Y9, 32+20+17+13+Y1+3+1P+1, 32+20+17+13+Y1+6+1P+1, 32+20+17+13+Y1+Y10, 32+20+17+13+Y1+Y9, 32+20+17+13+Y1+Y4, 32+20+17+13+Y1+Y3, 32+20+17+13+Y1+9+Y10, 32+20+17+13+Y1+9+Y9, 32+20+17+13+Y1+9+Y6, 32+20+17+13+Y1+9+Y5, 32+20+17+13+Y1+9+8+Y10, 32+20+17+13+Y1+9+8+Y9, 32+20+17+13+Y1+9+8+Y8, 32+20+17+13+Y1+9+8+Y7, 32+20+17+13+Y1+9+8+7+Y10, 32+20+17+13+Y1+9+8+7+Y9, 32+20+Z5+3+1P+1, 32+20+Z5+6+1P+1, 32+20+Z5+Y10, 32+20+Z5+Y9, 32+20+Z5+11+3+1P+1, 32+20+Z5+11+6+1P+1, 32+20+Z5+11+Y10, 32+20+Z5+

11+Y9, 32+20+Z5+11+10+3+1P+1, 32+20+Z5+11+10+6+ 1P+1, 32+20+Z5+11+10+Y10, 32+20+Z5+11+10+Y9, 32+20+Z5+Y2+3+1P+1, 32+20+Z5+Y2+6+1P+1, 32+20+ Z5+Y2+Y10, 32+20+Z5+Y2+Y9, 32+20+Z5+Y2+Y6, 32+20+Z5+Y2+Y5, 32+20+Z5+Y2+8+Y10, 32+20+Z5+ Y2+8+Y9, 32+20+Z5+Y2+8+Y8, 32+20+Z5+Y2+8+Y7, 32+20+Z5+Y2+8+7+Y10, 32+20+Z5+Y2+8+7+Y9, 32+20+Z5+12+3+1P+1, 32+20+Z5+12+6+1P+1, 32+20+ Z5+12+Y10, 32+20+Z5+12+Y9, 32+20+Z5+12+Y6, 32+20+Z5+12+Y5, 32+20+Z5+12+8+Y10, 32+20+Z5+12+ 8+Y9, 32+20+Z5+12+8+Y8, 32+20+Z5+12+8+Y7, 32+20+ Z5+12+8+7+Y10, 32+20+Z5+12+8+7+Y9, 32+20+Z5+12+ 11+3+1P+1, 32+20+Z5+12+11+6+1P+1, 32+20+Z5+12+ 11+Y10, 32+20+Z5+12+11+Y9, 32+20+Z5+Y1+3+1P+1, 32+20+Z5+Y1+6+1P+1, 32+20+Z5+Y1+Y10, 32+20+Z5+ Y1+Y9, 32+20+Z5+Y1+Y4, 32+20+Z5+Y1+Y3, 32+20+ Z5+Y1+9+Y10, 32+20+Z5+Y1+9+Y9, 32+20+Z5+Y1+9+ Y6, 32+20+Z5+Y1+9+Y5, 32+20+Z5+Y1+9+8+Y10, 32+20+Z5+Y1+9+8+Y9, 32+20+Z5+Y1+9+8+Y8, 32+20+ Z5+Y1+9+8+Y7, 32+20+Z5+Y1+9+8+7+Y10, 32+20+Z5+ Y1+9+8+7+Y9, 32+20+18+17+13+3+1P+1, 32+20+18+ 17+13+6+1P+1, 32+20+18+17+13+Y10, 32+20+18+17+ 13+Y9, 32+20+18+Z7+3+1P+1, 32+20+18+Z7+6+1P+1, 32+20+18+Z7+Y10, 32+20+18+Z7+Y9, 32+20+18+Z7+ 10+3+1P+1, 32+20+18+Z7+10+6+1P+1, 32+20+18+Z7+ 10+Y10, 32+20+18+Z7+10+Y9, 32+20+18+17+13+Y2+3+ 1P+1, 32+20+18+17+13+Y2+6+1P+1, 32+20+18+17+13+ Y2+Y10, 32+20+18+17+13+Y2+Y9, 32+20+18+17+13+ Y2+Y6, 32+20+18+17+13+Y2+Y5, 32+20+18+17+13+ Y2+8+Y10, 32+20+18+17+13+Y2+8+Y9, 32+20+18+17+ 13+Y2+8+Y8, 32+20+18+17+13+Y2+8+Y7, 32+20+18+ 17+13+Y2+8+7+Y10, 32+20+18+17+13+Y2+8+7+Y9, 32+20+18+Z6+3+1P+1, 32+20+18+Z6+6+1P+1, 32+20+ 18+Z6+Y10, 32+20+18+Z6+Y9, 32+20+18+Z6+Y6, 32+20+18+Z6+Y5, 32+20+18+Z6+8+Y10, 32+20+18+Z6+ 8+Y9, 32+20+18+Z6+8+Y8, 32+20+18+Z6+8+Y7, 32+20+ 18+Z6+8+7+Y10, 32+20+18+Z6+8+7+Y9, 32+20+18+Z6+ 11+3+1P+1, 32+20+18+Z6+11+6+1P+1, 32+20+18+Z6+ 11+Y10, 32+20+18+Z6+11+Y9, 32+20+18+17+13+Y1+3+ 1P+1, 32+20+18+17+13+Y1+6+1P+1, 32+20+18+17+13+ Y1+Y10, 32+20+18+17+13+Y1+Y9, 32+20+18+17+13+ Y1+Y4, 32+20+18+17+13+Y1+Y3, 32+20+18+17+13+ Y1+9+Y10, 32+20+18+17+13+Y1+9+Y9, 32+20+18+17+ 13+Y1+9+Y6, 32+20+18+17+13+Y1+9+Y5, 32+20+18+ 17+13+Y1+9+8+Y10, 32+20+18+17+13+Y1+9+8+Y9, 32+20+18+17+13+Y1+9+8+Y8, 32+20+18+17+13+Y1+9+ 8+Y7, 32+20+18+17+13+Y1+9+8+7+Y10, 32+20+18+ 17+13+Y1+9+8+7+Y9, 32+22+13+3+1P+1, 32+22+13+6+1P+ 1, 32+22+13+Y10, 32+22+13+Y9, 32+22+13+11+3+1P+1, 32+22+13+11+6+1P+1, 32+22+13+11+Y10, 32+22+13+ 11+Y9, 32+22+13+11+10+3+1P+1, 32+22+13+11+10+6+ 1P+1, 32+22+13+11+10+Y10, 32+22+13+11+10+Y9, 32+22+13+Y2+3+1P+1, 32+22+13+Y2+6+1P+1, 32+22+ 13+Y2+Y10, 32+22+13+Y2+Y9, 32+22+13+Y2+Y6, 32+22+13+Y2+Y5, 32+22+13+Y2+8+Y10, 32+22+13+ Y2+8+Y9, 32+22+13+Y2+8+Y8, 32+22+13+Y2+8+Y7, 32+22+13+Y2+8+7+Y10, 32+22+13+Y2+8+7+Y9, 32+22+ 13+12+3+1P+1, 32+22+13+12+6+1P+1, 32+22+13+12+ Y10, 32+22+13+12+Y9, 32+22+13+12+Y6, 32+22+13+ 12+Y5, 32+22+13+12+8+Y10, 32+22+13+12+8+Y9, 32+22+13+12+8+Y8, 32+22+13+12+8+Y7, 32+22+13+ 12+8+7+Y10, 32+22+13+12+8+7+Y9, 32+22+13+12+11+ 3+1P+1, 32+22+13+12+11+6+1P+1, 32+22+13+12+11+ Y10, 32+22+13+12+11+Y9, 32+22+13+Y1+3+1P+1, 32+22+13+Y1+6+1P+1, 32+22+13+Y1+Y10, 32+22+13+ Y1+Y9, 32+22+13+Y1+Y4, 32+22+13+Y1+Y3, 32+22+ 13+Y1+9+Y10, 32+22+13+Y1+9+Y9, 32+22+13+Y1+9+ Y6, 32+22+13+Y1+9+Y5, 32+22+13+Y1+9+8+Y10, 32+22+13+Y1+9+8+Y9, 32+22+13+Y1+9+8+Y8, 32+22+ 13+Y1+9+8+Y7, 32+22+13+Y1+9+8+7+Y10, 32+22+13+ Y1+9+8+7+Y9, 32+23+13+3+1P+1, 32+23+13+6+1P+1, 32+23+13+Y10, 32+23+13+Y9, 32+23+13+11+3+1P+1, 32+23+13+11+6+1P+1, 32+23+13+11+Y10, 32+23+13+ 11+Y9, 32+23+13+11+10+3+1P+1, 32+23+13+11+10+6+ 1P+1, 32+23+13+11+10+Y10, 32+23+13+11+10+Y9, 32+23+13+Y2+3+1P+1, 32+23+13+Y2+6+1P+1, 32+23+ 13+Y2+Y10, 32+23+13+Y2+Y9, 32+23+13+Y2+Y6, 32+23+13+Y2+Y5, 32+23+13+Y2+8+Y10, 32+23+13+ Y2+8+Y9, 32+23+13+Y2+8+Y8, 32+23+13+Y2+8+Y7, 32+23+13+Y2+8+7+Y10, 32+23+13+Y2+8+7+Y9, 32+23+ 13+12+3+1P+1, 32+23+13+12+6+1P+1, 32+23+13+12+ Y10, 32+23+13+12+Y9, 32+23+13+12+Y6, 32+23+13+ 12+Y5, 32+23+13+12+8+Y10, 32+23+13+12+8+Y9, 32+23+13+12+8+Y8, 32+23+13+12+8+Y7, 32+23+13+ 12+8+7+Y10, 32+23+13+12+8+7+Y9, 32+23+13+12+11+ 3+1P+1, 32+23+13+12+11+6+1P+1, 32+23+13+12+11+ Y10, 32+23+13+12+11+Y9, 32+23+13+Y1+3+1P+1, 32+23+13+Y1+6+1P+1, 32+23+13+Y1+Y10, 32+23+13+ Y1+Y9, 32+23+13+Y1+Y4, 32+23+13+Y1+Y3, 32+23+ 13+Y1+9+Y10, 32+23+13+Y1+9+Y9, 32+23+13+Y1+9+ Y6, 32+23+13+Y1+9+Y5, 32+23+13+Y1+9+8+Y10, 32+23+13+Y1+9+8+Y9, 32+23+13+Y1+9+8+Y8, 32+23+ 13+Y1+9+8+Y7, 32+23+13+Y1+9+8+7+Y10, 32+23+13+ Y1+9+8+7+Y9, 32+24+13+3+1P+1, 32+24+13+6+1P+1, 32+24+13+Y10, 32+24+13+Y9, 32+24+13+11+3+1P+1, 32+24+13+11+6+1P+1, 32+24+13+11+Y10, 32+24+13+ 11+Y9, 32+24+13+11+10+3+1P+1, 32+24+13+11+10+6+ 1P+1, 32+24+13+11+10+Y10, 32+24+13+11+10+Y9, 32+24+13+Y2+3+1P+1, 32+24+13+Y2+6+1P+1, 32+24+ 13+Y2+Y10, 32+24+13+Y2+Y9, 32+24+13+Y2+Y6, 32+24+13+Y2+Y5, 32+24+13+Y2+8+Y10, 32+24+13+ Y2+8+Y9, 32+24+13+Y2+8+Y8, 32+24+13+Y2+8+Y7, 32+24+13+Y2+8+7+Y10, 32+24+13+Y2+8+7+Y9, 32+24+ 13+12+3+1P+1, 32+24+13+12+6+1P+1, 32+24+13+12+ Y10, 32+24+13+12+Y9, 32+24+13+12+Y6, 32+24+13+ 12+Y5, 32+24+13+12+8+Y10, 32+24+13+12+8+Y9, 32+24+13+12+8+Y8, 32+24+13+12+8+Y7, 32+24+13+ 12+8+7+Y10, 32+24+13+12+8+7+Y9, 32+24+13+12+11+ 3+1P+1, 32+24+13+12+11+6+1P+1, 32+24+13+12+11+ Y10, 32+24+13+12+11+Y9, 32+24+13+Y1+3+1P+1, 32+24+13+Y1+6+1P+1, 32+24+13+Y1+Y10, 32+24+13+ Y1+Y9, 32+24+13+Y1+Y4, 32+24+13+Y1+Y3, 32+24+ 13+Y1+9+Y10, 32+24+13+Y1+9+Y9, 32+24+13+Y1+9+ Y6, 32+24+13+Y1+9+Y5, 32+24+13+Y1+9+8+Y10, 32+24+13+Y1+9+8+Y9, 32+24+13+Y1+9+8+Y8, 32+24+ 13+Y1+9+8+Y7, 32+24+13+Y1+9+8+7+Y10, 32+24+13+ Y1+9+8+7+Y9, 32+24+17+13+3+1P+1, 32+24+17+13+6+ 1, 32+24+17+13+Y10, 32+24+17+13+Y9, 32+24+Z7+3+ 1P+1, 32+24+Z7+6+1P+1, 32+24+Z7+Y10, 32+24+Z7+ Y9, 32+24+Z7+10+3+1P+1, 32+24+Z7+10+6+1P+1, 32+24+Z7+10+Y10, 32+24+Z7+10+Y9, 32+24+17+13+ Y2+3+1P+1, 32+24+17+13+Y2+6+1P+1, 32+24+17+13+ Y2+Y10, 32+24+17+13+Y2+Y9, 32+24+17+13+Y2+Y6, 32+24+17+13+Y2+Y5, 32+24+17+13+Y2+8+Y10, 32+24+ 17+13+Y2+8+Y9, 32+24+17+13+Y2+8+Y8, 32+24+17+ 13+Y2+8+Y7, 32+24+17+13+Y2+8+7+Y10, 32+24+17+ 13+Y2+8+7+Y9, 32+24+Z6+3+1P+1, 32+24+Z6+6+1P+1, 32+24+Z6+Y10, 32+24+Z6+Y9, 32+24+Z6+Y6, 32+24+ Z6+Y5, 32+24+Z6+8+Y10, 32+24+Z6+8+Y9, 32+24+Z6+ 8+Y8, 32+24+Z6+8+Y7, 32+24+Z6+8+7+Y10, 32+24+Z6+ 8+7+Y9, 32+24+Z6+11+3+1P+1, 32+24+Z6+11+6+1P+1, 32+24+Z6+11+Y10, 32+24+Z6+11+Y9, 32+24+17+13+ Y1+3+1P+1, 32+24+17+13+Y1+6+1P+1, 32+24+17+13+ Y1+Y10, 32+24+17+13+Y1+Y9, 32+24+17+13+Y1+Y4,

32+24+17+13+Y1+Y3, 32+24+17+13+Y1+9+Y10, 32+24+ 17+13+Y1+9+Y9, 32+24+17+13+Y1+9+Y6, 32+24+17+ 13+Y1+9+Y5, 32+24+17+13+Y1+9+8+Y10, 32+24+17+ 13+Y1+9+8+Y9, 32+24+17+13+Y1+9+8+Y8, 32+24+17+ 13+Y1+9+8+Y7, 32+24+17+13+Y1+9+8+7+Y10, 32+24+ 17+13+Y1+9+8+7+Y9, 32+25+13+3+1P+1, 32+25+13+6+ 1P+1, 32+25+13+Y10, 32+25+13+Y9, 32+25+13+11+3+ 1P+1, 32+25+13+11+6+1P+1, 32+25+13+11+Y10, 32+25+ 13+11+Y9, 32+25+13+11+10+3+1P+1, 32+25+13+11+10+ 6+1P+1, 32+25+13+11+10+Y10, 32+25+13+11+10+Y9, 32+25+13+Y2+3+1P+1, 32+25+13+Y2+6+1P+1, 32+25+ 13+Y2+Y10, 32+25+13+Y2+Y9, 32+25+13+Y2+Y6, 32+25+13+Y2+Y5, 32+25+13+Y2+8+Y10, 32+25+13+ Y2+8+Y9, 32+25+13+Y2+8+Y8, 32+25+13+Y2+8+Y7, 32+25+13+Y2+8+7+Y10, 32+25+13+Y2+8+7+Y9, 32+25+ 13+12+3+1P+1, 32+25+13+12+6+1P+1, 32+25+13+12+ Y10, 32+25+13+12+Y9, 32+25+13+12+Y6, 32+25+13+ 12+Y5, 32+25+13+12+8+Y10, 32+25+13+12+8+Y9, 32+25+13+12+8+Y8, 32+25+13+12+8+Y7, 32+25+13+ 12+8+7+Y10, 32+25+13+12+8+7+Y9, 32+25+13+12+11+ 3+1P+1, 32+25+13+12+11+6+1P+1, 32+25+13+12+11+ Y10, 32+25+13+12+11+Y9, 32+25+13+Y1+3+1P+1, 32+25+13+Y1+6+1P+1, 32+25+13+Y1+Y10, 32+25+13+ Y1+Y9, 32+25+13+Y1+Y4, 32+25+13+Y1+Y3, 32+25+ 13+Y1+9+Y10, 32+25+13+Y1+9+Y9, 32+25+13+Y1+9+ Y6, 32+25+13+Y1+9+Y5, 32+25+13+Y1+9+8+Y10, 32+25+13+Y1+9+8+Y9, 32+25+13+Y1+9+8+Y8, 32+25+ 13+Y1+9+8+Y7, 32+25+13+Y1+9+8+7+Y10, 32+25+13+ Y1+9+8+7+Y9, 32+25+Z4+3+1P+1, 32+25+Z4+6+1P+1, 32+25+Z4+Y10, 32+25+Z4+Y9, 32+25+Z4+11+3+1P+1, 32+25+Z4+11+6+1P+1, 32+25+Z4+11+Y10, 32+25+Z4+ 11+Y9, 32+25+Z4+11+10+3+1P+1, 32+25+Z4+11+10+6+ 1P+1, 32+25+Z4+11+10+Y10, 32+25+Z4+11+10+Y9, 32+25+Z4+Y2+3+1P+1, 32+25+Z4+Y2+6+1P+1, 32+25+ Z4+Y2+Y10, 32+25+Z4+Y2+Y9, 32+25+Z4+Y2+Y6, 32+25+Z4+Y2+Y5, 32+25+Z4+Y2+8+Y10, 32+25+Z4+ Y2+8+Y9, 32+25+Z4+Y2+8+Y8, 32+25+Z4+Y2+8+Y7, 32+25+Z4+Y2+8+7+Y10, 32+25+Z4+Y2+8+7+Y9, 32+25+Z4+12+3+1P+1, 32+25+Z4+12+6+1P+1, 32+25+ Z4+12+Y10, 32+25+Z4+12+Y9, 32+25+Z4+12+Y6, 32+25+Z4+12+Y5, 32+25+Z4+12+8+Y10, 32+25+Z4+12+ 8+Y9, 32+25+Z4+12+8+Y8, 32+25+Z4+12+8+Y7, 32+25+ Z4+12+8+7+Y10, 32+25+Z4+12+8+7+Y9, 32+25+Z4+12+ 11+3+1P+1, 32+25+Z4+12+11+6+1P+1, 32+25+Z4+12+ 11+Y10, 32+25+Z4+12+11+Y9, 32+25+Z4+Y1+3+1P+1, 32+25+Z4+Y1+6+1P+1, 32+25+Z4+Y1+Y10, 32+25+Z4+ Y1+Y9, 32+25+Z4+Y1+Y4, 32+25+Z4+Y1+Y3, 32+25+ Z4+Y1+9+Y10, 32+25+Z4+Y1+9+Y9, 32+25+Z4+Y1+9+ Y6, 32+25+Z4+Y1+9+Y5, 32+25+Z4+Y1+9+8+Y10, 32+25+Z4+Y1+9+8+Y9, 32+25+Z4+Y1+9+8+Y8, 32+25+ Z4+Y1+9+8+Y7, 32+25+Z4+Y1+9+8+7+Y10, 32+25+Z4+ Y1+9+8+7+Y9, 32+25+Z3+3+1P+1, 32+25+Z3+6+1P+1, 32+25+Z3+Y10, 32+25+Z3+Y9, 32+25+Z3+11+3+1P+1, 32+25+Z3+11+6+1P+1, 32+25+Z3+11+Y10, 32+25+Z3+ 11+Y9, 32+25+Z3+11+10+3+1P+1, 32+25+Z3+11+10+6+ 1P+1, 32+25+Z3+11+10+Y10, 32+25+Z3+11+10+Y9, 32+25+Z3+Y2+3+1P+1, 32+25+Z3+Y2+6+1P+1, 32+25+ Z3+Y2+Y10, 32+25+Z3+Y2+Y9, 32+25+Z3+Y2+Y6, 32+25+Z3+Y2+Y5, 32+25+Z3+Y2+8+Y10, 32+25+Z3+ Y2+8+Y9, 32+25+Z3+Y2+8+Y8, 32+25+Z3+Y2+8+Y7, 32+25+Z3+Y2+8+7+Y10, 32+25+Z3+Y2+8+7+Y9, 32+25+Z3+12+3+1P+1, 32+25+Z3+12+6+1P+1, 32+25+ Z3+12+Y10, 32+25+Z3+12+Y9, 32+25+Z3+12+Y6, 32+25+Z3+12+Y5, 32+25+Z3+12+8+Y10, 32+25+Z3+12+ 8+Y9, 32+25+Z3+12+8+Y8, 32+25+Z3+12+8+Y7, 32+25+ Z3+12+8+7+Y10, 32+25+Z3+12+8+7+Y9, 32+25+Z3+12+ 11+3+1P+1, 32+25+Z3+12+11+6+1P+1, 32+25+Z3+12+ 11+Y10, 32+25+Z3+12+11+Y9, 32+25+Z3+Y1+3+1P+1, 32+25+Z3+Y1+6+1P+1, 32+25+Z3+Y1+Y10, 32+25+Z3+ Y1+Y9, 32+25+Z3+Y1+Y4, 32+25+Z3+Y1+Y3, 32+25+ Z3+Y1+9+Y10, 32+25+Z3+Y1+9+Y9, 32+25+Z3+Y1+9+ Y6, 32+25+Z3+Y1+9+Y5, 32+25+Z3+Y1+9+8+Y10, 32+25+Z3+Y1+9+8+Y9, 32+25+Z3+Y1+9+8+Y8, 32+25+ Z3+Y1+9+8+Y7, 32+25+Z3+Y1+9+8+7+Y10, 32+25+Z3+ Y1+9+8+7+Y9, 32+25+Z2+3+1P+1, 32+25+Z2+6+1P+1, 32+25+Z2+Y10, 32+25+Z2+Y9, 32+25+Z2+11+3+1P+1, 32+25+Z2+11+6+1P+1, 32+25+Z2+11+Y10, 32+25+Z2+ 11+Y9, 32+25+Z2+11+10+3+1P+1, 32+25+Z2+11+10+6+ 1P+1, 32+25+Z2+11+10+Y10, 32+25+Z2+11+10+Y9, 32+25+Z2+Y2+3+1P+1, 32+25+Z2+Y2+6+1P+1, 32+25+ Z2+Y2+Y10, 32+25+Z2+Y2+Y9, 32+25+Z2+Y2+Y6, 32+25+Z2+Y2+Y5, 32+25+Z2+Y2+8+Y10, 32+25+Z2+ Y2+8+Y9, 32+25+Z2+Y2+8+Y8, 32+25+Z2+Y2+8+Y7, 32+25+Z2+Y2+8+7+Y10, 32+25+Z2+Y2+8+7+Y9, 32+25+Z2+12+3+1P+1, 32+25+Z2+12+6+1P+1, 32+25+ Z2+12+Y10, 32+25+Z2+12+Y9, 32+25+Z2+12+Y6, 32+25+Z2+12+Y5, 32+25+Z2+12+8+Y10, 32+25+Z2+12+ 8+Y9, 32+25+Z2+12+8+Y8, 32+25+Z2+12+8+Y7, 32+25+ Z2+12+8+7+Y10, 32+25+Z2+12+8+7+Y9, 32+25+Z2+12+ 11+3+1P+1, 32+25+Z2+12+11+6+1P+1, 32+25+Z2+12+ 11+Y10, 32+25+Z2+12+11+Y9, 32+25+Z2+Y1+3+1P+1, 32+25+Z2+Y1+6+1P+1, 32+25+Z2+Y1+Y10, 32+25+Z2+ Y1+Y9, 32+25+Z2+Y1+Y4, 32+25+Z2+Y1+Y3, 32+25+ Z2+Y1+9+Y10, 32+25+Z2+Y1+9+Y9, 32+25+Z2+Y1+9+ Y6, 32+25+Z2+Y1+9+Y5, 32+25+Z2+Y1+9+8+Y10, 32+25+Z2+Y1+9+8+Y9, 32+25+Z2+Y1+9+8+Y8, 32+25+ Z2+Y1+9+8+Y7, 32+25+Z2+Y1+9+8+7+Y10, 32+25+Z2+ Y1+9+8+7+Y9, 32+25+Z1+3+1P+1, 32+25+Z1+6+1P+1, 32+25+Z1+Y10, 32+25+Z1+Y9, 32+25+Z1+11+3+1P+1, 32+25+Z1+11+6+1P+1, 32+25+Z1+11+Y10, 32+25+Z1+ 11+Y9, 32+25+Z1+11+10+3+1P+1, 32+25+Z1+11+10+6+ 1P+1, 32+25+Z1+11+10+Y10, 32+25+Z1+11+10+Y9, 32+25+Z1+Y2+3+1P+1, 32+25+Z1+Y2+6+1P+1, 32+25+ Z1+Y2+Y10, 32+25+Z1+Y2+Y9, 32+25+Z1+Y2+Y6, 32+25+Z1+Y2+Y5, 32+25+Z1+Y2+8+Y10, 32+25+Z1+ Y2+8+Y9, 32+25+Z1+Y2+8+Y8, 32+25+Z1+Y2+8+Y7, 32+25+Z1+Y2+8+7+Y10, 32+25+Z1+Y2+8+7+Y9, 32+25+Z1+12+3+1P+1, 32+25+Z1+12+6+1P+1, 32+25+ Z1+12+Y10, 32+25+Z1+12+Y9, 32+25+Z1+12+Y6, 32+25+Z1+12+Y5, 32+25+Z1+12+8+Y10, 32+25+Z1+12+ 8+Y9, 32+25+Z1+12+8+Y8, 32+25+Z1+12+8+Y7, 32+25+ Z1+12+8+7+Y10, 32+25+Z1+12+8+7+Y9, 32+25+Z1+12+ 11+3+1P+1, 32+25+Z1+12+11+6+1P+1, 32+25+Z1+12+ 11+Y10, 32+25+Z1+12+11+Y9, 32+25+Z1+Y1+3+1P+1, 32+25+Z1+Y1+6+1P+1, 32+25+Z1+Y1+Y10, 32+25+Z1+ Y1+Y9, 32+25+Z1+Y1+Y4, 32+25+Z1+Y1+Y3, 32+25+ Z1+Y1+9+Y10, 32+25+Z1+Y1+9+Y9, 32+25+Z1+Y1+9+ Y6, 32+25+Z1+Y1+9+Y5, 32+25+Z1+Y1+9+8+Y10, 32+25+Z1+Y1+9+8+Y9, 32+25+Z1+Y1+9+8+Y8, 32+25+ Z1+Y1+9+8+Y7, 32+25+Z1+Y1+9+8+7+Y10, 32+25+Z1+ Y1+9+8+7+Y9, 33+5+1P+1, 34+5+1P+1, 35+5+1P+1, 36+1P+1, 37+1, 37+34+1, 37+35+1, 38+37+1, 38+37+34+ 1, 38+37+35+1, 39+37+1, 39+37+34+1, 39+37+35+1, 40+37+1, 40+37+34+1, 40+37+35+1, 41+37+1, 41+37+34+ 1, 41+37+35+1, 41+38+37+1, 41+38+37+34+1, 41+38+37+ 35+1, 41+39+37+1, 41+39+37+34+1, 41+39+37+35+1, 41+40+37+1, 41+40+37+34+1, 41+40+37+35+1, 42+37+1, 42+37+34+1, 42+37+35+1, 42+38+37+1, 42+38+37+34+1, 42+38+37+35+1, 42+39+37+1, 42+39+37+34+1, 42+39+ 37+35+1, 42+40+37+1, 42+40+37+34+1, 42+40+37+35+1, 42+41+37+1, 42+41+37+34+1, 42+41+37+35+1, 42+41+ 38+37+1, 42+41+38+37+34+1, 42+41+38+37+35+1, 42+41+39+37+1, 42+41+39+37+34+1, 42+41+39+37+35+ 1, 42+41+40+37+1, 42+41+40+37+34+1, 42+41+40+37+

35+1, 43+37+1, 43+37+34+1, 43+37+35+1, 43+38+37+1, 43+38+37+34+1, 43+38+37+35+1, 43+39+37+1, 43+39+37+34+1, 43+39+37+35+1, 43+40+37+1, 43+40+37+34+1, 43+40+37+35+1, 43+41+37+1, 43+41+37+34+1, 43+41+37+35+1, 43+41+38+37+1, 43+41+38+37+34+1, 43+41+38+37+35+1, 43+41+39+37+1, 43+41+39+37+34+1, 43+41+39+37+35+1, 43+41+40+37+1, 43+41+40+37+34+1, 43+41+40+37+35+1, 44+37+1, 44+37+34+1, 44+37+35+1, 44+38+37+1, 44+38+37+34+1, 44+38+37+35+1, 44+39+37+1, 44+39+37+34+1, 44+39+37+35+1, 44+41+37+1, 44+41+37+34+1, 44+41+37+35+1, 44+41+38+37+1, 44+41+38+37+34+1, 44+41+38+37+35+1, 44+41+39+37+1, 44+41+39+37+34+1, 44+41+39+37+35+1, 45+1;

wherein the following abbreviations are used: Y1 means 12+11+10; Y2 means 11+10+9; Y3 means 9+6+1P+1; Y4 means 9+3+1P+1; Y5 means 8+6+1P+1; Y6 means 8+3+1P+1; Y7 means 7+6+1P+1; Y8 means 7+3+1P+1; Y9 means 6+4+1P+1; Y10 means 6+3+1P+1; Z1 means 19+18+17+13; Z2 means 19+18+15+13; Z3 means 19+17+13; Z4 means 19+15+13; Z5 means 18+15+13; Z6 means 17+13+12; Z7 means 17+13+11; Z8 means 15+13+12; and wherein the list above is not to be construed as limiting with respect to further embodiments which are also possible based on the dependencies of the embodiments 1) to 45) as disclosed hereinabove and which are also intended. In the list above the numbers refer to the embodiments according to their numbering provided hereinabove whereas "+" indicates the dependency from another embodiment. The different individualized embodiments are separated by commas. In other words, "6+3+1P+1" for example refers to embodiment 6) depending on embodiment 3) depending on embodiment 1P) depending on embodiment 1), i.e. embodiment "6+3+1P+1" corresponds to embodiment 1) further limited by the features of embodiments 1P), 3) and 6).

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 45), or pharmaceutically acceptable salts thereof, are suitable for use as medicaments. In particular, compounds of formula (I) modulate the P2X$_7$ receptor, i.e. they act as P2X$_7$ receptor antagonists, and are useful for the prevention or treatment of diseases which are associated with the activation of the P2X$_7$ receptor such as pain; neurodegenerative and neuroinflammatory diseases; bone and joint diseases; obstructive diseases of the airways; cardiovascular diseases; eye diseases; skin diseases; abdominal and gastrointestinal tract diseases; genitourinary diseases; cancer; other auto-immune and allergic disorders; and other disorders with an inflammatory or immunological component.

In particular, the compounds of formula (I) according to any one of embodiments 1) to 45), or pharmaceutically acceptable salts thereof, are suitable for the prevention or treatment of pain. Pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain.

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Chronic articular pain conditions include especially rheumatoid arthritis, osteoarthritis, rheumatoid spondylitis, gouty arthritis and juvenile arthritis.

Pain associated with functional bowel disorders includes especially non-ulcer dyspepsia, non-cardiac chest pain and irritable bowel syndrome.

Further, the compounds of formula (I) according to any one of embodiments 1) to 45), or pharmaceutically acceptable salts thereof, are suitable for the prevention or treatment of neurodegenerative and neuroinflammatory diseases. Neurodegenerative and neuro-inflammatory diseases include Alzheimer's disease and other dementing disorders including, but not limited to, Creutzfeldt-Jakob disease (CJD) and new variant Creutzfeldt-Jakob disease (nvCJD); Amyotrophic lateral sclerosis, amyloidosis; multiple sclerosis and other demyelinating syndromes; cerebral atherosclerosis and vasculitis; temporal arteritis; myasthenia gravis; Huntington's disease; Lewy Body dementia; and Parkinson's disease.

Further, the compounds of formula (I) according to any one of embodiments 1) to 45), or pharmaceutically acceptable salts thereof, are suitable for the prevention or treatment of bone and joint diseases. Bone and joint diseases include arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; arthritides associated with or including osteoarthritis/osteoarthrosis, both primary and secondary to, for example, congenital hip dysplasia; cervical and lumbar spondylitis; Still's disease; seronegative spondyloarthropathies including ankylosing spondylitis, psoriatic arthritis, reactive arthritis and undifferentiated spondyloarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Familial Mediterranean fever, Muckle-Wells syndrome, and Familial Hibernian Fever, Kikuchi disease; and drug-induced arthalgias, tendonitis, and myopathies including dystrophies and other inflammatory myopathies.

Further, the compounds of formula (I) according to any one of embodiments 1) to 45), or pharmaceutically acceptable salts thereof, are suitable for the prevention or treatment of obstructive diseases of the airways. Obstructive diseases of the airways include asthma, including bronchial, allergic, intrinsic, and extrinsic asthma, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; and acute viral infection including the common cold, and infection due to respiratory syncytial virus, influenza, coronavirus (including SARS) and adenovirus.

Further, the compounds of formula (I) according to any one of embodiments 1) to 45), or pharmaceutically acceptable salts thereof, are suitable for the prevention or treatment of cardiovascular diseases. Cardiovascular diseases include atherosclerosis, affecting the coronary and peripheral circulation; pericarditis; myocarditis; inflammatory and autoimmune cardiomyopathies including myocardial sarcoid; ischaemic reperfusion injuries; endocarditis, valvulitis, and aortitis including infective (for example syphilitic); vasculitides; and disorders of the proximal and peripheral veins including phlebitis and thrombosis, including deep vein thrombosis and complications of varicose veins.

Further, the compounds of formula (I) according to any one of embodiments 1) to 45), or pharmaceutically acceptable salts thereof, are suitable for the prevention or treatment of eye diseases. Eye diseases include blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; and infections of the eyes including viral, fungal, and bacterial infections.

Further, the compounds of formula (I) according to any one of embodiments 1) to 45), or pharmaceutically acceptable salts thereof, are suitable for the prevention or treatment of skin diseases. Skin diseases include psoriasis, skin burn, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and noninfective; panniculitis; cutaneous lymphomas, non-melanoma skin cancer and other dysplastic lesions; and drug-induced disorders including fixed drug eruptions.

Further, the compounds of formula (I) according to any one of embodiments 1) to 45), or pharmaceutically acceptable salts thereof, are suitable for the prevention or treatment of abdominal and gastrointestinal tract diseases. Abdominal and gastrointestinal tract diseases include hepatitis, including autoimmune, alcoholic and viral hepatitis; fibrosis and cirrhosis of the liver; cholecystitis; pancreatitis, both acute and chronic; non-inflammatory diarrhea; glossitis, gingivitis, periodontitis; oesophagitis, including reflux; eosinophilic gastro-enteritis, mastocytosis, Crohn's disease, colitis including ulcerative colitis, proctitis, pruritis ani; Coeliac disease, irritable bowel disease/syndrome, and food-related allergies which may have effects remote from the gut, for example migraine, rhinitis or eczema; allograft rejection including acute and chronic allograft rejection following, for example, transplantation of kidney, heart, liver, lung, bone marrow, skin or cornea or following blood transfusion; and chronic graft versus host disease;

Further, the compounds of formula (I) according to any one of embodiments 1) to 45), or pharmaceutically acceptable salts thereof, are suitable for the prevention or treatment of genitourinary diseases. Genitourinary diseases include nephritis including interstitial and glomerulonephritis; nephrotic syndrome; cystitis including acute and chronic (interstitial) cystitis and Hunner's ulcer; acute and chronic urethritis, hemorrhagic cystitis, prostatitis, epididymitis, oophoritis and salpingitis; vulvovaginitis; Peyronie's disease; and erectile dysfunction, both male and female.

Further, the compounds of formula (I) according to any one of embodiments 1) to 45), or pharmaceutically acceptable salts thereof, are suitable for the prevention or treatment of cancer. The treatment of cancer includes the treatment of brain tumors, prostate, lung, breast, ovarian, bowel and colon, stomach, pancreatic, skin and bone marrow (including leukaemias) and lymphoproliferative systems, such as non-Hodgkin's and Hodgkin's lymphoma; including the prevention and treatment of metastatic disease and tumor recurrences, and paraneoplastic syndromes.

Further, the compounds of formula (I) according to any one of embodiments 1) to 45), or pharmaceutically acceptable salts thereof, are suitable for the prevention or treatment of other auto-immune and allergic disorders. Other auto-immune and allergic disorders include Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Further, the compounds of formula (I) according to any one of embodiments 1) to 45), or pharmaceutically acceptable salts thereof, are suitable for the prevention or treatment of other disorders with an inflammatory or immunological component. Other disorders with an inflammatory or immunological component include acquired immune deficiency syndrome (AIDS), leprosy, Sezary syndrome, and paraneoplastic syndromes.

Further, the compounds of formula (I) according to any one of embodiments 1) to 45), or pharmaceutically acceptable salts thereof, are suitable for the prevention or treatment of mood, depression, sleep and anxiety disorders.

Further, the compounds of formula (I) according to any one of embodiments 1) to 45), or pharmaceutically acceptable salts thereof, are suitable for the prevention or treatment of injury induced trauma and spinal cord injury.

Especially, compounds of formula (I) according to any one of embodiments 1) to 45), or pharmaceutically acceptable salts thereof, are suitable for the prevention or treatment of diseases selected from one, several or all of the following groups of diseases and disorders:
1) Pain, wherein pain refers to acute pain; chronic pain; pain associated with sprains and strains; chronic articular pain; pain associated with rheumatic fever; musculoskeletal pain; lower back and neck pain; inflammatory pain; neuropathic pain; visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;
Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);
Chronic articular pain conditions include especially rheumatoid arthritis, osteoarthritis, rheumatoid spondylitis, gouty arthritis and juvenile arthritis;
Pain associated with functional bowel disorders includes especially non-ulcer dyspepsia, non-cardiac chest pain and irritable bowel syndrome;
2) Neurodegenerative and neuro-inflammatory diseases such as Alzheimer's disease and other dementing disorders including, but not limited to, Creutzfeldt-Jakob disease (CJD) and new variant Creutzfeldt-Jakob disease (nvCJD); amyloidosis; Amyotrophic lateral sclerosis, multiple sclerosis and other demyelinating syndromes; cerebral atherosclerosis and vasculitis; temporal arteritis; myasthenia gravis; Huntington's disease; Lewy Body dementia; and Parkinson's disease;
3) Bone and joint diseases such as arthritides such as rheumatoid arthritis, osteoarthritis, gout or crystal arthropathy; intervertebral disc degeneration; temporomandibular joint degeneration; bone remodelling disease such as osteoporosis, Paget's disease or osteonecrosis; polychondritis; scleroderma; mixed connective tissue disorder; spondyloarthropathies; periodontal disease such as periodontitis; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; Muckle-Wells syndrome, and Familial Hibernian Fever, Kikuchi disease; and drug-induced arthalgias, tendonitis, and myopathies;
4) Obstructive diseases of the airways such as chronic obstructive pulmonary disease (COPD); cystic fibrosis; lung emphysema; sarcoidosis; farmer's lung and related diseases; lung fibrosis, including fibrosis complicating tuberculosis; and chronic cough associated with inflammatory and secretory conditions of the airways;
5) Cardiovascular diseases such as inflammatory and auto-immune cardiomyopathies;
6) Eye diseases such as degenerative or inflammatory disorders affecting the retina;
7) Skin diseases such as psoriasis, skin burn, atopic dermatitis, contact dermatitis or other eczematous dermatoses; and discoid lupus erythematosus;
8) Abdominal and gastrointestinal tract diseases such as fibrosis and cirrhosis of the liver; cholecystitis; pancreatitis, both acute and chronic; Crohn's disease; colitis including ulcerative colitis; and irritable bowel disease/syndrome;
9) Genitourinary diseases such as nephritis including interstitial and glomerulonephritis; nephrotic syndrome; and cystitis including acute and chronic (interstitial) cystitis; and
10) Other auto-immune and allergic disorders such as Hashimoto's thyroiditis, Graves' disease, Addison's disease, diabetes mellitus, idiopathic thrombocytopaenic purpura, eosinophilic fasciitis, hyper-IgE syndrome, and antiphospholipid syndrome.

Most preferably, compounds of formula (I) according to any one of embodiments 1) to 45), or pharmaceutically acceptable salts thereof, are suitable for the prevention or treatment of diseases selected from one, several or all of the following groups of diseases and disorders:
1) Pain, wherein pain refers to acute pain; chronic pain; pain associated with sprains and strains; chronic articular pain; pain associated with rheumatic fever; musculoskeletal pain (preferred); lower back and neck pain; inflammatory pain; neuropathic pain (preferred); visceral pain; pain associated with influenza or other viral infections; pain associated with cancer and tumor invasion; joint and bone pain; atypical facial pain; pain associated with migraine, toothache and dysmenorrhea; headache including tension headache and cluster headaches; pain associated with myocardial ischemia; pain associated with functional bowel disorders; sympathetically maintained pain; myositis; pain associated with cancer chemotherapy; and post operative pain;

Neuropathic pain includes especially diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia);

Chronic articular pain conditions include especially rheumatoid arthritis, osteoarthritis, rheumatoid spondylitis, gouty arthritis and juvenile arthritis;

Pain associated with functional bowel disorders includes especially non-ulcer dyspepsia, non-cardiac chest pain and irritable bowel syndrome;

2) Rheumatoid arthritis and osteoarthritis;
3) Chronic obstructive pulmonary disease (COPD); and
4) Crohn's disease.

The invention also relates to the use of a compound of formula (I) according to any one of embodiments 1) to 45) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 45).

A pharmaceutical composition according to the present invention contains at least one compound of formula (I) according to any one of embodiments 1) to 45) (or a pharmaceutically acceptable salt thereof) as the active agent and optionally carriers and/or diluents and/or adjuvants.

The compounds of formula (I) according to any one of embodiments 1) to 45) and their pharmaceutically acceptable salts can be used as medicaments, e.g. in the form of pharmaceutical compositions for enteral (such as especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 45), or a pharmaceutically acceptable salt thereof.

Any reference to a compound of formula (I), $(I_{Ar})$, $(I_{Sr1})$ or $(I_{Sr2})$ in this text is to be understood as referring also to the salts (and especially the pharmaceutically acceptable salts) of such compounds, as appropriate and expedient. The preferences indicated for the compounds of formula (I) of course apply mutatis mutandis to the compounds of formula $(I_{Ar})$, of formula $(I_{Sr1})$ and of formula $(I_{Sr2})$ as well as to the salts and pharmaceutically acceptable salts of the compounds of formula (I), of formula $(I_{Ar})$, of formula $(I_{Sr1})$ and of formula $(I_{Sr2})$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (RT) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$, $R^2$, $R^3$, $R^4$, $R^5$ and $R^6$ are as defined for formula (I). Other abbreviations used are defined in the experimental section.

In some instances the generic groups $R^1$, $R^2$, $R^3$, $R^4$, $R^5$ and $R^6$ might be incompatible with the assembly illustrated in the schemes below and will therefore require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups are as necessary in place.

Preparation of Compounds of Formula (I)

Compounds of formula (I) can be prepared (Scheme 1) by reaction of carboxylic acids of formula II with amines of formula III using standard amide coupling reagents such as TBTU, EDC.HCl/HOBt, HATU or PyBOP in the presence of a suitable base such as DIPEA or Et₃N and in a suitable solvent such as DCM, THF or DMF preferably at temperatures between RT and 45° C.

Compounds of formula (I) wherein $R^4$ represents —CH(OH)Me can be prepared by reduction of compounds of formula (I) wherein $R^4$ represents acetyl using a suitable reducing reagent such as NaBH₄ in a suitable solvent such as MeOH at temperatures around RT. Other primary or secondary alcohols may be prepared in analogy.

Compounds of formula (I) wherein $R^4$ represents —C(OH)Me₂ can be prepared from compounds of formula (I) wherein $R^4$ represents acetyl by addition of a methylmagnesium halide solution in the presence of a suitable solvent such as THF at temperatures between −10° C. and RT. Other tertiary alcohols may be prepared in analogy.

Compounds of formula (I) wherein $R^4$ represents hydroxy-$(C_2-C_4)$alkoxy can be prepared from compounds of formula (I) wherein $R^4$ represents tert-butyloxy-$(C_2-C_4)$alkoxy by treatment with a suitable acid such as TFA in a suitable solvent such as DCM at temperatures around RT.

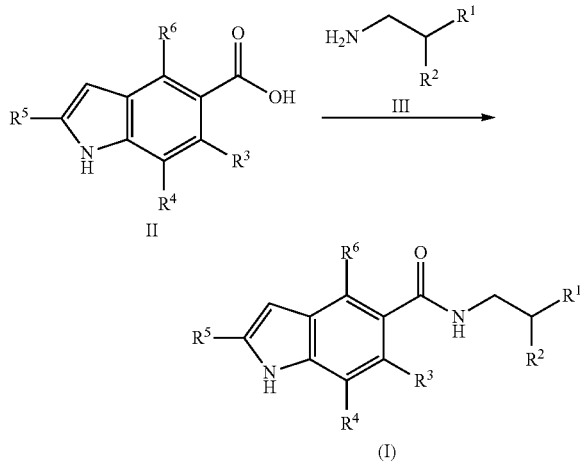

Scheme 1: General Synthesis of Compounds of Formula (I)

Compounds of formula Ia wherein Y represents N or CH (Scheme 2) can be prepared as previously described in Scheme 1.

Compounds of formula Ib wherein Y represents N or CH (Scheme 2) can be prepared by cleavage of the Boc protecting group in compounds of formula Ia by treatment with a suitable acid such as HCl or TFA in the presence of a suitable solvent such as dioxane, EtOAc or DCM at temperatures around RT.

Compounds of formula Ic wherein Y represents N or CH and wherein $R^{10}$ represents $(C_1-C_4)$alkyl (Scheme 2) can be prepared by reductive alkylation of amines of formula Ib with a suitable aldehyde or ketone in the presence of a suitable reducing agent such as $NaBH(OAc)_3$, $NaBH_3CN$ or $NaBH_4$ in a suitable solvent such as dichloroethane or mixture of solvents such as DCM/MeOH/AcOH at temperatures around RT.

Compounds of formula Id wherein Y represents N or CH and wherein $R^{10}$ represents $(C_1-C_4)$alkyl (Scheme 2) can be prepared by acylation of amines of formula Ib by treatment with a suitable acid chloride or acid anhydride in the presence of a suitable base such as $Et_3N$ or DIPEA and in a suitable solvent such as DCM or THF at temperatures between 0° C. and 50° C.

Compounds of formula Ie wherein Y represents N or CH and wherein $R^{10}$ represents $(C_1-C_4)$alkyl (Scheme 2) can be prepared by alkoxycarbonylation of amines of formula Ib by treatment with a suitable alkyl chloroformate in the presence of a suitable base such as $Et_3N$ or DIPEA and in a suitable solvent such as DCM or THF at temperatures between 0° C. and 50° C.

Compounds of formula If wherein Y represents N or CH and wherein $R^{10}$ represents $(C_1-C_4)$alkyl (Scheme 2) can be prepared by sulfonation of amines of formula Ib by treatment with a suitable alkyl sulfonyl chloride in the presence of a suitable base such as $Et_3N$ or DIPEA and in a suitable solvent such as DCM or THF at temperatures between 0° C. and 50° C.

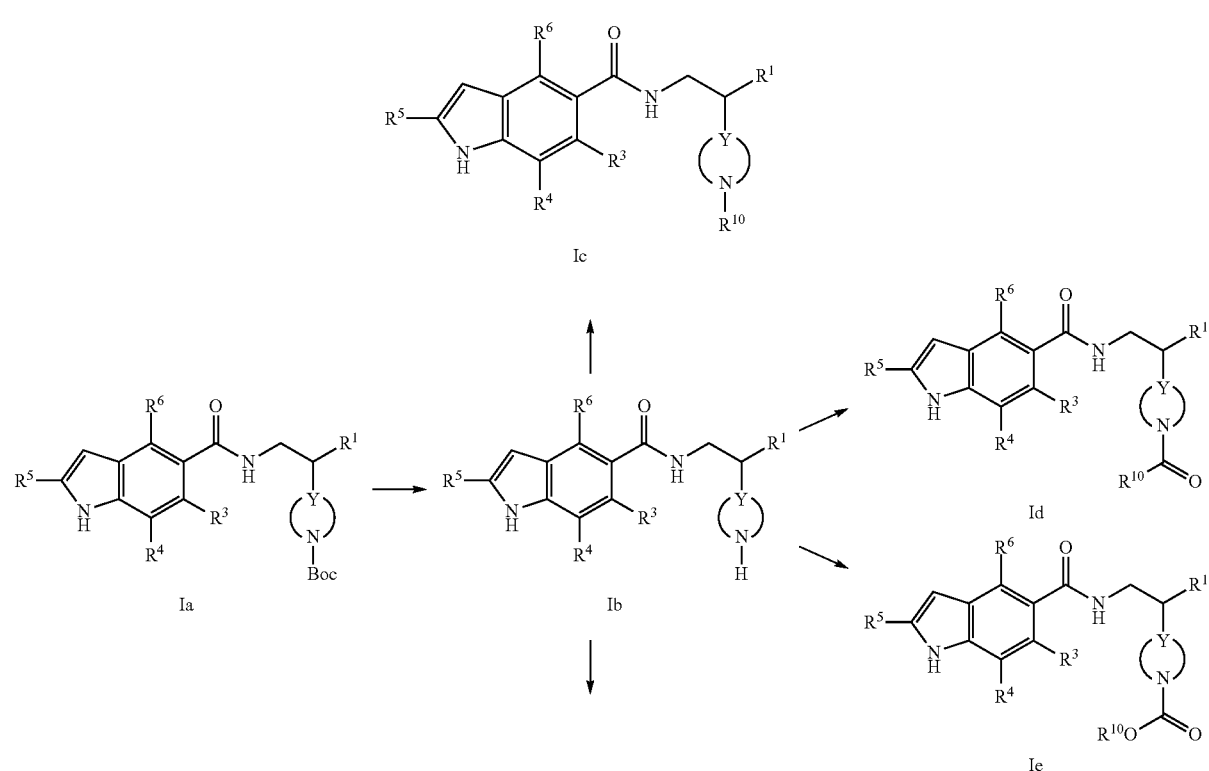

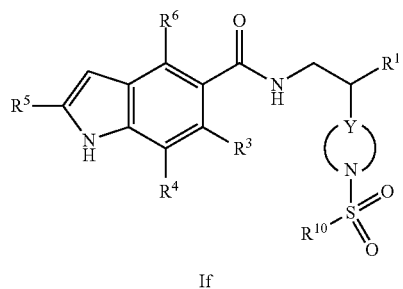

If

Scheme 2: Synthesis of Compounds of Formula I wherein $R^2$ Represents Heterocyclyl (Y Represents N or CH and $R^{10}$ Represents $(C_1-C_4)$Alkyl)

Indole carboxylic acids of formula IIa can be prepared according to the synthetic routes given in scheme 3.

Regioisomers of formula XII wherein Y represents methoxycarbonyl or cyano, together with various amounts of regioisomer XI, (Scheme 3) can be prepared by iodination of anilines of formula XIV, wherein Y represents methoxycarbonyl or cyano, using about 1.05 equivalents of a suitable iodinating reagent such as iodine in the presence of a catalyst such as silver sulfate and in a suitable solvent such as EtOH at temperatures around RT. The separation of both regioisomers can be achieved by standard CC.

Compounds of formula IX wherein $R^4$ represents hydrogen and wherein Y represents methoxycarbonyl or cyano (Scheme 3) can be prepared by Sonogashira type cross-coupling of iodides of formula XI wherein Y represents methoxycarbonyl or cyano with trimethylsilylacetylene in the presence of a suitable palladium catalyst such as bis(triphenylphosphine)palladium(II) dichloride, in the presence of a suitable copper catalyst such as copper iodide, in the presence of a ligand such as triphenylphosphine, in the presence of a suitable base such as $Et_3N$ and heating in a suitable solvent such as toluene at temperatures between 50° C. and 100° C.

Alternatively, compounds of formula IX wherein $R^4$ represents $(C_1-C_4)$alkyl or $(C_1-C_2)$alkoxy-$(C_1-C_4)$alkyl and wherein Y represents methoxycarbonyl or cyano (Scheme 3) can be prepared from iodides of formula VII wherein $R^4$ represents $(C_1-C_4)$alkyl or $(C_1-C_2)$alkoxy-$(C_1-C_4)$alkyl and wherein Y represents methoxycarbonyl or cyano using Sonogashira cross-coupling conditions such as those described above. Compounds of formula VII wherein $R^4$ represents $(C_1-C_4)$alkyl or $(C_1-C_2)$alkoxy-$(C_1-C_4)$alkyl and wherein Y represents methoxycarbonyl or cyano (Scheme 3) can be prepared by iodination of anilines of formula VIII wherein $R^4$ represents $(C_1-C_4)$alkyl or $(C_1-C_2)$alkoxy-$(C_1-C_4)$alkyl and wherein Y represents methoxycarbonyl or cyano following standard iodination conditions such as those previously described for the synthesis of compounds of formula XI and XII. Compounds of formula VIII wherein $R^4$ represents $(C_1-C_4)$alkyl or $(C_1-C_2)$alkoxy-$(C_1-C_4)$alkyl and Y represents methoxycarbonyl or cyano (Scheme 3) can be prepared by Negishi (or Suzuki, respectively) type cross-coupling of iodides of formula XII wherein Y represents methoxycarbonyl or cyano with organozinc reagents of type $R^4ZnX$ (or boronic acid of type $R^4B(OH)_2$, respectively) wherein $R^4$ represents $(C_1-C_4)$alkyl or $(C_1-C_2)$alkoxy-$(C_1-C_4)$alkyl and X represents chloro, bromo or $(C_1-C_4)$alkyl, in the presence of a suitable palladium catalyst such as $Pd(dppf)Cl_2.DCM$ (or bis(triphenylphosphine)palladium(II) dichloride and in the additional presence of a base such as $K_3PO_4$, respectively) and heating in a suitable solvent such as dioxane (or a mixture of toluene/water 20/1, respectively) at temperatures between 50° C. and 100° C. (or around 110° C., respectively).

Alternatively, compounds of formula VIII (Scheme 3) wherein $R^4$ represents $(C_3-C_4)$alkyl or $(C_1-C_2)$alkoxy-$(C_3-C_4)$alkyl and Y represents methoxycarbonyl or cyano (Scheme 3) can be prepared by Sonogashira type cross-coupling of iodides of formula XII wherein Y represents methoxycarbonyl or cyano with $(C_1-C_2)$alkylacetylene or $(C_1-C_2)$alkoxy-$(C_1-C_2)$alkylacetylene in the presence of a suitable palladium catalyst such as bis(triphenylphosphine)palladium(II) dichloride, in the presence of a suitable copper catalyst such as copper iodide, in the presence of a suitable base such as $Et_3N$ and heating in a suitable solvent such as THF at temperatures between RT and 80° C. The subsequent reduction of the triple bond can be carried out under hydrogenation conditions in the presence of a suitable catalyst such as $PtO_2$ and a suitable solvent such as EtOH at temperatures around RT. Alternatively, when using $(C_1-C_2)$ alkylacetylene as reagent, the subsequent hydration of the triple bond can be carried out by treatment with an acid such as p-toluenesulfonic acid in the presence of a suitable solvent such as toluene at temperatures around 80° C. and leads to compounds of formula VIII wherein $R^4$ represents $(C_2-C_4)$alkyl-carbonyl and Y represents methoxycarbonyl or cyano.

Alternatively, compounds of formula VIII wherein $R^4$ represents $(C_1-C_2)$alkoxy-$(C_2-C_4)$alkyl and Y represents methoxycarbonyl or cyano (Scheme 3) can be prepared by a two step procedure: (i) Suzuki type cross-coupling of iodides of formula XII wherein Y represents methoxycarbonyl or cyano with $(C_1-C_2)$alkoxy-vinyl boronic acid pinacol ester or $(C_1-C_2)$alkoxy-$(C_1-C_2)$alkyl-vinyl boronic acid pinacol ester reagents in the presence of a suitable palladium catalyst such as $Pd(OAc)_2$, a suitable ligand such as 2-dicyclohexylphosphino-2',6'-dimethoxybiphenyl and a base such as KOH and heating in a suitable solvent such as $CH_3CN$ at temperatures around 70° C. and (ii) reduction of the double bond under hydrogenation conditions such as those described above. Alternatively, compounds of formula VII wherein $R^4$ represents acetyl or ethyl, and Y represents methoxycarbonyl (Scheme 3) can be regioselectively prepared by Sonogashira type cross-coupling of iodides of formula XXXI wherein Y represents methoxycarbonyl with trimethylsilylacetylene following standard conditions such as those previously described for the synthesis of compounds of formula VIII. The subsequent reduction of the triple bond under hydrogenation conditions as those previously described for the synthesis of compounds of formula VIII delivers compounds of formula VII wherein $R^4$ represents ethyl and Y represents methoxycarbonyl. Alternatively, the subsequent hydration of the triple bond can be carried out by treatment with an acid such as p-toluenesulfonic acid in the presence of a suitable solvent such as toluene at temperatures around 80° C. and provides compounds of formula VII wherein $R^4$ represents acetyl and Y represents methoxycarbonyl. Compounds of formula XXXI wherein Y represents methoxycarbonyl or cyano can be prepared by bis-iodination of anilines of formula XIV wherein Y represents methoxycarbonyl or cyano following standard iodination conditions such as those previously described for the synthesis of compounds of formula XI and XII, but using about 2.2 equivalents of iodinating reagent.

Compounds of formula V wherein Y represents methoxycarbonyl or cyano (Scheme 3) can be prepared by protodesilylation of compounds of formula IX wherein Y represents methoxycarbonyl or cyano with a base such as potassium carbonate in the presence of a suitable solvent such as MeOH at temperatures around RT.

Compounds of formula IV wherein Y represents methoxycarbonyl or cyano (Scheme 3) can be prepared by rhodium-catalyzed cycloisomerization of anilines of formula V wherein Y represents methoxycarbonyl or cyano in the presence of a rhodium catalyst such as chloro(1,5-cyclooctadiene)rhodium(I) dimer and a ligand such as tris (4-fluorophenyl)phosphine and heating in a suitable solvent such as DMF at temperatures between 50° C. and 90° C.

Alternatively, compounds of formula IV wherein Y represents methoxycarbonyl or cyano (Scheme 3) can be prepared by copper-catalyzed cycloisomerization of anilines of formula IX wherein Y represents methoxycarbonyl or cyano using a suitable copper catalyst such as copper iodide and heating in a suitable solvent such as DMF at temperatures between 50° C. and 100° C.

Alternatively, compounds of formula IV wherein $R^4$ represents hydrogen and Y represents methoxycarbonyl (Scheme 3) can be prepared by simultaneous deiodination and desulfurization of methylsulfanyl indoles of formula XIII by treatment with a suitable catalyst such as Raney nickel in the presence of a suitable solvent such as EtOH at temperatures around RT.

Alternatively, compounds of formula IV wherein $R^4$ represents $(C_1-C_4)$alkyl and Y represents methoxycarbonyl (Scheme 3) can be prepared by desulfurization of methylsulfanyl indoles of formula VI wherein $R^4$ represents $(C_1-C_4)$alkyl by treatment with a suitable catalyst such as Raney nickel in the presence of a suitable solvent such as EtOH at temperatures around RT.

Compounds of formula VI wherein $R^4$ represents $(C_1-C_4)$ alkyl (Scheme 3) can be prepared from compounds of formula XIII by Negishi type cross-coupling following standard conditions such as those previously described for the synthesis of compounds of formula VIII.

Compounds of formula XIII (Scheme 3) can be prepared by Gassman indole synthesis by consecutive treatment of anilines of formula XII wherein Y represents methoxycarbonyl with (i) a chlorinating reagent such as N-chlorosuccinimide or tert-butyl hypochlorite, (ii) a methyl sulfanyl protected aldehyde such as methylthioacetaldehyde dimethylacetal in the presence for both steps of a suitable solvent such as DCM at temperatures between −50° C. and −78° C., (iii) a base such as $Et_3N$ in the presence of a suitable solvent such as chlorobenzene at temperatures between 80° C. and 120° C. and finally with (iv) an acid such as HCl in the presence of a solvent such as dioxane or $Et_2O$ at temperatures around RT.

Alternatively, compounds of formula IV wherein $R^3$ represents hydrogen, $R^6$ represents methyl (or ethyl, respectively) and Y represents methoxycarbonyl or cyano (Scheme 3) can be prepared by Suzuki type cross-coupling of chlorides of formula IV wherein $R^3$ represents hydrogen, $R^6$ represents chloro and Y represents methoxycarbonyl or cyano with trimethylboroxine (or vinyl boronic acid pinacol ester, respectively), in the presence of a suitable palladium catalyst such as [1,3-bis(2,6-diisopropylphenyl)imidazol-2-ylidene](3-chloropyridyl)palladium(II) dichloride, in the presence of a suitable base such as $K_2CO_3$ and heating in a suitable solvent such as dioxane at temperatures around 110° C. When using vinyl boronic acid pinacol ester as reagent, the subsequent reduction of the double bond was carried out under hydrogenation conditions such as those described above.

Alternatively, compounds of formula IV (Scheme 3) wherein $R^4$ represents hydroxy (or hydroxy-$(C_1-C_4)$alkyl respectively) and Y represents cyano can be prepared from methyl ether of formula IV wherein $R^4$ represents methoxy (or methoxy-$(C_1-C_4)$alkyl respectively) and Y represents cyano by treatment with $BBr_3$ in the presence of a suitable solvent such as DCM at temperatures between −78° C. and 55° C. The possible subsequent alkylation of the phenol of formula IV wherein $R^4$ represents hydroxy and Y represents cyano by treatment with $(C_1-C_4)$alkyl halide or $(C_1-C_4)$alkoxy-$(C_2-C_4)$alkyl halide in the presence of a suitable base such as $K_2CO_3$ and a suitable solvent such as DMF at temperatures between 0° C. and 80° C. provides compounds of formula IV wherein $R^4$ represents $(C_1-C_4)$alkoxy or $(C_1-C_4)$alkoxy-$(C_2-C_4)$alkoxy and Y represents cyano.

Carboxylic acid derivatives of formula IIa (Scheme 3) can be prepared by hydrolysis of methyl esters of formula IV wherein Y represents methoxycarbonyl by standard treatment with a suitable base such as LiOH, NaOH or KOH in the presence of water and a suitable organic solvent such as MeOH, EtOH or THF at temperatures between RT and 60° C.

Alternatively, carboxylic acid derivatives of formula IIa (Scheme 3) can be prepared by hydrolysis of nitriles of formula IV wherein Y represents cyano with a suitable base such as KOH or NaOH in the presence of water and optionally a suitable organic solvent such as 2-propanol at temperatures around 150° C.

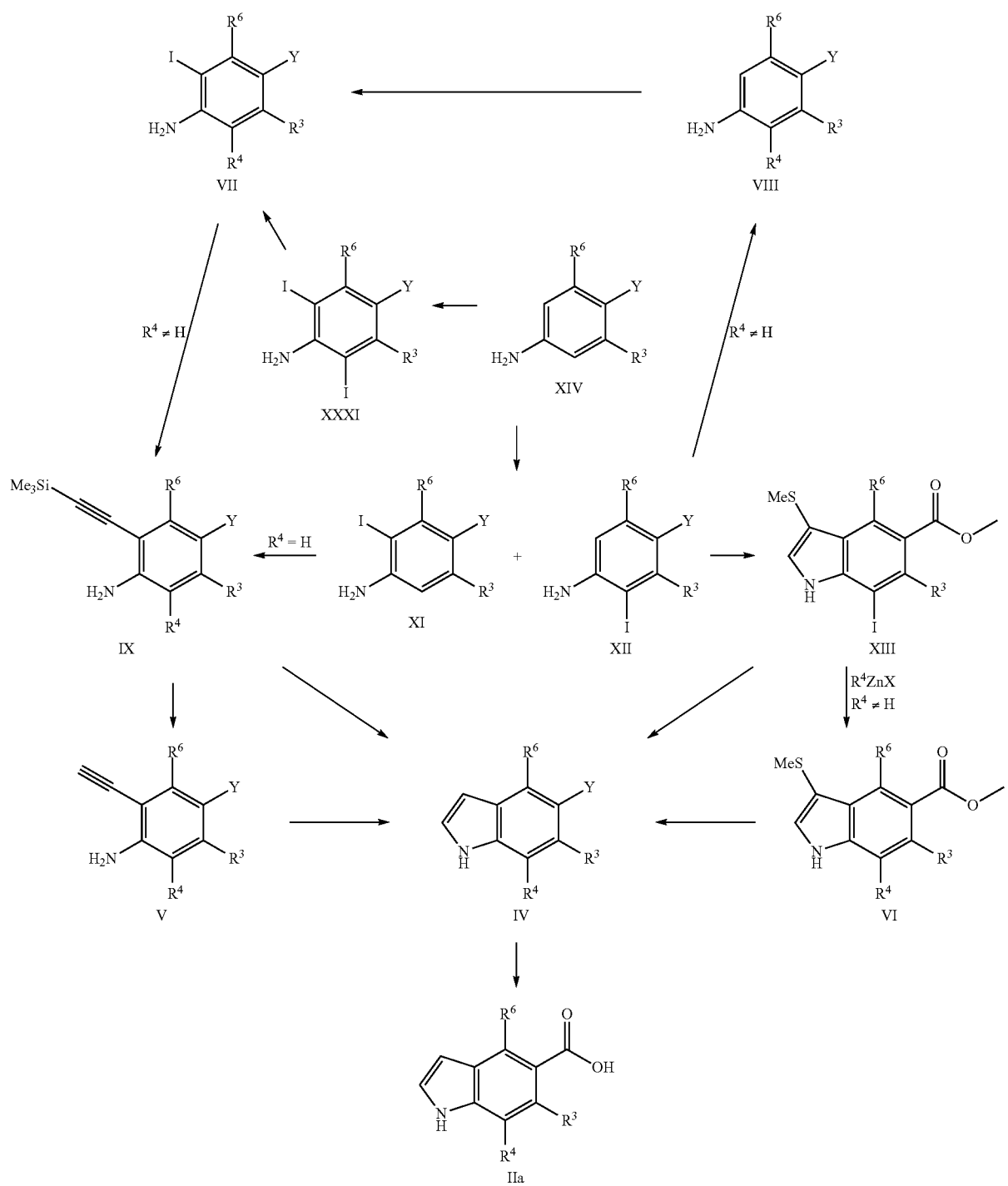

Scheme 3: Synthesis of Carboxylic Acid Intermediates of Formula II wherein $R^5$ Represents Hydrogen Indole carboxylic acids of formula IIb can be prepared according to the synthetic routes given in scheme 4.

Hydrazines of formula XVII (Scheme 4) can be prepared by diazotisation of anilines of formula XII with for instance sodium nitrite in a suitable solvent such as concentrated HCl and water at temperatures around 0° C. and subsequent reduction of the diazonium salt with for instance tin(II) chloride dihydrate in a suitable solvent such as HCl and water at temperatures between 0° C. and RT.

Indoles of formula XVIII (Scheme 4) can be prepared by Fisher indole reaction between hydrazine derivatives of formula XVII and ketones of formula $R^5COCH_2SMe$ wherein $R^5$ represents $(C_1-C_4)$alkyl in the presence of a suitable acid such as HCl and a suitable solvent such as EtOH at temperatures between 50° C. and 80° C.

Compounds of formula XVI wherein $R^4$ represents $(C_1-C_4)$alkyl, $(C_1-C_2)$alkoxy-$(C_1-C_4)$alkyl or $(C_1-C_4)$alkyl-carbonyl (Scheme 4) can be prepared from iodides of formula XVIII by Negishi, Sonogashira or Suzuki cross-coupling reactions following standard conditions such as those previously described for the synthesis of compounds of formula VIII. The possible subsequent reduction or hydration step can be carried out as previously described for the synthesis of compounds VIII.

Alternatively, compounds of formula XVI (Scheme 4) can be prepared from anilines of formula VIII wherein Y represents methoxycarbonyl by a similar two-step sequence (hydrazine formation and Fisher indole synthesis) using similar conditions such as those previously described for the synthesis of compounds of formula XVIII from compounds of formula XII.

Compounds of formula XV wherein $R^4$ represents fluoro, chloro, $(C_1-C_4)$alkyl, $(C_1-C_4)$alkoxy, $(C_1-C_4)$alkyl-carbonyl, $(C_1-C_2)$alkoxy-$(C_1-C_4)$alkyl or $(C_1-C_4)$alkoxy-$(C_2-C_4)$alkoxy (Scheme 4) can be prepared from compounds of formula XVI by desulfurization following standard conditions such as those previously described for the synthesis of compounds of formula IV.

Alternatively, compounds of formula XV wherein $R^4$ represents hydrogen can be prepared from compounds of formula XVIII by simultaneous deiodination and desulfurization following standard conditions such as those previously described for the synthesis of compounds of formula IV from compounds of formula XIII.

Carboxylic acid derivatives of formula IIb (Scheme 4) can be prepared by hydrolysis of methyl esters of formula XV following standard conditions such as those previously described for the synthesis of compounds of formula IIa.

Scheme 4: Synthesis of Carboxylic Acid Intermediates of Formula IIb wherein $R^5$ Represents $(C_1-C_4)$alkyl If not commercially available, aniline intermediates of formula XIV can be prepared according to procedures known in the art. Possible synthetic routes are outlined in Scheme 5 below.

Carboxylic acid derivatives of formula XX wherein $R^4$ represents hydrogen, $(C_1-C_4)$alkoxy, fluoro or chloro and $R^6$ represents fluoro, chloro or $(C_1-C_2)$fluoroalkyl can be prepared by oxidation of toluene derivatives of formula XIX wherein $R^4$ represents hydrogen, $(C_1-C_4)$alkoxy, fluoro or chloro and $R^6$ represents fluoro, chloro or $(C_1-C_2)$fluoroalkyl with a suitable oxidizing reagent such as $KMnO_4$ in the presence of water and a solvent such as pyridine at temperatures around 100° C. Toluene derivatives of formula XIX wherein $R^4$ represents $(C_1-C_4)$alkoxy can be prepared by treatment of phenols of formula XIX wherein $R^4$ represents hydroxy with a suitable base such as $Cs_2CO_3$ or $K_2CO_3$ and a suitable alkylating reagent such as $(C_1-C_4)$alkyl iodide or bromide in the presence of a suitable solvent such as DMF at temperatures around RT.

Alternatively, carboxylic acids derivatives of formula XX wherein $R^4$ represents hydrogen, $(C_1-C_4)$alkyl, $(C_1-C_4)$alkoxy, fluoro or chloro (Scheme 5) can be prepared by hydrolysis of nitriles of formula XXIII wherein $R^4$ represents hydrogen, $(C_1-C_4)$alkyl, $(C_1-C_4)$alkoxy, fluoro or chloro by treatment with a suitable base such as KOH or NaOH in the presence of water and a suitable organic solvent such as 2-propanol. An additional treatment with sodium nitrite in the presence of water and an acid such as

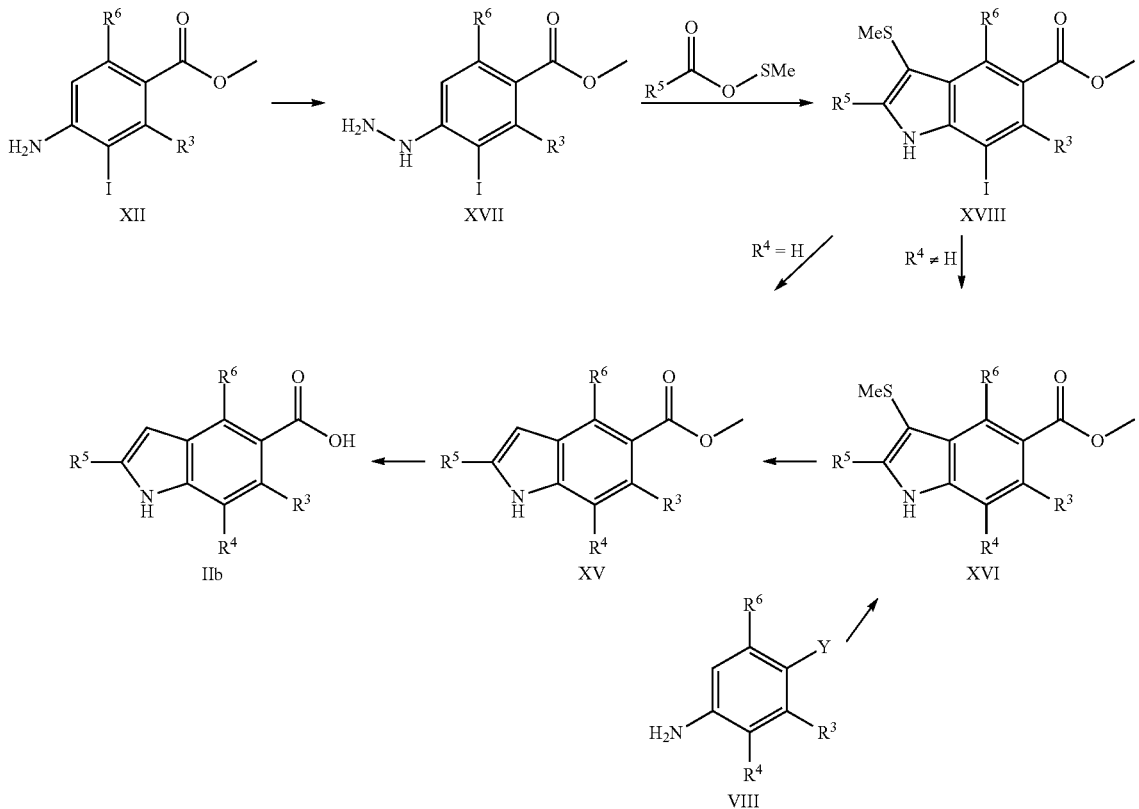

sulphuric acid at temperatures around 80° C. may be required for the hydrolysis of the primary amide intermediates. Nitriles of formula XXIII wherein $R^4$ represents hydrogen, $(C_1-C_4)$alkyl, $(C_1-C_4)$alkoxy, fluoro or chloro (Scheme 5) can be prepared by treatment of anilines of formula XXII wherein $R^4$ represents hydrogen, $(C_1-C_4)$alkyl, $(C_1-C_4)$alkoxy, fluoro or chloro with a suitable diazotisation reagent such as tert-butyl nitrite in the presence of a suitable cyanating reagent such as copper(I) cyanide in a suitable solvent such as $CH_3CN$ at temperatures between 0° C. and 80° C.

Alternatively, carboxylic acid derivatives of formula XX wherein $R^4$ represents $(C_1-C_4)$alkoxy (Scheme 5) can be prepared by nucleophilic aromatic substitution of fluorides of formula XX wherein $R^4$ represents fluoro with $(C_1-C_4)$-alcohol in the presence of a base such as $Cs_2CO_3$ and a suitable solvent such as DMF at temperatures between RT and 110° C.

Methyl esters of formula XXI wherein $R^N$ represents nitro (Scheme 5) can be prepared by treatment of carboxylic acids of formula XX with a suitable base such as $Cs_2CO_3$ or $K_2CO_3$ and a suitable alkylating reagent such as MeI in the presence of a suitable solvent such as DMF at temperatures around RT.

Alternatively, compounds of formula XXI wherein $R^N$ represents acetylamino and $R^6$ represents methyl or ethyl (Scheme 5) can be prepared from phenols of formula XXI wherein $R^N$ represents acetylamino and $R^6$ represents hydroxy following a two-step procedure: (i) triflate formation by treatment with trifluoromethanesulfonic anhydride in the presence of a base such as $Et_3N$ and a suitable solvent such as DCM at temperatures around RT and (ii) subsequent Suzuki type cross coupling with methyl- or ethyl-boronic acid in the presence of a suitable palladium catalyst such as $Pd(dppf)Cl_2.DCM$ and a base such as $K_3PO_4$ and heating in a suitable solvent such as THF at temperatures around 65° C.

Anilines of formula XIV wherein Y represents methoxycarbonyl (or VIII wherein $R^4$ represents $(C_1-C_4)$alkyl, $(C_1-C_4)$alkoxy, fluoro or chloro and Y represents methoxycarbonyl, respectively) (Scheme 5) can be prepared by reduction of nitrobenzene derivatives of formula XXI wherein $R^N$ represents nitro and $R^4$ represents hydrogen (or XXI wherein $R^N$ represents nitro and $R^4$ represents $(C_1-C_4)$ alkyl, $(C_1-C_4)$alkoxy, fluoro or chloro, respectively) with a suitable reducing reagent such as tin(II) chloride dihydrate in the presence of a suitable solvent such as DMF at temperatures around 100° C. or with zinc dust and ammonium formate in the presence of a suitable solvent such as MeOH at temperatures around RT.

Alternatively, anilines of formula XIV wherein Y represents methoxycarbonyl (or VIII wherein $R^4$ represents $(C_1-C_4)$alkyl, $(C_1-C_4)$alkoxy, fluoro or chloro and Y represents methoxycarbonyl, respectively) (Scheme 5) can be prepared by methanolysis of acetylated anilines of formula XXI wherein $R^N$ represents acetylamino and $R^4$ represents hydrogen (or XXI wherein $R^N$ represents acetylamino and $R^4$ represents $(C_1-C_4)$alkyl, $(C_1-C_4)$alkoxy, fluoro or chloro, respectively) with $K_2CO_3$ in the presence of MeOH at temperatures around RT.

Alternatively, anilines of formula XIV wherein $R^3$ represents hydrogen or chloro and Y represents cyano (or VIII wherein $R^4$ represents $(C_1-C_4)$alkyl, $(C_1-C_4)$alkoxy or chloro, $R^3$ represents hydrogen or chloro and Y represents cyano, respectively) (Scheme 5) can be prepared by palladium catalysed cyanation of bromides of formula XXXII wherein $R^3$ represents hydrogen or chloro and $R^4$ represents hydrogen, $(C_1-C_4)$alkyl, $(C_1-C_4)$alkoxy or chloro with zinc cyanide in the presence of a suitable palladium catalyst such as $Pd(PPh_3)_4$ and heating in a suitable solvent such as DMF at temperatures around 110° C.

Alternatively, anilines of formula XIV wherein Y represents methoxycarbonyl (or VIII wherein $R^4$ represents $(C_1-C_4)$alkyl, $(C_1-C_4)$alkoxy, fluoro or chloro and Y represents methoxycarbonyl, respectively) (Scheme 5) can be prepared by esterification of anilines of formula XIV wherein Y represents hydroxycarbonyl (or VIII wherein $R^4$ represents $(C_1-C_4)$alkyl, $(C_1-C_4)$alkoxy, fluoro or chloro and Y represents hydroxycarbonyl, respectively) by standard procedures as for example the treatment with acetylchloride in the presence of MeOH at temperatures around 65° C.

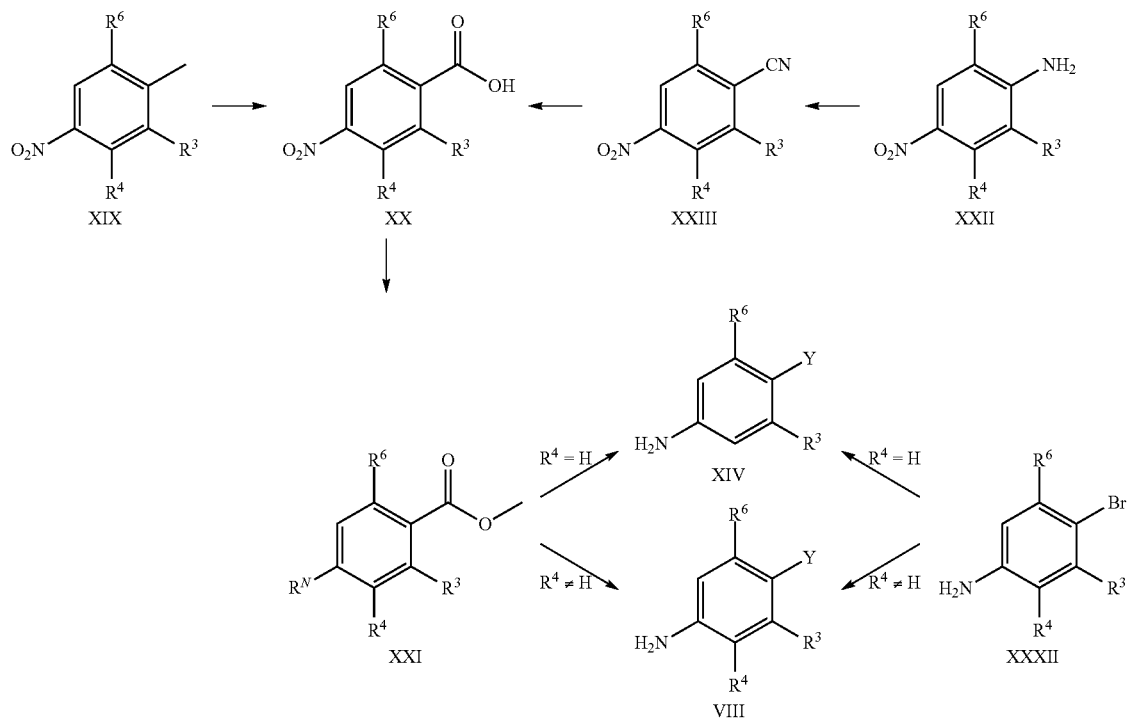

Scheme 5: Synthesis of Aniline Precursors XIV and VIII

If not commercially available, amine precursors of formula III can be prepared according to procedures described in WO2009/132000 or outlined in Scheme 6 below.

Amino nitriles of formula XXV wherein $NR^{11}R^{12}$ represents heterocyclyl which is unsubstituted, mono- or di-substituted, wherein the substituents are independently selected from $(C_1-C_4)$alkyl, $(C_1-C_4)$alkylcarbonyl, $(C_1-C_4)$alkoxycarbonyl, $(C_1-C_4)$alkylsulfonyl, and halogen; cycloalkylamino; cycloalkylmethylamino; N—$(C_1-C_4)$alkylamino; N,N-di-[$(C_1-C_4)$alkyl]-amino or N-arylmethyl-N—$(C_1-C_4)$alkyl-amino (Scheme 6) can be prepared by Strecker reaction between aldehydes of formula XXIV and amines of formula $R^{11}R^{12}NH$ in the presence of a suitable cyanating reagent such as TMSCN and a suitable Lewis acid catalyst such as $ZnI_2$ in a suitable mixture of solvents such as $Et_2O$/MeOH at temperatures between 0° C. and 80° C. The resulting nitriles of formula XXV can be transformed to diamines of formula IIIa (Scheme 6) by reduction under hydrogenation conditions in the presence of a suitable catalyst such as Raney nickel and a suitable solvent such as methanolic ammonia at temperatures around RT.

Nitroalkenes of formula XXVI (Scheme 6) can be prepared by Henry reaction between aldehydes of formula XXIV and nitromethane following a two step procedure: (i) treatment with a suitable base such as KOtBu in a suitable solvent such as tBuOH/THF at temperatures around 0° C. and (ii) treatment of the isolated β-nitro alcohol intermediates with a suitable dehydrating reagent such as acetyl anhydride in the presence of a base such as DMAP and in a suitable solvent such as DCM at temperatures around RT.

Ether derivatives of formula XXVII wherein $OR^{11}$ represents heterocyclyloxy; $(C_3-C_6)$cycloalkoxy or $(C_2-C_6)$alkoxy (Scheme 6) can be prepared by Michael addition of an alcohol of formula $R^{11}OH$ to a nitro alkene of formula XXVI in the presence of a suitable base such as NaH in a suitable solvent such as THF at temperatures between 0° C. and RT.

The obtained ether XXVII can be converted to amino ethers of formula IIIb (Scheme 6) by reduction of the nitro group under hydrogenation conditions in the presence of a suitable catalyst such as platinum dioxide and a suitable solvent such as EtOH at temperatures around RT.

If not commercially available, nitriles of formula XXIX (Scheme 6) can be prepared by a two step procedure: (i) arylation or heteroarylation of methylcyanoacetate by treatment with a bromoarene or bromoheteroarene of formula Br—$R^1$ in the presence of a suitable base such as KOtBu, a suitable palladium catalyst such as $Pd(OAc)_2$, a suitable ligand such as dppf in a suitable solvent such as dioxane as described in *J. Org. Chem.*, 2008, 73, 4, 1643-1645 and (ii) subsequent decarboxylation of the isolated methyl aryl- or heteroarylcyanoacetate intermediates by treatment with a suitable salt such as LiCl in a suitable mixture of solvents such as DMSO/water at temperatures around 140° C.

Alternatively, if not commercially available, nitriles of formula XXIX can be prepared according to *J. Am. Chem. Soc.*, 2011, 133, 6948-6951.

Cyano alkenes of formula XXX (Scheme 6) wherein $R^{11}$ and $R^{12}$, together with the carbon atom to which they are attached, represent heterocyclyl which is unsubstituted, mono- or di-substituted, wherein the substituents are independently selected from $(C_1-C_4)$alkyl, $(C_1-C_4)$alkylcarbonyl, $(C_1-C_4)$alkoxycarbonyl, $(C_1-C_4)$alkylsulfonyl, and halogen; $(C_3-C_6)$cycloalkyl which is unsubstituted or mono- or di-substituted with halogen or $(C_3-C_6)$alkyl can be prepared by Knoevenagel condensation of aryl- or heteroaryl-acetonitriles of formula XXIX with aldehydes or ketones of formula $R^{11}COR^{12}$ by treatment with a suitable base such as KOH or NaOMe in a suitable solvent such as MeOH at temperatures between 0° C. and 60° C.

The respective amines of formula IIIc (Scheme 6) can be prepared by reduction of cyano alkenes of formula XXX using a two step procedure: (i) hydrogenation in the presence of a suitable catalyst such as Pd/C followed by (ii) hydrogenation in the presence of a suitable catalyst such as Raney nickel, both steps being carried out in a suitable solvent such as methanolic ammonia at temperatures around RT.

Alternatively, amines of formula IIIc can be prepared by reduction of cyano alkenes of formula XXX in the presence of a suitable reducing reagent such as $BH_3$ THF complex in a suitable solvent such as THF at temperatures around 60° C.

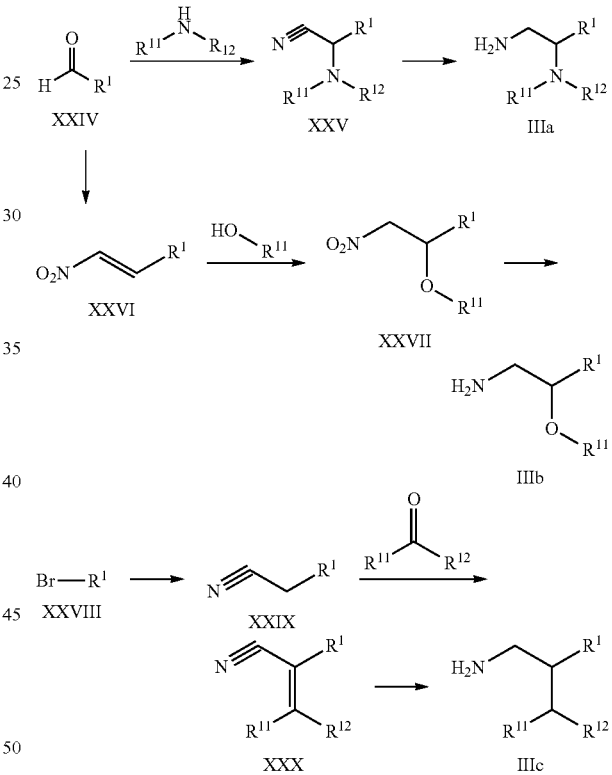

Scheme 6: Synthesis of Amine Intermediates of Formula III

EXPERIMENTAL PART

Abbreviations (as Used herein and in the Description above)
Ac acetyl
anh anhydrous
aq. Aqueous
ATP adenosine-5'-triphoshate
Boc tert-butoxycarbonyl
tBu tert-butyl
CC column chromatography
cDNA complementary desoxyribonucleic acid
CNS central nervous system DCM dichloromethane
DEA diethylamine
DIPEA diisopropylethylamine
DMAP 4-(dimethylamino)pyridine
DMEM dulbecco's modified eagle's medium
DMF dimethylformamide
DMSO dimethylsulfoxide
DNA desoxyribonucleic acid
dppf 1,1'-bis(diphenylphosphino)ferrocene
EDC.HCl N-(3-dimethylaminopropyl)-N'-ethylcarbodiimide hydrochloride
eq equivalent
Et ethyl
FCS fetal calf serum
FLIPR fluorescent imaging plate reader
h hour(s)
HATU 2-(7-aza-1H-benzotriazole-1-yl)-1,1,3,3-tetramethyluronium hexafluorophosphate
Hept heptanes
HOBT 1-hydroxybenzotriazole hydrate
HV high vacuum
LC-MS liquid chromatography-mass spectrometry
M molar(ity)
Me methyl
min minute(s)
MS mass spectrometry
NCS N-chlorosuccinimide
NMR nuclear magnetic resonance
ON overnight
PBS phosphate buffered saline
PEPPSI™-IPr [1,3-bis(2,6-Diisopropylphenyl)imidazol-2-ylidene](3-chloropyridyl)palladium(II) dichloride
PG protecting group
Ph phenyl
PyBOP benzotriazole-1-yl-oxy-tris-pyrrolidino-phosphonium hexafluorophosphate
RNA ribonucleic acid
RT room temperature
sat. saturated
TBTU O-(benzotriazol-1-yl)-N,N,N',N'-tetramethyluronium tetrafluoroborate
TFA trifluoroacetic acid
THF tetrahydrofuran
TMS trimethylsilyl
$t_R$ retention time
UV ultra-violet
Vis visible A. Characterization Methods Used NMR: Brucker Avance 400, 400 MHz; chemical shifts are given in ppm relative to the solvent used; multiplicities: s=singlet, d=doublet, t=triplet, q=quadruplet, m=multiplet, br=broad, coupling constants are given in Hz.

LC-MS (I): Thermo Finnigan MSQ Surveyor MS with Agilent 1100 Binary Pump and DAD. Eluents (acidic conditions): A: $H_2O$+0.04% TFA; B: $CH_3CN$; gradient: 5% B→95% B; runtime: 1.5 min; flow: 4.5 mL/min; detection: UV/Vis+MS, $t_R$ is given in min.

LC-MS (A): column Zorbax SB-AQ, 3.5 μm, 4.6×50 mm
LC-MS (B): column Waters XBridge C18, 2.5 μm, 4.6×30 mm
LC-MS (C): column Waters Atlantis T3, 5 μm, 4.6×30 mm;

Eluents (basic conditions): A: $H_2O$+13 mmol/L $NH_4OH$; B: $CH_3CN$; gradient: 5% B→95% B; runtime: 1.5 min; flow: 4.5 mL/min:

LC-MS (D): column Waters XBridge C18, 5 μm, 4.6×50 mm.
LC-MS (D*): column Zorbax Extend C18, 5 μm, 4.6×50 mm.

LC-MS (II): Dionex Ultimate 3000 with Thermo MSQ MS, HPG-3000 pump and photodiode array detector
Eluents (basic conditions): A: $H_2O$+0.05% $NH_4OH$+2% $CH_3CN$; B: $CH_3CN$; gradient: 5% B→95% B; runtime: 2.0 min; flow: 1.8 mL/min; detection: UV/Vis+MS, $t_R$ is given in min.

LC-MS (E): column Ascentis Express C18, 2.7 μm, 2.1×50 mm
LC-MS (F): similar to E except that runtime is 1.1 min
Eluents (acidic conditions): A: $H_2O$+0.05% HCOOH; B: $CH_3CN$+0.05% HCOOH; gradient: 5% B→95% B; runtime: 2.0 min; flow: 1.4 mL/min; detection: UV/Vis+MS, $t_R$ is given in min.

LC-MS (G): column Ascentis Express C18, 2.7 μm, 2.1×50 mm

B. Purification Methods Used

Preparative LC-MS (A): flow: 75 mL/min. Detection: UV/Vis and/or MS.

Additional information for the purification are summerized in the tables below using following explanations:

XBridge: column Waters XBridge C18, 10 μm, 30×75 mm
Atlantis: column Waters Atlantis T3, 10 μm, 30×75 mm
Acidic: eluant: A=$H_2O$ with 0.5% HCOOH, B=$CH_3CN$
Basic: eluant: A=$H_2O$ with 0.125% $NH_4OH$, B=$CH_3CN$
Lipophilic gradient: 30% B→95% B over 4 min then 95% B over 2 min
Normal gradient: 20% B→95% B over 4 min then 95% B over 2 min
Polar gradient: 10% B→95% B over 4 min then 95% B over 2 min
Very polar gradient: 5% B→50% B over 3 min then 50% B→95% B over 1 min and finally 95% B over 2 min

|  | XBridge | | Atlantis |
|---|---|---|---|
|  | acidic | basic | acidic |
| Lipophilic gradient | Method II | | |
| Normal gradient | Method VII | Method IV | Method I |
| Polar gradient | Method VI | Method V | Method VIII |
| Very polar gradient | Method III | | Method IX |

Preparative LC-MS (B): flow: mL/min. Detection: UV/Vis and/or MS.

XBridge: column Waters XBridge C18 OBD™, 5 μm, 19×50 mm
Acidic: eluant: A=$H_2O$ with 0.1% HCOOH, B=$CH_3CN$ with 0.1% HCOOH
Basic: eluant: A=$H_2O$ with 0.1% $NH_4OH$, B=$CH_3CN$ with 0.1% $NH_4OH$
Normal gradient: 25% B over 0.2 min, 25%→35% B over 0.1 min, 35%→65% B over 2.9 min, 65%→95% B over 0.1 min and finally 95% B over 1 min
Polar gradient: 10% B over 0.2 min, 10%→20% B over 0.1 min, 20%→50% B over 2.9 min, 50%→95% B over 0.1 min and finally 95% B over 1 min
Very polar gradient: 5% B over 0.3 min, 5%→35% B over 2.9 min, 35%→95% B over 0.1 min and finally 95% B over 1 min.

|  | acidic | basic |
|---|---|---|
| Normal gradient | | Method 5 |
| Polar gradient | Method 2 | Method 4 |
| Very polar gradient | Method 1 | Method 3 |

Column chromatography (CC) was performed using silica gel 60 Merck (0.063-0.200 mm) or using prepacked cartridges (SNAP KP-SIL™, SNAP KP-NH™, Isolute™ Silica II, Isolute™ NH₂ or Isolute™ C¹⁸) from Biotage. Additional information for the purification are summarized in the table below:

|  | SNAP KP-SIL ™ | Isolute ™ Silica II | SNAP KP-NH ™ |
|---|---|---|---|
| Hept/EtOAc | Method b | Method c |  |
| EtOAc/MeOH | Method e | Method g | Method f |
| DCM/MeOH | Method i | Method d | Method a |
| Hept/EtOAc/MeOH | Method h |  |  |

The following examples illustrate the invention but do not at all limit the scope thereof.

PREPARATION OF PRECURSORS AND INTERMEDIATES

A. Synthesis of Carboxylic Acids

A.1. Synthesis of 4-chloro-1H-indole-5-carboxylic acid

A.1.a. Methyl 4-amino-2-chlorobenzoate

To a solution of 4-amino-2-chlorobenzoic acid (54.2 mmol) in MeOH (325 mL) was added dropwise acetylchloride (163 mmol) and the mixture was refluxed for 5 h. It was concentrated in vacuo and partitioned between EtOAc and a sat. solution of NaHCO₃. The organic phase was washed with a sat. solution of NaHCO₃, dried over MgSO₄ and concentrated in vacuo to give the title compound as beige solid.

LC-MS (B): $t_R$=0.57 min; [M+CH₃CN+H]+: 227.30

A.1.b. Mixture of methyl 4-amino-2-chloro-3-iodobenzoate and methyl 4-amino-2-chloro-5-iodobenzoate To a suspension of methyl 4-amino-2-chlorobenzoate (55.8 mmol) in EtOH (558 mL) was added iodine (58.6 mmol) and silver sulfate (55.8 mmol). The mixture was stirred for 15 min, filtered and the filtrate was concentrated in vacuo. The residue was partitioned between DCM and a 1M aq. solution of NaOH. The organic phase was washed with a 1M aq. solution of NaOH, dried over MgSO₄ and concentrated in vacuo. The crude was purified by CC (SNAP KP-SIL™ from Biotage) using Hept/EtOAc/MeOH from 89/11/1 to 81/19/1 to give the mixture of regioisomers as salmon solid. The mixture was enriched from 59 to 66% in methyl 4-amino-2-chloro-3-iodobenzoate by recrystallisation in Hept/EtOAc 75/25, separation of the solid methyl 4-amino-2-chloro-5-iodobenzoate by filtration and evaporation of the mother liquid.

LC-MS (B): $t_R$=0.72 min; [M+CH₃CN+H]+: 352.79

In addition, pure methyl 4-amino-2-chloro-5-iodobenzoate regioisomer was isolated as pink to orange solid.

LC-MS (B): $t_R$=0.75 min; [M+CH₃CN+H]+: 352.80

A.1.c. Methyl 4-amino-2-chloro-3-((trimethylsilyl)ethynyl)benzoate

A solution of mixture of methyl 4-amino-2-chloro-3-iodobenzoate and methyl 4-amino-2-chloro-5-iodobenzoate from previous step (13.3 mmol) in Et₃N (110 mL) and toluene (110 mL) was heated to 60° C. under argon and treated with PPh₃ (1.33 mmol), CuI (1.33 mmol), Pd(PPh₃)₂Cl₂ (0.66 mmol) and trimethylsilylacetylene (19.9 mmol). The mixture was stirred for 30 min at 60° C. and 1 h at 70° C., quenched with a 10% aq. solution of NH₄Cl and extracted with EtOAc. The organic phase was washed with brine, dried over MgSO4 and concentrated in vacuo. The crude was purified by CC (SNAP KP-SIL™ from Biotage) using Hept/EtOAc from 1/0 to 8/2 to give the title compound (second eluting product) as light yellow solid.

LC-MS (B): $t_R$=0.93 min; [M+CH₃CN+H]+: 322.70

In addition, methyl 4-amino-2-chloro-5-((trimethylsilyl)ethynyl)benzoate was isolated as orange solid (first eluting product).

LC-MS (B): $t_R$=0.97 min; [M+CH₃CN+H]+: 323.22

A.1.d. Methyl 4-amino-2-chloro-3-ethynylbenzoate

To a solution of methyl 4-amino-2-chloro-3-((trimethylsilyl)ethynyl)benzoate (8.81 mmol) in MeOH (8.81 mL) was added K₂CO₃ (9.69 mmol). The mixture was stirred for 15 min and the solvent was evaporated off. The residue was partitioned between DCM and water. The organic phase was dried over MgSO₄ and concentrated in vacuo. The crude was purified by CC (Isolute™ Silica II from Biotage) using DCM to give the title compound as yellowish solid.

LC-MS (B): $t_R$=0.66 min; [M+H]+: 210.04

A.1.e. Methyl 4-chloro-1H-indole-5-carboxylate

To a mixture of methyl 4-amino-2-chloro-3-ethynylbenzoate (5.57 mmol), chloro(1,5-cyclooctadiene)rhodium(I) dimer (0.28 mmol) and tris(4-fluorophenyl)phosphine (3.34 mmol) was added under argon degassed DMF (28 mL). The mixture was heated to 85° C. for 50 min, cooled to RT and partitioned between Et₂O and water. The organic phase was washed with brine, dried over MgSO₄ and concentrated in vacuo. The crude was purified by CC (SNAP KP-SIL™ from Biotage) using Hept/DCM 1/0 to 0/1 to give the title compound as brownish solid.

LC-MS (B): $t_R$=0.69 min; [M+H]+: 210.14

A.1.f. 4-Chloro-1H-indole-5-carboxylic acid (Saponification I)

To a suspension of methyl 4-chloro-1H-indole-5-carboxylate (4 mmol) in MeOH (24 mL) was added a 2M aq. solution of LiOH (4 mL). The mixture was stirred for 5 h at 65° C. then ON at 45° C. It was evaporated off and partitioned between EtOAc and H₂O. The aq. phase was acidified with a 25% solution of HCl and extracted 3 times with DCM. The combined organic phases were dried over MgSO₄ and concentrated in vacuo to give the title compound as off-white solid.

LC-MS (A): $t_R$=0.65 min; [M+H]+: 196.06

A.2. Synthesis of 4-chloro-7-methyl-1H-indole-5-carboxylic acid

A.2.a. Methyl 4-chloro-7-iodo-3-(methylthio)-1H-indole-5-carboxylate (Gassman Indole)

To a suspension of methyl 4-amino-2-chloro-5-iodobenzoate (6.21 mmol) in anh. DCM (29 mL) was added at −60° C. NCS (7.45 mmol) and the mixture was stirred for 10 min. A solution of (methylthio)acetaldehyde dimethyl acetal (7.45 mmol) in anh. DCM (5.8 mL) was added at −60° C. and the mixture was stirred allowing temperature to reach −30° C. A solution of Et₃N (7.45 mmol) in anh. DCM (5 mL) was added at −30° C. and the mixture was stirred allowing temperature to reach RT. It was concentrated in vacuo, PhCl (17.4 mL) and Et₃N (20.5 mmol) were added and the mixture was heated to 125° C. and stirred for 2 h. The volatiles were evaporated off and the residue was taken up in Et₂O (28.7 mL) and treated with a 4M solution of HCl in dioxane (11 mL) for 30 min. It was partitioned between EtOAc and a sat. solution of NaHCO₃, the organic phase was dried over MgSO₄ and concentrated in vacuo. The crude was purified by CC (SNAP KP-SIL™ from Biotage) using Hept/EtOAc from 9/1 to 65/35 to give the title compound as yellow solid.

LC-MS (A): $t_R$=0.93 min; [M+H]+: 381.71

A.2.b. Methyl 4-chloro-7-meth yl-3-(methylthio)-1H-indole-5-carboxylate

To a solution of methyl 4-chloro-7-iodo-3-(methylthio)-1H-indole-5-carboxylate (0.42 mmol) in dioxane (1 mL) was added under argon a 2M solution of methylzinc chloride in THF (1.04 mmol) and a solution of Pd(dppf)Cl₂.DCM (0.03 mmol) in dioxane (0.5 mL). The mixture was stirred ON at 65° C. in a sealed vial, diluted with EtOAc and washed with a sat. solution of Rochelle salt and brine. The organic phase was dried over MgSO₄ and concentrated in vacuo. The crude was purified by CC (SNAP KP-SIL™ from Biotage) using DCM to give the title compound as yellow solid.

LC-MS (A): $t_R$=0.86 min; [M+H]+: 270.11

A.2.c. Methyl 4-chloro-7-methyl-1H-indole-5-carboxylate

To a solution of methyl 4-chloro-7-methyl-3-(methylthio)-1H-indole-5-carboxylate (0.24 mmol) in EtOH (4.11 mL) was added Actimet M Raney Nickel (14 mg). The mixture was stirred for 2 h at RT and filtered over a pad of celite. The filtrate was concentrated in vacuo to give the title compound as white solid.

LC-MS (A): $t_R$=0.82 min; [M+H]+: 224.16

A.2.d. 4-Chloro-7-methyl-1H-indole-5-carboxylic acid (Saponification II)

To a solution of methyl 4-chloro-7-methyl-1H-indole-5-carboxylate (0.11 mmol) in MeOH (0.4 mL), THF (0.4 mL) and H₂O (0.4 mL) was added LiOH.H₂O (0.44 mmol). The mixture was stirred for 2 h at 60° C. It was evaporated off and partitioned between EtOAc and H₂O. The aq. phase was acidified with a 25% solution of HCl and extracted 3 times with EtOAc. The combined organic phases were dried over MgSO₄ and concentrated in vacuo to give the title compound as pink solid.

LC-MS (A): $t_R$=0.69 min; [M+H]+: 209.98

A.3. Synthesis of 4-chloro-2-methyl-1H-indole-5-carboxylic acid

A.3.a. Methyl 2-chloro-4-hydrazinyl-5-iodobenzoate

To a solution of methyl 4-amino-2-chloro-5-iodobenzoate (6.42 mmol) in 37% HCl (4.40 mL) was added dropwise at 0° C. a solution of sodium nitrite (7.49 mmol) in water (2.15 mL). The mixture was stirred for 15 min at 0° C. and a solution of tin(II) chloride dihydrate (16 mmol) in water (1 mL) and 37% HCl (4.28 mL) was added dropwise at 0° C. The mixture was stirred for 15 min and quenched with consecutive addition of water, a 10% solution of Na₂CO₃ and a 20% solution of NaOH. It was extracted 3 times with DCM, the combined organic phases were dried over MgSO₄ and concentrated in vacuo. The crude was purified by CC (SNAP KP-SIL™ from Biotage) using Hept/EtOAc from 95/5 to 62/38 to give the title compound as beige solid.

LC-MS (A): $t_R$=0.73 min; [M+CH₃CN+H]+: 367.75

A.3.b. Methyl 4-chloro-7-iodo-2-methyl-3-(methylthio)-1H-indole-5-carboxylate To a solution of methyl 2-chloro-4-hydrazinyl-5-iodobenzoate (0.76 mmol) in a 1.25 M solution of HCl in EtOH (1.8 mL) was added 1-methylthio-2-propanone (1.38 mmol). The mixture was stirred for 2 h at 65° C. and filtered. The filtrate was concentrated in vacuo and the crude was purified by preparative LC-MS using method I.

LC-MS (A): $t_R$=0.96 min; [M+H]+: 395.73

A.3.c. Methyl 4-chloro-2-methyl-1H-indole-5-carboxylate

This compound was prepared using a method analogous to that of methyl 4-chloro-7-methyl-1H-indole-5-carboxylate, methyl 4-chloro-7-iodo-2-methyl-3-(methylthio)-1H-indole-5-carboxylate replacing 4-chloro-7-methyl-3-(methylthio)-1H-indole-5-carboxylate except that the reaction mixture was stirred for 48 h at RT and further additions of Actimet M Raney Nickel was required until completion of the reaction.

LC-MS (A): $t_R$=0.83 min; [M+H]+: 224.10

A.3.d. 4-Chloro-2-methyl-1H-indole-5-carboxylic acid

This compound was prepared using a method analogous to that of 4-chloro-1H-indole-5-carboxylic acid, methyl 4-chloro-2-methyl-1H-indole-5-carboxylate replacing methyl 4-chloro-1H-indole-5-carboxylate.

LC-MS (A): $t_R$=0.69 min; [M+H]+: 210.04

A.4. Synthesis of 4,6-dichloro-1H-indole-5-carboxylic acid

A.4.a. 2,6-Dichloro-4-nitrobenzoic acid

A solution of 1,3-dichloro-2-methyl-5-nitrobenzene (4.85 mmol) in pyridine (5 mL) and water (10 mL) was heated to 90° C. and KMnO₄ (29.1 mmol) was added portionwise. The mixture was refluxed for 2 h and stirred ON at RT. It was heated to 90° C., additional amount of KMnO₄ (12.7 mmol) was added and it was refluxed for 7 h. The mixture was filtered, the filtrate was basified with a 1M solution of NaOH until pH 12-13 and washed with EtOAc. The aq. phase was acidified with a 1M solution of HCl until pH 1-2 and extracted 3 times with EtOAc. The combined organic phases were dried over MgSO₄ and concentrated in vacuo to give the crude acid as orange solid.

LC-MS (A): $t_R$=0.45 min
LC-MS (D*): $t_R$=0.17 min; [M−H]−: 234.01

A.4.b. Methyl 2,6-dichloro-4-nitrobenzoate

To a solution of 2,6-dichloro-4-nitrobenzoic acid (1.63 mmol) in DMF (5 mL) was added cesium carbonate (2.44 mmol). The suspension was stirred for 30 min at RT and MeI (1.63 mmol) was added. The mixture was stirred for 2 h, quenched with water and extracted 3 times with EtOAc. The combined organic phases were dried and concentrated in vacuo to give the title compound as yellow solid.

LC-MS (A): $t_R$=0.88 min $^1$H NMR ((CD$_3$)$_2$SO) δ: 8.48 (s, 2 H), 3.99 (s, 3 H)

A.4.c. Methyl 4-amino-2,6-dichlorobenzoate

To a solution of methyl 2,6-dichloro-4-nitrobenzoate (1.44 mmol) in DMF (2 mL) was added tin(II) chloride dihydrate (5.04 mmol). The mixture was stirred at 100° C. for 40 min under microwave condition and quenched with water. It was basified with a 1M solution of NaOH until pH 11-12 and extracted 3 times with EtOAc. The combined organic phases were washed with brine, dried over MgSO$_4$ and concentrated in vacuo. The crude was purified by CC (SNAP KP-NH™ from Biotage) using Hept/EtOAc from 1/0 to 1/1 to give the title compound as yellow solid.

LC-MS (A): $t_R$=0.78 min; [M+H]+: 220.07

A.4.d. Methyl 4-amino-2,6-dichloro-3-iodobenzoate

This compound was prepared using a method analogous to that of the mixture of methyl 4-amino-2-chloro-3-iodobenzoate and methyl 4-amino-2-chloro-5-iodobenzoate, methyl 4-amino-2,6-dichlorobenzoate replacing methyl 4-amino-2-chlorobenzoate except that no purification was done.

LC-MS (A): $t_R$=0.86 min; [M+CH$_3$CN+H]+: 386.57

A.4.e. Methyl 4-amino-2,6-dichloro-3-((trimethylsilyl)ethynyl)benzoate

This compound was prepared using a method analogous to that of methyl 4-amino-2-chloro-3-((trimethylsilyl)ethynyl)benzoate, methyl 4-amino-2,6-dichloro-3-iodobenzoate replacing the mixture of methyl 4-amino-2-chloro-3-iodobenzoate and methyl 4-amino-2-chloro-5-iodobenzoate.

LC-MS (A): $t_R$=1.00 min; [M+H]+: 316.07

A.4.f. Methyl 4-amino-2,6-dichloro-3-ethynylbenzoate

This compound was prepared using a method analogous to that of methyl 4-amino-2-chloro-3-ethynylbenzoate, methyl 4-amino-2,6-dichloro-3-((trimethylsilyl)ethynyl)benzoate replacing methyl 4-amino-2-chloro-3-((trimethylsilyl)ethynyl)benzoate.

LC-MS (A): $t_R$=0.83 min; [M+H]+: 243.91

A.4.g. Methyl 4,6-dichloro-1H-indole-5-carboxylate

This compound was prepared using a method analogous to that of methyl 4-chloro-1H-indole-5-carboxylate, methyl 4-amino-2,6-dichloro-3-ethynylbenzoate replacing methyl 4-amino-2-chloro-3-ethynylbenzoate.

LC-MS (A): $t_R$=0.84 min $^1$H NMR ((CD$_3$)$_2$SO) δ: 11.79 (s, 1 H), 7.62 (dd, J$_1$=2.9 Hz, J$_2$=2.5 Hz, 1 H), 7.59 (d, J=0.9 Hz, 1 H), 6.58 (m, 1 H), 3.91 (s, 3 H)

A.4.h. 4,6-Dichloro-1H-indole-5-carboxylic acid

This compound was prepared using a method analogous to that of 4-chloro-7-methyl-1H-indole-5-carboxylic acid, methyl 4,6-dichloro-1H-indole-5-carboxylate replacing methyl 4-chloro-7-methyl-1H-indole-5-carboxylate.

LC-MS (A): $t_R$=0.68 min

LC-MS (D*): $t_R$=0.15 min; [M–H]–: 228.06

A.5. Synthesis of 4-chloro-7-isobutyl-1H-indole-5-carboxylic acid

A.5.a. Methyl 4-amino-2-chloro-5-isobutylbenzoate

To a solution of methyl 4-amino-2-chloro-5-iodobenzoate (3.36 mmol) in toluene/water 20/1 (40 mL) was added under argon K$_3$PO$_4$ (11.8 mmol), PdCl$_2$(PPh$_3$)$_2$ (0.34 mmol) and (2-methylpropyl)boronic acid (6.72 mmol). The mixture was heated ON at 110° C. in a sealed vial, quenched with water and extracted with EtOAc. The organic phase was washed with brine, dried over MgSO4 and concentrated in vacuo. The crude was purified by CC (SNAP KP-Sil™ from Biotage) using Hept/EtOAc from 1/0 to 0/1 to give the title compound as yellow oil.

LC-MS (A): $t_R$=0.90 min; [M+CH$_3$CN+H]+: 283.06

A.5.b. Methyl 4-amino-2-chloro-3-iodo-5-isobutylbenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-isobutylbenzoate replacing methyl 4-amino-2-chlorobenzoate.

LC-MS (A): $t_R$=0.97 min; [M+CH$_3$CN+H]+: 408.77

A.5.c. Methyl 4-amino-2-chloro-5-isobutyl-3-((trimethylsilyl)ethynyl)benzoate This compound was prepared using a method analogous to that of methyl 4-amino-2-chloro-3-((trimethylsilyl)ethynyl)benzoate, methyl 4-amino-2-chloro-3-iodo-5-isobutylbenzoate replacing the mixture of methyl 4-amino-2-chloro-3-iodobenzoate and methyl 4-amino-2-chloro-5-iodobenzoate.

LC-MS (A): $t_R$=1.07 min; [M+H]+: 337.90

A.5.d. Methyl 4-amino-2-chloro-3-ethynyl-5-isobutylbenzoate

This compound was prepared using a method analogous to that of methyl 4-amino-2-chloro-3-ethynylbenzoate, methyl 4-amino-2-chloro-5-isobutyl-3-((trimethylsilyl)ethynyl)benzoate replacing methyl 4-amino-2-chloro-3-((trimethylsilyl)ethynyl)benzoate.

LC-MS (A): $t_R$=0.94 min; [M+H]+: 266.07

A.5.e. Methyl 4-chloro-7-isobutyl-1H-indole-5-carboxylate

This compound was prepared using a method analogous to that of methyl 4-chloro-1H-indole-5-carboxylate, methyl 4-amino-2-chloro-3-ethynyl-5-isobutylbenzoate replacing methyl 4-amino-2-chloro-3-ethynylbenzoate.

LC-MS (A): $t_R$=0.94 min; [M+H]+: 266.16

A.5.f. 4-Chloro-7-isobutyl-1H-indole-5-carboxylic acid

This compound was prepared using a method analogous to that of 4-chloro-7-methyl-1H-indole-5-carboxylic acid, methyl 4-chloro-7-isobutyl-1H-indole-5-carboxylate replacing methyl 4-chloro-7-methyl-1H-indole-5-carboxylate.

LC-MS (A): $t_R$=0.82 min, [M+H]+: 252.06

A.6. Synthesis of 4-chloro-7-(3-methoxypropyl)-1H-indole-5-carboxylic acid

A.6.a. Methyl 4-amino-2-chloro-5-(3-methoxyprop-1-yn-1-yl)benzoate

To a mixture of methyl 4-amino-2-chloro-5-iodobenzoate (3.51 mmol), Pd(PPh$_3$)$_2$Cl$_2$ (0.18 mmol) and CuI (0.18 mmol) was sequentially added under argon THF (12 mL), Et$_3$N (14 mmol) and methyl propargyl ether (14 mmol). The mixture was stirred for 1 h at RT, diluted with EtOAc and filtered. The filtrate was concentrated in vacuo and the crude was purified by CC (SNAP KP-Sil™ from Biotage) using Hept/EtOAc from 85/15 to 40/60 to give the title compound as orange solid.

LC-MS (A): $t_R$=0.82 min, [M+H]+: 253.99

A.6.b. Methyl 4-amino-2-chloro-5-(3-methoxypropyyl)benzoate

To a solution of methyl 4-amino-2-chloro-5-(3-methoxyprop-1-yn-1-yl)benzoate (3.48 mmol) in EtOH (14 mL) was added PtO$_2$ (0.35 mmol). The mixture was stirred under a hydrogen atmosphere for 2 h. It was filtered over Celite, washed with EtOH and concentrated in vacuo. The crude was purified by CC (SNAP KP-Sil™ from Biotage) using Hept/EtOAc from 1/0 to 8/2 to give the title compound as yellow oil.

LC-MS (A): $t_R$=0.80 min, [M+H]+: 257.90

A.6.c. Methyl 4-amino-2-chloro-3-iodo-5-(3-methoxypropyl)benzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-(3-methoxypropyl)benzoate replacing methyl 4-amino-2-chlorobenzoate.

LC-MS (A): $t_R$=0.90 min; [M+H]+: 383.91

A.6.d. Methyl 4-amino-2-chloro-5-(3-methoxypropyl)-3-((trimethylsilyl)ethynyl)benzoate This compound was prepared using a method analogous to that of methyl 4-amino-2-chloro-3-((trimethylsilyl)ethynyl)benzoate, methyl 4-amino-2-chloro-3-iodo-5-(3-methoxypropyl)benzoate replacing the mixture of methyl 4-amino-2-chloro-3-iodobenzoate and methyl 4-amino-2-chloro-5-iodobenzoate.

LC-MS (A): $t_R$=1.00 min; [M+H]+: 353.85

A.6.e. Methyl 4-amino-2-chloro-3-ethynyl-5-(3-methoxypropyl)benzoate

This compound was prepared using a method analogous to that of methyl 4-amino-2-chloro-3-ethynylbenzoate, methyl 4-amino-2-chloro-5-(3-methoxypropyl)-3-((trimethylsilyl)ethynyl)benzoate replacing methyl 4-amino-2-chloro-3-((trimethylsilyl)ethynyl)benzoate.

LC-MS (A): $t_R$=0.85 min; [M+H]+: 281.83

A.6.f. Methyl 4-chloro-7-(3-methoxypropyl)-1H-indole-5-carboxylate

This compound was prepared using a method analogous to that of methyl 4-chloro-1H-indole-5-carboxylate, methyl 4-amino-2-chloro-3-ethynyl-5-(3-methoxypropyl)benzoate replacing methyl 4-amino-2-chloro-3-ethynylbenzoate.

LC-MS (A): $t_R$=0.86 min; [M+H]+: 282.07

A.6.g. 4-Chloro-7-(3-methoxypropyl)-1H-indole-5-carboxylic acid

This compound was prepared using a method analogous to that of 4-chloro-7-methyl-1H-indole-5-carboxylic acid, methyl 4-chloro-7-(3-methoxypropyl)-1H-indole-5-carboxylate replacing methyl 4-chloro-7-methyl-1H-indole-5-carboxylate.

LC-MS (A): $t_R$=0.72 min, [M+H]+: 268.07

A.7. Synthesis of 4-methyl-1H-indole-5-carboxylic acid

A.7.a. Methyl 4-methyl-1H-indole-5-carboxylate

Methyl 4-chloro-1H-indole-5-carboxylate (0.48 mmol), K$_2$CO$_3$ (1.91 mmol) and PEPPSI™-IPr (0.05 mmol) were placed in a pressure vessel and anh. dioxane (2 mL) and trimethylboroxine (0.23 mL) were added sequentially. The tube was sealed under argon and heated at 115° C. After 17 h, the reaction mixture was cooled to RT, filtered over a pad of Celite and the cake was washed with EtOAc. The filtrate was concentrated in vacuo and the crude was purified by CC (SNAP KP-Sil™ from Biotage) using Hept/EtOAc from 96/4 to 50/50 to give the title compound as white solid.

LC-MS (A): $t_R$=0.78 min, [M+H]+: 190.10

A.7.b. 4-Methyl-1H-indole-5-carboxylic acid

This compound was prepared using a method analogous to that of 4-chloro-7-methyl-1H-indole-5-carboxylic acid, methyl 4-methyl-1H-indole-5-carboxylate replacing methyl 4-chloro-7-methyl-1H-indole-5-carboxylate except that the reaction mixture was stirred for 16 h at 60° C.

LC-MS (A): $t_R$=0.64 min

LC-MS (D*): $t_R$=0.15 min, [M−H]−: 173.91

A.8. Synthesis of 4-ethyl-1H-indole-5-carboxylic acid

A.8.a. Methyl 4-vinyl-1H-indole-5-carboxylate

This compound was prepared using a method analogous to that of methyl 4-methyl-1H-indole-5-carboxylate, vinylboronic acid pinacol ester replacing trimethylboroxine.

LC-MS (A): $t_R$=0.80 min, [M+H]+: 202.20

A.8.b. Methyl 4-ethyl-1H-indole-5-carboxylate

To a solution of methyl 4-vinyl-1H-indole-5-carboxylate (0.21 mmol) in EtOH (2 mL) was added platinum dioxide (0.021 mmol). The mixture was stirred under a hydrogen atmosphere for 2 h, filtered over Celite and concentrated in vacuo to give the title compound as pinkish solid.

LC-MS (A): $t_R$=0.83 min, [M+H]+: 204.18

A.8.c. 4-Ethyl-1H-indole-5-carboxylic acid

This compound was prepared using a method analogous to that of 4-chloro-7-methyl-1H-indole-5-carboxylic acid, methyl 4-methyl-1H-indole-5-carboxylate replacing methyl 4-chloro-7-methyl-1H-indole-5-carboxylate.

LC-MS (A): $t_R$=0.70 min, [M+CH$_3$CN+H]+: 231.08

A.9. Synthesis of 4-chloro-7-acetyl-1H-indole-5-carboxylic acid

A.9.a. Methyl 4-amino-2-chloro-3,5-diiodobenzoate

To a suspension of methyl 4-amino-2-chlorobenzoate (10.8 mmol) in EtOH (100 mL) was added iodine (23.7 mmol) and silver sulfate (10.8 mmol) under argon. The mixture was stirred for 2 h, filtered and the filtrate was treated with a 10% aq. solution of sodium thiosulfate. After evaporation of EtOH, the residue was partitioned between EtOAc and a 1M aq. solution of NaOH. The organic phase was washed with a 1M aq. solution of NaOH and brine, dried over MgSO$_4$ and concentrated in vacuo. The crude was purified by CC using DCM and the solid was triturated in CH$_3$CN and filtered to give the title compound as beige solid.

LC-MS (A): $t_R$=0.92 min
$^1$H NMR ((CD$_3$)$_2$SO) δ: 8.13 (s, 1 ), 6.02 (s, 2 ), 3.79 (s, 3 )

A.9.b. Methyl 4-amino-2-chloro-3-iodo-5-((trimethylsilyl)ethynyl)benzoate

A solution of methyl 4-amino-2-chloro-3,5-diiodobenzoate (9.6 mmol) in Et$_3$N (80 mL) and toluene (80 mL) was treated under argon with PPh$_3$ (0.96 mmol), CuI (4.80 mmol), Pd(PPh$_3$)$_2$Cl$_2$ (0.48 mmol) and trimethylsilylacetylene (10.1 mmol). The mixture was stirred for 2 h at RT, quenched with a 10% aq. solution of NH$_4$Cl and extracted with EtOAc. The organic phase was washed with brine, dried over MgSO$_4$ and concentrated in vacuo. The crude was purified by CC (SNAP KP-SIL™ from Biotage) using Hept/EtOAc from 100/0 to 85/15 to give the title compound as light orange solid.

LC-MS (A): $t_R$=1.05 min; [M+H]+: 408.02

A.9.c. Methyl 5-acetyl-4-amino-2-chloro-3-iodobenzoate

A solution of methyl 4-amino-2-chloro-3-iodo-5-((trimethylsilyl)ethynyl)benzoate (4.39 mmol) in toluene (20 mL) was treated with 4-toluene sulfonic acid monohydrate (11 mmol). The mixture was stirred for 3 h at 80° C. and poured into water. The aq. phase was basified with a 32% aq. solution of NaOH until pH=12-13 and extracted with EtOAc. The organic phase was washed with brine, dried over MgSO$_4$ and concentrated in vacuo. The crude was purified by CC (SNAP KP-SIL™ from Biotage) using Hept/EtOAc from 100/0 to 75/25 to give the title compound as light yellow solid.

LC-MS (A): $t_R$=0.88 min
$^1$H NMR ((CD$_3$)$_2$SO) δ: 8.37 (s, 1 ), 8.00 (s br, 2 ), 3.83 (s, 3 ), 2.63 (s, 3 )

A.9.d. Methyl 5-acetyl-4-amino-2-chloro-3-((trimethylsilyl)ethynyl)benzoate

This compound was prepared using a method analogous to that of methyl 4-amino-2-chloro-3-((trimethylsilyl)ethynyl)benzoate, methyl 5-acetyl-4-amino-2-chloro-3-iodobenzoate replacing the mixture of methyl 4-amino-2-chloro-3-iodobenzoate and methyl 4-amino-2-chloro-5-iodobenzoate.

LC-MS (A): $t_R$=1.03 min; [M+H]+: 324.25

A.9.e. Methyl 5-acetyl-4-amino-2-chloro-3-ethynylbenzoate

This compound was prepared using a method analogous to that of methyl 4-amino-2-chloro-3-ethynylbenzoate, methyl 5-acetyl-4-amino-2-chloro-3-((trimethylsilyl)ethynyl)benzoate replacing methyl 4-amino-2-chloro-3-((trimethylsilyl)ethynyl)benzoate.

LC-MS (A): $t_R$=0.84 min; [M+H]+: 251.99

A.9.f. Methyl 7-acetyl-4-chloro-1H-indole-5-carboxylate

This compound was prepared using a method analogous to that of methyl 4-chloro-1H-indole-5-carboxylate, methyl 5-acetyl-4-amino-2-chloro-3-ethynylbenzoate replacing methyl 4-amino-2-chloro-3-ethynylbenzoate.

LC-MS (A): $t_R$=0.83 min
$^1$H NMR ((CD$_3$)$_2$SO) δ: 11.96 (s, 1 ), 8.32 (s, 1 ), 7.56 (dd, J$_1$=J$_2$=2.9 Hz, 1 ), 6.74 (dd, J$_1$=2.1 Hz, J$_2$=3.2 Hz, 1 ), 3.92 (s, 3 ), 2.72 (s, 3 )

A.9.g. 7-Acetyl-4-chloro-1H-indole-5-carboxylic acid

This compound was prepared using a method analogous to that of 4-chloro-7-methyl-1H-indole-5-carboxylic acid, methyl 7-acetyl-4-chloro-1H-indole-5-carboxylate replacing methyl 4-chloro-7-methyl-1H-indole-5-carboxylate.

LC-MS (A): $t_R$=0.69 min
$^1$H NMR ((CD$_3$)$_2$SO) δ: 13.25 (s, 1 ), 11.91 (s, 1 ), 8.34 (s, 1 ), 7.54 (dd, J$_1$=J$_2$=2.9 Hz, 1 ), 6.72 (dd, J$_1$=2.1 Hz, J$_2$=3.1 Hz, 1 ), 2.72 (s, 3 )

A.10. Synthesis of 7-methyl-4-(trifluoromethyl)-1H-indole-5-carboxylic acid

A.10.a. Methyl 4-amino-2-(trifluoromethyl)benzoate

This compound was prepared using a method analogous to that of methyl 4-amino-2-chlorobenzoate, 4-amino-2-(trifluoromethyl)benzoic acid replacing 4-amino-2-chlorobenzoic acid.

LC-MS (A): $t_R$=0.77 min, [M+H]+: 220.04

A.10.b. Methyl 4-amino-5-iodo-2-(trifluoromethyl)benzoate

This compound was prepared using a method analogous to that of the mixture of methyl 4-amino-2-chloro-3-iodobenzoate and methyl 4-amino-2-chloro-5-iodobenzoate, methyl 4-amino-2-(trifluoromethyl)benzoate replacing methyl 4-amino-2-chlorobenzoate except that only the 5-iodo regioisomer was isolated.

LC-MS (A): $t_R$=0.88 min, [M+H]+: 345.7

A.10.c. Methyl 4-amino-5-methyl-2-(trifluoromethyl)benzoate

To a solution of methyl 4-amino-5-iodo-2-(trifluoromethyl)benzoate (24.6 mmol) in dioxane (49 mL) was added under argon a 2M solution of methylzinc chloride in THF (61.6 mmol) followed by Pd(dppf)Cl$_2$.DCM (1.72 mmol). The mixture was stirred for 30 min at 65° C. in a sealed vial, diluted with EtOAc and filtered. The filtrate was washed with a sat. solution of Rochelle salt and with brine, dried over MgSO$_4$ and concentrated in vacuo. The crude was purified by CC (SNAP KP-SIL™ from Biotage) using DCM to give the title compound as brown solid.
LC-MS (A): $t_R$=0.81 min; [M+H]+: 234.01

A.10.d. Methyl 4-amino-3-iodo-5-methyl-2-(trifluoromethyl)benzoate

This compound was prepared using a method analogous to that of the mixture of methyl 4-amino-2-chloro-3-iodobenzoate and methyl 4-amino-2-chloro-5-iodobenzoate, methyl 4-amino-5-methyl-2-(trifluoromethyl)benzoate replacing methyl 4-amino-2-chlorobenzoate except that the reaction mixture was stirred for 7 h at 50° C.
LC-MS (A): $t_R$=0.88 min, [M+H]+: 400.78

A.10.e. Methyl 4-amino-5-methyl-2-(trifluoromethyl)-3-((trimethylsilyl)ethynyl)benzoate This compound was prepared using a method analogous to that of methyl 4-amino-2-chloro-3-((trimethylsilyl)ethynyl)benzoate, methyl 4-amino-3-iodo-5-methyl-2-(trifluoromethyl)benzoate replacing the mixture of methyl 4-amino-2-chloro-3-iodobenzoate and methyl 4-amino-2-chloro-5-iodobenzoate except that the reaction mixture was stirred for 3 h30 at 70° C.
LC-MS (A): $t_R$=1.02 min; [M+H]+: 330.09

A.10.f. Methyl 4-amino-3-ethynyl-5-methyl-2-(trifluoromethyl)benzoate

This compound was prepared using a method analogous to that of methyl 4-amino-2-chloro-3-ethynylbenzoate, methyl 4-amino-5-methyl-2-(trifluoromethyl)-3-((trimethylsilyl) ethynyl)benzoate replacing methyl 4-amino-2-chloro-3-((trimethylsilyl)ethynyl)benzoate.
LC-MS (A): $t_R$=0.85 min; [M+H]+: 257.90

A.10.g. Methyl 7-methyl-4-(trifluoromethyl)-1H-indole-5-carboxylate

This compound was prepared using a method analogous to that of methyl 4-chloro-1H-indole-5-carboxylate, methyl 4-amino-3-ethynyl-5-methyl-2-(trifluoromethyl)benzoate replacing methyl 4-amino-2-chloro-3-ethynylbenzoate.
LC-MS (A): $t_R$=0.86 min
$^1$H NMR ((CD$_3$)$_2$SO) δ: 11.87 (s, 1 H), 7.68 (dd, $J_1$=$J_2$=2.8 Hz, 1 H), 7.22 (s, 1 H), 6.65 (m, 1 H), 3.85 (s, 3 H), 2.58 (s, 3 H)

A.10.h. 7-Methyl-4-(trifluoromethyl)-1H-indole-5-carboxylic acid

This compound was prepared using a method analogous to that of 4-chloro-7-methyl-1H-indole-5-carboxylic acid, methyl 7-methyl-4-(trifluoromethyl)-1H-indole-5-carboxylate replacing methyl 4-chloro-7-methyl-1H-indole-5-carboxylate except that the reaction mixture was stirred ON at 60° C.
LC-MS (A): $t_R$=0.73 min
$^1$H NMR ((CD$_3$)$_2$SO) δ: 13.07 (s br, 1 H), 11.79 (s, 1 H), 7.65 (dd, $J_1$=$J_2$=2.7 Hz, 1 H), 7.21 (s, 1 H), 6.63 (m, 1 H), 2.57 (s, 3 H)

A.11. Synthesis of 4,7-dimethyl-1H-indole-5-carboxylic acid

A.11.a. 4-Amino-2,5-dimethylbenzonitrile

4-Bromo-2,5-dimethylaniline (5 mmol), zinc cyanide (6 mmol) and Pd(PPh$_3$)$_4$ (0.1 mmol) were placed in a pressure vessel and anh. DMF (3 mL) was added. The tube was sealed under argon and heated at 110° C. After 35 h, it was quenched with a 10% Na$_2$CO$_3$ solution and extracted three times with EtOAc. The organic phase was washed with a sat. NaHCO$_3$ solution, dried over MgSO$_4$ and concentrated in vacuo. The crude was purified by CC (SNAP KP-Sil™ from Biotage) using Hept/EtOAc from 92/8 to 40/60 to give the title compound as white solid.
LC-MS (A): $t_R$=0.72 min, [M+H]+: 147.16

A.11.b. 4-Amino-3-iodo-2,5-dimethylbenzonitrile

This compound was prepared using a method analogous to that of the mixture of methyl 4-amino-2-chloro-3-iodobenzoate and methyl 4-amino-2-chloro-5-iodobenzoate, 4-amino-2,5-dimethylbenzonitrile replacing methyl 4-amino-2-chlorobenzoate.
LC-MS (A): $t_R$=0.85 min; [M+CH$_3$CN+H]+: 313.83

A.11.c. 4-Amino-2,5-dimethyl-3-((trimethylsilyl)ethynyl)benzonitrile

This compound was prepared using a method analogous to that of methyl 4-amino-2-chloro-3-((trimethylsilyl)ethynyl)benzoate, 4-amino-3-iodo-2,5-dimethylbenzonitrile replacing the mixture of methyl 4-amino-2-chloro-3-iodobenzoate and methyl 4-amino-2-chloro-5-iodobenzoate.
LC-MS (A): $t_R$=1.00 min; [M+H]+: 243.13

A.11.d. 4-Amino-3-ethynyl-2,5-dimethylbenzonitrile

This compound was prepared using a method analogous to that of methyl 4-amino-2-chloro-3-ethynylbenzoate, 4-amino-2,5-dimethyl-3-((trimethylsilyl)ethynyl)benzonitrile replacing methyl 4-amino-2-chloro-3-((trimethylsilyl)ethynyl)benzoate.
LC-MS (A): $t_R$=0.81 min; [M+CH$_3$CN+H]+: 212.12

A.11.e. 4,7-Dimethyl-1H-indole-5-carbonitrile

This compound was prepared using a method analogous to that of methyl 4-chloro-1H-indole-5-carboxylate, 4-amino-3-ethynyl-2,5-dimethylbenzonitrile replacing methyl 4-amino-2-chloro-3-ethynylbenzoate.
LC-MS (A): $t_R$=0.81 min; [M+CH$_3$CN+H]+: 212.13
$^1$H NMR ((CD$_3$)$_2$SO) δ: 11.64 (s br, 1 H), 7.52 (dd, $J_1$=$J_2$=2.8 Hz, 1 H), 7.17 (s, 1 H), 6.67 (dd, $J_1$=2.9 Hz, $J_2$=1.9 Hz, 1 H), 2.63 (s, 3 H), 2.47 (s, 3 H)

A.11.f. 4,7-Dimethyl-1H-indole-5-carboxylic acid

To a solution of 4,7-dimethyl-1H-indole-5-carbonitrile (0.19 mmol) in EtOH (1 mL) was added a 4M KOH solution (3.9 mL) and the mixture was heated for 18 h at 120° C. It was partitioned between water and EtOAc, the aqueous phase was acidified with a 25% HCl solution until pH 1-2 and extracted three times with EtOAc. The organic phases were dried over MgSO$_4$ and concentrated in vacuo to give the title compound as white solid.
LC-MS (A): $t_R$=0.68 min; [M+H]+: 190.18

A.12. Synthesis of 4-chloro-7-ethyl-1H-indole-5-carboxylic acid

A.12.a. Methyl 4-amino-2-chloro-5-ethynyl-3-iodobenzoate

This compound was prepared using a method analogous to that of methyl 4-amino-2-chloro-3-ethynylbenzoate, methyl 4-amino-2-chloro-3-iodo-5-((trimethylsilyl)ethynyl) benzoate replacing methyl 4-amino-2-chloro-3-((trimethylsilyl)ethynyl)benzoate.

LC-MS (A): $t_R$=0.88 min
$^1$H NMR ((CD$_3$)$_2$SO) δ: 7.76 (s, 1 H), 6.17 (s, 2 H), 4.65 (s, 1 H), 3.78 (s, 3 H)

A.12.b. Methyl 4-amino-2-chloro-5-ethyl-3-iodobenzoate

To a solution of methyl 4-amino-2-chloro-5-ethynyl-3-iodobenzoate (0.99 mmol) in EtOH (4 mL) was added platinum dioxide (0.099 mmol). The mixture was stirred under a hydrogen atmosphere for 1 h, filtered over Celite and concentrated in vacuo. The crude was purified by CC using DCM to give the title compound as light yellow solid.

LC-MS (A): $t_R$=0.90 min, [M+H]+: 339.83

A.12.c. Methyl 4-amino-2-chloro-5-ethyl-3-((trimethylsilyl)ethynyl)benzoate

This compound was prepared using a method analogous to that of methyl 4-amino-2-chloro-3-((trimethylsilyl)ethynyl)benzoate, methyl 4-amino-2-chloro-5-ethyl-3-iodobenzoate replacing the mixture of methyl 4-amino-2-chloro-3-iodobenzoate and methyl 4-amino-2-chloro-5-iodobenzoate except that the reaction was stirred for 30 min at 80° C.

LC-MS (A): $t_R$=1.03 min; [M+H]+: 310.22

A.12.d. Methyl 4-amino-2-chloro-5-ethyl-3-ethynylbenzoate

This compound was prepared using a method analogous to that of methyl 4-amino-2-chloro-3-ethynylbenzoate, methyl 4-amino-2-chloro-5-ethyl-3-((trimethylsilyl)ethynyl)benzoate replacing methyl 4-amino-2-chloro-3-((trimethylsilyl)ethynyl)benzoate.

LC-MS (A): $t_R$=0.86 min; [M+H]+: 238.21

A.12.e. Methyl 4-chloro-7-ethyl-1H-indole-5-carboxylate

This compound was prepared using a method analogous to that of methyl 4-chloro-1H-indole-5-carboxylate, methyl 4-amino-2-chloro-5-ethyl-3-ethynylbenzoate replacing methyl 4-amino-2-chloro-3-ethynylbenzoate.

LC-MS (A): $t_R$=0.86 min, [M+H]+: 238.05

A.12.f. 4-Chloro-7-ethyl-1H-indole-5-carboxylic acid

This compound was prepared using a method analogous to that of 4-chloro-7-methyl-1H-indole-5-carboxylic acid, methyl 7-methyl-4-(trifluoromethyl)-1H-indole-5-carboxylate replacing methyl 4-chloro-7-methyl-1H-indole-5-carboxylate.

LC-MS (A): $t_R$=0.73 min, [M+H]+: 224.20

A.13. Synthesis of 7-chloro-4-methyl-1H-indole-5-carboxylic acid

A.13.a. Methyl 4-acetamido-5-chloro-2-(((trifluoromethyl)sulfonyl)oxy)benzoate To a solution of methyl 4-acetamido-5-chloro-2-hydroxybenzoate (20.5 mmol) in DCM (100 mL) was added at 0° C. Et$_3$N (22.6 mmol) and trifluoromethanesulfonic anhydride (22.6 mmol). The mixture was stirred for 1 h at RT, quenched with a sat. solution of NaHCO$_3$ and extracted with DCM. The organic phase was washed with brine, dried over MgSO$_4$ and concentrated in vacuo. The crude was purified by CC (SNAP KP-Sil™ from Biotage) using Hept/EtOAc from 100/0 to 65/35 to give the title compound as light yellow solid.

LC-MS (A): $t_R$=0.90 min
$^1$H NMR ((CD$_3$)$_2$SO) δ: 9.94 (s, 1 H), 8.35 (s, 1 H), 8.14 (s, 1 H), 3.88 (s, 3 H), 2.23 (s, 3H)

A.13.b. Methyl 4-acetamido-5-chloro-2-methylbenzoate

A suspension of methyl 4-acetamido-5-chloro-2-(((trifluoromethyl)sulfonyl)oxy)benzoate (2.61 mmol), K$_3$PO$_4$ (5.23 mmol), methylboronic acid (5.23 mmol) and Pd(dppf)Cl$_2$.DCM (0.26 mmol) in THF (26 mL) was stirred under argon for 2 h at 65° C. The reaction mixture was quenched with a sat. solution of NaHCO$_3$ and extracted three times with EtOAc. The organic phase was washed with brine, dried over MgSO$_4$ and concentrated in vacuo. The crude was purified by CC (SNAP KP-Sil™ from Biotage) using Hept/EtOAc from 100/0 to 60/40 to give the title compound as white solid.

LC-MS (A): $t_R$=0.77 min, [M+H]+: 241.90

A.13.c. Methyl 4-amino-5-chloro-2-methylbenzoate

To a solution of methyl 4-acetamido-5-chloro-2-methylbenzoate (2.25 mmol) in MeOH (14 mL) was added K$_2$CO$_3$ (2.48 mmol). The suspension was stirred for 3 days at RT, MeOH was evaporated off and the residue was partitioned between EtOAc and a 1M solution of HCl. The aq. phase was extracted twice with EtOAc and the combined organic phases were washed with brine, dried over MgSO$_4$ and concentrated in vacuo. The crude was purified by CC (SNAP KP-Sil™ from Biotage) using Hept/EtOAc from 100/0 to 80/20 to give the title compound as white solid.

LC-MS (A): $t_R$=0.81 min, [M+H]+: 200.12

A.13.d. Methyl 4-amino-5-chloro-3-iodo-2-methylbenzoate

This compound was prepared using a method analogous to that of the mixture of methyl 4-amino-2-chloro-3-iodobenzoate and methyl 4-amino-2-chloro-5-iodobenzoate, methyl 4-amino-5-chloro-2-methylbenzoate replacing methyl 4-amino-2-chlorobenzoate except that the reaction mixture was stirred for 1 h at RT.

LC-MS (A): $t_R$=0.91 min
$^1$H NMR ((CD$_3$)$_2$SO) δ: 7.76 (s, 1 H), 6.02 (s, 2 H), 3.77 (s, 3 H), 2.65 (s, 3 H)

A.13.e. Methyl 4-amino-5-chloro-2-methyl-3-((trimethylsilyl)ethynyl)benzoate This compound was prepared using a method analogous to that of methyl 4-amino-2-chloro-3-((trimethylsilyl)ethynyl)benzoate, methyl 4-amino-5-chloro-3-iodo-2-methyl benzoate replacing the mixture of methyl 4-amino-2-chloro-3-iodobenzoate and methyl 4-amino-2-chloro-5-iodobenzoate.

LC-MS (A): $t_R$=1.06 min; [M+H]+: 296.14

A.13.f. Methyl 4-amino-5-chloro-3-ethynyl-2-methylbenzoate

This compound was prepared using a method analogous to that of methyl 4-amino-2-chloro-3-ethynylbenzoate, methyl 4-amino-5-chloro-2-methyl-3-((trimethylsilyl)ethynyl)benzoate replacing methyl 4-amino-2-chloro-3-((trimethylsilyl)ethynyl)benzoate.

LC-MS (A): $t_R$=0.88 min; [M+H]+: 224.03

A.13.g. Methyl 7-chloro-4-methyl-1H-indole-5-carboxylate

This compound was prepared using a method analogous to that of methyl 4-chloro-1H-indole-5-carboxylate, methyl 4-amino-5-chloro-3-ethynyl-2-methylbenzoate replacing methyl 4-amino-2-chloro-3-ethynylbenzoate.

LC-MS (A): $t_R$=0.86 min, [M+H]+: 223.46

A.13.h. 7-Chloro-4-methyl-1H-indole-5-carboxylic acid

This compound was prepared using a method analogous to that of 4-chloro-7-methyl-1H-indole-5-carboxylic acid, methyl 7-chloro-4-methyl-1H-indole-5-carboxylate replacing methyl 4-chloro-7-methyl-1H-indole-5-carboxylate.

LC-MS (A): $t_R$=0.72 min $^1$H NMR ((CD$_3$)$_2$SO) δ: 12.62 (s, 1 H), 11.77 (s, 1 H), 7.67 (s, 1 H), 7.49 (dd, J$_1$=J$_2$=2.8 Hz, 1 H), 6.78 (dd, J$_1$=2.0 Hz, J$_2$=3.0 Hz, 1 H), 2.75 (s, 3 H)

A.14. Synthesis of 7-methoxy-4-methyl-1H-indole-5-carboxylic acid

A.14.a. 5-Methoxy-2-methyl-4-nitrobenzonitrile

To a solution of CuCN (25.2 mmol) in CH$_3$CN (32 mL) was added tert-butylnitrite (19.8 mmol) at RT followed by a suspension of 5-methoxy-2-methyl-4-nitroaniline (11 mmol) in CH$_3$CN (5 mL) at 0° C. The mixture was stirred for 1 h at 85° C. then ON at RT, quenched with a 10% solution of Na$_2$CO$_3$ and extracted three times with EtOAc. The organic phases were washed with brine, dried over MgSO$_4$ and concentrated in vacuo. The crude was purified by CC (SNAP KP-Sil™ from Biotage) using Hept/EtOAc from 100/0 to 85/15 to give the title compound as orange solid.

LC-MS (A): $t_R$=0.82 min $^1$H NMR ((CD$_3$)$_2$SO) δ: 8.00 (s, 1 H), 7.88 (s, 1 H), 3.95 (s, 3 H), 2.47 (s, 3 H)

A.14.b. 5-Methoxy-2-methyl-4-nitrobenzoic acid

To a suspension of 5-methoxy-2-methyl-4-nitrobenzonitrile (1.92 mmol) in 2-propanol (4.3 mL) and water (4.3 mL) was added KOH (9.6 mmol). The mixture was stirred for 2 h at 70° C., diluted with water and extracted three times with EtOAc. The organic phases were washed with brine, dried over MgSO$_4$ and concentrated in vacuo. The crude was dissolved in water (1 mL) and H$_2$SO$_4$ (2.9 mL) and the mixture was heated to 80° C. Sodium nitrite (3.46 mmol) was added dropwise and the reaction mixture was stirred for 45 min at 80° C. It was diluted with water and extracted three times with EtOAc. The organic phase was dried over MgSO$_4$ and concentrated in vacuo to give the crude title compound as orange solid.

LC-MS (A): $t_R$=0.82 min

LC-MS (D*): $t_R$=0.17 min; [M−H]−: 210.19

A.14.c. Methyl 5-methoxy-2-methyl-4-nitrobenzoate

This compound was prepared using a method analogous to that of methyl 4-amino-2-chlorobenzoate, 5-methoxy-2-methyl-4-nitrobenzoic acid replacing 4-amino-2-chlorobenzoic acid.

LC-MS (A): $t_R$=0.85 min $^1$H NMR ((CD$_3$)$_2$SO) δ: 7.87 (s, 1 H), 7.64 (s, 1 H), 3.95 (s, 3 H), 3.89 (s, 3 H), 2.46 (s, 3H)

A.14.d. Methyl 4-amino-5-methoxy-2-methylbenzoate

To a solution of methyl 5-methoxy-2-methyl-4-nitrobenzoate (2.13 mmol) in MeOH (21 mL) was added zinc dust (21.3 mmol) at RT followed by ammonium formate (21.3 mmol) at 0° C. The mixture was stirred for 1 h at RT, filtered over Celite and the filtrate was concentrated in vacuo. The residue was partitioned between EtOAc and a sat. solution of NaHCO$_3$. The organic phase was washed with brine, dried over MgSO$_4$ and concentrated in vacuo. The crude was purified by CC using DCM/MeOH from 100/0 to 99/1 to give the title compound as light yellow solid.

LC-MS (A): $t_R$=0.71 min; [M+H]+: 196.15

A.14.e. Methyl 4-amino-3-iodo-5-methoxy-2-methylbenzoate

This compound was prepared using a method analogous to that of the mixture of methyl 4-amino-2-chloro-3-iodobenzoate and methyl 4-amino-2-chloro-5-iodobenzoate, methyl 4-amino-5-methoxy-2-methylbenzoate replacing methyl 4-amino-2-chlorobenzoate except that the reaction mixture was stirred for 1 h at RT.

LC-MS (A): $t_R$=0.87 min, [M+H]+: 321.73

A.14.f. Methyl 4-amino-5-methoxy-2-methyl-3-((trimethylsilyl)ethynyl)benzoate This compound was prepared using a method analogous to that of methyl 4-amino-2-chloro-3-((trimethylsilyl)ethynyl)benzoate, methyl 4-amino-3-iodo-5-methoxy-2-methyl benzoate replacing the mixture of methyl 4-amino-2-chloro-3-iodobenzoate and methyl 4-amino-2-chloro-5-iodobenzoate.

LC-MS (A): $t_R$=1.01 min; [M+H]+: 292.21

A.14.g. Methyl 4-amino-3-ethynyl-5-methoxy-2-methylbenzoate

This compound was prepared using a method analogous to that of methyl 4-amino-2-chloro-3-ethynylbenzoate, methyl 4-amino-5-methoxy-2-methyl-3-((trimethylsilyl)ethynyl)benzoate replacing methyl 4-amino-2-chloro-3-((trimethylsilyl)ethynyl)benzoate.

LC-MS (A): $t_R$=0.83 min; [M+H]+: 220.13

A.14.h. Methyl 7-methoxy-4-methyl-1H-indole-5-carboxylate

This compound was prepared using a method analogous to that of methyl 4-chloro-1H-indole-5-carboxylate, methyl 4-amino-3-ethynyl-5-methoxy-2-methylbenzoate replacing methyl 4-amino-2-chloro-3-ethynylbenzoate.

LC-MS (A): $t_R$=0.81 min; [M+H]+: 220.07

A.14.i. 7-Methoxy-4-methyl-1H-indole-5-carboxylic acid

This compound was prepared using a method analogous to that of 4-chloro-7-methyl-1H-indole-5-carboxylic acid, methyl 7-methoxy-4-methyl-1H-indole-5-carboxylate replacing methyl 4-chloro-7-methyl-1H-indole-5-carboxylate.

LC-MS (A): $t_R$=0.67 min; [M+H]+: 206.15

A.15. Synthesis of 4-chloro-7-ethoxy-1H-indole-5-carboxylic acid

A.15.a. 4-Amino-2-chloro-5-methoxybenzonitrile

This compound was prepared using a method analogous to that of 4-amino-2,5-dimethylbenzonitrile, 4-bromo-5-chloro-2-methoxyaniline replacing 4-bromo-2,5-dimethyl aniline except that the reaction mixture was stirred ON at 110° C.

LC-MS (A): $t_R$=0.76 min, [M+H]+: 183.19

A.15.b. 4-Amino-2-chloro-3-iodo-5-methoxybenzonitrile

This compound was prepared using a method analogous to that of the mixture of methyl 4-amino-2-chloro-3-iodobenzoate and methyl 4-amino-2-chloro-5-iodobenzoate, 4-amino-2-chloro-5-methoxybenzonitrile replacing methyl 4-amino-2-chlorobenzoate except that the reaction mixture was stirred for 45 min at RT.

LC-MS (A): $t_R$=0.86 min
$^1$H NMR ((CD$_3$)$_2$SO) δ: 7.33 (s, 1 H), 6.11 (s, 2 H), 3.85 (s, 3 H)

A.15.c. 4-Amino-2-chloro-5-methoxy-3-((trimethylsilyl)ethynyl)benzonitrile

This compound was prepared using a method analogous to that of methyl 4-amino-2-chloro-3-((trimethylsilyl)ethynyl)benzoate, 4-amino-2-chloro-3-iodo-5-methoxybenzonitrile replacing the mixture of methyl 4-amino-2-chloro-3-iodobenzoate and methyl 4-amino-2-chloro-5-iodobenzoate.

LC-MS (A): $t_R$=1.00 min; [M+H]+: 279.04

A.15.d. 4-Amino-2-chloro-3-ethynyl-5-methoxybenzonitrile

This compound was prepared using a method analogous to that of methyl 4-amino-2-chloro-3-ethynylbenzoate, 4-amino-2-chloro-5-methoxy-3-((trimethylsilyl)ethynyl) benzonitrile replacing methyl 4-amino-2-chloro-3-((trimethylsilyl)ethynyl)benzoate.

LC-MS (A): $t_R$=0.82 min; [M+CH$_3$CN+H]+: 248.23

A.15.e. 4-Chloro-7-methoxy-1H-indole-5-carbonitrile

This compound was prepared using a method analogous to that of methyl 4-chloro-1H-indole-5-carboxylate, 4-amino-2-chloro-3-ethynyl-5-methoxybenzonitrile replacing methyl 4-amino-2-chloro-3-ethynylbenzoate.

LC-MS (A): $t_R$=0.83 min, [M+CH$_3$CN+H]+: 248.23
$^1$H NMR ((CD$_3$)$_2$SO) δ: 12.23 (s, 1 H), 7.56 (d, J=3.1 Hz, 1 H), 7.14 (s, 1 H), 6.61 (d, J=3.1 Hz, 1 H), 3.99 (s, 3 H)

A.15.f. 4-Chloro-7-hydroxy-1H-indole-5-carbonitrile

To a solution of 4-chloro-7-methoxy-1H-indole-5-carbonitrile (2.53 mmol) in DCM (106 mL) was added dropwise a 1M solution of BBr$_3$ in DCM (14.8 mmol) at −78° C. The mixture was allowed to warm up to RT and stirred for 15 h at 45° C. then for 4 h30 at 55° C. It was quenched with MeOH (40 mL) and concentrated in vacuo. The crude was purified by CC (SNAP KP-Sil™ from Biotage) using EtOAc/MeOH from 100/0 to 90/10 to give the title compound as brownish solid.

LC-MS (A): $t_R$=0.75 min
$^1$H NMR ((CD$_3$)$_2$SO) δ: 11.99 (s, 1 H), 10.69 (s, 1 H), 7.54 (dd, J$_1$=J$_2$=2.8 Hz, 1 H), 6.80 (s, 1 H), 6.57 (m, 1 H)

A.15.g. 4-Chloro-7-ethoxy-1H-indole-5-carbonitrile

To a solution of 4-chloro-7-hydroxy-1H-indole-5-carbonitrile (1.31 mmol) in DMF (2.6 mL) was added at 0° C. K$_2$CO$_3$ (1.58 mmol) and ethyl bromide (1.44 mmol). The mixture was stirred ON at RT, quenched with water and extracted with EtOAc. The organic phase was dried over MgSO$_4$ and concentrated in vacuo. The crude was purified by CC (SNAP KP-Sil™ from Biotage) using Hept/EtOAc from 100/0 to 50/50 to give the title compound as white solid.

LC-MS (A): $t_R$=0.88 min, [M+CH$_3$CN+H]+: 262.10

A.15.h. 4-Chloro-7-ethoxy-1H-indole-5-carboxylic acid

This compound was prepared using a method analogous to that of 4,7-dimethyl-1H-indole-5-carboxylic acid, 4-chloro-7-ethoxy-1H-indole-5-carbonitrile replacing 4,7-dimethyl-1H-indole-5-carbonitrile.

LC-MS (A): $t_R$=0.73 min; [M+H]+: 240.05

A.16. Synthesis of 4-chloro-7-propyl-1H-indole-5-carboxylic acid

A.16.a. Methyl 4-amino-2-chloro-5-propylbenzoate

This compound was prepared using a method analogous to that of methyl 4-amino-2-chloro-5-isobutylbenzoate, 1-propylboronic acid replacing (2-methylpropyl)boronic acid.

LC-MS (A): $t_R$=0.86 min; [M+H]+: 228.15

A.16.b. Methyl 4-amino-2-chloro-3-iodo-5-propylbenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-propylbenzoate replacing methyl 4-amino-2-chlorobenzoate.

LC-MS (A): $t_R$=0.94 min; [M+H]+: 353.66

A.16.c. Methyl 4-amino-2-chloro-5-propyl-3-((trimethylsilyl)ethynyl)benzoate This compound was prepared using a method analogous to that of methyl 4-amino-2-chloro-3-((trimethylsilyl)ethynyl)benzoate, methyl 4-amino-2-chloro-3-iodo-5-propylbenzoate replacing the mixture of methyl 4-amino-2-chloro-3-iodobenzoate and methyl 4-amino-2-chloro-5-iodobenzoate.

LC-MS (A): $t_R$=1.05 min; [M+H]+: 324.10

A.16.d. Methyl 4-amino-2-chloro-3-ethynyl-5-propylbenzoate

This compound was prepared using a method analogous to that of methyl 4-amino-2-chloro-3-ethynylbenzoate, methyl 4-amino-2-chloro-5-propyl-3-((trimethylsilyl)ethynyl)benzoate replacing methyl 4-amino-2-chloro-3-((trimethylsilyl)ethynyl)benzoate.

LC-MS (A): $t_R$=0.90 min; [M+H]+: 252.25

A.16.e. Methyl 4-chloro-7-propyl-1H-indole-5-carboxylate

This compound was prepared using a method analogous to that of methyl 4-chloro-1H-indole-5-carboxylate, methyl 4-amino-2-chloro-3-ethynyl-5-propylbenzoate replacing methyl 4-amino-2-chloro-3-ethynylbenzoate.

LC-MS (A): $t_R$=0.91 min; [M+H]+: 252.21

A.16.f. 4-Chloro-7-propyl-1H-indole-5-carboxylic acid

This compound was prepared using a method analogous to that of 4-chloro-7-methyl-1H-indole-5-carboxylic acid, methyl 4-chloro-7-propyl-1H-indole-5-carboxylate replacing methyl 4-chloro-7-methyl-1H-indole-5-carboxylate.

LC-MS (A): $t_R$=0.78 min, [M+H]+: 238.19

A.17. Synthesis of 7-(2-(tert-butoxy)ethoxy)-4-chloro-1H-indole-5-carboxylic acid

A.17.a. 7-(2-(tert-Butoxy)ethoxy)-4-chloro-1H-indole-5-carbonitrile

This compound was prepared using a method analogous to that of 4-chloro-7-ethoxy-1H-indole-5-carbonitrile, 2-(2-bromoethoxy)-2-methylpropane replacing ethyl bromide except that the reaction mixture was stirred for 8 h at 80° C.

LC-MS (A): $t_R$=0.94 min, [M+CH$_3$CN+H]+: 334.12

A.17.b. 7-(2-(tert-Butoxy)ethoxy)-4-chloro-1H-indole-5-carboxylic acid

This compound was prepared using a method analogous to that of 4,7-dimethyl-1H-indole-5-carboxylic acid, 7-(2-(tert-butoxy)ethoxy)-4-chloro-1H-indole-5-carbonitrile replacing 4,7-dimethyl-1H-indole-5-carbonitrile.

LC-MS (A): $t_R$=0.80 min; [M+CH$_3$CN+H]+: 353.16

$^1$H NMR ((CD$_3$)$_2$SO) δ: 12.86 (s very br, 1 H), 11.74 (s, 1 H), 7.43 (dd, J$_1$=J$_2$=2.7 Hz, 1H), 7.17 (s, 1 H), 6.58 (m, 1 H), 4.26 (m, 2 H), 3.74 (m, 2 H), 1.18 (s, 9 H)

A.18. Synthesis of 4-chloro-7-methoxy-1H-indole-5-carboxylic acid

A.18.a. 1-Chloro-4-methoxy-2-methyl-5-nitrobenzene

To a suspension of 4-chloro-5-methyl-2-nitrophenol (5.33 mmol) and K$_2$CO$_3$ (10.70 mmol) in DMF (11 mL) was added methyl iodide (5.86 mmol) and the mixture was stirred for 6 h at RT. It was quenched with half saturated NaHCO$_3$ solution and extracted three times with EtOAc. The organic phases were dried over MgSO$_4$ and concentrated in vacuo. The crude was purified by CC (Isolute Flash Si II from Biotage) using Hept/EtOAc from 85/15 to 80/20 to give the title compound as yellow solid.

LC-MS (A): $t_R$=0.88 min $^1$H NMR ((CD$_3$)$_2$SO) δ: 8.01 (s, 1 H), 7.44 (s, 1 H), 3.93 (s, 3 H), 2.42 (s, 3 H)

A.18.b. 2-Chloro-5-methoxy-4-nitrobenzoic acid

To a suspension of 1-chloro-4-methoxy-2-methyl-5-nitrobenzene (4.32 mmol) in H$_2$O (207 mL) was added KMnO$_4$ (17.30 mmol) and the mixture was refluxed for 3 h and filtered to remove solids. The filtrate was quenched with a 40% NaHSO$_3$ solution, acidified with a 1M HCl solution until pH 1-2 and extracted three times with EtOAc. The organic phases were dried over MgSO$_4$ and concentrated in vacuo to give the title compound as light yellow solid.

LC-MS (A): $t_R$=0.69 min

LC-MS (D*): $t_R$=0.26 min, [M−H]−: 230.04

A.18.c. 4-Amino-2-chloro-5-methoxybenzoic acid

This compound was prepared using a method analogous to that of methyl 4-amino-2,6-dichlorobenzoate, 2-chloro-5-methoxy-4-nitrobenzoic acid replacing methyl 2,6-dichloro-4-nitrobenzoate except that the mixture was heated for 15 min at 100° C. under microwave conditions.

LC-MS (A): $t_R$=0.59 min; [M+CH$_3$CN+H]+: 242.70

A.18.d. Methyl 4-amino-2-chloro-5-methoxybenzoate

This compound was prepared using a method analogous to that of methyl 4-amino-2-chlorobenzoate, 4-amino-2-chloro-5-methoxybenzoic acid replacing 4-amino-2-chlorobenzoic acid.

LC-MS (A): $t_R$=0.75 min; [M+H]+: 216.14

A.18.e. Methyl 4-amino-2-chloro-3-iodo-5-methoxybenzoate

This compound was prepared using a method analogous to that of the mixture of methyl 4-amino-2-chloro-3-iodobenzoate and methyl 4-amino-2-chloro-5-iodobenzoate, methyl 4-amino-2-chloro-5-methoxybenzoate replacing methyl 4-amino-2-chlorobenzoate.

LC-MS (A): $t_R$=0.85 min; [M+H]+: 341.67

A.18.f. Methyl 4-amino-2-chloro-5-methoxy-3-((trimethylsilyl)ethynyl)benzoate This compound was prepared using a method analogous to that of methyl 4-amino-2-chloro-3-((trimethylsilyl)ethynyl)benzoate, methyl 4-amino-2-chloro-3-iodo-5-methoxybenzoate replacing the mixture of methyl 4-amino-2-chloro-3-iodobenzoate and methyl 4-amino-2-chloro-5-iodobenzoate.

LC-MS (A): $t_R$=0.99 min; [M+H]+: 311.94

A.18.g. Methyl 4-amino-2-chloro-3-ethynyl-5-methoxybenzoate

This compound was prepared using a method analogous to that of methyl 4-amino-2-chloro-3-ethynylbenzoate, methyl 4-amino-2-chloro-5-methoxy-3-((trimethylsilyl)

ethynyl)-benzoate replacing methyl 4-amino-2-chloro-3-((trimethylsilyl)ethynyl)benzoate.

LC-MS (A): $t_R$=0.81 min; [M+H]+: 240.02

A.18.h. Methyl 4-chloro-7-methoxy-1H-indole-5-carboxylate

This compound was prepared using a method analogous to that of methyl 4-chloro-1H-indole-5-carboxylate, methyl 4-amino-2-chloro-3-ethynyl-5-methoxybenzoate replacing methyl 4-amino-2-chloro-3-ethynylbenzoate.

LC-MS (A): $t_R$=0.82 min; [M+H]+: 239.95

A.18.i 4-Chloro-7-methoxy-1H-indole-5-carboxylic acid

This compound was prepared using a method analogous to that of 4-chloro-7-methyl-1H-indole-5-carboxylic acid, methyl 4-chloro-7-methoxy-1H-indole-5-carboxylate replacing methyl 4-chloro-7-methyl-1H-indole-5-carboxylate.

LC-MS (A): $t_R$=0.68 min, [M+H]+: 226.08

A.19. Synthesis of 4,7-difluoro-1H-indole-5-carboxylic acid

A.19.a. Methyl 2,5-difluoro-4-nitrobenzoate

This compound was prepared using a method analogous to that of methyl 4-amino-2-chlorobenzoate, 2,5-difluoro-4-nitrobenzoic acid replacing 4-amino-2-chlorobenzoic acid.

LC-MS (A): $t_R$=0.80 min
$^1$H NMR ((CD$_3$)$_2$SO) δ: 8.31 (dd, $J_1$=6.0 Hz, $J_2$=9.7 Hz, 1 H), 8.07 (dd, $J_1$=5.8 Hz, $J_2$=10.9 Hz, 1 H), 3.92 (s, 3 H)

A.19.b. Methyl 4-amino-2,5-difluorobenzoate

This compound was prepared using a method analogous to that of methyl 4-amino-5-methoxy-2-methylbenzoate, methyl 2,5-difluoro-4-nitrobenzoate replacing methyl 5-methoxy-2-methyl-4-nitrobenzoate.

LC-MS (A): $t_R$=0.70 min, [M+H]+: 188.22

A.19.c. Methyl 4-amino-2,5-difluoro-3-iodobenzoate

This compound was prepared using a method analogous to that of the mixture of methyl 4-amino-2-chloro-3-iodobenzoate and methyl 4-amino-2-chloro-5-iodobenzoate, methyl 4-amino-2,5-difluorobenzoate replacing methyl 4-amino-2-chlorobenzoate except that the reaction mixture was stirred for 1 h at RT.

LC-MS (A): $t_R$=0.81 min
$^1$H NMR ((CD$_3$)$_2$SO) δ: 7.52 (dd, $J_1$=6.7 Hz, $J_2$=11.7 Hz, 1 H), 6.43 (s, 2 H), 3.78 (s, 3 H)

A.19.d. Methyl 4-amino-2,5-difluoro-3-((trimethylsilyl)ethynyl)benzoate

This compound was prepared using a method analogous to that of methyl 4-amino-2-chloro-3-((trimethylsilyl)ethynyl)benzoate, methyl 4-amino-2,5-difluoro-3-iodobenzoate replacing the mixture of methyl 4-amino-2-chloro-3-iodobenzoate and methyl 4-amino-2-chloro-5-iodobenzoate.

LC-MS (A): $t_R$=0.98 min; [M+H]+: 284.22

A.19.e. Methyl 4-amino-3-ethynyl-2,5-difluorobenzoate

This compound was prepared using a method analogous to that of methyl 4-amino-2-chloro-3-ethynylbenzoate, methyl 4-amino-2,5-difluoro-3-((trimethylsilyl)ethynyl)benzoate replacing methyl 4-amino-2-chloro-3-((trimethylsilyl)ethynyl)benzoate.

LC-MS (A): $t_R$=0.78 min
$^1$H NMR ((CD$_3$)$_2$SO) δ: 7.48 (dd, $J_1$=6.6 Hz, $J_2$=11.8 Hz, 1 H), 6.66 (s, 2 H), 4.80 (s, 1H), 3.78 (s, 3 H)

A.19.f. Methyl 4,7-difluoro-1H-indole-5-carboxylate

This compound was prepared using a method analogous to that of methyl 4-chloro-1H-indole-5-carboxylate, methyl 4-amino-3-ethynyl-2,5-difluorobenzoate replacing methyl 4-amino-2-chloro-3-ethynylbenzoate.

LC-MS (A): $t_R$=0.79 min, [M+H]+: 212.21

A.19.g. 4,7-Difluoro-1H-indole-5-carboxylic acid

This compound was prepared using a method analogous to that of 4-chloro-7-methyl-1H-indole-5-carboxylic acid, methyl 4,7-difluoro-1H-indole-5-carboxylate replacing methyl 4-chloro-7-methyl-1H-indole-5-carboxylate.

LC-MS (A): $t_R$=0.64 min
$^1$H NMR ((CD$_3$)$_2$SO) δ: 12.96 (s, 1 H), 12.29 (s, 1 H), 7.56 (dd, $J_1$=$J_2$=2.6 Hz, 1 H), 7.32 (dd, $J_1$=4.9 Hz, $J_2$=11.3 Hz, 1 H), 6.73 (m, 1 H)

A.20. Synthesis of 4-fluoro-7-methoxy-1H-indole-5-carboxylic acid

A.20.a. 2-Fluoro-5-methoxy-4-nitrobenzoic acid

To a suspension of 2,5-difluoro-4-nitrobenzoic acid (2.46 mmol) and Cs$_2$CO$_3$ (12.3 mmol) in DMF was added MeOH (16.5 mmol) and the mixture was stirred for 3 h30 at RT. It was diluted with water, acidified with a 1M solution of HCl until pH=1-2 and extracted three times with EtOAc. The organic phases were washed with brine, dried over MgSO$_4$ and concentrated in vacuo to give the title compound as light yellow solid.

LC-MS (A): $t_R$=0.67 min
$^1$H NMR ((CD$_3$)$_2$SO) δ: 13.96 (s br, 1 H), 8.03 (d, J=9.6 Hz, 1 H), 7.68 (d, J=5.8 Hz, 1H), 3.97 (s, 3 H)

A.20.b. Methyl 2-fluoro-5-methoxy-4-nitrobenzoate

This compound was prepared using a method analogous to that of methyl 4-amino-2-chlorobenzoate, 2-fluoro-5-methoxy-4-nitrobenzoic acid replacing 4-amino-2-chlorobenzoic acid.

LC-MS (A): $t_R$=0.81 min
$^1$H NMR ((CD$_3$)$_2$SO) δ: 8.09 (d, J=9.7 Hz, 1 ), 7.70 (d, J=5.7 Hz, 1 ), 3.98 (s, 3 ), 3.92 (s, 3 )

A.20.c. Methyl 4-amino-2-fluoro-5-methoxybenzoate

This compound was prepared using a method analogous to that of methyl 4-amino-5-methoxy-2-methylbenzoate, methyl 2-fluoro-5-methoxy-4-nitrobenzoate replacing methyl 5-methoxy-2-methyl-4-nitrobenzoate.

LC-MS (A): $t_R$=0.70 min, [M+H]+: 200.19

A.20.d. Methyl 4-amino-2-fluoro-3-iodo-5-methoxybenzoate

This compound was prepared using a method analogous to that of the mixture of methyl 4-amino-2-chloro-3-iodobenzoate and methyl 4-amino-2-chloro-5-iodobenzoate, methyl 4-amino-2-fluoro-5-methoxybenzoate replacing methyl 4-amino-2-chlorobenzoate except that the reaction mixture was stirred for 2 h at RT.

LC-MS (A): $t_R$=0.83 min, [M+H]+: 325.97

A.20.e. Methyl 4-amino-2-fluoro-5-methoxy-3-((trimethylsilyl)ethynyl)benzoate This compound was prepared using a method analogous to that of methyl 4-amino-2-chloro-3-((trimethylsilyl)ethynyl)benzoate, methyl 4-amino-2-fluoro-3-iodo-5-methoxy benzoate replacing the mixture of methyl 4-amino-2-chloro-3-iodobenzoate and methyl 4-amino-2-chloro-5-iodobenzoate.

LC-MS (A): $t_R$=0.97 min; [M+H]+: 296.03

A.20.f. Methyl 4-amino-3-ethynyl-2-fluoro-5-methoxybenzoate

This compound was prepared using a method analogous to that of methyl 4-amino-2-chloro-3-ethynylbenzoate, methyl 4-amino-2-fluoro-5-methoxy-3-((trimethylsilyl)ethynyl)benzoate replacing methyl 4-amino-2-chloro-3-((trimethylsilyl)ethynyl)benzoate.

LC-MS (A): $t_R$=0.78 min; [M+H]+: 223.92

A.20.g. Methyl 4-fluoro-7-methoxy-1H-indole-5-carboxylate

This compound was prepared using a method analogous to that of methyl 4-chloro-1H-indole-5-carboxylate, methyl 4-amino-3-ethynyl-2-fluoro-5-methoxybenzoate replacing methyl 4-amino-2-chloro-3-ethynylbenzoate.

LC-MS (A): $t_R$=0.78 min, [M+H]+: 223.76

$^1$H NMR ((CD$_3$)$_2$SO) δ: 11.96 (s, 1 ), 7.41 (dd, J$_1$=J$_2$=2.6 Hz, 1 ), 6.99 (d, J=4.9 Hz, 1 ), 6.62 (m, 1 ), 3.95 (s, 3 ), 3.85 (s, 3 )

A.20.h. 4-Fluoro-7-methoxy-1H-indole-5-carboxylic acid

This compound was prepared using a method analogous to that of 4-chloro-7-methyl-1H-indole-5-carboxylic acid, methyl 4-fluoro-7-methoxy-1H-indole-5-carboxylate replacing methyl 4-chloro-7-methyl-1H-indole-5-carboxylate.

LC-MS (A): $t_R$=0.64 min, [M+H]+: 210.15

B. Synthesis of Amines

B.1. Synthesis of 2-alkyl/(hetero)aryl-2-aminoethanamine

B.1.a. Strecker Reaction (General Procedure I)

To a suspension of the corresponding aldehyde (24.6 mmol) in anh. Et$_2$O (8 mL) was slowly added at RT, TMSCN (27 mmol) followed by ZnI$_2$ (1.23 mmol). The mixture was cooled to 0° C. and a solution of the corresponding amine (24.6 mmol) in anh. MeOH (20 mL) was added dropwise (when the amine was a HCl salt, 24.6 mmol of TEA were additionally added). The mixture was heated at 70° C. for 1 to 6 h then cooled to RT. It was quenched with a 10% Na$_2$CO$_3$ aq. solution and extracted 3 times with EtOAc. The combined organic phases were dried over MgSO$_4$ and concentrated in vacuo. The crude was purified by CC (KP-NH™ from Biotage) to isolate the desired α-amino-nitrile (see table below).

| Name | type | tR (min) | [M + H]+ |
|---|---|---|---|
| 2-morpholino-2-(2-(trifluoromethyl)pyrimidin-5-yl)acetonitrile | B | 0.65 | [M + MeCN + H]+: 313.99 |
| 2-(6-chloropyridin-3-yl)-2-(4,4-difluoropiperidin-1-yl)acetonitrile | B | 0.76 | 272.25 |
| 2-(2-methylpyrimidin-5-yl)-2-morpholinoacetonitrile | B | 0.39 | 219.41 |
| 2-(4,4-difluoropiperidin-1-yl)-2-(2-methylpyrimidin-5-yl)acetonitrile | B | 0.59 | 253.05 |
| 2-(6-methylpyridin-3-yl)-2-morpholinoacetonitrile | B | 0.29 | 218.11 |
| 2-(4,4-difluoropiperidin-1-yl)-2-(2-(trifluoromethyl)pyrimidin-5-yl)acetonitrile | B | 0.80 | [M + MeCN + H]+: 347.93 |
| 2-(2-cyclopropylpyrimidin-5-yl)-2-morpholinoacetonitrile | B | 0.55 | 245.06 |
| 2-morpholino-2-(6-(trifluoromethyl)pyridin-3-yl)acetonitrile | B | 0.68 | 272.01 |
| 2-(6-methoxypyridin-3-yl)-2-morpholinoacetonitrile | B | 0.57 | 234.33 |
| 2-(dimethylamino)-2-(2-methylpyrimidin-5-yl)acetonitrile | B | 0.39 | 177.46 |
| 2-(azetidin-1-yl)-2-(2-methylpyrimidin-5-yl)acetonitrile | B | 0.35 | 189.47 |
| 2-(2-methylpyrimidin-5-yl)-2-(pyrrolidin-1-yl)acetonitrile | B | 0.44 | 203.46 |
| 2-(diethylamino)-2-(2-methylpyrimidin-5-yl)acetonitrile | B | 0.58 | 205.14 |
| 2-(2-methylpyrimidin-5-yl)-2-(piperidin-1-yl)acetonitrile | B | 0.59 | 217.11 |
| 2-(4-fluorophenyl)-2-morpholinoacetonitrile | B | 0.70 | 221.06 |
| 2-(3,5-difluorophenyl)-2-morpholinoacetonitrile | B | 0.74 | 239.05 |
| 2-(6-chloropyridin-3-yl)-2-morpholinoacetonitrile | A | 0.70 | 238.26 |
| 2-morpholino-2-(pyrimidin-5-yl)acetonitrile | E | 0.30 | 205.3 |
| 2-(piperidin-1-yl)-2-(pyrimidin-5-yl)acetonitrile | E | 0.72 | 203.26 |
| 2-(1-methyl-1H-pyrazol-4-yl)-2-morpholinoacetonitrile | E | 0.35 | 207.27 |
| 2-(1-methyl-1H-pyrazol-4-yl)-2-(piperidin-1-yl)acetonitrile | F | 0.56 | 205.3 |
| 2-(piperidin-1-yl)-2-(2,4,6-trifluorophenyl)acetonitrile | F | 0.89 | 255.16 |
| 2-(2,4-difluorophenyl)-2-(piperidin-1-yl)acetonitrile | F | 0.91 | 237.23 |
| 2-(5-fluoropyridin-2-yl)-2-(piperidin-1-yl)acetonitrile | F | 0.74 | 220.26 |
| 2-morpholino-2-(2,4,6-trifluorophenyl)acetonitrile | F | 0.66 | 257.12 |
| 2-(2,4-difluorophenyl)-2-morpholinoacetonitrile | F | 0.68 | 239.21 |
| 2-(2-fluorophenyl)-2-morpholinoacetonitrile | F | 0.64 | 221.26 |
| 2-(5-fluoropyridin-2-yl)-2-morpholinoacetonitrile | F | 0.48 | 222.26 |
| 2-(3-fluorophenyl)-2-morpholinoacetonitrile | F | 0.68 | 221.25 |
| 2-(4-chlorophenyl)-2-morpholinoacetonitrile | A | 0.83 | 237.08 |
| 2-(2,4-dichlorophenyl)-2-morpholinoacetonitrile | A | 0.89 | 270.98 |
| 2-(4-chloro-2-fluorophenyl)-2-morpholinoacetonitrile | A | 0.84 | 255.02 |
| 2-(2,6-dimethylmorpholino)-2-(2-methylpyrimidin-5-yl)acetonitrile | A | 0.66 | 247.32 |
| 2-(3-fluorophenyl)-2-(piperidin-1-yl)acetonitrile | F | 0.93 | 219.28 |
| 2-(piperidin-1-yl)-2-(4-(trifluoromethyl)phenyl)acetonitrile | F | 1.02 | 269.14 |
| 2-(3,4-difluorophenyl)-2-(piperidin-1-yl)acetonitrile | F | 0.96 | 237.22 |

-continued

| Name | LC-MS type | tR (min) | [M + H]+ |
|---|---|---|---|
| 2-(6-chloropyridin-3-yl)-2-(piperidin-1-yl)acetonitrile | F | 0.82 | 236.21 |
| 2-morpholino-2-(p-tolyl)acetonitrile | F | 0.74 | 217.28 |
| 2-morpholino-2-(4-(trifluoromethoxy)phenyl)acetonitrile | F | 0.84 | 287.08 |
| 2-morpholino-2-(4-(trifluoromethyl)phenyl)acetonitrile | F | 0.81 | 271.1 |
| 2-(3,4-difluorophenyl)-2-morpholinoacetonitrile | F | 0.72 | 239.2 |
| 2-(3,5-dimethylisoxazol-4-yl)-2-morpholinoacetonitrile | E | 0.63 | 222.25 |
| 2-(3,5-dimethylisoxazol-4-yl)-2-(piperidin-1-yl)acetonitrile | E | 1.07 | 220.28 |
| 2-(piperidin-1-yl)-2-(p-tolyl)acetonitrile | F | 0.98 | 215.29 |
| 2-(6-chloropyridin-3-yl)-2-(piperidin-1-yl)acetonitrile | F | 0.82 | 236.21 |
| 2-(4-phenoxyphenyl)-2-(piperidin-1-yl)acetonitrile | F | 1.09 | 293.16 |
| 2-morpholino-2-(4-phenoxyphenyl)acetonitrile | F | 0.89 | 295.13 |
| 2-(4-methoxyphenyl)-2-morpholinoacetonitrile | F | 0.67 | 233.24 |
| 2-(5-methylpyrazin-2-yl)-2-(piperidin-1-yl)acetonitrile | F | 0.64 | 217.3 |
| 2-(isothiazol-5-yl)-2-(piperidin-1-yl)acetonitrile | F | 0.76 | 208.2 |
| 2-(piperidin-1-yl)-2-(thiazol-5-yl)acetonitrile | F | 0.66 | 208.22 |
| 2-(5-methylpyrazin-2-yl)-2-morpholinoacetonitrile | F | 0.39 | 219.26 |
| 2-morpholino-2-(thiazol-5-yl)acetonitrile | F | 0.39 | 210.2 |
| 2-(2-oxa-5-azabicyclo[2.2.1]heptan-5-yl)-2-(2-methylpyrimidin-5-yl)acetonitrile | A | 0.54 | 231.16 |
| 2-(piperidin-1-yl)-2-(pyridazin-3-yl)acetonitrile | E | 0.65 | 203.27 |
| 2-(2-hydroxypyridin-4-yl)-2-(piperidin-1-yl)acetonitrile | E | 0.64 | 218.25 |
| tert-butyl 1-(cyano(2-methylpyrimidin-5-yl)methyl)piperidine-4-carboxylate | E | 1.09 | 317.23 |
| 2-(4-methylpiperidin-1-yl)-2-(2-methylpyrimidin-5-yl)acetonitrile | E | 0.95 | 231.27 |
| 2-(2-methylpiperidin-1-yl)-2-(2-methylpyrimidin-5-yl)acetonitrile | E | 0.93 | 231.26 |
| 2-(4-fluoropiperidin-1-yl)-2-(2-methylpyrimidin-5-yl)acetonitrile | E | 0.64 | 235.24 |
| 2-(3,3-difluoropiperidin-1-yl)-2-(2-methylpyrimidin-5-yl)acetonitrile | E | 0.75 | 253.16 |
| 2-(azepan-1-yl)-2-(2-methylpyrimidin-5-yl)acetonitrile | F | 0.71 | 231.26 |
| 2-(2-methylpyrimidin-5-yl)-2-(1,4-oxazepan-4-yl)acetonitrile | E | 0.50 | 233.24 |
| 2-(3,3-difluoropyrrolidin-1-yl)-2-(2-methylpyrimidin-5-yl)acetonitrile | E | 0.66 | 239.19 |
| 2-(cyclopentylamino)-2-(2-methylpyrimidin-5-yl)acetonitrile | E | 0.71 | 217.28 |
| 2-((cyclopentylmethyl)amino)-2-(2-methylpyrimidin-5-yl)acetonitrile | E | 0.90 | 231.28 |
| 2-(isobutylamino)-2-(2-methylpyrimidin-5-yl)acetonitrile | E | 0.72 | 205.29 |
| 2-(isobutyl(methyl)amino)-2-(2-methylpyrimidin-5-yl)acetonitrile | E | 0.97 | 219.29 |
| 2-(benzyl(methyl)amino)-2-(2-methylpyrimidin-5-yl)acetonitrile | E | 0.99 | 253.17 |
| tert-butyl 4-(cyano(2-methylpyrimidin-5-yl)methyl)piperazine-1-carboxylate | F | 0.68 | 318.2 |
| 2-morpholino-2-(pyridazin-3-yl)acetonitrile | E | 0.24 | 205.24 |
| 2-morpholino-2-(2-hydroxypyridin-4-yl)acetonitrile | E | 0.25 | 220.23 |
| 2-(1,1-dioxidothiomorpholino)-2-(2-methylpyrimidin-5-yl)acetonitrile | F | 0.28 | 267.09 |
| 2-(6-oxa-3-azabicyclo[3.1.1]heptan-3-yl)-2-(2-methylpyrimidin-5-yl)acetonitrile | A | 0.56 | 231.13 |

B.1.b. Hydrogenation of Nitrile (General Procedure II)

To a solution of the α-amino-nitrile (4.38 mmol) from the previous step in a 7M solution of NH$_3$ in MeOH (32 mL) were added at 0° C. a 4% solution of thiophene in diisopropylether (0.16 mL) and Actimet M Raney nickel. The mixture was allowed to warm to RT and stirred under a hydrogen atmosphere for 30 h. It was filtered over Celite, washed with MeOH and concentrated in vacuo. The amine was optionally transformed to its HCl salt by dissolution in Et$_2$O (8.8 mL), addition of a 4M HCl solution in dioxane (4.4 mL) at 0° C. and filtration of the formed solid.

| Name | LC-MS type | tR (min) | [M + H]+ |
|---|---|---|---|
| 2-morpholino-2-(2-(trifluoromethyl)pyrimidin-5-yl)ethanamine | B | 0.40 | 277.09 |
| 2-(6-chloropyridin-3-yl)-2-(4,4-difluoropiperidin-1-yl)ethanamine | B | 0.50 | 276.30 |
| 2-(2-methylpyrimidin-5-yl)-2-morpholinoethanamine | B | 0.21 | 223.10 |
| 2-(4,4-difluoropiperidin-1-yl)-2-(2-methylpyrimidin-5-yl)ethanamine | B | 0.40 | 257.07 |
| 2-(6-methylpyridin-3-yl)-2-morpholinoethanamine | B | 0.12 | 222.12 |
| 2-(4,4-difluoropiperidin-1-yl)-2-(2-(trifluoromethyl)pyrimidin-5-yl)ethanamine | B | 0.55 | 311.39 |
| 2-(2-cyclopropylpyrimidin-5-yl)-2-morpholinoethanamine | B | 0.34 | 249.10 |
| 2-morpholino-2-(6-(trifluoromethyl)pyridin-3-yl)ethanamine | B | 0.41 | 276.10 |
| 2-(6-methoxypyridin-3-yl)-2-morpholinoethanamine | B | 0.28 | 238.09 |
| N1,N1-dimethyl-1-(2-methylpyrimidin-5-yl)ethane-1,2-diamine | B | 0.10 | 181.20 |
| 2-(azetidin-1-yl)-2-(2-methylpyrimidin-5-yl)ethanamine | B | 0.10 | 193.18 |
| 2-(2-methylpyrimidin-5-yl)-2-(pyrrolidin-1-yl)ethanamine | B | 0.13 | 207.15 |
| N1,N1-diethyl-1-(2-methylpyrimidin-5-yl)ethane-1,2-diamine | B | 0.15 | 209.19 |
| 2-(2-methylpyrimidin-5-yl)-2-(piperidin-1-yl)ethanamine | B | 0.19 | 221.19 |
| 2-(4-fluorophenyl)-2-morpholinoethanamine | B | 0.31 | 225.12 |
| 2-(3,5-difluorophenyl)-2-morpholinoethanamine | B | 0.41 | 242.98 |
| 2-(6-chloropyridin-3-yl)-2-morpholinoethanamine | A | 0.43 | 242.11 |
| 2-(pyridin-3-yl)-2-morpholinoethanamine (side-product from hydrogenation of 2-(6-chloropyridin-3-yl)-2-morpholinoacetonitrile) | A | 0.17 | 208.48 |
| 2-morpholino-2-(pyrimidin-5-yl)ethanamine | F | 0.16 | 209.3 |
| 2-(piperidin-1-yl)-2-(pyrimidin-5-yl)ethanamine | F | 0.41 | 207.3 |
| 2-(1-methyl-1H-pyrazol-4-yl)-2-morpholinoethanamine | F | 0.19 | 211.28 |
| 2-(1-methyl-1H-pyrazol-4-yl)-2-(piperidin-1-yl)ethanamine | F | 0.53 | 209.32 |
| 2-(piperidin-1-yl)-2-(2,4,6-trifluorophenyl)ethanamine | F | 0.79 | 259.16 |
| 2-(2,4-difluorophenyl)-2-(piperidin-1-yl)ethanamine | F | 0.78 | 241.25 |
| 2-(5-fluoropyridin-2-yl)-2-(piperidin-1-yl)ethanamine | F | 0.55 | 224.3 |
| 2-morpholino-2-(2,4,6-trifluorophenyl)ethanamine | F | 0.56 | 261.13 |
| 2-(2,4-difluorophenyl)-2-morpholinoethanamine | F | 0.53 | 243.23 |
| 2-(2-fluorophenyl)-2-morpholinoethanamine | F | 0.49 | 225.27 |

| Name | LC-MS type | tR (min) | [M + H]+ |
|---|---|---|---|
| 2-(5-fluoropyridin-2-yl)-2-morpholinoethanamine | F | 0.35 | 226.27 |
| 2-(3-fluorophenyl)-2-morpholinoethanamine | F | 0.50 | 225.27 |
| 2-(4-chlorophenyl)-2-morpholinoethanamine | A | 0.46 | 241.23 |
| 2-(2,4-dichlorophenyl)-2-morpholinoethanamine | A | 0.57 | 275.33 |
| 2-(4-chloro-2-fluorophenyl)-2-morpholinoethanamine | A | 0.54 | 259.29 |
| 2-(2,6-dimethylmorpholino)-2-(2-methylpyrimidin-5-yl)ethanamine | A | 0.41 | 251.36 |
| 2-(3-fluorophenyl)-2-(piperidin-1-yl)ethanamine | F | 0.78 | 223.3 |
| 2-(piperidin-1-yl)-2-(4-(trifluoromethyl)phenyl)ethanamine | F | 0.91 | 273.2 |
| 2-(3,4-difluorophenyl)-2-(piperidin-1-yl)ethanamine | F | 0.87 | 241.24 |
| 2-(6-chloropyridin-3-yl)-2-(piperidin-1-yl)ethanamine | F | 0.63 | 240.21 |
| 2-(pyridin-3-yl)-2-(piperidin-1-yl)ethanamine (side-product from hydrogenation of 2-(6-chloropyridin-3-yl)-2-(piperidin-1-yl)acetonitrile) | F | 0.54 | 206.3 |
| 2-morpholino-2-(p-tolyl)ethanamine | F | 0.58 | 221.31 |
| 2-morpholino-2-(4-(trifluoromethoxy)phenyl)ethanamine | F | 0.70 | 291.12 |
| 2-morpholino-2-(4-(trifluoromethyl)phenyl)ethanamine | F | 0.67 | 275.11 |
| 2-(3,4-difluorophenyl)-2-morpholinoethanamine | F | 0.58 | 243.22 |
| 2-(3,5-dimethylisoxazol-4-yl)-2-morpholinoethanamine | F | 0.38 | 226.3 |
| 2-(3,5-dimethylisoxazol-4-yl)-2-(piperidin-1-yl)ethanamine | F | 0.58 | 224.3 |
| 2-(piperidin-1-yl)-2-(p-tolyl)ethanamine | F | 0.93 | 219.33 |
| 2-(6-chloropyridin-3-yl)-2-(piperidin-1-yl)ethanamine | F | 0.62 | 240.21 |
| 2-(4-phenoxyphenyl)-2-(piperidin-1-yl)ethanamine | F | 1.05 | 297.19 |
| 2-morpholino-2-(4-phenoxyphenyl)ethanamine | F | 0.76 | 299.17 |
| 2-(4-methoxyphenyl)-2-morpholinoethanamine | F | 0.50 | 237.27 |
| 2-(5-methylpyrazin-2-yl)-2-(piperidin-1-yl)ethanamine | F | 0.52 | 221.33 |
| 2-(isothiazol-5-yl)-2-(piperidin-1-yl)ethanamine | F | 0.54 | 212.29 |
| 2-(piperidin-1-yl)-2-(thiazol-5-yl)ethanamine | F | 0.50 | 212.26 |
| 2-(5-methylpyrazin-2-yl)-2-morpholinoethanamine | F | 0.27 | 223.3 |
| 2-morpholino-2-(thiazol-5-yl)ethanamine | F | 0.23 | 214.25 |
| 2-(2-oxa-5-azabicyclo[2.2.1]heptan-5-yl)-2-(2-methylpyrimidin-5-yl)ethanamine | A | 0.27 | 235.17 |
| 2-(piperidin-1-yl)-2-(pyridazin-3-yl)ethanamine | F | 0.43 | 207.3 |
| 4-(2-amino-1-(piperidin-1-yl)ethyl)pyridin-2-ol | F | 0.37 | 222.26 |
| tert-butyl 1-(2-amino-1-(2-methylpyrimidin-5-yl)ethyl)piperidine-4-carboxylate | F | 0.62 | 321.25 |
| 2-(4-methylpiperidin-1-yl)-2-(2-methylpyrimidin-5-yl)ethanamine | F | 0.53 | 235.28 |
| 2-(2-methylpiperidin-1-yl)-2-(2-methylpyrimidin-5-yl)ethanamine | F | 0.52 | 235.28 |
| 2-(4-fluoropiperidin-1-yl)-2-(2-methylpyrimidin-5-yl)ethanamine | F | 0.38 | 239.23 |
| 2-(3,3-difluoropiperidin-1-yl)-2-(2-methylpyrimidin-5-yl)ethanamine | F | 0.44 | 257.17 |
| 2-(azepan-1-yl)-2-(2-methylpyrimidin-5-yl)ethanamine | F | 0.56 | 235.28 |
| 2-(2-methylpyrimidin-5-yl)-2-(1,4-oxazepan-4-yl)ethanamine | F | 0.31 | 237.25 |
| 2-(3,3-difluoropyrrolidin-1-yl)-2-(2-methylpyrimidin-5-yl)ethanamine | F | 0.38 | 243.2 |
| N1-cyclopentyl-1-(2-methylpyrimidin-5-yl)ethane-1,2-diamine | F | 0.44 | 221.29 |
| N1-(cyclopentylmethyl)-1-(2-methylpyrimidin-5-yl)ethane-1,2-diamine | F | 0.54 | 235.3 |
| N1-isobutyl-1-(2-methylpyrimidin-5-yl)ethane-1,2-diamine | F | 0.44 | 209.3 |
| N1-isobutyl-N1-methyl-1-(2-methylpyrimidin-5-yl)ethane-1,2-diamine | F | 0.57 | 223.3 |
| N1-benzyl-N1-methyl-1-(2-methylpyrimidin-5-yl)ethane-1,2-diamine | F | 0.61 | 257.18 |
| tert-butyl 4-(2-amino-1-(2-methylpyrimidin-5-yl)ethyl)piperazine-1-carboxylate | F | 0.54 | 322.25 |
| 2-morpholino-2-(pyridazin-3-yl)ethanamine | F | 0.17 | 209.3 |
| 4-(2-amino-1-morpholinoethyl)pyridin-2-ol | F | 0.12 | 224.3 |
| 4-(2-amino-1-(2-methylpyrimidin-5-yl)ethyl)thiomorpholine 1,1-dioxide | F | 0.15 | 271.1 |
| 2-(6-oxa-3-azabicyclo[3.1.1]heptan-3-yl)-2-(2-methylpyrimidin-5-yl)ethanamine | A | 0.33 | 235.22 |

B.2. Synthesis of 2-alkyl/cycloalkyl-2-heteroaryl-ethanamine

B.2.a. Synthesis of tert-butyl 4-(2-amino-1-(pyridin-3-yl)ethyl)piperidine-1-carboxylate B.2.a.1. tert-Butyl 4-((6-chloropyridin-3-yl)(cyano)methylene)piperidine-1-carboxylate To a solution of 2-(6-chloro-3-pyridinyl)acetonitrile (6.52 mmol) in MeOH (26 mL) was added a 30% solution of NaOMe in MeOH (13 mmol) followed by 1-Boc-4-piperidone (6.52 mmol). The mixture was heated to 70° C. for 5 h, poured into cold $H_2O$ and extracted 3 times with EtOAc. The combined organic phases were dried over $MgSO_4$ and concentrated in vacuo. The crude was purified by CC (KP-Sil™ from Biotage) using Hept/EtOAc from 1/0 to 7/3 to give the title compound as colorless oil.

LC-MS (B): $t_R$=0.85 min; [M+$CH_3CN$+H]+: 375.32

B.2.a.2. tert-Butyl 4-(2-amino-1-(pyridin-3-yl)ethylidene)piperidine-1-carboxylate This compound was prepared using a method analogous to that of general procedure II (hydrogenation of nitrile), tert-butyl 4-((6-chloropyridin-3-yl)(cyano)methylene)piperidine-1-carboxylate replacing α-amino-nitrile. The crude was purified by preparative LC-MS method I to give the title compound as white solid.

LC-MS (B): $t_R$=0.43 min; [M+H]+: 304.11

B.2.a.3. tert-Butyl 4-(2-amino-1-(pyridin-3-yl)ethyl)piperidine-1-carboxylate

To a solution of tert-butyl 4-(2-amino-1-(pyridin-3-yl)ethylidene)piperidine-1-carboxylate (1.27 mmol) in a 7M solution of $NH_3$ in MeOH (20 mL) was added 10% palladium on activated charcoal (135 mg). The mixture was stirred under a hydrogen atmosphere for 2 h 30 min. It was filtered over Celite, washed with MeOH and concentrated in vacuo to give the title compound as white foam.

LC-MS (B): $t_R$=0.42 min; [M+H]+: 306.31

B.2.b. Synthesis of 2-(2-methylpyrimidin-5-yl)-2-(tetrahydro-2H-pyran-4-yl)ethanamine

B.2.b.1. 2-(2-Methylpyrimidin-5-yl)acetonitrile

This compound was synthesized according to *JACS*, 2011, 133, 6948-6951

To a solution of 5-bromo-2-methylpyrimidine (5.78 mmol) and 4-isoxazoleboronic acid pinacol ester (6.07 mmol) in DMSO (40 mL) was added a solution of potassium fluoride (17.30 mmol) in water (17 mL). The mixture was flushed with argon, Pd(dppf)Cl$_2$.DCM (0.58 mmol) was added and the mixture was heated for 48 h at 130° C. It was filtered over a pad of Celite and washed with EtOAc. The filtrate was partitioned between water and EtOAc and the aqueous phase was extracted twice with EtOAc. The combined organic phases were dried over MgSO$_4$ and concentrated in vacuo. The crude was purified by CC using DCM/MeOH from 1/0 to 95/5 to give the title compound as brown oil.

LC-MS (A): $t_R$=0.43 min; [M+H]+: 134.10

B.2.b.2. 2-(Dihydro-2H-pyran-4(3H)-ylidene)-2-(2-methylpyrimidin-5-yl)acetonitrile This compound was prepared using a method analogous to that of tert-butyl 4-((6-chloropyridin-3-yl)(cyano)methylene)piperidine-1-carboxylate, 2-(2-methylpyrimidin-5-yl)acetonitrile replacing 2-(6-chloro-3-pyridinyl)acetonitrile and tetrahydro-4H-pyran-4-one replacing 1-Boc-4-piperidone except that the reaction mixture was stirred for 20 min at 50° C.

LC-MS (A): $t_R$=0.61 min; [M+H]+: 216.09

B.2.b.3. 2-(2-Methylpyrimidin-5-yl)-2-(tetrahydro-2H-pyran-4-yl)ethanamine

To a solution of 2-(dihydro-2H-pyran-4(3H)-ylidene)-2-(2-methylpyrimidin-5-yl)acetonitrile (0.22 mmol) in a 7M solution of NH$_3$ in MeOH (3 mL) was added 10% palladium on activated charcoal (24 mg). The mixture was stirred under a hydrogen atmosphere for 24 h. It was filtered over Celite and the filtrate was treated with Actimet M Raney nickel (25 mg) at 0° C. The mixture was allowed to warm to RT and stirred under a hydrogen atmosphere for 4 h. It was filtered over Celite, washed with DCM/MeOH 8/2 and concentrated in vacuo to give the title compound as orange oil.

LC-MS (A): $t_R$=0.38 min; [M+H]+: 222.14

B.2.c. Synthesis of 2-(6-chloropyridin-3-yl)-2-cyclohexylethanamine

B.2.c.1. 2-(6-Chloropyridin-3-yl)-2-cyclohexylideneacetonitrile

To a solution of KOH (1.32 mmol) in MeOH (1.5 mL) was added at 0° C. 2-(6-chloro-3-pyridinyl)acetonitrile (1.32 mmol) followed by cyclohexanone (1.32 mmol). The mixture was stirred ON allowing temperature to reach RT. It was quenched with a sat. solution of NH$_4$Cl, diluted with water and extracted 3 times with EtOAc. The combined organic phases were dried over MgSO$_4$ and concentrated in vacuo to give the crude as orange oil.

LC-MS (A): $t_R$=0.90 min; [M+H]+: 233.15

B.2.c.2. 2-(6-Chloropyridin-3-yl)-2-cyclohexylethanamine

To a solution of 2-(6-chloropyridin-3-yl)-2-cyclohexylideneacetonitrile (1.28 mmol) in THF (3 mL) was added a 1M solution of BH$_3$ in THF (3.83 mmol). The mixture was heated for 3 h at 60° C. and quenched at 0° C. with MeOH followed by water. The volatiles were evaporated off and the residue diluted with water and acidified with a 1M solution of HCl until pH 1-2. The aqueous phase was washed 3 times with EtOAc, acidified with a 32% solution of NaOH until pH 13-14 and extracted 3 times with EtOAc. The combined organic phases were dried over MgSO$_4$ and concentrated in vacuo to give the title compound as light yellow oil.

LC-MS (A): $t_R$=0.63 min; [M+H]+: 239.17

B.2.d. Synthesis of 2-(6-chloropyridin-3-yl)-4-methylpentan-1-amine

B.2.d.1. 2-(6-Chloropyridin-3-yl)-4-methylpent-2-enenitrile

This compound was prepared using a method analogous to that of 2-(6-chloropyridin-3-yl)-2-cyclohexylideneacetonitrile, isobutyraldehyde replacing cyclohexanone except that the reaction mixture was stirred for 30 min at 0° C.

LC-MS (A): $t_R$=0.88 min; [M+H]+: 207.16

B.2.d.2. 2-(6-Chloropyridin-3-yl)-4-methylpentan-1-amine

This compound was prepared using a method analogous to that of 2-(6-chloropyridin-3-yl)-2-cyclohexylethanamine, 2-(6-chloropyridin-3-yl)-4-methylpent-2-enenitrile replacing 2-(6-chloropyridin-3-yl)-2-cyclohexylideneacetonitrile except that the reaction mixture was stirred for 30 min at 60° C.

LC-MS (A): $t_R$=0.59 min; [M+H]+: 213.16

B.2.e. Synthesis of 3-Ethyl-2-(pyrimidin-5-yl)pentan-1-amine

B.2.e.1. 3-Ethyl-2-(pyrimidin-5-yl)pent-2-enenitrile

This compound was prepared using a method analogous to that of tert-butyl 4-((6-chloropyridin-3-yl)(cyano)methylene)piperidine-1-carboxylate, 5-pyrimidineacetonitrile replacing 2-(6-chloro-3-pyridinyl)acetonitrile and 3-pentanone replacing 1-Boc-4-piperidone except that the reaction mixture was stirred ON at 50° C.

LC-MS (A): $t_R$=0.76 min; [M+H]+: 188.24

B.2.e.2. 3-Ethyl-2-(pyrimidin-5-yl)pentan-1-amine

This compound was prepared using a method analogous to that of 2-(2-methylpyrimidin-5-yl)-2-(tetrahydro-2H-pyran-4-yl)ethanamine, 3-ethyl-2-(pyrimidin-5-yl)pent-2-enenitrile replacing 2-(dihydro-2H-pyran-4(3H)-ylidene)-2-(2-methylpyrimidin-5-yl)acetonitrile.

LC-MS (A): $t_R$=0.50 min; [M+CH$_3$CN+H]+: 235.18

B.2.f. 2-(4,4-Difluorocyclohexyl)-2-(2-methylpyrimidin-5-yl)ethanamine

B.2.f.1. 2-(4,4-Difluorocyclohexylidene)-2-(2-methylpyrimidin-5-yl)acetonitrile This compound was prepared using a method analogous to that of 2-(6-chloropyridin-3-yl)-2-cyclohexylideneacetonitrile, 2-(2-methylpyrimidin-5-yl)acetonitrile replacing 2-(6-chloro-3-pyridinyl)acetonitrile and 4,4-difluorocyclohexanone replacing cyclohexanone except that the reaction mixture was stirred for 2 h 30 min at 50° C.
LC-MS (A): $t_R$=0.76 min; [M+H]+: 250.11

B.2.f.2. 2-(4,4-Difluorocyclohexyl)-2-(2-methylpyrimidin-5-yl)ethanamine

This compound was prepared using a method analogous to that of 2-(2-methylpyrimidin-5-yl)-2-(tetrahydro-2H-pyran-4-yl)ethanamine, 2-(4,4-difluorocyclohexylidene)-2-(2-methylpyrimidin-5-yl)acetonitrile replacing 2-(dihydro-2H-pyran-4(3H)-ylidene)-2-(2-methylpyrimidin-5-yl) acetonitrile.
LC-MS (A): $t_R$=0.50 min; [M+CH$_3$CN+H]+: 297.26

B.3. Synthesis of 2-alkoxy/cycloalkoxy-2-heteroarylethanamine

B.3.a. Synthesis of 2-(cyclopentyloxy)-2-(2-methylpyrimidin-5-yl)ethanamine

B.3.a.1. 1-(2-Methylpyrimidin-5-yl)-2-nitroethanol

To a mixture of 2-methyl-pyrimidine-5-carbaldehyde (13.9 mmol) and nitromethane (22.2 mmol) in THF (8.33 mL) and tBuOH (8.33 mL) was added portionwise at 0° C. tBuOK (0.83 mmol). The mixture was stirred for 5 min at 0° C., quenched with water and volatiles were evaporated off. The residue was partitioned between water and EtOAc. The organic phase was dried over MgSO$_4$ and concentrated in vacuo. The crude was purified by CC using Hept/EtOAc from 1/1 to 0/1 to give the title compound as yellowish solid.
LC-MS (A): $t_R$=0.40 min; [M+H]+: 184.13

B.3.a.2. 2-Methyl-5-(2-nitrovinyl) pyrimidine

To a solution of 1-(2-methylpyrimidin-5-yl)-2-nitroethanol (6.73 mmol) in DCM (33.6 mL) was added DMAP (0.34 mmol) followed by Ac$_2$O (7.40 mmol). The mixture was stirred for 3 days at RT, quenched with a sat. solution of NaHCO$_3$ and extracted 3 times with DCM. The combined organic phases were dried over MgSO$_4$ and concentrated in vacuo. The crude was purified by CC using Hept/EtOAc from 75/25 to 30/70 to give the title compound as yellow solid.
LC-MS (A): $t_R$=0.56 min; [M+CH$_3$CN+H]+: 207.42

B.3.a.3. 5-(1-(Cyclopentyloxy)-2-nitroethyl)-2-methylpyrimidine

To a suspension of tBuOK (1.31 mmol) in THF (3.84 mL) and tBuOH (0.77 mL) under argon was added cyclopentanol (1.15 mmol). The mixture was cooled to 0° C. and a solution of 2-methyl-5-(2-nitrovinyl)pyrimidine (0.77 mmol) in THF (0.5 mL) was added dropwise. It was stirred for 5 min at 0° C. then for 30 min at RT, quenched with a 2M solution of HCl and filtered over a pad of celite. The filtrate was diluted with water and extracted twice with EtOAc. The combined organic phases were dried over MgSO$_4$ and concentrated in vacuo. The crude was purified by CC using Hept/EtOAc from 1/0 to 0/1 to give the title compound as white solid.
LC-MS (A): $t_R$=0.79 min; [M+H]+: 252.16

B.3.a.4. 2-(Cyclopentyloxy)-2-(2-methylpyrimidin-5-yl)ethanamine

To a solution of 5-(1-(cyclopentyloxy)-2-nitroethyl)-2-methylpyrimidine (0.22 mmol) in EtOH (1.45 mL) was added 10% palladium on activated charcoal (7.8 mg). The mixture was stirred under a hydrogen atmosphere for 3 h. It was filtered over Celite and the filtrate was concentrated in vacuo to give the title compound as yellow oil.
LC-MS (B): $t_R$=0.49 min; [M+CH$_3$CN+H]+: 263.22

B.3.b. Synthesis of 2-ethoxy-2-(2-methylpyrimidin-5-yl)ethanamine

B.3.b.1. 5-(1-Ethoxy-2-nitroethyl)-2-methylpyrimidine

This compound was prepared using a method analogous to that of 5-(1-(cyclopentyloxy)-2-nitroethyl)-2-methylpyrimidine, ethanol replacing cyclopentanol.
LC-MS (A): $t_R$=0.63 min; [M+H]+: 212.17

B.3.b.2. 2-Ethoxy-2-(2-methylpyrimidin-5-yl)ethanamine

This compound was prepared using a method analogous to that of 2-(cyclopentyloxy)-2-(2-methylpyrimidin-5-yl) ethanamine, 5-(1-ethoxy-2-nitroethyl)-2-methylpyrimidine replacing 5-(1-(cyclopentyloxy)-2-nitroethyl)-2-methylpyrimidine except that 10% palladium on activated charcoal was replaced by platinum dioxide and the reaction mixture was stirred ON.
LC-MS (C): $t_R$=0.31 min; [M+CH$_3$CN+H]+: 223.21

B.3.c. Synthesis of 2-(cyclohexyloxy)-2-(2-methylpyrimidin-5-yl)ethanamine

B.3.c.1. 5-(1-(Cyclohexyloxy)-2-nitroethyl)-2-methylpyrimidine

To a suspension of NaH (1.70 mmol) in THF (1.89 mL) was added at 0° C. cyclohexanol (6 mmol). The mixture was stirred for 5 min and a solution of 2-methyl-5-(2-nitrovinyl) pyrimidine (0.30 mmol) in THF (2 mL) was added dropwise at 0° C. It was stirred for 5 min at 0° C. then for 1.5 h allowing temperature to reach 10° C. It was quenched with AcOH and filtered over a pad of celite. The cake was washed with EtOAc and the filtrate was concentrated in vacuo. The crude was purified by CC using Hept/EtOAc from 8/2 to 25/75 to give the title compound as yellow oil.
LC-MS (A): $t_R$=0.83 min; [M+H]+: 266.24

B.3.c.2. 2-(Cyclohexyloxy)-2-(2-methylpyrimidin-5-yl)ethanamine

This compound was prepared using a method analogous to that of 2-(cyclopentyloxy)-2-(2-methylpyrimidin-5-yl) ethanamine, 5-(1-(cyclohexyloxy)-2-nitroethyl)-2-methylpyrimidine replacing 5-(1-(cyclopentyloxy)-2-nitroethyl)-2-methylpyrimidine except that platinum dioxide was used as catalyst instead of 10% palladium on activated charcoal and the reaction mixture was stirred ON.
LC-MS (A): $t_R$=0.52 min; [M+H]+: 235.91

B.3.d. Synthesis of 2-(2-methylpyrimidin-5-yl)-2-((tetrahydro-2H-pyran-4-yl)oxy)ethanamine

B.3.d.1. 2-Methyl-5-(2-nitro-1-((tetrahydro-2H-pyran-4-yl)oxy)ethyl)pyrimidine This compound was prepared using a method analogous to that of 5-(1-(cyclohexyloxy)-2-nitroethyl)-2-methylpyrimidine, tetrahydro-2H-pyran-4-ol replacing cyclohexanol.
LC-MS (A): $t_R$=0.62 min; [M+H]+: 267.93

B.3.d.2. 2-(2-Methylpyrimidin-5-yl)-2-((tetrahydro-2H-pyran-4-yl)oxy)ethanamine This compound was prepared using a method analogous to that of 2-(cyclopentyloxy)-2-(2-methylpyrimidin-5-yl)ethanamine, 2-methyl-5-(2-nitro-1-((tetrahydro-2H-pyran-4-yl)oxy)ethyl)pyrimidine replacing 5-(1-(cyclopentyloxy)-2-nitroethyl)-2-methylpyrimidine except that platinum dioxide was used as catalyst instead of 10% palladium on activated charcoal and the reaction mixture was stirred for 1.5 h.

LC-MS (A): $t_R$=0.39 min; [M+H]+: 238.20

B.3.e. Synthesis of 2-(2-methylpyrimidin-5-yl)-2-(pentan-3-yloxy)ethanamine

B.3.e.1. 2-Methyl-5-(2-nitro-1-(pentan-3-yloxy)ethyl)pyrimidine

This compound was prepared using a method analogous to that of 5-(1-(cyclohexyloxy)-2-nitroethyl)-2-methylpyrimidine, 3-pentanol replacing cyclohexanol.

LC-MS (A): $t_R$=0.81 min; [M+H]+: 254.18

B.4. 2-(2-methylpyrimidin-5-yl)-2-(pentan-3-yloxy)ethanamine

This compound was prepared using a method analogous to that of 2-(cyclopentyloxy)-2-(2-methylpyrimidin-5-yl)ethanamine, 2-methyl-5-(2-nitro-1-(pentan-3-yloxy)ethyl)pyrimidine replacing 5-(1-(cyclopentyloxy)-2-nitroethyl)-2-methylpyrimidine except that platinum dioxide was used as catalyst instead of 10% palladium on activated charcoal and the reaction mixture was stirred ON.

LC-MS (A): $t_R$=0.51 min; [M+H]+: 225.04

C. Chiral Separation of Amines of Formula (III)

C.1. Synthesis of 2-(2-methylpyrimidin-5-yl)-2-morpholinoethanamine (Enantiomer A) and 2-(2-methylpyrimidin-5-yl)-2-morpholinoethanamine (Enantiomer B)

2-(2-Methylpyrimidin-5-yl)-2-morpholinoethanamine as racemate was separated into the two enantiomers using preparative chiral HPLC (Daicel, ChiralPak IC, 5 μm, 20×250 mm, $CH_3CN$/(EtOH+0.1% DEA) 90/10, flow: 18 mL/min, detection: UV 210 nm).

Both enantiomers were characterized by analytical chiral HPLC (Daicel, ChiralPak IC, 5 μm, 4.6×250 mm, $CH_3CN$/(EtOH+0.1% DEA) 90/10, flow: 0.8 mL/min, detection: UV 210 to 280 nm)

Enantiomer A: $t_R$=12.63 min

Enantiomer B: $t_R$=17.92 min

Both enantiomers were transformed to their HCl salt following the procedure described above (under B.1.b)

Enantiomer A: LC-MS (A): $t_R$=0.36 min; [M+H]+: 223.21

Enantiomer B: LC-MS (A): $t_R$=0.36 min; [M+H]+: 223.18

PREPARATION OF EXAMPLES

A. Synthesis of Compounds of Formula I (General Procedure for Amide Coupling)

To a solution of the respective carboxylic acid precursor of formula II (0.23 mmol) in a mixture of DCM/DMF (0.4 mL) were consecutively added DIPEA (0.69 mmol), HOBt (0.28 mmol) and EDC.HCl (0.28 mmol) followed by a solution of the respective amine precursor of formula III (0.25 mmol) in DCM (0.1 mL). The mixture was stirred ON at RT, diluted with DCM and washed twice with a 5% solution of $KHSO_4$ (when appropriate), with a sat. solution of $NaHCO_3$ and with brine (when appropriate). The organic phase was dried over $MgSO_4$ and concentrated in vacuo. The crude was purified using conditions which are detailed in the table below.

All compounds in the following table were synthesized according to the aforementioned general procedure except compounds which are marked with "see below under section B" or "see below under section C"; such compounds were synthesized according to the specific procedures given in sections "B. Chiral separation of compounds of formula (I)" or "C. Post amide coupling steps" below.

| | | | LC-MS | | |
|---|---|---|---|---|---|
| Compound | Name | Purification method | type | tR (min) | [M + H]+ |
| Example 1 | rac-4-Chloro-1H-indole-5-carboxylic acid [2-morpholin-4-yl-2-(2-trifluoromethyl-pyrimidin-5-yl)-ethyl]-amide | a + IV | C | 0.65 | 453.94 |
| Example 2 | rac-4-Chloro-1H-indole-5-carboxylic acid [2-(6-chloro-pyridin-3-yl)-2-(4,4-difluoro-piperidin-1-yl)-ethyl]-amide | b | B | 0.61 | 452.88 |
| Example 3 | 4-Chloro-1H-indole-5-carboxylic acid [2-(2-methyl-pyrimidin-5-yl)-2-morpholin-4-yl-ethyl]-amide (enantiomer A) | see below under section B. | | | |
| Example 4 | 4-Chloro-1H-indole-5-carboxylic acid [2-(2-methyl-pyrimidin-5-yl)-2-morpholin-4-yl-ethyl]-amide (enantiomer B) | see below under section B. | | | |
| Example 5 | 4-Chloro-1H-indole-5-carboxylic acid [2-(4,4-difluoro-piperidin-1-yl)-2-(2-methyl-pyrimidin-5-yl)-ethyl]-amide (enantiomer A) | see below under section B. | | | |
| Example 6 | 4-Chloro-1H-indole-5-carboxylic acid [2-(4,4-difluoro-piperidin-1-yl)-2-(2-methyl-pyrimidin-5-yl)-ethyl]-amide (enantiomer B) | see below under section B. | | | |

-continued

| Compound | Name | Purification method | LC-MS type | tR (min) | [M + H]+ |
|---|---|---|---|---|---|
| Example 7 | rac-4-Chloro-1H-indole-5-carboxylic acid [2-(6-methyl-pyridin-3-yl)-2-morpholin-4-yl-ethyl]-amide | IV | B | 0.40 | 398.83 |
| Example 8 | rac-4-Chloro-1H-indole-5-carboxylic acid [2-(4,4-difluoro-piperidin-1-yl)-2-(2-trifluoromethyl-pyrimidin-5-yl)-ethyl]-amide | c + d | B | 0.77 | 488.45 |
| Example 9 | rac-4-Chloro-1H-indole-5-carboxylic acid [2-(2-cyclopropyl-pyrimidin-5-yl)-2-morpholin-4-yl-ethyl]-amide | IV | B | 0.48 | 425.78 |
| Example 10 | rac-4-Chloro-1H-indole-5-carboxylic acid [2-morpholin-4-yl-2-(6-trifluoromethyl-pyridin-3-yl)-ethyl]-amide | IV | B | 0.56 | 453.25 |
| Example 11 | rac-4-Chloro-1H-indole-5-carboxylic acid [2-(6-methoxy-pyridin-3-yl)-2-morpholin-4-yl-ethyl]-amide | IV | B | 0.48 | 414.98 |
| Example 12 | rac-4-Chloro-1H-indole-5-carboxylic acid [2-dimethylamino-2-(2-methyl-pyrimidin-5-yl)-ethyl]-amide | V + d | B | 0.40 | 358.00 |
| Example 13 | rac-4-Chloro-1H-indole-5-carboxylic acid [2-azetidin-1-yl-2-(2-methyl-pyrimidin-5-yl)-ethyl]-amide | V + d | B | 0.42 | 369.80 |
| Example 14 | rac-4-Chloro-1H-indole-5-carboxylic acid [2-(2-methyl-pyrimidin-5-yl)-2-pyrrolidin-1-yl-ethyl]-amide | V + d | B | 0.42 | 384.05 |
| Example 15 | rac-4-Chloro-1H-indole-5-carboxylic acid [2-diethylamino-2-(2-methyl-pyrimidin-5-yl)-ethyl]-amide | IV | B | 0.43 | 385.79 |
| Example 16 | rac-4-Chloro-1H-indole-5-carboxylic acid [2-(2-methyl-pyrimidin-5-yl)-2-piperidin-1-yl-ethyl]-amide | IV | B | 0.43 | 398.37 |
| Example 17 | rac-4-Chloro-1H-indole-5-carboxylic acid [2-(4-fluoro-phenyl)-2-morpholin-4-yl-ethyl]-amide | IV + e | B | 0.53 | 401.73 |
| Example 18 | rac-4-Chloro-1H-indole-5-carboxylic acid [2-(3,5-difluoro-phenyl)-2-morpholin-4-yl-ethyl]-amide | IV + e | B | 0.56 | 420.01 |
| Example 19 | rac-4-{2-[(4-Chloro-1H-indole-5-carbonyl)-amino]-1-pyridin-3-yl-ethyl}-piperidine-1-carboxylic acid tent-butyl ester | f | B | 0.61 | 483.56 |
| Example 20 | rac-4-Chloro-1H-indole-5-carboxylic acid (2-piperidin-4-yl-2-pyridin-3-yl-ethyl)-amide | see below under section C. | | | |
| Example 21 | rac-4-Chloro-1H-indole-5-carboxylic acid [2-(1-methyl-piperidin-4-yl)-2-pyridin-3-yl-ethyl]-amide formic acid salt | see below under section C. | | | |
| Example 22 | rac-4-Chloro-1H-indole-5-carboxylic acid [2-(1-acetyl-piperidin-4-yl)-2-pyridin-3-yl-ethyl]-amide | see below under section C. | | | |
| Example 23 | rac-4-Chloro-1H-indole-5-carboxylic acid [2-(1-methanesulfonyl-piperidin-4-yl)-2-pyridin-3-yl-ethyl]-amide | see below under section C. | | | |
| Example 24 | rac-4-Chloro-1H-indole-5-carboxylic acid [2-(6-chloro-pyridin-3-yl)-2-morpholin-4-yl-ethyl]-amide | e | A | 0.60 | 418.95 |

-continued

| Compound | Name | Purification method | LC-MS type | tR (min) | [M + H]+ |
|---|---|---|---|---|---|
| Example 25 | rac-4-Chloro-1H-indole-5-carboxylic acid (2-morpholin-4-yl-2-pyridin-3-yl-ethyl)-amide | e | A | 0.61 | 385.05 |
| Example 26 | rac-4-Chloro-1H-indole-5-carboxylic acid (2-morpholin-4-yl-2-pyrimidin-5-yl-ethyl)-amide | 3 | E | 0.62 | 386.17 |
| Example 27 | rac-4-Chloro-1H-indole-5-carboxylic acid (2-piperidin-1-yl-2-pyrimidin-5-yl-ethyl)-amide | 4 | E | 0.89 | 384.17 |
| Example 28 | rac-4-Chloro-1H-indole-5-carboxylic acid [2-(1-methyl-1H-pyrazol-4-yl)-2-morpholin-4-yl-ethyl]-amide | 4 | E | 0.67 | 388.18 |
| Example 29 | rac-4-Chloro-1H-indole-5-carboxylic acid [2-(1-methyl-1H-pyrazol-4-yl)-2-piperidin-1-yl-ethyl]-amide | 4 | E | 0.96 | 386.16 |
| Example 30 | rac-4-Chloro-1H-indole-5-carboxylic acid [2-piperidin-1-yl-2-(2,4,6-trifluoro-phenyl)-ethyl]-amide | 5 | E | 1.41 | 436.05 |
| Example 31 | rac-4-Chloro-1H-indole-5-carboxylic acid [2-(2,4-difluoro-phenyl)-2-piperidin-1-yl-ethyl]-amide | 5 | E | 1.39 | 418.08 |
| Example 32 | rac-4-Chloro-1H-indole-5-carboxylic acid [2-(5-fluoro-pyridin-2-yl)-2-piperidin-1-yl-ethyl]-amide | 5 | E | 1.18 | 401.16 |
| Example 33 | rac-4-Chloro-1H-indole-5-carboxylic acid [2-morpholin-4-yl-2-(2,4,6-trifluoro-phenyl)-ethyl]-amide | 5 | E | 1.08 | 437.71 |
| Example 34 | rac-4-Chloro-1H-indole-5-carboxylic acid [2-(2,4-difluoro-phenyl)-2-morpholin-4-yl-ethyl]-amide | 5 | E | 1.06 | 420.05 |
| Example 35 | rac-4-Chloro-1H-indole-5-carboxylic acid [2-(2-fluoro-phenyl)-2-morpholin-4-yl-ethyl]-amide | 4 | E | 1.02 | 402.11 |
| Example 36 | rac-4-Chloro-1H-indole-5-carboxylic acid [2-(5-fluoro-pyridin-2-yl)-2-morpholin-4-yl-ethyl]-amide | 4 | E | 0.86 | 403.11 |
| Example 37 | rac-4-Chloro-1H-indole-5-carboxylic acid [2-(3-fluoro-phenyl)-2-morpholin-4-yl-ethyl]-amide | 4 | E | 1.03 | 402.11 |
| Example 38 | rac-4-Chloro-1H-indole-5-carboxylic acid [2-(4-chloro-phenyl)-2-morpholin-4-yl-ethyl]-amide | b + VI | A | 0.65 | 418.22 |
| Example 39 | rac-4-Chloro-1H-indole-5-carboxylic acid [2-(2,4-dichloro-phenyl)-2-morpholin-4-yl-ethyl]-amide | VI | A | 0.67 | 452.40 |
| Example 40 | rac-4-Chloro-1H-indole-5-carboxylic acid [2-(4-chloro-2-fluoro-phenyl)-2-morpholin-4-yl-ethyl]-amide | VI | A | 0.66 | 436.41 |
| Example 41 | 4-Chloro-1H-indole-5-carboxylic acid [2-(2,6-dimethyl-morpholin-4-yl)-2-(2-methyl-pyrimidin-5-yl)-ethyl]-amide (mixture A of stereoisomers) | VI | A | 0.58 | 428.06 |
| Example 42 | 4-Chloro-1H-indole-5-carboxylic acid [2-(2,6-dimethyl-morpholin-4-yl)-2-(2-methyl-pyrimidin-5-yl)-ethyl]-amide (mixture B of stereoisomers) | VI | A | 0.62 | 428.05 |

-continued

|  |  |  |  | LC-MS | |
| --- | --- | --- | --- | --- | --- |
| Compound | Name | Purification method | type | tR (min) | [M + H]+ |
| Example 43 | rac-4-Chloro-1H-indole-5-carboxylic acid [2-(3-fluoro-phenyl)-2-piperidin-1-yl-ethyl]-amide | 1 | E | 1.34 | 400.14 |
| Example 44 | rac-4-Chloro-1H-indole-5-carboxylic acid [2-piperidin-1-yl-2-(4-trifluoromethyl-phenyl)-ethyl]-amide | 2 | E | 1.47 | 450.08 |
| Example 45 | rac-4-Chloro-1H-indole-5-carboxylic acid [2-(3,4-difluoro-phenyl)-2-piperidin-1-yl-ethyl]-amide | 1 | E | 1.37 | 418.07 |
| Example 46 | rac-4-Chloro-1H-indole-5-carboxylic acid (2-piperidin-1-yl-2-pyridin-3-yl-ethyl)-amide | 1 | E | 0.96 | 383.16 |
| Example 47 | rac-4-Chloro-1H-indole-5-carboxylic acid (2-morpholin-4-yl-2-p-tolyl-ethyl)-amide | 1 | E | 1.07 | 398.14 |
| Example 48 | rac-4-Chloro-1H-indole-5-carboxylic acid [2-morpholin-4-yl-2-(4-trifluoromethoxy-phenyl)-ethyl]-amide | 2 | E | 1.19 | 468.06 |
| Example 49 | rac-4-Chloro-1H-indole-5-carboxylic acid [2-morpholin-4-yl-2-(4-trifluoromethyl-phenyl)-ethyl]-amide | 2 | E | 1.16 | 452.05 |
| Example 50 | rac-4-Chloro-1H-indole-5-carboxylic acid [2-(3,4-difluoro-phenyl)-2-morpholin-4-yl-ethyl]-amide | 1 | E | 1.04 | 420.06 |
| Example 51 | rac-4-Chloro-1H-indole-5-carboxylic acid [2-(2-methyl-pyrimidin-5-yl)-2-(tetrahydro-pyran-4-yl)-ethyl]-amide | d | A | 0.65 | 399.07 |
| Example 52 | rac-4-Chloro-1H-indole-5-carboxylic acid [2-cyclopentyloxy-2-(2-methyl-pyrimidin-5-yl)-ethyl]-amide | I | A | 0.81 | 399.01 |
| Example 53 | rac-4-Chloro-1H-indole-5-carboxylic acid [2-(3,5-dimethyl-isoxazol-4-yl)-2-morpholin-4-yl-ethyl]-amide | 1 | E | 0.61 | 403.12 |
| Example 54 | rac-4-Chloro-1H-indole-5-carboxylic acid [2-(3,5-dimethyl-isoxazol-4-yl)-2-piperidin-1-yl-ethyl]-amide | 1 | E | 0.54 | 401.15 |
| Example 55 | rac-4-Chloro-1H-indole-5-carboxylic acid (2-piperidin-1-yl-2-p-tolyl-ethyl)-amide | 1 | E | 0.70 | 396.16 |
| Example 56 | rac-4-Chloro-1H-indole-5-carboxylic acid [2-(6-chloro-pyridin-3-yl)-2-piperidin-1-yl-ethyl]-amide | 1 | E | 0.57 | 417.07 |
| Example 57 | rac-4-Chloro-1H-indole-5-carboxylic acid [2-(4-phenoxy-phenyl)-2-piperidin-1-yl-ethyl]-amide | 2 | E | 0.86 | 474.12 |
| Example 58 | rac-4-Chloro-1H-indole-5-carboxylic acid [2-morpholin-4-yl-2-(4-phenoxy-phenyl)-ethyl]-amide | 2 | E | 0.84 | 476.12 |
| Example 59 | rac-4-Chloro-1H-indole-5-carboxylic acid [2-(4-methoxy-phenyl)-2-morpholin-4-yl-ethyl]-amide | 1 | E | 0.57 | 414.08 |
| Example 60 | rac-4-Chloro-1H-indole-5-carboxylic acid [2-(5-methyl-pyrazin-2-yl)-2-piperidin-1-yl-ethyl]-amide | 1 | E | 0.50 | 398.14 |
| Example 61 | rac-4-Chloro-1H-indole-5-carboxylic acid (2-isothiazol-5-yl-2-piperidin-1-yl-ethyl)-amide | 1 | E | 0.54 | 389.14 |

-continued

| Compound | Name | Purification method | LC-MS type | tR (min) | [M + H]+ |
|---|---|---|---|---|---|
| Example 62 | rac-4-Chloro-1H-indole-5-carboxylic acid (2-piperidin-1-yl-2-thiazol-5-yl-ethyl)-amide | 1 | E | 0.45 | 389.11 |
| Example 63 | rac-4-Chloro-1H-indole-5-carboxylic acid [2-(5-methyl-pyrazin-2-yl)-2-morpholin-4-yl-ethyl]-amide | 1 | E | 0.51 | 400.13 |
| Example 64 | rac-4-Chloro-1H-indole-5-carboxylic acid (2-morpholin-4-yl-2-thiazol-5-yl-ethyl)-amide | 1 | E | 0.57 | 391.08 |
| Example 65 | rac-4-Chloro-1H-indole-5-carboxylic acid [2-(6-chloro-pyridin-3-yl)-2-cyclohexyl-ethyl]-amide | b + d | A | 0.92 | 416.12 |
| Example 66 | rac-4-Chloro-1H-indole-5-carboxylic acid [2-(6-chloro-pyridin-3-yl)-4-methyl-pentyl]-amide | b + d | A | 0.89 | 389.90 |
| Example 67 | rac-4-Chloro-1H-indole-5-carboxylic acid [2-ethoxy-2-(2-methyl-pyrimidin-5-yl)-ethyl]-amide | I | A | 0.71 | 358.96 |
| Example 68 | 4-Chloro-1H-indole-5-carboxylic acid [2-(2-methyl-pyrimidin-5-yl)-2-(2-oxa-5-aza-bicyclo[2.2.1]hept-5-yl)-ethyl]-amide (mixture of stereoisomers) | V + VI | A | 0.52 | 411.99 |
| Example 69 | rac-4-Chloro-1H-indole-5-carboxylic acid [2-cyclohexyloxy-2-(2-methyl-pyrimidin-5-yl)-ethyl]-amide | b | A | 0.84 | 413.01 |
| Example 70 | rac-4-Chloro-1H-indole-5-carboxylic acid [2-(2-methyl-pyrimidin-5-yl)-2-(tetrahydro-pyran-4-yloxy)-ethyl]-amide | precipitate from CH$_3$CN | A | 0.69 | 415.15 |
| Example 71 | rac-4-Chloro-1H-indole-5-carboxylic acid [2-(1-ethyl-propoxy)-2-(2-methyl-pyrimidin-5-yl)-ethyl]-amide | precipitate from CH$_3$CN | A | 0.83 | 401.01 |
| Example 72 | rac-4-Chloro-2-methyl-1H-indole-5-carboxylic acid [2-(2-methyl-pyrimidin-5-yl)-2-morpholin-4-yl-ethyl]-amide | V + e | A | 0.56 | 414.00 |
| Example 73 | rac-4-Chloro-1H-indole-5-carboxylic acid (2-piperidin-1-yl-2-pyridazin-3-yl-ethyl)-amide | 1 | G | 0.42 | 384.17 |
| Example 74 | rac-4-Chloro-1H-indole-5-carboxylic acid [2-(2-hydroxypyridin-4-yl)-2-piperidin-1-yl-ethyl]-amide | 1 | G | 0.35 | 399.16 |
| Example 75 | rac-1-[2-[(4-Chloro-1H-indole-5-carbonyl)-amino]-1-(2-methyl-pyrimidin-5-yl)-ethyl]-piperidine-4-carboxylic acid tert-butyl ester | 1 | G | 0.74 | 498.25 |
| Example 76 | rac-4-Chloro-1H-indole-5-carboxylic acid [2-(4-methyl-piperidin-1-yl)-2-(2-methyl-pyrimidin-5-yl)-ethyl]-amide | 1 | G | 0.50 | 412.15 |
| Example 77 | 4-Chloro-1H-indole-5-carboxylic acid [(R)-2-(2-methyl-piperidin-1-yl)-2-(2-methyl-pyrimidin-5-yl)-ethyl]-amide (mixture of stereoisomers) | 1 | G | 0.49 | 412.16 |
| Example 78 | rac-4-Chloro-1H-indole-5-carboxylic acid [2-(4-fluoro-piperidin-1-yl)-2-(2-methyl-pyrimidin-5-yl)-ethyl]-amide | 1 | G | 0.50 | 416.13 |
| Example 79 | rac-4-Chloro-1H-indole-5-carboxylic acid [2-(3,3-difluoro-piperidin-1-yl)-2-(2-methyl-pyrimidin-5-yl)-ethyl]-amide | 2 | G | 0.91 | 434.10 |

-continued

| Compound | Name | Purification method | LC-MS type | tR (min) | [M + H]+ |
|---|---|---|---|---|---|
| Example 80 | rac-4-Chloro-1H-indole-5-carboxylic acid [2-azepan-1-yl-2-(2-methyl-pyrimidin-5-yl)-ethyl]-amide | 1 | G | 0.51 | 412.14 |
| Example 81 | rac-4-Chloro-1H-indole-5-carboxylic acid [2-(2-methyl-pyrimidin-5-yl)-2-[1,4]oxazepan-4-yl-ethyl]-amide | 1 | G | 0.45 | 414.13 |
| Example 82 | rac-4-Chloro-1H-indole-5-carboxylic acid [2-(3,3-difluoro-pyrrolidin-1-yl)-2-(2-methyl-pyrimidin-5-yl)-ethyl]-amide | 2 | G | 0.85 | 420.12 |
| Example 83 | rac-4-Chloro-1H-indole-5-carboxylic acid [2-cyclopentylamino-2-(2-methyl-pyrimidin-5-yl)-ethyl]-amide | 1 | G | 0.50 | 398.17 |
| Example 84 | rac-4-Chloro-1H-indole-5-carboxylic acid [2-(cyclopentylmethyl-amino)-2-(2-methyl-pyrimidin-5-yl)-ethyl]-amide | 1 | G | 0.58 | 412.16 |
| Example 85 | rac-4-Chloro-1H-indole-5-carboxylic acid [2-isobutylamino-2-(2-methyl-pyrimidin-5-yl)-ethyl]-amide | 1 | G | 0.48 | 386.16 |
| Example 86 | rac-4-Chloro-1H-indole-5-carboxylic acid [2-(isobutyl-methyl-amino)-2-(2-methyl-pyrimidin-5-yl)-ethyl]-amide | 1 | G | 0.56 | 400.17 |
| Example 87 | rac-4-Chloro-1H-indole-5-carboxylic acid [2-(benzyl-methyl-amino)-2-(2-methyl-pyrimidin-5-yl)-ethyl]-amide | 2 | G | 0.74 | 434.14 |
| Example 88 | rac-4-Chloro-1H-indole-5-carboxylic acid (3-ethyl-2-pyrimidin-5-yl-pentyl)-amide | VII + d | A | 0.83 | 371.01 |
| Example 89 | rac-4-[2-[(4-Chloro-1H-indole-5-carbonyl)-amino]-1-(2-methyl-pyrimidin-5-yl)-ethyl]-piperazine-1-carboxylic acid tert-butyl ester | 2 | E | 0.93 | 499.23 |
| Example 90 | rac-4-Chloro-1H-indole-5-carboxylic acid (2-morpholin-4-yl-2-pyridazin-3-yl-ethyl)-amide | 1 | E | 0.46 | 386.15 |
| Example 91 | rac-4-Chloro-1H-indole-5-carboxylic acid [2-morpholin-4-yl-2-(2-hydroxypyridin-4-yl)-ethyl]-amide | 1 | E | 0.41 | 401.13 |
| Example 92 | rac-4-Chloro-1H-indole-5-carboxylic acid [2-(1,1-dioxo-thiomorpholin-4-yl)-2-(2-methyl-pyrimidin-5-yl)-ethyl]-amide | 1 | E | 0.62 | 448.11 |
| Example 93 | rac-4-Chloro-1H-indole-5-carboxylic acid [2-(4,4-difluoro-cyclohexyl)-2-(2-methyl-pyrimidin-5-yl)-ethyl]-amide | e | A | 0.79 | 433.06 |
| Example 94 | rac-4,6-Dichloro-1H-indole-5-carboxylic acid [2-(2-methyl-pyrimidin-5-yl)-2-morpholin-4-yl-ethyl]-amide | III + d | A | 0.55 | 433.82 |
| Example 95 | 4-Chloro-1H-indole-5-carboxylic acid [2-(2-methyl-pyrimidin-5-yl)-2-(6-oxa-3-aza-bicyclo[3.1.1]hept-3-yl)-ethyl]-amide (mixture of stereoisomers) | VIII | A | 0.54 | 411.98 |
| Example 96 | 4-Chloro-7-methyl-1H-indole-5-carboxylic acid [2-(2-methyl-pyrimidin-5-yl)-2-morpholin-4-yl-ethyl]-amide (enantiomer A) | see below under section B. | | | |
| Example 97 | 4-Chloro-7-methyl-1H-indole-5-carboxylic acid [2-(2-methyl-pyrimidin-5-yl)-2-morpholin-4-yl-ethyl]-amide (enantiomer B) | see below under section B. | | | |

-continued

| Compound | Name | Purification method | LC-MS type | tR (min) | [M + H]+ |
|---|---|---|---|---|---|
| Example 98 | rac-4-Chloro-7-isobutyl-1H-indole-5-carboxylic acid [2-(2-methyl-pyrimidin-5-yl)-2-morpholin-4-yl-ethyl]-amide | IV + g | A | 0.65 | 456.12 |
| Example 99 | rac-4-Chloro-7-(3-methoxy-propyl)-1H-indole-5-carboxylic acid [2-(2-methyl-pyrimidin-5-yl)-2-morpholin-4-yl-ethyl]-amide | h | A | 0.59 | 472.21 |
| Example 100 | rac-4-Methyl-1H-indole-5-carboxylic acid [2-(2-methyl-pyrimidin-5-yl)-2-morpholin-4-yl-ethyl]-amide | d | A | 0.51 | 380.04 |
| Example 101 | rac-4-Ethyl-1H-indole-5-carboxylic acid [2-(2-methyl-pyrimidin-5-yl)-2-morpholin-4-yl-ethyl]-amide | d | A | 0.55 | 394.06 |
| Example 102 | rac-7-Acetyl-4-chloro-1H-indole-5-carboxylic acid [2-(2-methyl-pyrimidin-5-yl)-2-morpholin-4-yl-ethyl]-amide | d | A | 0.56 | 441.93 |
| Example 103 | rac-7-Methyl-4-trifluoromethyl-1H-indole-5-carboxylic acid [2-(2-methyl-pyrimidin-5-yl)-2-morpholin-4-yl-ethyl]-amide | e | A | 0.58 | 447.94 |
| Example 104 | rac-4,7-Dimethyl-1H-indole-5-carboxylic acid [2-(2-methyl-pyrimidin-5-yl)-2-morpholin-4-yl-ethyl]-amide | e | A | 0.54 | 394.10 |
| Example 105 | 4-Methyl-1H-indole-5-carboxylic acid [2-(2-methyl-pyrimidin-5-yl)-2-morpholin-4-yl-ethyl]-amide (enantiomer A) | i | A | 0.51 | 380.01 |
| | | For chiral characterization, see below under section B | | | |
| Example 106 | 4-Methyl-1H-indole-5-carboxylic acid [2-(2-methyl-pyrimidin-5-yl)-2-morpholin-4-yl-ethyl]-amide (enantiomer B) | i | A | 0.51 | 380.01 |
| | | For chiral characterization, see below under section B | | | |
| Example 107 | rac-4-Chloro-7-ethyl-1H-indole-5-carboxylic acid [2-(2-methyl-pyrimidin-5-yl)-2-morpholin-4-yl-ethyl]-amide | e | A | 0.58 | 427.98 |
| Example 108 | rac-7-Chloro-4-methyl-1H-indole-5-carboxylic acid [2-(2-methyl-pyrimidin-5-yl)-2-morpholin-4-yl-ethyl]-amide | d | A | 0.56 | 414.09 |
| Example 109 | rac-7-Methoxy-4-methyl-1H-indole-5-carboxylic acid [2-(2-methyl-pyrimidin-5-yl)-2-morpholin-4-yl-ethyl]-amide | d | A | 0.54 | 410.07 |
| Example 110 | rac-4-Chloro-7-ethoxy-1H-indole-5-carboxylic acid [2-(2-methyl-pyrimidin-5-yl)-2-morpholin-4-yl-ethyl]-amide | e | A | 0.59 | 443.99 |
| Example 111 | rac-4-Chloro-7-propyl-1H-indole-5-carboxylic acid [2-(2-methyl-pyrimidin-5-yl)-2-morpholin-4-yl-ethyl]-amide | d | A | 0.62 | 442.24 |
| Example 112 | rac-7-(2-tert-Butoxy-ethoxy)-4-chloro-1H-indole-5-carboxylic acid [2-(2-methyl-pyrimidin-5-yl)-2-morpholin-4-yl-ethyl]-amide | VIII | A | 0.66 | 516.16 |
| Example 113 | rac-4-Chloro-7-(2-hydroxy-ethoxy)-1H-indole-5-carboxylic acid [2-(2-methyl-pyrimidin-5-yl)-2-morpholin-4-yl-ethyl]-amide | see below under section C. | | | |
| Example 114 | 4-Chloro-7-methoxy-1H-indole-5-carboxylic acid [2-(2-methyl-pyrimidin-5-yl)-2-morpholin-4-yl ethyl]-amide (enantiomer A) | d | A | 0.55 | 430.24 |
| | | For chiral characterization, see below under section B | | | |
| Example 115 | 4-Chloro-7-methoxy-1H-indole-5-carboxylic acid [2-(2-methyl-pyrimidin-5-yl)-2-morpholin-4-yl-ethyl]-amide (enantiomer B) | d | A | 0.55 | 430.24 |
| | | For chiral characterization, see below under section B | | | |

-continued

| Compound | Name | Purification method | LC-MS type | tR (min) | [M + H]+ |
|---|---|---|---|---|---|
| Example 116 | rac-4-Chloro-7-(1-hydroxy-1-methyl-ethyl)-1H-indole-5-carboxylic acid [2-(2-methyl-pyrimidin-5-yl)-2-morpholin-4-yl-ethyl]-amide | see below under section C. | | | |
| Example 117 | rac-4,7-Difluoro-1H-indole-5-carboxylic acid [2-(2-methyl-pyrimidin-5-yl)-2-morpholin-4-yl-ethyl]-amide | d | A | 0.55 | 402.11 |
| Example 118 | rac-4-Fluoro-7-methoxy-1H-indole-5-carboxylic acid [2-(2-methyl-pyrimidin-5-yl)-2-morpholin-4-yl-ethyl]-amide | d | A | 0.55 | 413.88 |
| Example 119 | 4-Chloro-7-ethyl-1H-indole-5-carboxylic acid [2-(2-methyl-pyrimidin-5-yl)-2-morpholin-4-yl-ethyl]-amide (enantiomer A) | d For chiral characterization, see below under section B | A | 0.58 | 428.21 |

B. Chiral Separation of Compounds of Formula (I)

Example 3

4-Chloro-1H-indole-5-carboxylic acid [2-(2-methyl-pyrimidin-5-yl)-2-morpholin-4-yl-ethyl]-amide (Enantiomer A) and Example 4

4-Chloro-1H-indole-5-carboxylic acid [2-(2-methyl-pyrimidin-5-yl)-2-morpholin-4-yl-ethyl]-amide (Enantiomer B)

4-Chloro-1H-indole-5-carboxylic acid [2-(2-methyl-pyrimidin-5-yl)-2-morpholin-4-yl-ethyl]-amide as racemate was prepared according to the general procedure for amide coupling engaging 4-chloro-1H-indole-5-carboxylic acid as carboxylic acid precursor II and 2-(2-methylpyrimidin-5-yl)-2-morpholinoethanamine as amine precursor III.

LC-MS (B): $t_R$=0.41 min; [M+H]+: 400.02

The racemate was separated into the two enantiomers using preparative chiral HPLC (Daicel, ChiralPak AD-H, 5 μm, 20×250 mm, Hept/(EtOH+0.1% DEA) 50/50, flow: 16 mL/min, detection: UV 230 nm).

Both enantiomers were characterized by analytical chiral HPLC (Daicel, ChiralPak AD-H, 5 μm, 4.6×250 mm, (Hept+0.05% DEA)/(EtOH+0.05% DEA) 50/50, flow: 0.8 mL/min, detection: UV 210 to 280 nm)

Enantiomer A: $t_R$=8.67 min (Example 3)
Enantiomer B: $t_R$=10.70 min (Example 4)

Example 5

4-Chloro-1H-indole-5-carboxylic acid [2-(4,4-difluoro-piperidin-1-yl)-2-(2-methyl-pyrimidin-5-yl)-ethyl]-amide (Enantiomer A) and Example 6

4-Chloro-1H-indole-5-carboxylic acid [2-(4,4-difluoro-piperidin-1-yl)-2-(2-methyl-pyrimidin-5-yl)-ethyl]-amide (Enantiomer B)

4-Chloro-1H-indole-5-carboxylic acid [2-(4,4-difluoro-piperidin-1-yl)-2-(2-methyl-pyrimidin-5-yl)-ethyl]-amide as racemate was prepared according to the general procedure for amide coupling engaging 4-chloro-1H-indole-5-carboxylic acid as carboxylic acid precursor II and 2-(4,4-difluoropiperidin-1-yl)-2-(2-methylpyrimidin-5-yl)ethanamine as amine precursor III.

LC-MS (B): $t_R$=0.52 min; [M+H]+: 434.33

The racemate was separated into the two enantiomers using preparative chiral HPLC (Daicel, ChiralPak AD-H, 5 μm, 20×250 mm, Hept/(EtOH+0.1% DEA) 50/50, flow: 16 mL/min, detection: UV 210 nm).

Both enantiomers were characterized by analytical chiral HPLC (Daicel, ChiralPak AD-H, 5 μm, 4.6×250 mm, (Hept+0.05% DEA)/(EtOH+0.05% DEA) 50/50, flow: 0.8 mL/min, detection: UV 210 to 280 nm)

Enantiomer A: $t_R$=8.72 min (Example 5)
Enantiomer B: $t_R$=10.92 min (Example 6)

Example 96

4-Chloro-7-methyl-1H-indole-5-carboxylic acid [2-(2-methyl-pyrimidin-5-yl)-2-morpholin-4-yl-ethyl]-amide (Enantiomer A) and Example 97

4-Chloro-7-methyl-1H-indole-5-carboxylic acid [2-(2-methyl-pyrimidin-5-yl)-2-morpholin-4-yl-ethyl]-amide (Enantiomer B)

4-Chloro-7-methyl-1H-indole-5-carboxylic acid [2-(2-methyl-pyrimidin-5-yl)-2-morpholin-4-yl-ethyl]-amide as racemate was prepared according to the general procedure for amide coupling engaging 4-chloro-7-methyl-1H-indole-5-carboxylic acid as carboxylic acid precursor II and 2-(2-methylpyrimidin-5-yl)-2-morpholinoethanamine as amine precursor III.

LC-MS (A): $t_R$=0.55 min; [M+H]+: 414.03

The racemate was separated into the two enantiomers using preparative chiral HPLC (Daicel, ChiralPak AD-H, 5 μm, 20×250 mm, Hept/(EtOH+0.1% DEA) 70/30, flow: 20 mL/min, detection: UV 230 nm).

Both enantiomers were characterized by analytical chiral HPLC (Daicel, ChiralPak AD-H, 5 μm, 4.6×250 mm, (Hept+0.05% DEA)/(EtOH+0.05% DEA) 70/30, flow: 1.0 mL/min, detection: UV 210 to 280 nm)

Enantiomer A: $t_R$=10.43 min (Example 96)
Enantiomer B: $t_R$=13.21 min (Example 97)

Example 105

4-Methyl-1H-indole-5-carboxylic acid [2-(2-methyl-pyrimidin-5-yl)-2-morpholin-4-yl-ethyl]-amide (Enantiomer A) and

Example 106

4-Methyl-1H-indole-5-carboxylic acid [2-(2-methyl-pyrimidin-5-yl)-2-morpholin-4-yl-ethyl]-amide (Enantiomer B)

Example 105 (or example 106 respectively) was synthesized according to the aforementioned general amide coupling procedure using 2-(2-methylpyrimidin-5-yl)-2-morpholinoethanamine (Enantiomer A) as chiral amines of formula III (or 2-(2-methylpyrimidin-5-yl)-2-morpholinoethanamine (Enantiomer B) respectively).

Both enantiomers were characterized by analytical chiral HPLC (Daicel, ChiralPak AD-H, 5 μm, 4.6×250 mm, (Hept+0.05% DEA)/(EtOH+0.05% DEA) 50/50, flow: 1.2 mL/min, detection: UV 210 to 280 nm)
Enantiomer A: $t_R$=8.16 min (Example 105)
Enantiomer B: $t_R$=6.35 min (Example 106)

Example 114

4-Chloro-7-methoxy-1H-indole-5-carboxylic acid [2-(2-methyl-pyrimidin-5-yl)-2-morpholin-4-yl-ethyl]-amide (Enantiomer A) and

Example 115

4-Chloro-7-methoxy-1H-indole-5-carboxylic acid [2-(2-methyl-pyrimidin-5-yl)-2-morpholin-4-yl-ethyl]-amide (Enantiomer B)

Example 114 (or example 115 respectively) was synthesized according to the aforementioned general amide coupling procedure using 2-(2-methylpyrimidin-5-yl)-2-morpholinoethanamine (Enantiomer A) as chiral amines of formula III (or 2-(2-methylpyrimidin-5-yl)-2-morpholinoethanamine (Enantiomer B) respectively).

Both enantiomers were characterized by analytical chiral HPLC (Daicel, ChiralPak ID, 5 μm, 4.6×250 mm, CH₃CN/(EtOAc+0.1% DEA) 40/60, flow: 1.0 mL/min, detection: UV 210 to 280 nm)
Enantiomer A: $t_R$=5.40 min (Example 114)
Enantiomer B: $t_R$=6.79 min (Example 115)

Example 119

4-Chloro-7-ethyl-1H-indole-5-carboxylic acid [2-(2-methyl-pyrimidin-5-yl)-2-morpholin-4-yl-ethyl]-amide (Enantiomer A)

Example 119 was synthesized according to the aforementioned general amide coupling procedure using 2-(2-methylpyrimidin-5-yl)-2-morpholinoethanamine (Enantiomer A) as chiral amines of formula III.

It was characterized by analytical chiral HPLC (Daicel, ChiralPak ID, 5 μm, 4.6×250 mm, Hept/(EtOAc+0.1% DEA) 10/90, flow: 1.4 mL/min, detection: UV 210 to 280 nm)

Enantiomer A: $t_R$=5.61 min (Example 119) ($t_R$=8.09 min for the other enantiomer)

C. Post Amide Coupling Steps

Example 20 rac-4-Chloro-1H-indole-5-carboxylic acid (2-piperidin-4-yl-2-pyridin-3-yl-ethyl)-amide dihydrochloride To a solution of 4-{2-[(4-Chloro-1H-indole-5-carbonyl)-amino]-1-pyridin-3-yl-ethyl}-piperidine-1-carboxylic acid tert-butyl ester (Example 19) (0.42 mmol) in EtOAc (2 mL) was added dropwise a 4M solution of HCl in dioxane (4.18 mmol). The mixture was stirred for 4 h at RT and concentrated in vacuo to give the title compound as light pink solid.
LC-MS (A): $t_R$=0.43 min; [M+H]+: 383.01

Example 21 rac-4-Chloro-1H-indole-5-carboxylic acid [2-(1-methyl-piperidin-4-yl)-2-pyridin-3-yl-ethyl]-amide formate To a solution of 4-chloro-1H-indole-5-carboxylic acid (2-piperidin-4-yl-2-pyridin-3-yl-ethyl)-amide dihydrochloride (Example 20) (0.13 mmol) in DCM (1 mL) and MeOH (2 mL) was added AcOH (0.16 mmol) followed by a 37% aqueous solution of formaldehyde (0.17 mmol) and by sodium triacetoxyborohydride (0.18 mmol). The mixture was stirred for 5 h at RT and an additional amount of sodium triacetoxyborohydride (0.18 mmol) was added. It was stirred ON at RT, quenched with a sat. solution of NaHCO₃ and extracted twice with DCM. The aqueous phase was further basified with a 1M solution of NaOH until pH 13-14 and extracted twice with DCM. The combined organic phases were dried over MgSO₄ and concentrated in vacuo. The crude was purified by preparative LC-MS using method III to give the title compound as white solid.
LC-MS (A): $t_R$=0.44 min; [M+H]+: 397.04

Example 22 rac-4-Chloro-1H-indole-5-carboxylic acid [2-(1-acetyl-piperidin-4-yl)-2-pyridin-3-yl-ethyl]-amide To a suspension of 4-chloro-1H-indole-5-carboxylic acid (2-piperidin-4-yl-2-pyridin-3-yl-ethyl)-amide dihydrochloride (Example 20) (0.13 mmol) and Et₃N (0.66 mmol) in DCM (1 mL) was added at 0° C. acetyl chloride (0.16 mmol). The mixture was stirred for 1.5 h at 0° C., quenched with a sat. solution of NaHCO₃ and extracted 3 times with EtOAc. The combined organic phases were washed with brine, dried over MgSO₄ and concentrated in vacuo. The crude was purified by preparative LC-MS using method III to give the title compound as white solid.
LC-MS (A): $t_R$=0.54 min; [M+H]+: 424.99

Example 23 rac-4-Chloro-1H-indole-5-carboxylic acid [2-(1-methanesulfonyl-piperidin-4-yl)-2-pyridin-3-yl-ethyl]-amide To a suspension of 4-chloro-1H-indole-5-carboxylic acid (2-piperidin-4-yl-2-pyridin-3-yl-ethyl)-amide dihydrochloride (Example 20) (0.13 mmol) and Et₃N (0.66 mmol) in DCM (1 mL) was added at 0° C. methanesulfonyl chloride (0.16 mmol). The mixture was stirred for 1.5 h at 0° C., quenched with a sat. solution of NaHCO₃ and extracted 3 times with EtOAc. The combined organic phases were washed with brine, dried over MgSO₄ and concentrated in vacuo. The crude was purified by preparative LC-MS using method III and additionally by CC (Isolute™ Silica II from Biotage) using DCM/MeOH 94/6 to give the title compound as white solid.

LC-MS (A): $t_R$=0.57 min; [M+H]+: 460.94

Example 113 rac-4-Chloro-7-(2-hydroxy-ethoxy)-1H-indole-5-carboxylic acid [2-(2-methyl-pyrimidin-5-yl)-2-morpholin-4-yl-ethyl]-amide To a solution of rac-7-(2-tert-butoxy-ethoxy)-4-chloro-1H-indole-5-carboxylic acid [2-(2-methyl-pyrimidin-5-yl)-2-morpholin-4-yl-ethyl]-amide (example 112) (0.047 mmol) in DCM (0.19 mL) was added TFA (0.18 mL). The mixture was stirred for 2 h at RT, concentrated in vacuo and coevaporated with toluene. The crude was purified by preparative LC-MS using method IX to give the title compound as beige solid LC-MS (A): $t_R$=0.51 min; [M+H]+: 460.02

Example 116 rac-4-Chloro-7-(1-hydroxy-1-methyl-ethyl)-1H-indole-5-carboxylic acid [2-(2-methyl-pyrimidin-5-yl)-2-morpholin-4-yl-ethyl]-amide To a solution of rac-7-acetyl-4-chloro-1H-indole-5-carboxylic acid [2-(2-methyl-pyrimidin-5-yl)-2-morpholin-4-yl-ethyl]-amide (0.05 mmol) in THF (1 mL) was added dropwise at −10° C. a 3M solution of methylmagnesium bromide in diethyl ether (0.54 mmol). The mixture was stirred for 2 h at RT and cooled to 0° C. It was quenched with a sat. solution of NH₄Cl and extracted three times with EtOAc. The organic phases were washed with brine, dried over MgSO₄ and concentrated in vacuo. The crude was purified by CC (Isolute™ Silica II from Biotage) using DCM/MeOH 90/10 to give the title compound as light yellow solid.

LC-MS (A): $t_R$=0.54 min; [M+H]+: 458.24

BIOLOGICAL ASSAYS

A. In Vitro Assay

The P2X₇ receptor antagonistic activity of the compounds of formula (I) is determined in accordance with the following experimental method.

B. Experimental Method:

Cell Line Generation and YO-PRO Assay

Cell line generation was performed in general according to established molecular cloning protocols. Specifically, RNA was extracted from human whole blood using the Qiagen RNeasy kit (Qiagen, CH) according to the manufacturer's instructions. Subsequently cDNA was made (Superscript II, Invitrogen AG, CH) and the human P2X7 gene (genbank ref. BC011913) was amplified with the following primers: ATCGCGGCCGCTCAGTAAGGACTCTT-GAAGCCACT and CGCCGCTAGCACCACCATGCCG-GCCTGCTGCAGCTGCA. The amplified sequence was subsequently ligated into a pcDNA3.1 (+) NotI, NheI digested plasmid. Human embryonic kidney (HEK) cells (ATCC CRL—1573, Manassas, Va., USA) were transfected with the pcDNA3.1 (+).hP2X7 plasmid using lipofectamine 2000 (Invitrogen AG, CH) according to the manufacturer's instructions. Following a 24 h exposure to DNA, cells were trypsinized and re-seeded at low density in the presence of 250 μg Geneticin. Geneticin resistant cells were then selected during two consecutive rounds of cloning by serial limiting dilution with visual inspection. Individual clones were screened for P2X7 expression by applying ATP and recording the resultant uptake of YO-PRO1. Specific cell clones were chosen based on RNA and protein expression. HEK cells stably expressing P2X7 were used to screen drugs using the YO-PRO1 assay. Cells were grown to confluency in adherent culture at 37° C. in a humidified 5% CO₂ incubator (split 1/5 every 3-4 days with DMEM, 10% FCS, 1% Penicillin/Streptomycin, 250 μg/ml Geneticin). Adherent cells were detached by incubation with Trypsine (1 ml per 165 cm² dish) for 2 minutes, then washed off with 10 ml PBS (without Mg²⁺ and Ca²⁺), and resuspended in DMEM, 10% FCS, 1% Penicillin/Streptomycin, no Geneticin. 10'000 cells per well (48 hours before the assay) or 25'000 cells per well (Vi-cell XR (Beckman Coulter) (24 hours before the assay) in 50 μl full medium were seeded on 384-well black-wall, clear bottom plates, that were coated before with 10 μl per well Poly-L-Lysine, incubated for 30-60 minutes at 37° C. and washed once with PBS. Medium was removed from cells and 50 μl of assay buffer containing 0.5 μM YO-PRO-1 was added into the wells. Solutions of antagonist compounds were prepared by serial dilutions of a 10 mM DMSO solution of the antagonist into PBS using a BioMek (Beckman Coulter). Each concentration was performed in duplicate. For IC₅₀ measurements 10 concentration points were measured (10 μM being the highest concentration followed by 9 serial dilution steps 1/3). The cells were incubated with the antagonists of the present invention together with ATP at a final concentration of 250 μM for 90 minutes. During this time period, four time points were taken. Each time point comprised the average of several measurements made within a few seconds. Fluorescence was measured in the FLIPR tetra (Molecular Devices) using the filters appropriate for YO-PRO-1 fluorescence (excitation 485/20, emission 530/25). The FLIPR tetra was equipped with Molecular Devices Screen Works system control software to define and run experimental protocols. For antagonist activity measurements, the maximal intensity was expressed as a percentage of that induced by the EC₅₀ value for agonist activation (0.25 mM ATP for HEK-293 cells expressing human recombinant P2X7 receptor). For IC50 measurements the maximum intensity is plotted against the concentration of compound to determine IC50 values.

Antagonistic activities with respect to the P2X₇ receptor (IC₅₀ values) of exemplified compounds are displayed in Table 1.

TABLE 1

| Compound | IC₅₀ [nM] | Compound | IC₅₀ [nM] | Compound | IC₅₀ [nM] |
|---|---|---|---|---|---|
| Example 1 | 3.9 | Example 2 | 4.3 | Example 3 | 7.9 |
| Example 4 | 9.4 | Example 5 | 7.9 | Example 6 | 6.8 |
| Example 7 | 19 | Example 8 | 12 | Example 9 | 7.7 |
| Example 10 | 5.1 | Example 11 | 14 | Example 12 | 2295 |

TABLE 1-continued

| Compound | IC$_{50}$ [nM] | Compound | IC$_{50}$ [nM] | Compound | IC$_{50}$ [nM] |
|---|---|---|---|---|---|
| Example 13 | 831 | Example 14 | 286 | Example 15 | 85 |
| Example 16 | 9.7 | Example 17 | 9.2 | Example 18 | 19 |
| Example 19 | 35 | Example 20 | 447 | Example 21 | 584 |
| Example 22 | 126 | Example 23 | 56 | Example 24 | 4.7 |
| Example 25 | 32 | Example 26 | 10 | Example 27 | 8.7 |
| Example 28 | 66 | Example 29 | 161 | Example 30 | 1305 |
| Example 31 | 251 | Example 32 | 232 | Example 33 | 301 |
| Example 34 | 61 | Example 35 | 161 | Example 36 | 265 |
| Example 37 | 32 | Example 38 | 15 | Example 39 | 455 |
| Example 40 | 73 | Example 41 | 651 | Example 42 | 36 |
| Example 43 | 163 | Example 44 | 889 | Example 45 | 83 |
| Example 46 | 39 | Example 47 | 54 | Example 48 | 134 |
| Example 49 | 34 | Example 50 | 13 | Example 51 | 16 |
| Example 52 | 32 | Example 53 | 1990 | Example 54 | 1851 |
| Example 55 | 774 | Example 56 | 8.8 | Example 57 | 187 |
| Example 58 | 102 | Example 59 | 55 | Example 60 | 232 |
| Example 61 | 15 | Example 62 | 48 | Example 63 | 257 |
| Example 64 | 53 | Example 65 | 76 | Example 66 | 32 |
| Example 67 | 636 | Example 68 | 2057 | Example 69 | 61 |
| Example 70 | 91 | Example 71 | 22 | Example 72 | 463 |
| Example 73 | 1014 | Example 74 | 193 | Example 75 | 258 |
| Example 76 | 348 | Example 77 | 87 | Example 78 | 12 |
| Example 79 | 9.3 | Example 80 | 25 | Example 81 | 26 |
| Example 82 | 34 | Example 83 | 162 | Example 84 | 1473 |
| Example 85 | 303 | Example 86 | 280 | Example 87 | 2647 |
| Example 88 | 15 | Example 89 | 277 | Example 90 | 1615 |
| Example 91 | 353 | Example 92 | 98 | Example 93 | 12 |
| Example 94 | 211 | Example 95 | 28 | Example 96 | 9.6 |
| Example 97 | 10 | Example 98 | 10 | Example 99 | 21 |
| Example 100 | 19 | Example 101 | 30 | Example 102 | 33 |
| Example 103 | 26 | Example 104 | 35 | Example 105 | 20 |
| Example 106 | 25 | Example 107 | 15 | Example 108 | 11 |
| Example 109 | 25 | Example 110 | 13 | Example 111 | 18 |
| Example 112 | 32 | Example 113 | 21 | Example 114 | 14 |
| Example 115 | 8.2 | Example 116 | 149 | Example 117 | 118 |
| Example 118 | 20 | Example 119 | 16 | | |

The invention claimed is:

1. A compound of the formula (I),

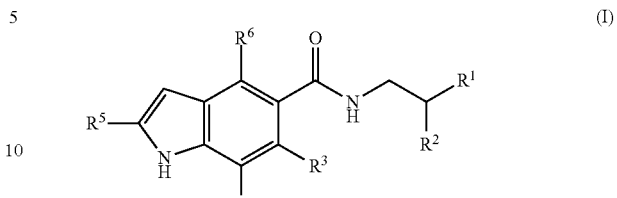

wherein

R$^1$ represents a heteroaryl or an aryl group which groups are independently unsubstituted, mono-, di-, or tri-substituted, wherein the substituents are independently selected from the group consisting of (C$_1$-C$_4$)alkyl, (C$_3$-C$_6$)cycloalkyl, (C$_1$-C$_4$)alkoxy, (C$_1$-C$_3$)fluoroalkyl, (C$_1$-C$_3$)fluoroalkoxy, hydroxy, halogen and phenoxy;

R$^2$ represents heterocyclyl which is unsubstituted, mono- or di-substituted, wherein the substituents are independently selected from (C$_1$-C$_4$)alkyl, (C$_1$-C$_4$)alkylcarbonyl, (C$_1$-C$_4$)alkoxycarbonyl, (C$_1$-C$_4$)alkylsulfonyl, and halogen;

heterocyclyloxy;

(C$_3$-C$_6$)cycloalkyl which is unsubstituted or mono- or di-substituted with halogen;

(C$_3$-C$_6$)cycloalkyloxy;

N—(C$_3$-C$_6$)cycloalkyl-amino;

N—(C$_3$-C$_6$)cycloalkylmethyl-amino;

(C$_3$-C$_6$)alkyl;

(C$_2$-C$_6$)alkoxy;

N—($C_1$-$C_4$)alkylamino;
N,N-di-[($C_1$-$C_4$)alkyl]-amino; or
N-arylmethyl-N—($C_1$-$C_4$)alkyl-amino;
$R^3$ represents hydrogen or halogen;
$R^4$ represents hydrogen, fluoro, chloro, ($C_1$-$C_4$)alkyl, ($C_1$-$C_4$)alkoxy, ($C_1$-$C_4$)alkyl-carbonyl, hydroxy-($C_1$-$C_4$)alkyl, hydroxy-($C_2$-$C_4$)alkoxy, ($C_1$-$C_2$)alkoxy-($C_1$-$C_4$)alkyl or ($C_1$-$C_4$)alkoxy -($C_2$-$C_4$)alkoxy;
$R^5$ represents hydrogen or ($C_1$-$C_4$)alkyl; and
$R^6$ represents fluoro, chloro, methyl, ethyl or ($C_1$-$C_2$)fluoroalkyl;
or a salt of such a compound.

2. The compound of formula (I) according to claim 1, wherein
$R^1$ represents a 5- or 6-membered monocyclic heteroaryl group which is unsubstituted, mono- or di-substituted, wherein the substituents are independently selected from the group consisting of ($C_1$-$C_4$)alkyl, ($C_3$-$C_6$)cycloalkyl, ($C_1$-$C_4$)alkoxy, ($C_1$-$C_3$)fluoroalkyl and halogen;
$R^2$ represents
heterocyclyl which is unsubstituted, mono- or di-substituted, wherein the substituents are independently selected from methyl and fluoro; or
($C_3$-$C_6$)cycloalkyl which is unsubstituted or mono- or di-substituted with fluoro;
$R^3$ represents hydrogen;
$R^4$ represents hydrogen or ($C_1$-$C_4$)alkyl;
$R^5$ represents hydrogen; and
$R^6$ represents chloro or methyl;
or a salt of such a compound.

3. The compound of formula (I) according to claim 1, wherein
$R^1$ represents a 5- or 6-membered monocyclic heteroaryl or a phenyl group which groups are independently unsubstituted, mono- or di-substituted, wherein the substituents are independently selected from the group consisting of ($C_1$-$C_4$)alkyl, ($C_3$-$C_6$)cycloalkyl, ($C_1$-$C_3$)fluoroalkyl and halogen;
or a salt of such a compound.

4. The compound of formula (I) according to claim 2, wherein
$R^2$ represents heterocyclyl which is unsubstituted or mono- or di-substituted with fluoro;
or a salt of such a compound.

5. The compound of formula (I) according to claim 3, wherein
$R^2$ represents ($C_3$-$C_6$)alkyl; or ($C_3$-$C_6$)cycloalkyl which is unsubstituted or mono- or di-substituted with fluoro;
or a salt of such a compound.

6. The compound of formula (I) according to claim 1, which is also a compound of formula ($I_{Ar}$)

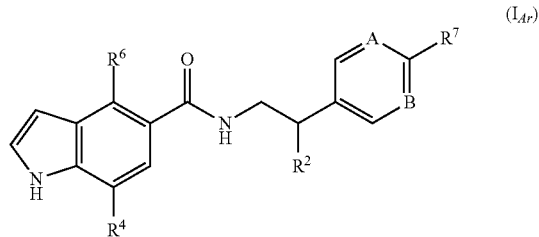

wherein
A represents N or CH;
B represents N or CH;
$R^2$ represents heterocyclyl which is unsubstituted or mono- or di-substituted with fluoro, wherein the heterocyclyl is selected from pyrrolidinyl, piperidinyl, tetrahydropyranyl, morpholinyl, azepanyl, 1,4-oxazepanyl and 6-oxa-3-azabicyclo[3.1.1]heptanyl; or
$R^2$ represents cyclohexyl which is unsubstituted or mono- or di-substituted with fluoro;
$R^4$ represents hydrogen, fluoro, chloro, ($C_1$-$C_4$)alkyl, ($C_1$-$C_4$)alkoxy, hydroxy-($C_2$-$C_4$)alkoxy or ($C_1$-$C_2$)alkoxy-($C_1$-$C_4$)alkyl;
$R^6$ represents fluoro, chloro, methyl, ethyl or ($C_1$-$C_2$)fluoroalkyl; and
$R^7$ represents hydrogen, halogen, ($C_1$-$C_4$)alkyl, ($C_3$-$C_6$)cycloalkyl, ($C_1$-$C_4$)alkoxy or ($C_1$-$C_3$)fluoroalkyl;
or a salt of such a compound.

7. The compound of formula ($I_{Ar}$) according to claim 6, wherein
A and B represent N and $R^7$ represents hydrogen, methyl, cyclopropyl or trifluoromethyl; or
A represents N, B represents CH and $R^7$ represents chloro, methyl, methoxy or trifluoromethyl; or
A and B represent CH and $R^7$ represents fluoro or chloro;
$R^2$ represents 3,3-difluoro-pyrrolidin-1-yl, piperidin-1-yl, 4-fluoro-piperidin-1-yl, 3,3-difluoro-piperidin-1-yl, 4,4-difluoro-piperidin-1-yl, tetrahydropyran-4-yl, morpholin-4-yl, azepan-1-yl, 1,4-oxazepan-4-yl, or 6-oxa-3-azabicyclo[3.1.1]heptan-3-yl;
$R^4$ represents hydrogen, chloro, methyl, ethyl, n-propyl, iso-butyl, methoxy, ethoxy, 2-hydroxy-ethoxy or 3-methoxy-prop-1-yl;
$R^6$ represents fluoro, chloro, methyl, ethyl or trifluoromethyl;
or a salt of such a compound.

8. The compound of formula ($I_{Ar}$) according to claim 6, wherein
A and B represent N;
or a salt of such a compound.

9. The compound of formula (I) according to claim 1, wherein
$R^6$ represents chloro;
or a salt of such a compound.

10. The compound of formula (I) according to claim 1, wherein
$R^6$ represents methyl;
or a salt of such a compound.

11. The compound of formula (I) according to claim 1, selected from the group consisting of:
4-Chloro-1H-indole-5-carboxylic acid [2-morpholin-4-yl-2-(2-trifluoromethyl-pyrimidin-5-yl)-ethyl]-amide;
4-Chloro-1H-indole-5-carboxylic acid [2-(6-chloro-pyridin-3-yl)-2-(4,4-difluoro-piperidin-1-yl)-ethyl]-amide;
4-Chloro-1H-indole-5-carboxylic acid [(R)-2-(2-methyl-pyrimidin-5-yl)-2-morpholin-4-yl-ethyl]-amide;
4-Chloro-1H-indole-5-carboxylic acid [(S)-2-(2-methyl-pyrimidin-5-yl)-2-morpholin-4-yl-ethyl]-amide;
4-Chloro-1H-indole-5-carboxylic acid [(R)-2-(4,4-difluoro-piperidin-1-yl)-2-(2-methyl-pyrimidin-5-yl)-ethyl]-amide;
4-Chloro-1H-indole-5-carboxylic acid [(S)-2-(4,4-difluoro-piperidin-1-yl)-2-(2-methyl-pyrimidin-5-yl)-ethyl]-amide;
4-Chloro-1H-indole-5-carboxylic acid [2-(6-methyl-pyridin-3-yl)-2-morpholin-4-yl-ethyl]-amide;
4-Chloro-1H-indole-5-carboxylic acid [2-(4,4-difluoro-piperidin-1-yl)-2-(2-trifluoromethyl-pyrimidin-5-yl)-ethyl]-amide;
4-Chloro-1H-indole-5-carboxylic acid [2-(2-cyclopropyl-pyrimidin-5-yl)-2-morpholin-4-yl-ethyl]-amide;

4-Chloro-1H-indole-5-carboxylic acid [2-morpholin-4-yl-2-(6-trifluoromethyl-pyridin-3-yl)-ethyl]-amide;
4-Chloro-1H-indole-5-carboxylic acid [2-(6-methoxy-pyridin-3-yl)-2-morpholin-4-yl-ethyl]-amide;
4-Chloro-1H-indole-5-carboxylic acid [2-dimethylamino-2-(2-methyl-pyrimidin-5-yl)-ethyl]-amide;
4-Chloro-1H-indole-5-carboxylic acid [2-azetidin-1-yl-2-(2-methyl-pyrimidin-5-yl)-ethyl]-amide;
4-Chloro-1H-indole-5-carboxylic acid [2-(2-methyl-pyrimidin-5-yl)-2-pyrrolidin-1-yl-ethyl]-amide;
4-Chloro-1H-indole-5-carboxylic acid [2-diethylamino-2-(2-methyl-pyrimidin-5-yl)-ethyl]-amide;
4-Chloro-1H-indole-5-carboxylic acid [2-(2-methyl-pyrimidin-5-yl)-2-piperidin-1-yl-ethyl]-amide;
4-Chloro-1H-indole-5-carboxylic acid [2-(4-fluoro-phenyl)-2-morpholin-4-yl-ethyl]-amide;
4-Chloro-1H-indole-5-carboxylic acid [2-(3,5-difluoro-phenyl)-2-morpholin-4-yl-ethyl]-amide;
4-{2-[(4-Chloro-1H-indole-5-carbonyl)-amino]-1-pyridin-3-yl-ethyl}-piperidine-1-carboxylic acid tert-butyl ester;
4-Chloro-1H-indole-5-carboxylic acid (2-piperidin-4-yl-2-pyridin-3-yl-ethyl)-amide;
4-Chloro-1H-indole-5-carboxylic acid [2-(1-methyl-piperidin-4-yl)-2-pyridin-3-yl-ethyl]-amide;
4-Chloro-1H-indole-5-carboxylic acid [2-(1-acetyl-piperidin-4-yl)-2-pyridin-3-yl-ethyl]-amide;
4-Chloro-1H-indole-5-carboxylic acid [2-(1-methanesulfonyl-piperidin-4-yl)-2-pyridin-3-yl-ethyl]-amide;
4-Chloro-1H-indole-5-carboxylic acid [2-(6-chloro-pyridin-3-yl)-2-morpholin-4-yl-ethyl]-amide;
4-Chloro-1H-indole-5-carboxylic acid (2-morpholin-4-yl-2-pyridin-3-yl-ethyl)-amide;
4-Chloro-1H-indole-5-carboxylic acid (2-morpholin-4-yl-2-pyrimidin-5-yl-ethyl)-amide;
4-Chloro-1H-indole-5-carboxylic acid (2-piperidin-1-yl-2-pyrimidin-5-yl-ethyl)-amide;
4-Chloro-1H-indole-5-carboxylic acid [2-(1-methyl-1H-pyrazol-4-yl)-2-morpholin-4-yl-ethyl]-amide;
4-Chloro-1H-indole-5-carboxylic acid [2-(1-methyl-1H-pyrazol-4-yl)-2-piperidin-1-yl-ethyl]-amide;
4-Chloro-1H-indole-5-carboxylic acid [2-piperidin-1-yl-2-(2,4,6-trifluoro-phenyl)-ethyl]-amide;
4-Chloro-1H-indole-5-carboxylic acid [2-(2,4-difluoro-phenyl)-2-piperidin-1-yl-ethyl]-amide;
4-Chloro-1H-indole-5-carboxylic acid [2-(5-fluoro-pyridin-2-yl)-2-piperidin-1-yl-ethyl]-amide;
4-Chloro-1H-indole-5-carboxylic acid [2-morpholin-4-yl-2-(2,4,6-trifluoro-phenyl)-ethyl]-amide;
4-Chloro-1H-indole-5-carboxylic acid [2-(2,4-difluoro-phenyl)-2-morpholin-4-yl-ethyl]-amide;
4-Chloro-1H-indole-5-carboxylic acid [2-(2-fluoro-phenyl)-2-morpholin-4-yl-ethyl]-amide;
4-Chloro-1H-indole-5-carboxylic acid [2-(5-fluoro-pyridin-2-yl)-2-morpholin-4-yl-ethyl]-amide;
4-Chloro-1H-indole-5-carboxylic acid [2-(3-fluoro-phenyl)-2-morpholin-4-yl-ethyl]-amide;
4-Chloro-1H-indole-5-carboxylic acid [2-(4-chloro-phenyl)-2-morpholin-4-yl-ethyl]-amide;
4-Chloro-1H-indole-5-carboxylic acid [2-(2,4-dichloro-phenyl)-2-morpholin-4-yl-ethyl]-amide;
4-Chloro-1H-indole-5-carboxylic acid [2-(4-chloro-2-fluoro-phenyl)-2-morpholin-4-yl-ethyl]-amide;
4-Chloro-1H-indole-5-carboxylic acid [2-(cis-2,6-dimethyl-morpholin-4-yl)-2-(2-methyl-pyrimidin-5-yl)-ethyl]-amide;
4-Chloro-1H-indole-5-carboxylic acid [2-(trans-2,6-dimethyl-morpholin-4-yl)-2-(2-methyl-pyrimidin-5-yl)-ethyl]-amide;
4-Chloro-1H-indole-5-carboxylic acid [2-(3-fluoro-phenyl)-2-piperidin-1-yl-ethyl]-amide;
4-Chloro-1H-indole-5-carboxylic acid [2-piperidin-1-yl-2-(4-trifluoromethyl-phenyl)-ethyl]-amide;
4-Chloro-1H-indole-5-carboxylic acid [2-(3,4-difluoro-phenyl)-2-piperidin-1-yl-ethyl]-amide;
4-Chloro-1H-indole-5-carboxylic acid (2-piperidin-1-yl-2-pyridin-3-yl-ethyl)-amide;
4-Chloro-1H-indole-5-carboxylic acid (2-morpholin-4-yl-2-p-tolyl-ethyl)-amide;
4-Chloro-1H-indole-5-carboxylic acid [2-morpholin-4-yl-2-(4-trifluoromethoxy-phenyl)-ethyl]-amide;
4-Chloro-1H-indole-5-carboxylic acid [2-morpholin-4-yl-2-(4-trifluoromethyl-phenyl)-ethyl]-amide;
4-Chloro-1H-indole-5-carboxylic acid [2-(3,4-difluoro-phenyl)-2-morpholin-4-yl-ethyl]-amide;
4-Chloro-1H-indole-5-carboxylic acid [2-(2-methyl-pyrimidin-5-yl)-2-(tetrahydro-pyran-4-yl)-ethyl]-amide;
4-Chloro-1H-indole-5-carboxylic acid [2-cyclopentyloxy-2-(2-methyl-pyrimidin-5-yl)-ethyl]-amide;
4-Chloro-1H-indole-5-carboxylic acid [2-(3,5-dimethyl-isoxazol-4-yl)-2-morpholin-4-yl-ethyl]-amide;
4-Chloro-1H-indole-5-carboxylic acid [2-(3,5-dimethyl-isoxazol-4-yl)-2-piperidin-1-yl-ethyl]-amide;
4-Chloro-1H-indole-5-carboxylic acid (2-piperidin-1-yl-2-p-tolyl-ethyl)-amide;
4-Chloro-1H-indole-5-carboxylic acid [2-(6-chloro-pyridin-3-yl)-2-piperidin-1-yl-ethyl]-amide;
4-Chloro-1H-indole-5-carboxylic acid [2-(4-phenoxy-phenyl)-2-piperidin-1-yl-ethyl]-amide;
4-Chloro-1H-indole-5-carboxylic acid [2-morpholin-4-yl-2-(4-phenoxy-phenyl)-ethyl]-amide;
4-Chloro-1H-indole-5-carboxylic acid [2-(4-methoxy-phenyl)-2-morpholin-4-yl-ethyl]-amide;
4-Chloro-1H-indole-5-carboxylic acid [2-(5-methyl-pyrazin-2-yl)-2-piperidin-1-yl-ethyl]-amide;
4-Chloro-1H-indole-5-carboxylic acid (2-isothiazol-5-yl-2-piperidin-1-yl-ethyl)-amide;
4-Chloro-1H-indole-5-carboxylic acid (2-piperidin-1-yl-2-thiazol-5-yl-ethyl)-amide;
4-Chloro-1H-indole-5-carboxylic acid [2-(5-methyl-pyrazin-2-yl)-2-morpholin-4-yl-ethyl]-amide;
4-Chloro-1H-indole-5-carboxylic acid (2-morpholin-4-yl-2-thiazol-5-yl-ethyl)-amide;
4-Chloro-1H-indole-5-carboxylic acid [2-(6-chloro-pyridin-3-yl)-2-cyclohexyl-ethyl]-amide;
4-Chloro-1H-indole-5-carboxylic acid [2-(6-chloro-pyridin-3-yl)-4-methyl-pentyl]-amide;
4-Chloro-1H-indole-5-carboxylic acid [2-ethoxy-2-(2-methyl-pyrimidin-5-yl)-ethyl]-amide;
4-Chloro-1H-indole-5-carboxylic acid [2-(2-methyl-pyrimidin-5-yl)-2-(2-oxa-5-azabicyclo[2.2.1]hept-5-yl)-ethyl]-amide;
4-Chloro-1H-indole-5-carboxylic acid [2-cyclohexyloxy-2-(2-methyl-pyrimidin-5-yl)-ethyl]-amide;
4-Chloro-1H-indole-5-carboxylic acid [2-(2-methyl-pyrimidin-5-yl)-2-(tetrahydro-pyran-4-yloxy)-ethyl]-amide;
4-Chloro-1H-indole-5-carboxylic acid [2-(1-ethyl-propoxy)-2-(2-methyl-pyrimidin-5-yl)-ethyl]-amide;
4-Chloro-2-methyl-1H-indole-5-carboxylic acid [2-(2-methyl-pyrimidin-5-yl)-2-morpholin-4-yl-ethyl]-amide;

4-Chloro-1H-indole-5-carboxylic acid (2-piperidin-1-yl-2-pyridazin-3-yl-ethyl)-amide;
4-Chloro-1H-indole-5-carboxylic acid [2-(2-hydroxy-pyridin-4-yl)-2-piperidin-1-yl-ethyl]-amide;
1-[2-[(4-Chloro-1H-indole-5-carbonyl)-amino]-1-(2-methyl-pyrimidin-5-yl)-ethyl]-piperidine-4-carboxylic acid tert-butyl ester;
4-Chloro-1H-indole-5-carboxylic acid [2-(4-methyl-piperidin-1-yl)-2-(2-methyl-pyrimidin-5-yl)-ethyl]-amide;
4-Chloro-1H-indole-5-carboxylic acid [(R)-2-(2-methyl-piperidin-1-yl)-2-(2-methyl-pyrimidin-5-yl)-ethyl]-amide;
4-Chloro-1H-indole-5-carboxylic acid [2-(4-fluoro-piperidin-1-yl)-2-(2-methyl-pyrimidin-5-yl)-ethyl]-amide;
4-Chloro-1H-indole-5-carboxylic acid [2-(3,3-difluoro-piperidin-1-yl)-2-(2-methyl-pyrimidin-5-yl)-ethyl]-amide;
4-Chloro-1H-indole-5-carboxylic acid [2-azepan-1-yl-2-(2-methyl-pyrimidin-5-yl)-ethyl]-amide;
4-Chloro-1H-indole-5-carboxylic acid [2-(2-methyl-pyrimidin-5-yl)-2-[1,4]oxazepan-4-yl-ethyl]-amide;
4-Chloro-1H-indole-5-carboxylic acid [2-(3,3-difluoro-pyrrolidin-1-yl)-2-(2-methyl-pyrimidin-5-yl)-ethyl]-amide;
4-Chloro-1H-indole-5-carboxylic acid [2-cyclopentyl-amino-2-(2-methyl-pyrimidin-5-yl)-ethyl]-amide;
4-Chloro-1H-indole-5-carboxylic acid [2-(cyclopentylmethyl-amino)-2-(2-methyl-pyrimidin-5-yl)-ethyl]-amide;
4-Chloro-1H-indole-5-carboxylic acid [2-isobutylamino-2-(2-methyl-pyrimidin-5-yl)-ethyl]-amide;
4-Chloro-1H-indole-5-carboxylic acid [2-(isobutyl-methyl-amino)-2-(2-methyl-pyrimidin-5-yl)-ethyl]-amide;
4-Chloro-1H-indole-5-carboxylic acid [2-(benzyl-methyl-amino)-2-(2-methyl-pyrimidin-5-yl)-ethyl]-amide;
4-Chloro-1H-indole-5-carboxylic acid (3-ethyl-2-pyrimidin-5-yl-pentyl)-amide;
4-[2-[(4-Chloro-1H-indole-5-carbonyl)-amino]-1-(2-methyl-pyrimidin-5-yl)-ethyl]-piperazine-1-carboxylic acid tert-butyl ester;
4-Chloro-1H-indole-5-carboxylic acid (2-morpholin-4-yl-2-pyridazin-3-yl-ethyl)-amide;
4-Chloro-1H-indole-5-carboxylic acid [2-morpholin-4-yl-2-(2-hydroxypyridin-4-yl)-ethyl]-amide;
4-Chloro-1H-indole-5-carboxylic acid [2-(1,1-dioxo-thiomorpholin-4-yl)-2-(2-methyl-pyrimidin-5-yl)-ethyl]-amide;
4-Chloro-1H-indole-5-carboxylic acid [2-(4,4-difluoro-cyclohexyl)-2-(2-methyl-pyrimidin-5-yl)-ethyl]-amide;
4,6-Dichloro-1H-indole-5-carboxylic acid [2-(2-methyl-pyrimidin-5-yl)-2-morpholin-4-yl-ethyl]-amide;
4-Chloro-1H-indole-5-carboxylic acid [2-(2-methyl-pyrimidin-5-yl)-2-(6-oxa-3-azabicyclo[3.1.1]hept-3-yl)-ethyl]-amide;
4-Chloro-7-methyl-1H-indole-5-carboxylic acid [(R)-2-(2-methyl-pyrimidin-5-yl)-2-morpholin-4-yl-ethyl]-amide;
4-Chloro-7-methyl-1H-indole-5-carboxylic acid [(S)-2-(2-methyl-pyrimidin-5-yl)-2-morpholin-4-yl-ethyl]-amide;
4-Chloro-7-isobutyl-1H-indole-5-carboxylic acid [2-(2-methyl-pyrimidin-5-yl)-2-morpholin-4-yl-ethyl]-amide;
4-Chloro-7-(3-methoxy-propyl)-1H-indole-5-carboxylic acid [2-(2-methyl-pyrimidin-5-yl)-2-morpholin-4-yl-ethyl]-amide;
4-Methyl-1H-indole-5-carboxylic acid [2-(2-methyl-pyrimidin-5-yl)-2-morpholin-4-yl-ethyl]-amide;
4-Ethyl-1H-indole-5-carboxylic acid [2-(2-methyl-pyrimidin-5-yl)-2-morpholin-4-yl-ethyl]-amide;
7-Acetyl-4-chloro-1H-indole-5-carboxylic acid [2-(2-methyl-pyrimidin-5-yl)-2-morpholin-4-yl-ethyl]-amide;
7-Methyl-4-trifluoromethyl-1H-indole-5-carboxylic acid [2-(2-methyl-pyrimidin-5-yl)-2-morpholin-4-yl-ethyl]-amide;
4,7-Dimethyl-1H-indole-5-carboxylic acid [2-(2-methyl-pyrimidin-5-yl)-2-morpholin-4-yl-ethyl]-amide;
4-Methyl-1H-indole-5-carboxylic acid [(S)-2-(2-methyl-pyrimidin-5-yl)-2-morpholin-4-yl-ethyl]-amide;
4-Methyl-1H-indole-5-carboxylic acid [(R)-2-(2-methyl-pyrimidin-5-yl)-2-morpholin-4-yl-ethyl]-amide;
4-Chloro-7-ethyl-1H-indole-5-carboxylic acid [2-(2-methyl-pyrimidin-5-yl)-2-morpholin-4-yl-ethyl]-amide;
7-Chloro-4-methyl-1H-indole-5-carboxylic acid [2-(2-methyl-pyrimidin-5-yl)-2-morpholin-4-yl-ethyl]-amide;
7-Methoxy-4-methyl-1H-indole-5-carboxylic acid [2-(2-methyl-pyrimidin-5-yl)-2-morpholin-4-yl-ethyl]-amide;
4-Chloro-7-ethoxy-1H-indole-5-carboxylic acid [2-(2-methyl-pyrimidin-5-yl)-2-morpholin-4-yl-ethyl]-amide;
4-Chloro-7-propyl-1H-indole-5-carboxylic acid [2-(2-methyl-pyrimidin-5-yl)-2-morpholin-4-yl-ethyl]-amide;
7-(2-tert-Butoxy-ethoxy)-4-chloro-1H-indole-5-carboxylic acid [2-(2-methyl-pyrimidin-5-yl)-2-morpholin-4-yl-ethyl]-amide;
4-Chloro-7-(2-hydroxy-ethoxy)-1H-indole-5-carboxylic acid [2-(2-methyl-pyrimidin-5-yl)-2-morpholin-4-yl-ethyl]-amide;
4-Chloro-7-methoxy-1H-indole-5-carboxylic acid [(S)-2-(2-methyl-pyrimidin-5-yl)-2-morpholin-4-yl-ethyl]-amide;
4-Chloro-7-methoxy-1H-indole-5-carboxylic acid [(R)-2-(2-methyl-pyrimidin-5-yl)-2-morpholin-4-yl-ethyl]-amide;
4-Chloro-7-(1-hydroxy-1-methyl-ethyl)-1H-indole-5-carboxylic acid [2-(2-methyl-pyrimidin-5-yl)-2-morpholin-4-yl-ethyl]-amide;
4,7-Difluoro-1H-indole-5-carboxylic acid [2-(2-methyl-pyrimidin-5-yl)-2-morpholin-4-yl-ethyl]-amide; and
4-Fluoro-7-methoxy-1H-indole-5-carboxylic acid [2-(2-methyl-pyrimidin-5-yl)-2-morpholin-4-yl-ethyl]-amide;
or a salt of such a compound.

12. The compound of formula ($I_{Ar}$) according to claim 7, wherein A and B represent N:
or a pharmaceutically acceptable salt thereof.

13. A pharmaceutical composition containing, as active principle, the compound of formula (I) according to claim 1, or a pharmaceutically acceptable salt thereof, and at least one therapeutically inert excipient.

14. A method for the treatment of a disease selected from spinal cord injury, stroke, epilepsy, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, osteoporosis, and ischemic heart disease, comprising administering to a subject a pharmaceutically active amount of the compound of formula (I) according to claim 1, or a pharmaceutically acceptable salt thereof.

15. A method for the treatment of a disease selected from spinal cord injury, stroke, epilepsy, amyotrophic lateral sclerosis, pain, rheumatoid arthritis, asthma, chronic obstructive pulmonary disease, lung emphysema, glomerulonephritis, irritable bowel syndrome, psoriasis, atopic dermatitis, Crohn's disease, ulcerative colitis, diabetes mellitus, osteoporosis, and ischemic heart disease, comprising administering to a subject a pharmaceutically active amount of a compound according to claim 11, or a pharmaceutically acceptable salt thereof.

16. The compound of formula ($I_{Ar}$) according to claim 8, wherein
   $R^6$ represents chloro;
or a salt of such a compound.

17. The compound of formula ($I_{Ar}$) according to claim 8, wherein
   $R^6$ represents methyl;
or a salt of such a compound.

18. The compound of formula ($I_{Ar}$) according to claim 12, wherein
   $R^6$ represents chloro;
or a salt of such a compound.

19. The compound of formula ($I_{Ar}$) according to claim 12, wherein
   $R^6$ represents methyl;
or a salt of such a compound.

* * * * *